United States Patent
Chakravarty et al.

(10) Patent No.: US 9,422,267 B2
(45) Date of Patent: *Aug. 23, 2016

(54) FUSED PYRIMIDINE COMPOUNDS AND USE THEREOF

(71) Applicant: Medivation Technologies, Inc., San Francisco, CA (US)

(72) Inventors: Sarvajit Chakravarty, Mountain View, CA (US); Roopa Rai, San Carlos, CA (US); Michael John Green, Half Moon Bay, CA (US)

(73) Assignee: Medivation Technologies, Inc., San Francisco, CA (US)

( * ) Notice: Subject to any disclaimer, the term of this patent is extended or adjusted under 35 U.S.C. 154(b) by 124 days.

This patent is subject to a terminal disclaimer.

(21) Appl. No.: 14/141,003

(22) Filed: Dec. 26, 2013

(65) Prior Publication Data

US 2014/0179668 A1    Jun. 26, 2014

Related U.S. Application Data

(60) Provisional application No. 61/746,088, filed on Dec. 26, 2012, provisional application No. 61/798,842, filed on Mar. 15, 2013.

(51) Int. Cl.

| | | |
|---|---|---|
| C07D 401/14 | (2006.01) | |
| C07D 403/14 | (2006.01) | |
| C07D 413/14 | (2006.01) | |
| C07D 417/14 | (2006.01) | |
| C07D 491/107 | (2006.01) | |
| A61K 31/502 | (2006.01) | |
| C07D 405/14 | (2006.01) | |
| C07F 9/6558 | (2006.01) | |

(52) U.S. Cl.
CPC ............ *C07D 401/14* (2013.01); *C07D 403/14* (2013.01); *C07D 405/14* (2013.01); *C07D 413/14* (2013.01); *C07D 417/14* (2013.01); *C07D 491/107* (2013.01); *C07F 9/65583* (2013.01)

(58) Field of Classification Search
None
See application file for complete search history.

(56) References Cited

U.S. PATENT DOCUMENTS

| | | | |
|---|---|---|---|
| 5,739,127 | A | 4/1998 | Schohe-Loop et al. |
| 7,381,714 | B2 | 6/2008 | Elzein et al. |
| 7,511,045 | B2 | 3/2009 | Hoenke et al. |
| 7,514,417 | B2 | 4/2009 | Elzein et al. |
| 7,648,986 | B2 | 1/2010 | Nagarathnam et al. |
| 7,989,463 | B2 | 8/2011 | De et al. |
| 2006/0281771 | A1 | 12/2006 | Baumann et al. |
| 2007/0259846 | A1 | 11/2007 | Hoenke et al. |
| 2011/0124623 | A1 | 5/2011 | Wittman et al. |
| 2011/0251181 | A1 | 10/2011 | Banka et al. |
| 2013/0085135 | A1 | 4/2013 | Banka et al. |

FOREIGN PATENT DOCUMENTS

| | | |
|---|---|---|
| CN | 102584828 A | 7/2012 |
| WO | 03/059913 A1 | 7/2003 |
| WO | 2006/046135 A2 | 5/2006 |
| WO | 2006/067614 A2 | 6/2006 |
| WO | 2006/111549 A1 | 10/2006 |
| WO | 2006/125190 A1 | 11/2006 |
| WO | 2006/125211 A1 | 11/2006 |
| WO | 2007/023382 A2 | 3/2007 |
| WO | 2009/050199 A1 | 4/2009 |
| WO | 2009/050236 A1 | 4/2009 |
| WO | 2009/050248 A1 | 4/2009 |
| WO | 2009/143058 A1 | 11/2009 |
| WO | 2014/105958 A2 | 7/2014 |

OTHER PUBLICATIONS

Weroha et al J.Mammary Gland Biol. Neoplasia, vol. 13, p. 471-483 (2008).*

(Continued)

*Primary Examiner* — Emily Bernhardt

(74) *Attorney, Agent, or Firm* — Morrison & Foerster LLP

(57) ABSTRACT

The present invention provides fused pyrimidine compounds of the general Formula (I):

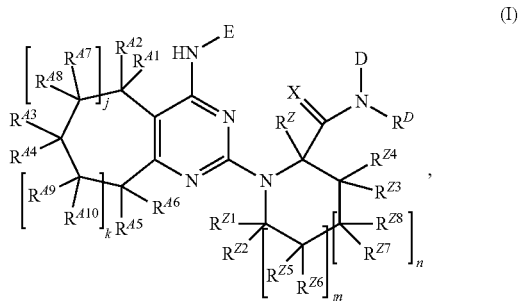

or a salt thereof, wherein the variables are as defined in the specification. Fused pyrimidine compounds of the general Formula (I) are provided as kinase inhibitors, such as multi-kinase inhibitors. In one aspect, fused pyrimidine compounds of the general Formula (I) are provided as IGF-IR inhibitors. The compounds may be used in a method of treating cancer. Pharmaceutical compositions containing a fused pyrimidine compounds of the general Formula (I) and a pharmaceutically acceptable carrier are also provided, as are kits containing a fused pyrimidine compound of the general Formula (I) or salt thereof and instructions for use, e.g., in a method of treating cancer.

138 Claims, 4 Drawing Sheets

(56) References Cited

OTHER PUBLICATIONS

Chen et al. Chin J Cancer; 2013; vol. 32 Issue 5, pp. 242-252.*
Cancer Drug Design and Discovery, Neidle, Stephen,ed. (Elsevier/Academic Press), pp. 427-431 (2008).*
Akil et al., "Fine-Tuning Roles of Endogenous Brain-Derived Neurotrophic Factor, TrkB and Sortilin in Colorectal Cancer Cell Survival", PLoS One, vol. 6, Issue 9, Sep. 2011, 15 pages.
Asgharzadeh et al., "Prognostic Significance of Gene Expression Profiles of Metastatic Neuroblastomas Lacking MYCN Gene Amplification", Journal of the National Cancer Institute, vol. 98, No. 17, Sep. 6, 2006, pp. 1193-1203.
Aware et al., "Cyclopentyl-Pyrimidine based Analogues as Novel and Potent IGF-1R Inhibitor", European Journal of Medicinal Chemistry, vol. 92, Mar. 6, 2015, pp. 246-256.
Belli et al., "AC220, A Uniquely Potent and Selective FLT3 Inhibitor, Enhances the Cytotoxiceffects of Chemotherapeutic Agents in Cell Culture and in Mouse Tumor Xenografts", Ambit Biosciences,, 2009, 1 page.
Betts et al., "Impact of Physicochemical and Structural Properties on the Pharmacokinetics of a Series of α1L-Adrenoceptor Antagonists", Drug Metabolism and Disposition, vol. 35, No. 8, May 14, 2007, pp. 1435-1445.
Brodeur et al., "Trk Receptor Expression and Inhibition in Neuroblastomas", Clin. Cancer Res., vol. 15, No. 10, May 15, 2009, pp. 3244-3250.
Dang et al., "Expression of Nerve Growth Factor Receptors is Correlated with Progression and Prognosis of Human Pancreatic Cancer", Gastroenterology, vol. 21, No. 5, 2006, pp. 850-858.
Elzein et al., "N6-Cycloalkyl-2-Substituted Adenosine Derivatives as Selective, High Affinity Adenosine A1 Receptor Agonists", Bioorganic & Medicinal Chemistry Letters, vol. 17, Issue 1, Jan. 1, 2007, pp. 161-166.
Fathi et al., "Treatment of FLT3-ITD acute myeloid leukemia", American Journal of Blood Research, vol. 1, No. 2, Sep. 9, 2011, pp. 175-189.
Gualberto et al., "Emerging role of Insulin-like Growth Factor Receptor Inhibitors in Oncology: Early Clinical Trial Results and Future Directions", Oncogene, vol. 28, 2009, pp. 3009-3021.
Ho et al., "Resistance to Chemotherapy Mediated by TrkB in Neuroblastomas1", Cancer Research, vol. 62, No. 22, Nov. 15, 2002, pp. 6462-6466.
Huang et al., "TRK Receptors: Roles in Neuronal Signal Transduction", Annu. Rev. Biochem, vol. 72, 2003, pp. 609-642.
Li et al., "AMG 925 Is a Dual FLT3/CDK4 Inhibitor with the Potential to Overcome FLT3 Inhibitor Resistance in Acute Myeloid Leukemia", Molecular Cancer Therapeutics, vol. 14, No. 2, Feb. 2015, pp. 375-383.
Li et al., "TrkBT1 Induces Liver Metastasis of Pancreatic Cancer Cells by Sequestering Rho GDP Dissociation Inhibitor and Promoting RhoA Activation", Cancer Res., vol. 69, No. 19, Oct. 1, 2009, pp. 7851-7859.
Liu et al., "siRNA Directed against TrkA Sensitizes Human Pancreatic Cancer Cells to Apoptosis Induced by Gemcitabine Through an Inactivation of PI3K/Akt-Dependent Pathway", Oncology Reports, vol. 18, No. 3, 2007, pp. 673-677.
Ma et al., "Expression of Nerve Growth Factor and Tyrosine Kinase Receptor A and Correlation with Perineural Invasion in Pancreatic Cancer", Gastroenterology, vol. 23, No. 12, May 2008, pp. 1852-1859.

Matsumoto et al., "Expression of Brain-Derived Neurotrophic Factor and p145TrkB Affects Survival, Differentiation, and Invasiveness of Human Neuroblastoma Cells1", Cancer Research, vol. 55, Apr. 15, 1995, pp. 1798-1806.
Miknyoczki et al., "Neurotrophins and Trk Receptors in Human Pancreatic Ductal Adenocarcinoma: Expression Patterns and Effects ON in vitroInvasive Behavior", Int. J. Cancer, vol. 81, No. 3, 1999, pp. 417-427.
Nakagawara, et al., "Expression and Function of TRK-B and BDNF in Human Neuroblastomas", Molecular and Cellular Biology, vol. 14, No. 1, Jan. 1994, pp. 759-767.
Okada et al., "Nerve Growth Factor Stimulates MMP-2 Expression and Activity and Increases Invasion by Human Pancreatic Cancer Cells", Clinical & Experimental Metastasis, vol. 21, No. 4, 2004, pp. 285-292.
International Preliminary Report on Patentability received for PCT Patent Application No. PCT/US2013/077817, mailed on Jul. 9, 2015, 7 pages.
International Search Report for PCT Patent Application No. PCT/US2013/077817, mailed on Apr. 23, 2014, 4 pages.
Written Opinion received for PCT Patent Application No. PCT/US2013/077817, mailed on Apr. 23, 2014, 5 pages.
Rodon et al., "Early Drug Development of Inhibitors of the Insulin-like Growth Factor-I Receptor Pathway: Lessons from the First Clinical Trials", Mol. Cancer Ther., vol. 7, No. 9, Sep. 2008, pp. 2575-2588.
Sakamoto et al., "Expression of TRK Tyrosine Kinase Receptor is a Biologic Marker for Cell Proliferation and Perineural Invasion of Human Pancreatic Ductal Adenocarcinoma", Oncology Reports, vol. 8, Issue 3, May 2001, pp. 477-484.
Samani et al., "The Role of the IGF System in Cancer Growth and Metastasis: Overview and Recent Insights", Endocrine Reviews, vol. 28, No. 1, Feb. 2007, pp. 20-47.
Sasahira et al., "Tropomyosin Receptor Kinases B and C are Tumor Progressive and Metastatic Marker in Colorectal Carcinoma", Human Pathology, vol. 44, No. 6, 2013, pp. 1098-1106.
Sasine et al., "Emerging Strategies for High-Risk and Relapsed/Refractory Acute Myeloid Leukemia: Novel Agents and Approaches Currently in Clinical Trials", Blood Reviews, vol. 29, Issue 1, Jan. 2015, pp. 1-9.
Sclabas et al., "Overexpression of Tropomysin-Related Kinase B in Metastatic Human Pancreatic Cancer Cells", Clinical Cancer Research, vol. 11, Jan. 15, 2005, pp. 440-449.
Tollefson et al., "1-(2-Ethoxyethyl)-1H-pyrazolo[4,3-d]Pyrimidines as Potent Phosphodiesterase 5 (PDE5) Inhibitors", Bioorganic & Medicinal Chemistry Letters, vol. 20, 2010, pp. 3120-3124.
Xu et al., "Design, Synthesis and Biological Evaluation of FLT3 Covalent Inhibitors with a Resorcylic Acid Core", Bioorganic & Medicinal Chemistry, vol. 22, Issue 23, Dec. 1, 2014, pp. 6625-6637.
Yu et al., "Overexpression of TrkB Promotes the Progression of Colon Cancer", APMIS, vol. 118, No. 3, 2010, pp. 188-195.
Zarrinkar et al., "AC220 is a Uniquely Potent and Selective Inhibitor of FLT3 for the Treatment of Acute Myeloid Leukemia (AML)", Blood, vol. 114, No. 14, Oct. 1, 2009, pp. 2984-2992.
International Search Report received for PCT Patent Application No. PCT/US2015/038140, mailed on Jan. 12, 2016, 5 pages.
Written Opinion received for PCT Patent Application No. PCT/US2015/038140, mailed on Jan. 12, 2016, 8 pages.

\* cited by examiner

Figure 1. Cpd 8b reduces tumor burden in COLO205 xenograft model of human colon cancer
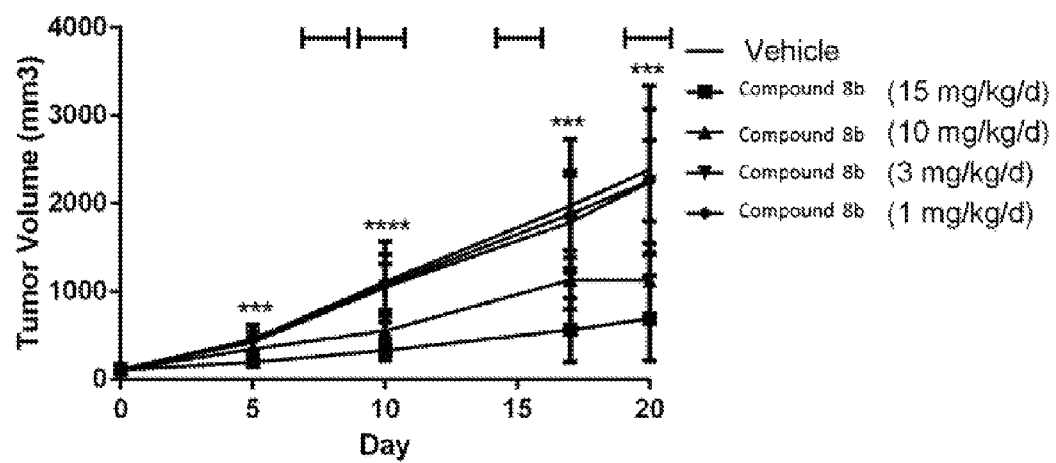

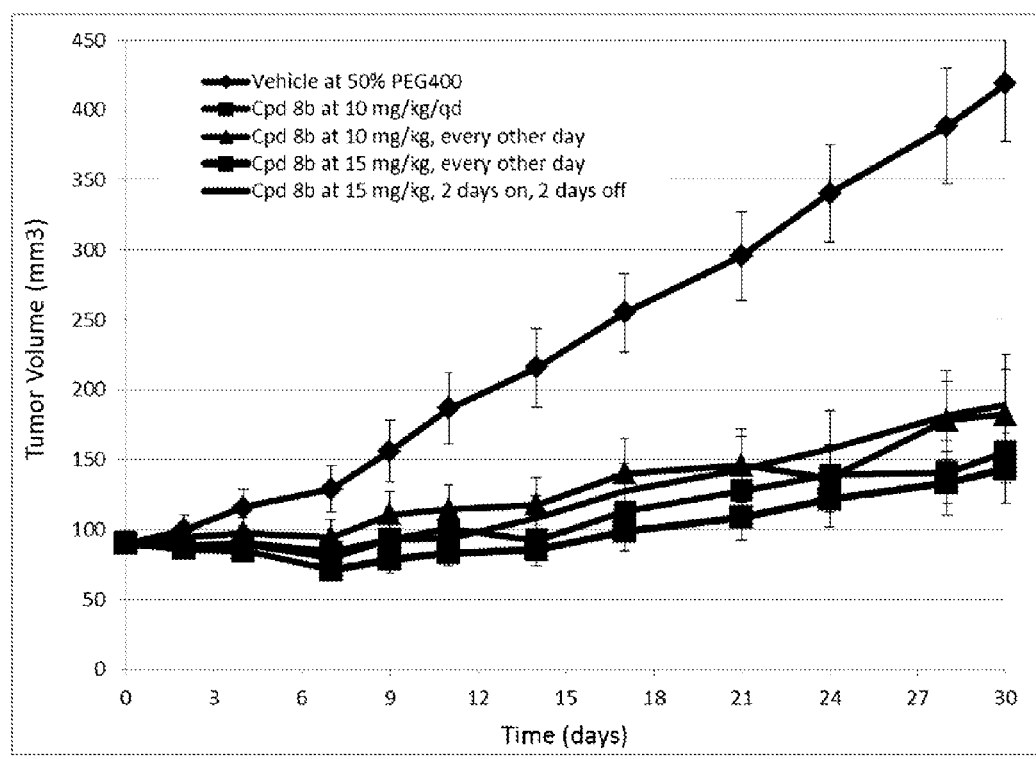
Figure 2. Cpd 8b reduces tumor burden in MCF7 xenograft model of human breast cancer Figure 3. Effect of Cpd 8b on body weight in COLO205 xenograft model of human colon cancer
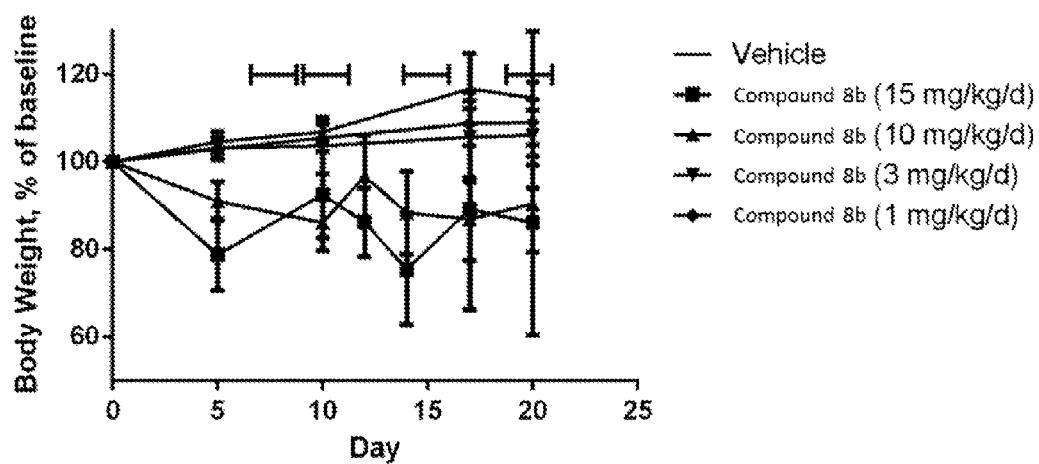

Figure 4. Effect of Cpd 8b on body weight in MCF7 xenograft model of human breast cancer
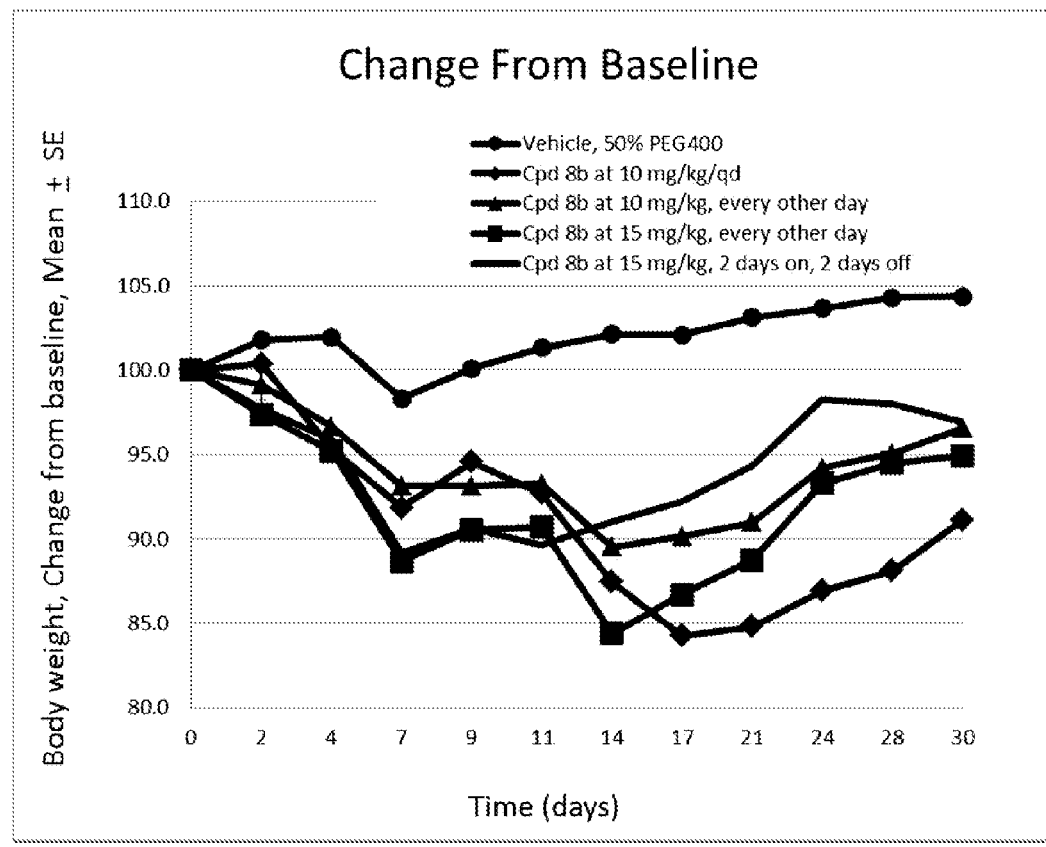

FUSED PYRIMIDINE COMPOUNDS AND USE THEREOF

CROSS-REFERENCE TO RELATED APPLICATIONS

This application claims the priority benefit of U.S. Provisional Patent Application No. 61/746,088, filed Dec. 26, 2012 and U.S. Provisional Patent Application No. 61/798,842, filed Mar. 15, 2013, the disclosures of which are incorporated by reference in their entireties.

BACKGROUND OF THE INVENTION

The insulin-like growth factor-I receptor (IGF-IR) is a tyrosine kinase membrane receptor having a structure very similar to that of the insulin receptor (IR). The structure of IGF-IR consists of two extracellular α-chains that form the ligand-binding domain and two β-chains that make up the transmembrane and intracellular domains. IGF-IR is the primary receptor for insulin-like growth factor IGF-I, although IGF-II and insulin can also bind with less affinity. Upon ligand binding, IGF-IR is activated, resulting in autophosphorylation of tyrosines on the intracellular β-subunit. IGF-IR then phosphorylates intracellular proteins such as the insulin receptor substrates 1 to 4 (IRS1-IRS4) and Shc. These substrates, in turn, initiate phosphorylation cascades that activate the phosphatidylinositol 3-kinase (PI-3K)/protein kinase B (Akt) or mitogen-activated protein kinase (MAPK) pathways (Samani et al. *Endocr. Rev.* 28:20-47 (2007)).

Through activation of these signaling cascades, IGF-IR has been implicated in cancer. The exact role of IGF-IR in cancer, however, remains uncertain and appears to vary according to tumor or cell type. For example, some tumors may depend on IGF-IR signaling for survival, whereas others rely on IGF-IR for proliferation. Yet other tumors may employ IGF-IR overexpression as a mechanism of resistance against cytotoxic agents such as anti-cancer drugs (Rodon et al. *Mol. Cancer Ther.* 7:2575-2588 (2008)). Accordingly, inhibition of IGF-IR is an attractive drug strategy for cancer treatment.

Although IGF-IR was first cloned in the 1980s, drug development to target IGF-IR has been slow to develop. Currently, there are close to 30 drug candidates that target IGF-IR in various clinical phases including both monoclonal antibodies and small molecule tyrosine kinase inhibitors, but no molecule has yet received FDA approval for cancer treatment (Rodon et al. *Mol. Cancer Ther.* 7:2575-2588 (2008); Gualberto et al. *Oncogene* 28:3009-3021 (2009)). There remains a clear need to target IGF-IR through the development of potent inhibitors of this receptor.

BRIEF SUMMARY OF THE INVENTION

Fused pyrimidine compounds of the general Formula (I) are described as new kinase modulators, such as modulators of anyone or more of the kinases of Tables B7-B13. The fused pyrimidine compounds of the general Formula (I) in one aspect are multi-kinase modulators. In one aspect, the fused pyrimidine compounds of the general Formula (I) are described as new insulin-like growth factor-I receptor modulators. Other compounds are also detailed herein. Compositions and kits comprising a compound are provided, as are methods of using and making the compounds. Other fused pyrimidine compounds are also provided. Compounds of the invention may also find use in treating of cancer. Compounds of the invention may also find use in treating diseases and/or conditions in which modulation of a kinase (e.g., one or more of the kinases of Tables B7-B13) may be implicated in therapy. Compounds of the invention may also find use in treating diseases and/or conditions in which modulation of insulin-like growth factor-I receptors may be implicated in therapy. Compounds disclosed herein may find use in the methods disclosed herein, including use in treating, preventing, delaying the onset and/or delaying the development of cancer in an individual in need thereof, such as a human.

In one variation, provided are compounds of the Formula (I):

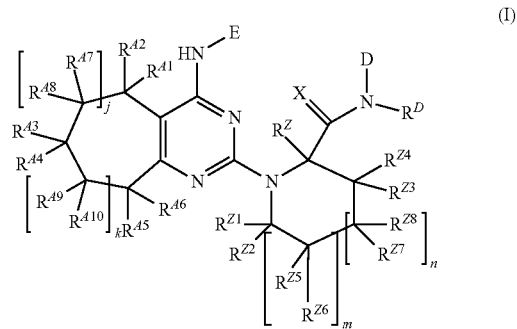

or a salt thereof, wherein:

D is hydrogen, substituted or unsubstituted $C_1$-$C_6$ alkyl, substituted or unsubstituted aryl, substituted or unsubstituted heteroaryl, substituted or unsubstituted $C_3$-$C_8$ cycloalkyl, substituted or unsubstituted heterocyclyl, or taken together with $R^D$ and the nitrogen to which they are attached to form a substituted or unsubstituted heterocyclyl;

E is substituted or unsubstituted heteroaryl;

each j, k, m, and n is independently 0 or 1;

each $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ where present, is independently hydrogen, substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —OC$(O)R^8$, —$C(O)R^9$, substituted or unsubstituted $C_3$-$C_8$ cycloalkyl, substituted or unsubstituted heterocyclyl, substituted or unsubstituted aryl, substituted or unsubstituted heteroaryl, or taken together with a geminal $R^{A(1-10)}$ group and the carbon to which they are attached to form carbonyl, thiocarbonyl, a $C_3$-$C_6$ cycloalkyl, or a heterocyclyl;

$R^D$ is hydrogen, substituted or unsubstituted $C_1$-$C_6$ alkyl, or taken together with D and the nitrogen to which they are attached to form a substituted or unsubstituted heterocyclyl;

X is O or S;

$R^Z$ is hydrogen, or substituted or unsubstituted $C_1$-$C_6$ alkyl;

each $R^{Z1}$ and $R^{Z2}$ is independently hydrogen, or substituted or unsubstituted $C_1$-$C_6$ alkyl, or $R^{Z1}$ and $R^{Z2}$ are taken together with the carbon to which they are attached to form a carbonyl or a $C_3$-$C_6$ cycloalkyl;

each $R^{Z3}$, $R^{Z4}$, $R^{Z5}$, $R^{Z6}$, $R^{Z7}$ and $R^{Z8}$, where present, is independently hydrogen, substituted or unsubstituted $C_1$-$C_6$ alkyl, halo, hydroxy, —$OR^1$, —O—$C_1$-$C_6$ alkylene-P(O)(OH)$_2$, —SH, —$S(O)_pR^2$, —$NR^3R^4$, —$C(O)NR^5R^6$, —$C(O)OR^7$, —OC(O)$R^8$, —$C(O)R^9$, substituted or unsubstituted $C_3$-$C_8$ cycloalkyl, substituted or unsubstituted heterocyclyl, substituted or unsubstituted aryl, substituted or unsubstituted heteroaryl, or taken together with a geminal $R^{Z(3-8)}$ group and the carbon to which they are attached to form carbonyl, thiocarbonyl or a $C_3$-$C_6$ cycloalkyl;

each p is independently 0, 1 or 2;

each $R^1$ is independently a substituted or unsubstituted $C_1$-$C_6$ alkyl, substituted or unsubstituted $C_3$-$C_8$ cycloalkyl, or substituted or unsubstituted aryl;

each $R^2$ is independently a substituted or unsubstituted $C_1$-$C_6$ alkyl, substituted or unsubstituted $C_3$-$C_8$ cycloalkyl, substituted or unsubstituted aryl or hydroxyl;

each $R^3$, $R^4$, $R^5$, $R^6$ and $R^7$ is independently hydrogen, substituted or unsubstituted $C_1$-$C_6$ alkyl, or substituted or unsubstituted $C_3$-$C_8$ cycloalkyl; and each $R^8$ and $R^9$ is independently hydrogen, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl.

In one variation, the compound is of Formula I, or a salt thereof, and j and k are each 0. In another variation, $R^{A1}$, $R^{A2}$, $R^{A3}$, $R^{A4}$, $R^{A5}$ and $R^{A6}$ are each hydrogen. In another variation, $R^{A1}$ and $R^{A2}$ are each $C_1$-$C_6$ alkyl and $R^{A3}$, $R^{A4}$, $R^{A5}$ and $R^{A6}$ are each hydrogen. In another variation, $R^{A1}$ and $R^{A2}$ are each methyl. In another variation, $R^{A3}$ and $R^{A4}$ are each $C_1$-$C_6$ alkyl and $R^{A1}$, $R^{A2}$, $R^{A5}$ and $R^{A6}$ are each hydrogen. In another variation, $R^{A3}$ and $R^{A4}$ are each methyl. In another variation, $R^{A5}$ and $R^{A6}$ are each $C_1$-$C_6$ alkyl and $R^{A1}$, $R^{A2}$, $R^{A3}$ and $R^{A4}$ are each hydrogen. In another variation, $R^{A5}$ and $R^{A6}$ are each methyl. In another variation, $R^{A3}$ and $R^{A4}$ are taken together to form substituted or unsubstituted cyclopropyl and $R^{A1}$, $R^{A2}$, $R^{A5}$ and $R^{A6}$ are each hydrogen. In another variation, $R^{A3}$ and $R^{A4}$ are taken together to form substituted or unsubstituted oxiranyl and $R^{A1}$, $R^{A2}$, $R^{A5}$ and $R^{A6}$ are each hydrogen. In another variation, $R^{A3}$ and $R^{A4}$ are taken together to form carbonyl and $R^{A1}$, $R^{A2}$, $R^{A5}$ and $R^{A6}$ are each hydrogen. In another variation, $R^{A3}$ and $R^{A4}$ are taken together to form thiocarbonyl and $R^{A1}$, $R^{A2}$, $R^{A5}$ and $R^{A6}$ are each hydrogen. In another variation, $R^{A3}$ and $R^{A4}$ are each halogen and $R^{A1}$, $R^{A2}$, $R^{A5}$ and $R^{A6}$ are each hydrogen. In another variation, $R^{A3}$ and $R^{A4}$ are each fluorine.

In another variation, the compound is of Formula I, or a salt thereof, and j is 1 and k is 0. In another variation, $R^{A1}$, $R^{A2}$, $R^{A3}$, $R^{A4}$, $R^{A5}$, $R^{A6}$, $R^{A7}$ and $R^{A8}$ are each hydrogen.

In another variation, j and k are each 1. In another variation, $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ are each hydrogen.

In another variation, the compound is of Formula I, or a salt thereof, and m and n are each 0. In another variation, each $R^{Z1}$, $R^{Z2}$, $R^{Z3}$ and $R^{Z4}$ is hydrogen.

In another variation, the compound is of Formula I, or a salt thereof, and m is 1 and n is 0. In another variation, each $R^{Z1}$, $R^{Z2}$, $R^{Z3}$ and $R^{Z4}$ is hydrogen. In another variation, $R^{Z5}$ and $R^{Z6}$ are each hydrogen. In another variation, $R^{Z5}$ is hydroxy and $R^{Z6}$ is hydrogen. In another variation, $R^{Z3}$ is hydroxy and $R^{Z4}$ is hydrogen. In another variation, $R^{Z5}$ is $C_1$-$C_6$ alkoxy and $R^{Z6}$ is hydrogen. In another variation, $R^{Z5}$ is methoxy. In another variation, $R^{Z5}$ is halogen and $R^{Z6}$ is hydrogen. In another variation, $R^{Z5}$ is fluorine. In another variation, $R^{Z5}$ and $R^{Z6}$ are each substituted or unsubstituted $C_1$-$C_6$ alkyl. In another variation, $R^{Z5}$ and $R^{Z6}$ are each methyl. In another variation, $R^{Z5}$ is substituted or unsubstituted heteroaryl and $R^{Z6}$ is hydrogen. In another variation, $R^{Z5}$ is substituted tetrazolyl. In another variation, $R^{Z5}$ and $R^{Z6}$ are each halogen. In another variation, $R^{Z5}$ and $R^{Z6}$ are each fluorine. In another variation, $R^{Z5}$ is —O—$C_1$-$C_6$ alkylene-P(O)(OH)$_2$, and $R^{Z6}$ is hydrogen. In another variation, $R^{Z5}$ is —OC(O)$R^8$ and $R^{Z6}$ is hydrogen.

In another variation, the compound is of Formula I, or a salt thereof, and m and n are each 1. In another variation, $R^{Z3}$, $R^{Z4}$, $R^{Z5}$, $R^{Z6}$, $R^{Z7}$ and $R^{Z8}$ are each hydrogen. In another variation, $R^Z$ is hydrogen. In another variation, $R^Z$ is substituted or unsubstituted $C_1$-$C_6$ alkyl. In another variation, $R^Z$ is unsubstituted $C_1$-$C_6$ alkyl. In another variation, $R^Z$ is methyl.

In another variation, the compound is of Formula I, or a salt thereof, and $R^D$ is hydrogen. In another variation, $R^D$ is substituted or unsubstituted $C_1$-$C_6$ alkyl.

In another variation, the compound is of Formula I, or a salt thereof, and D is hydrogen. In another variation, D is substituted or unsubstituted $C_1$-$C_6$ alkyl. In another variation, D is substituted or unsubstituted phenyl, substituted or unsubstituted pyridyl, substituted or unsubstituted pyrimidyl, substituted or unsubstituted pyrazinyl, substituted or unsubstituted thiazolyl, substituted or unsubstituted thiadiazolyl, substituted or unsubstituted $C_3$-$C_8$ cycloalkyl, or substituted or unsubstituted heterocyclyl. In another variation, D is substituted or unsubstituted phenyl. In another variation, D is substituted or unsubstituted pyridyl. In another variation, D is unsubstituted pyridyl. In another variation, D is substituted pyridyl. In another variation, D is selected from the group consisting of 3-pyridyl and 6-fluoro-3-pyridyl. In another variation, D is substituted or unsubstituted pyrimidyl. In another variation, D is unsubstituted pyrimidyl. In another variation, D is pyrimid-5-yl. In another variation, D is substituted pyrimidyl. In another variation, D is substituted or unsubstituted pyrazinyl. In another variation, D is pyrazin-2-yl. In another variation, D is substituted pyrazinyl. In another variation, D is substituted or unsubstituted thiazolyl. In another variation, D is unsubstituted thiazolyl. In another variation, D is substituted thiazolyl. In another variation, D is 5-chlorothiazol-2-yl. In another variation, D is substituted or unsubstituted thiadiazolyl. In another variation, D is unsubstituted thiadiazolyl. In another variation, D is substituted or unsubstituted $C_3$-$C_8$ cycloalkyl. In another variation, D is substituted or unsubstituted heterocyclyl. In another variation, D is substituted or unsubstituted pyrrolidin-3-yl. In another variation, D is substituted or unsubstituted piperidin-3-yl. In another variation, D is 1-(2-amino-2-methylpropanoyl)piperidin-3-yl. In another variation, D is 1-isopropylpiperidin-3-yl. In another variation, D is taken together with $R^D$ and the nitrogen to which they are attached to form a substituted or unsubstituted heterocyclyl. In another variation, D is taken together with $R^D$ and the nitrogen to which they are attached to form a substituted azetidinyl. In another variation, D is taken together with $R^D$ and the nitrogen to which they are attached to form 3-aminoazetidinyl.

In another variation, the compound is of Formula I, or a salt thereof, and E is a substituted or unsubstituted 5-membered heteroaryl. In another variation, E is a substituted or unsubstituted pyrazolyl. In another variation, E is a substituted pyrazolyl. In another variation, E is selected from the group consisting of 5-cyclopropylpyrazol-3-yl, 5-cyclopentylpyrazol-3-yl, 5-(isopropyl)pyrazol-3-yl, 3-cyclopropylpyrazol-5-yl, 3-cyclopentylpyrazol-5-yl and 3-(isopropyl)pyrazol-5-yl. In another variation, E is a substituted or unsubstituted imidazolyl. In another variation, E is a substituted or unsubstituted isoxazolyl. In another variation, E is a substituted or unsubstituted oxazole. In another variation, E is a substituted or unsubstituted thiazole.

In another variation, the compound of Formula I, or a salt thereof, is selected from the group consisting of:

1-(4-(5-cyclopropyl-1H-pyrazol-3-ylamino)-6,7-dihydro-5H-cyclopenta[d]pyrimidin-2-yl)-N-(6-fluoropyridin-3-yl)-2-methylpyrrolidine-2-carboxamide;

1-(4-(5-cyclopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;

1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide;

1-(4-(5-cyclopentyl-1H-pyrazol-3-ylamino)-6,7-dihydro-5H-cyclopenta[d]pyrimidin-2-yl)-N-(6-fluoropyridin-3-yl)pyrrolidine-2-carboxamide;

1-(4-(5-cyclopropyl-1H-pyrazol-3-ylamino)-6,7-dihydro-5H-cyclopenta[d]pyrimidin-2-yl)-N-(6-fluoropyridin-3-yl)azetidine-2-carboxamide;

1-(4-(5-cyclopropyl-1H-pyrazol-3-ylamino)-6,7-dihydro-5H-cyclopenta[d]pyrimidin-2-yl)-N-(pyrazin-2-yl)pyrrolidine-2-carboxamide;

1-(4-(5-cyclopropyl-1H-pyrazol-3-ylamino)-6,7-dihydro-5H-cyclopenta[d]pyrimidin-2-yl)-N-(pyrimidin-5-yl)pyrrolidine-2-carboxamide;

N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

1-(4-(5-cyclopropyl-1H-pyrazol-3-ylamino)-6,7-dihydro-5H-cyclopenta[d]pyrimidin-2-yl)-N-(6-fluoropyridin-3-yl)piperidine-2-carboxamide;

1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;

1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;

N-(6-fluoropyridin-3-yl)-1-(4-(3-isopropylisoxazol-5-ylamino)-6,7-dihydro-5H-cyclopenta[d]pyrimidin-2-yl)pyrrolidine-2-carboxamide;

N-(6-fluoropyridin-3-yl)-1-(4-(5-isopropyl-1H-pyrazol-3-ylamino)-5,6,7,8-tetrahydroquinazolin-2-yl)pyrrolidine-2-carboxamide;

1-(4-(5-cyclopropyl-1H-pyrazol-3-ylamino)-5,6,7,8-tetrahydroquinazolin-2-yl)-N-(6-fluoropyridin-3-yl)pyrrolidine-2-carboxamide;

1-(4-(5-cyclopentyl-1H-pyrazol-3-ylamino)-5,6,7,8-tetrahydroquinazolin-2-yl)-N-(6-fluoropyridin-3-yl)pyrrolidine-2-carboxamide;

N-(6-fluoropyridin-3-yl)-1-(4-(5-isopropyl-1H-pyrazol-3-ylamino)-6,7-dihydro-5H-cyclopenta[d]pyrimidin-2-yl)piperidine-2-carboxamide;

1-(4-(5-cyclopentyl-1H-pyrazol-3-ylamino)-6,7-dihydro-5H-cyclopenta[d]pyrimidin-2-yl)-N-(6-fluoropyridin-3-yl)piperidine-2-carboxamide;

1-(4-(5-isopropyl-1H-pyrazol-3-ylamino)-6,7-dihydro-5H-cyclopenta[d]pyrimidin-2-yl)pyrrolidine-2-carboxamide;

1-(4-(5-isopropyl-1H-pyrazol-3-ylamino)-6,7-dihydro-5H-cyclopenta[d]pyrimidin-2-yl)-N-methylpyrrolidine-2-carboxamide;

1-(4-(5-isopropyl-1H-pyrazol-3-ylamino)-6,7-dihydro-5H-cyclopenta[d]pyrimidin-2-yl)-N,N-dimethylpyrrolidine-2-carboxamide;

1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;

1-(4-((5-isopropyl-1H-pyrazol-3-yl)amino)-6,7-dihydro-5H-cyclopenta[d]pyrimidin-2-yl)-N-(pyrrolidin-3-yl)pyrrolidine-2-carboxamide;

(3-aminoazetidin-1-yl)(1-(4-((5-isopropyl-1H-pyrazol-3-yl)amino)-6,7-dihydro-5H-cyclopenta[d]pyrimidin-2-yl)pyrrolidin-2-yl)methanone;

1-(4-((5-cyclopropyl-1H-pyrazol-3-yl)amino)-6,7-dihydro-5H-cyclopenta[d]pyrimidin-2-yl)-N-(thiazol-2-yl)pyrrolidine-2-carboxamide;

1-(4-((5-cyclopropyl-1H-pyrazol-3-yl)amino)-6,7-dihydro-5H-cyclopenta[d]pyrimidin-2-yl)-2-methyl-N-(pyrimidin-4-yl)pyrrolidine-2-carboxamide;

1-(4-((5-isopropyl-1H-pyrazol-3-yl)amino)-6,7-dihydro-5H-cyclopenta[d]pyrimidin-2-yl)-N-(piperidin-3-yl)pyrrolidine-2-carboxamide;

N-(1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;

N-(6-aminopyridin-3-yl)-1-(4-((5-cyclopropyl-1H-pyrazol-3-yl)amino)-6,7-dihydro-5H-cyclopenta[d]pyrimidin-2-yl)pyrrolidine-2-carboxamide;

1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

N-(6-fluoropyridin-3-yl)-1-(4-((5-(1-methylcyclopropyl)-1H-pyrazol-3-yl)amino)-6,7-dihydro-5H-cyclopenta[d]pyrimidin-2-yl)pyrrolidine-2-carboxamide;

N-(6-fluoropyridin-3-yl)-1-(4-((5-isopropyl-1H-pyrazol-3-yl)amino)-6,7-dihydro-5H-cyclopenta[d]pyrimidin-2-yl)-4,4-dimethylpyrrolidine-2-carboxamide 1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;

1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;

4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

4,4-difluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

3-((2-(2-(((6-fluoropyridin-3-yl)carbamoyl)pyrrolidin-1-yl)-6,7-dihydro-5H-cyclopenta[d]pyrimidin-4-yl)amino)-1H-pyrazole-5-carboxamide;

N-(6-fluoropyridin-3-yl)-1-(4-(((1-isopropyl-1H-imidazol-4-yl)amino)-6,7-dihydro-5H-cyclopenta[d]pyrimidin-2-yl)pyrrolidine-2-carboxamide;

4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;

2-((2-(2-(((6-fluoropyridin-3-yl)carbamoyl)pyrrolidin-1-yl)-6,7-dihydro-5H-cyclopenta[d]pyrimidin-4-yl)amino)oxazole-5-carboxamide;

N-(6-fluoropyridin-3-yl)-1-(4-((5-(1-hydroxycyclopropyl)-1H-pyrazol-3-yl)amino)-6,7-dihydro-5H-cyclopenta[d]pyrimidin-2-yl)pyrrolidine-2-carboxamide;

N-(6-fluoropyridin-3-yl)-4-hydroxy-1-(4-(((1-isopropyl-1H-imidazol-4-yl)amino)-6,7-dihydro-5H-cyclopenta[d]pyrimidin-2-yl)pyrrolidine-2-carboxamide;

2-((2-(2-(((6-fluoropyridin-3-yl)carbamoyl)pyrrolidin-1-yl)-6,7-dihydro-5H-cyclopenta[d]pyrimidin-4-yl)amino)thiazole-5-carboxamide;

N-(6-fluoropyridin-3-yl)-1-(4-((2-isopropyl-1H-imidazol-5-yl)amino)-6,7-dihydro-5H-cyclopenta[d]pyrimidin-2-yl)pyrrolidine-2-carboxamide;

N-(6-fluoropyridin-3-yl)-1-(4-((5-isopropyl-1H-pyrazol-3-yl)amino)-5,5-dimethyl-6,7-dihydro-5H-cyclopenta[d]pyrimidin-2-yl)pyrrolidine-2-carboxamide;

N-(6-fluoropyridin-3-yl)-1-(4-((5-isopropyl-1H-pyrazol-3-yl)amino)-7,7-dimethyl-6,7-dihydro-5H-cyclopenta[d]pyrimidin-2-yl)pyrrolidine-2-carboxamide;

N-(6-fluoropyridin-3-yl)-1-(4-((5-isopropyl-1H-pyrazol-3-yl)amino)-5,7-dihydrospiro[cyclopenta[d]pyrimidine-6,1'-cyclopropan]-2-yl)pyrrolidine-2-carboxamide;

N-(6-fluoropyridin-3-yl)-1-(4-((5-isopropyl-1H-pyrazol-3-yl)amino)-6-oxo-6,7-dihydro-5H-cyclopenta[d]pyrimidin-2-yl)pyrrolidine-2-carboxamide;

N-(6-fluoropyridin-3-yl)-1-(4-((5-isopropyl-1H-pyrazol-3-yl)amino)-6,6-dimethyl-6,7-dihydro-5H-cyclopenta[d]pyrimidin-2-yl)pyrrolidine-2-carboxamide;

1-(6,6-difluoro-4-((5-isopropyl-1H-pyrazol-3-yl)amino)-6,7-dihydro-5H-cyclopenta[d]pyrimidin-2-yl)-N-(6-fluoropyridin-3-yl)pyrrolidine-2-carboxamide;

N-(6-fluoropyridin-3-yl)-1-(4-((5-isopropyl-1H-pyrazol-3-yl)amino)-5,7-dihydrospiro[cyclopenta[d]pyrimidine-6,2'-oxiran]-2-yl)pyrrolidine-2-carboxamide;

N-(6-fluoropyridin-3-yl)-1-(4-((5-isopropyl-1H-pyrazol-3-yl)amino)-6-thioxo-6,7-dihydro-5H-cyclopenta[d]pyrimidin-2-yl)pyrrolidine-2-carboxamide;

1-(4-(5-cyclopropyl-1H-pyrazol-3-ylamino)-6,7-dihydro-5H-cyclopenta[d]pyrimidin-2-yl)pyrrolidine-2-carboxamide;

N-(6-fluoropyridin-3-yl)-1-(4-((5-isopropyl-1H-pyrazol-3-yl)amino)-6,7-dihydro-5H-cyclopenta[d]pyrimidin-2-yl)-N-methylpyrrolidine-2-carboxamide;

1-(4-((5-cyclopropyl-1H-pyrazol-3-yl)amino)-5,6,7,8-tetrahydroquinazolin-2-yl)-N-(thiazol-2-yl)pyrrolidine-2-carboxamide;

1-(4-((5-cyclopropyl-1H-pyrazol-3-yl)amino)-6,7,8,9-tetrahydro-5H-cyclohepta[d]pyrimidin-2-yl)-N-(thiazol-2-yl)pyrrolidine-2-carboxamide;

(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid;

1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;

2-fluoro-5-(1-(4-((5-isopropyl-1H-pyrazol-3-yl)amino)-6,7-dihydro-5H-cyclopenta[d]pyrimidin-2-yl)pyrrolidine-2-carboxamido)pyridine 1-oxide;

2-(2-(((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 1-oxide;

2-(2-(((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 3-oxide;

N-(6-hydroxypyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

1-(4-((5-isopropyl-1H-pyrazol-3-yl)amino)-6,7-dihydro-5H-cyclopenta[d]pyrimidin-2-yl)-N-(6-oxo-1,6-dihydropyridin-3-yl)pyrrolidine-2-carboxamide;

1-(5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

1-(5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

1-(4-((5-hydroxy-1H-pyrazol-3-yl)amino)-6,7-dihydro-5H-cyclopenta[d]pyrimidin-2-yl)-N-(6-hydroxypyridin-3-yl)pyrrolidine-2-carboxamide;

1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

1-(4-(5-isopropyl-1H-pyrazol-3-ylamino)-6,7-dihydro-5H-cyclopenta[d]pyrimidin-2-yl)-N-(pyrimidin-4-yl)pyrrolidine-2-carboxamide;

N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;

4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

N-(6-aminopyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(1-(4-(5-isopropyl-1H-pyrazol-3-ylamino)-6,7-dihydro-5H-cyclopenta[d]pyrimidin-2-yl)pyrrolidin-2-yl)(piperidin-1-yl)methanone;

(1-(4-(5-isopropyl-1H-pyrazol-3-ylamino)-6,7-dihydro-5H-cyclopenta[d]pyrimidin-2-yl)pyrrolidin-2-yl)(morpholino)methanone;

N-(6-fluoropyridin-3-yl)-1-(4-(5-(2-hydroxypropan-2-yl)-1H-pyrazol-3-ylamino)-6,7-dihydro-5H-cyclopenta[d]pyrimidin-2-yl)pyrrolidine-2-carboxamide;

3-(2-(2-(6-fluoropyridin-3-ylcarbamoyl)pyrrolidin-1-yl)-6,7-dihydro-5H-cyclopenta[d]pyrimidin-4-ylamino)-5-isopropyl-1H-pyrazole 2-oxide;

N-(6-fluoropyridin-3-yl)-1-(4-(1-hydroxy-5-isopropyl-1H-pyrazol-3-ylamino)-6,7-dihydro-5H-cyclopenta[d]pyrimidin-2-yl)pyrrolidine-2-carboxamide;

1-(4-(5-isopropyl-1H-pyrazol-3-ylamino)-6,7-dihydro-5H-cyclopenta[d]pyrimidin-2-yl)-N-(6-(methylthio)pyridin-3-yl)pyrrolidine-2-carboxamide;

N-(6-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

N-(6-fluoropyridin-3-yl)-1-(4-(5-isopropyl-1H-pyrazol-3-ylamino)-6,7-dihydro-5H-cyclopenta[d]pyrimidin-2-yl)-4-oxopyrrolidine-2-carboxamide;

N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;

N-(2-hydroxyethyl)-1-(4-(5-isopropyl-1H-pyrazol-3-ylamino)-6,7-dihydro-5H-cyclopenta[d]pyrimidin-2-yl)pyrrolidine-2-carboxamide;

N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carbothioamide;

N-(2-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

N-(furan-2-ylmethyl)-1-(4-(5-isopropyl-1H-pyrazol-3-ylamino)-6,7-dihydro-5H-cyclopenta[d]pyrimidin-2-yl)pyrrolidine-2-carboxamide;

N-((1H-pyrazol-5-yl)methyl)-1-(4-(5-isopropyl-1H-pyrazol-3-ylamino)-6,7-dihydro-5H-cyclopenta[d]pyrimidin-2-yl)pyrrolidine-2-carboxamide;

1-(4-(5-isopropyl-1H-pyrazol-3-ylamino)-6,7-dihydro-5H-cyclopenta[d]pyrimidin-2-yl)-N-((1-methyl-1H-pyrazol-5-yl)methyl)pyrrolidine-2-carboxamide;

1-(4-(5-isopropyl-1H-pyrazol-3-ylamino)-6,7-dihydro-5H-cyclopenta[d]pyrimidin-2-yl)-N-(oxazol-2-ylmethyl)pyrrolidine-2-carboxamide;

1-(4-(5-isopropyl-1H-pyrazol-3-ylamino)-6,7-dihydro-5H-cyclopenta[d]pyrimidin-2-yl)-N-(thiazol-2-ylmethyl)pyrrolidine-2-carboxamide;

N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;

N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;

1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;

N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;

N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;

N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;

N-(2-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide; and N-(6-fluoropyridin-3-yl)-1-(4-(5-isopropyl-1H-pyrazol-3-ylamino)-6,7-dihydro-5H-cyclopenta[d]pyrimidin-2-yl)-N-methylpyrrolidine-2-carboxamide.

In another variation, the compound of Formula I, or a salt thereof, is selected from the group consisting of:

(R)-1-(4-(5-cyclopropyl-1H-pyrazol-3-ylamino)-6,7-dihydro-5H-cyclopenta[d]pyrimidin-2-yl)-N-(6-fluoropyridin-3-yl)-2-methylpyrrolidine-2-carboxamide;

(S)-1-(4-(5-cyclopropyl-1H-pyrazol-3-ylamino)-6,7-dihydro-5H-cyclopenta[d]pyrimidin-2-yl)-N-(6-fluoropyridin-3-yl)-2-methylpyrrolidine-2-carboxamide;

(R)-1-(4-(5-cyclopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide;

(R)-1-(4-(5-cyclopentyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(S)-1-(4-(5-cyclopentyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)-N-(6-fluoropyridin-3-yl)azetidine-2-carboxamide;

(S)-1-(4-(5-cyclopropyl-1H-pyrazol-3-ylamino)-6,7-dihydro-5H-cyclopenta[d]pyrimidin-2-yl)-N-(6-fluoropyridin-3-yl)azetidine-2-carboxamide;

(R)-1-(4-(5-cyclopropyl-1H-pyrazol-3-ylamino)-6,7-dihydro-5H-cyclopenta[d]pyrimidin-2-yl)-N-(pyrazin-2-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)-N-(pyrazin-2-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)-N-(pyrimidin-5-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)-N-(pyrimidin-5-yl)pyrrolidine-2-carboxamide;

(R)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)-N-(6-fluoropyridin-3-yl)piperidine-2-carboxamide;

(S)-1-(4-(5-cyclopropyl-1H-pyrazol-3-ylamino)-6,7-dihydro-5H-cyclopenta[d]pyrimidin-2-yl)-N-(6-fluoropyridin-3-yl)piperidine-2-carboxamide;

(2R,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;

(2S,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;

(2R,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;

(2S,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;

(2R,3R)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;

(2S,3S)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;

(2R,3S)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;

(2S,3R)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;

(R)—N-(6-fluoropyridin-3-yl)-1-(4-(3-isopropylisoxazol-5-ylamino)-6,7-dihydro-5H-cyclopenta[d]pyrimidin-2-yl)pyrrolidine-2-carboxamide;

(S)—N-(6-fluoropyridin-3-yl)-1-(4-(3-isopropylisoxazol-5-ylamino)-6,7-dihydro-5H-cyclopenta[d]pyrimidin-2-yl)pyrrolidine-2-carboxamide;

(R)—N-(6-fluoropyridin-3-yl)-1-(4-(5-isopropyl-1H-pyrazol-3-ylamino)-5,6,7,8-tetrahydroquinazolin-2-yl)pyrrolidine-2-carboxamide;

(S)—N-(6-fluoropyridin-3-yl)-1-(4-(5-isopropyl-1H-pyrazol-3-ylamino)-5,6,7,8-tetrahydroquinazolin-2-yl)pyrrolidine-2-carboxamide;

(R)-1-(4-(5-cyclopropyl-1H-pyrazol-3-ylamino)-5,6,7,8-tetrahydroquinazolin-2-yl)-N-(6-fluoropyridin-3-yl)pyrrolidine-2-carboxamide;

(S)-1-(4-(5-cyclopropyl-1H-pyrazol-3-ylamino)-5,6,7,8-tetrahydroquinazolin-2-yl)-N-(6-fluoropyridin-3-yl)pyrrolidine-2-carboxamide;

(R)-1-(4-(5-cyclopentyl-1H-pyrazol-3-ylamino)-5,6,7,8-tetrahydroquinazolin-2-yl)-N-(6-fluoropyridin-3-yl)pyrrolidine-2-carboxamide;

(S)-1-(4-(5-cyclopentyl-1H-pyrazol-3-ylamino)-5,6,7,8-tetrahydroquinazolin-2-yl)-N-(6-fluoropyridin-3-yl)pyrrolidine-2-carboxamide;

(R)—N-(6-fluoropyridin-3-yl)-1-(4-(5-isopropyl-1H-pyrazol-3-ylamino)-6,7-dihydro-5H-cyclopenta[d]pyrimidin-2-yl)piperidine-2-carboxamide;

(S)—N-(6-fluoropyridin-3-yl)-1-(4-(5-isopropyl-1H-pyrazol-3-ylamino)-6,7-dihydro-5H-cyclopenta[d]pyrimidin-2-yl)piperidine-2-carboxamide;

(R)-1-(4-(5-cyclopentyl-1H-pyrazol-3-ylamino)-6,7-dihydro-5H-cyclopenta[d]pyrimidin-2-yl)-N-(6-fluoropyridin-3-yl)piperidine-2-carboxamide;

(S)-1-(4-(5-cyclopentyl-1H-pyrazol-3-ylamino)-6,7-dihydro-5H-cyclopenta[d]pyrimidin-2-yl)-N-(6-fluoropyridin-3-yl)piperidine-2-carboxamide;

(R)-1-(4-(5-isopropyl-1H-pyrazol-3-ylamino)-6,7-dihydro-5H-cyclopenta[d]pyrimidin-2-yl)pyrrolidine-2-carboxamide;

(S)-1-(4-(5-isopropyl-1H-pyrazol-3-ylamino)-6,7-dihydro-5H-cyclopenta[d]pyrimidin-2-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-methylpyrrolidine-2-carboxamide;

(S)-1-(4-(5-isopropyl-1H-pyrazol-3-ylamino)-6,7-dihydro-5H-cyclopenta[d]pyrimidin-2-yl)-N-methylpyrrolidine-2-carboxamide;

(R)-1-(4-(5-isopropyl-1H-pyrazol-3-ylamino)-6,7-dihydro-5H-cyclopenta[d]pyrimidin-2-yl)-N,N-dimethylpyrrolidine-2-carboxamide;

(S)-1-(4-(5-isopropyl-1H-pyrazol-3-ylamino)-6,7-dihydro-5H-cyclopenta[d]pyrimidin-2-yl)-N,N-dimethylpyrrolidine-2-carboxamide;

(2R,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;

(2S,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;

(2R,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;

(2S,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;

(R)-1-(4-((5-isopropyl-1H-pyrazol-3-yl)amino)-6,7-dihydro-5H-cyclopenta[d]pyrimidin-2-yl)-N—((R)-pyrrolidin-3-yl)pyrrolidine-2-carboxamide;

(S)-1-(4-((5-isopropyl-1H-pyrazol-3-yl)amino)-6,7-dihydro-5H-cyclopenta[d]pyrimidin-2-yl)-N—((S)-pyrrolidin-3-yl)pyrrolidine-2-carboxamide;

(R)-1-(4-((5-isopropyl-1H-pyrazol-3-yl)amino)-6,7-dihydro-5H-cyclopenta[d]pyrimidin-2-yl)-N—((S)-pyrrolidin-3-yl)pyrrolidine-2-carboxamide;

(S)-1-(4-((5-isopropyl-1H-pyrazol-3-yl)amino)-6,7-dihydro-5H-cyclopenta[d]pyrimidin-2-yl)-N—((R)-pyrrolidin-3-yl)pyrrolidine-2-carboxamide;

(R)-(3-aminoazetidin-1-yl)(1-(4-((5-isopropyl-1H-pyrazol-3-yl)amino)-6,7-dihydro-5H-cyclopenta[d]pyrimidin-2-yl)pyrrolidin-2-yl)methanone;

(S)-(3-aminoazetidin-1-yl)(1-(4-((5-isopropyl-1H-pyrazol-3-yl)amino)-6,7-dihydro-5H-cyclopenta[d]pyrimidin-2-yl)pyrrolidin-2-yl)methanone;

(R)-1-(4-((5-cyclopropyl-1H-pyrazol-3-yl)amino)-6,7-dihydro-5H-cyclopenta[d]pyrimidin-2-yl)-N-(thiazol-2-yl)pyrrolidine-2-carboxamide;

(S)-1-(4-((5-cyclopropyl-1H-pyrazol-3-yl)amino)-6,7-dihydro-5H-cyclopenta[d]pyrimidin-2-yl)-N-(thiazol-2-yl)pyrrolidine-2-carboxamide;

(R)-1-(4-((5-cyclopropyl-1H-pyrazol-3-yl)amino)-6,7-dihydro-5H-cyclopenta[d]pyrimidin-2-yl)-2-methyl-N-(pyrimidin-4-yl)pyrrolidine-2-carboxamide;

(S)-1-(4-((5-cyclopropyl-1H-pyrazol-3-yl)amino)-6,7-dihydro-5H-cyclopenta[d]pyrimidin-2-yl)-2-methyl-N-(pyrimidin-4-yl)pyrrolidine-2-carboxamide;

(R)-1-(4-((5-isopropyl-1H-pyrazol-3-yl)amino)-6,7-dihydro-5H-cyclopenta[d]pyrimidin-2-yl)-N—((R)-piperidin-3-yl)pyrrolidine-2-carboxamide;

(S)-1-(4-((5-isopropyl-1H-pyrazol-3-yl)amino)-6,7-dihydro-5H-cyclopenta[d]pyrimidin-2-yl)-N—((S)-piperidin-3-yl)pyrrolidine-2-carboxamide;

(R)-1-(4-((5-isopropyl-1H-pyrazol-3-yl)amino)-6,7-dihydro-5H-cyclopenta[d]pyrimidin-2-yl)-N—((S)-piperidin-3-yl)pyrrolidine-2-carboxamide;

(S)-1-(4-((5-isopropyl-1H-pyrazol-3-yl)amino)-6,7-dihydro-5H-cyclopenta[d]pyrimidin-2-yl)-N—((R)-piperidin-3-yl)pyrrolidine-2-carboxamide;

(R)—N—((R)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(S)—N—((S)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(R)—N—((S)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(S)—N—((R)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(2R,4R)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;

(2S,4S)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;

(2R,4S)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;

(2S,4R)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;

(R)—N-(6-aminopyridin-3-yl)-1-(4-((5-cyclopropyl-1H-pyrazol-3-yl)amino)-6,7-dihydro-5H-cyclopenta[d]pyrimidin-2-yl)pyrrolidine-2-carboxamide;

(S)—N-(6-aminopyridin-3-yl)-1-(4-((5-cyclopropyl-1H-pyrazol-3-yl)amino)-6,7-dihydro-5H-cyclopenta[d]pyrimidin-2-yl)pyrrolidine-2-carboxamide;

(2R,4R)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2S,4S)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2R,4S)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2S,4R)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2R,4R)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(2S,4S)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(2R,4S)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(2S,4R)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;
(R)—N-(6-fluoropyridin-3-yl)-1-(4-((5-(1-methylcyclopropyl)-1H-pyrazol-3-yl)amino)-6,7-dihydro-5H-cyclopenta[d]pyrimidin-2-yl)pyrrolidine-2-carboxamide;
(S)—N-(6-fluoropyridin-3-yl)-1-(4-((5-(1-methylcyclopropyl)-1H-pyrazol-3-yl)amino)-6,7-dihydro-5H-cyclopenta[d]pyrimidin-2-yl)pyrrolidine-2-carboxamide;
(R)—N-(6-fluoropyridin-3-yl)-1-(4-((5-isopropyl-1H-pyrazol-3-yl)amino)-6,7-dihydro-5H-cyclopenta[d]pyrimidin-2-yl)-4,4-dimethylpyrrolidine-2-carboxamide
(S)—N-(6-fluoropyridin-3-yl)-1-(4-((5-isopropyl-1H-pyrazol-3-yl)amino)-6,7-dihydro-5H-cyclopenta[d]pyrimidin-2-yl)-4,4-dimethylpyrrolidine-2-carboxamide;
(2R,4R)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;
(2S,4S)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;
(2R,4S)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;
(2S,4R)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;
(2R,4R)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;
(2S,4S)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;
(2R,4S)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;
(2S,4R)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;
(2R,4R)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(2S,4S)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(2R,4S)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(2S,4R)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(R)-4,4-difluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(S)-4,4-difluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(R)-3-((2-(2-((6-fluoropyridin-3-yl)carbamoyl)pyrrolidin-1-yl)-6,7-dihydro-5H-cyclopenta[d]pyrimidin-4-yl)amino)-1H-pyrazole-5-carboxamide;
(S)-3-((2-(2-((6-fluoropyridin-3-yl)carbamoyl)pyrrolidin-1-yl)-6,7-dihydro-5H-cyclopenta[d]pyrimidin-4-yl)amino)-1H-pyrazole-5-carboxamide;
(R)—N-(6-fluoropyridin-3-yl)-1-(4-((1-isopropyl-1H-imidazol-4-yl)amino)-6,7-dihydro-5H-cyclopenta[d]pyrimidin-2-yl)pyrrolidine-2-carboxamide;
(S)—N-(6-fluoropyridin-3-yl)-1-(4-((1-isopropyl-1H-imidazol-4-yl)amino)-6,7-dihydro-5H-cyclopenta[d]pyrimidin-2-yl)pyrrolidine-2-carboxamide;
(2R,4R)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;
(2S,4S)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;
(2R,4S)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;
(2S,4R)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;
(R)-2-((2-(2-((6-fluoropyridin-3-yl)carbamoyl)pyrrolidin-1-yl)-6,7-dihydro-5H-cyclopenta[d]pyrimidin-4-yl)amino)oxazole-5-carboxamide;
(S)-2-((2-(2-((6-fluoropyridin-3-yl)carbamoyl)pyrrolidin-1-yl)-6,7-dihydro-5H-cyclopenta[d]pyrimidin-4-yl)amino)oxazole-5-carboxamide;
(R)—N-(6-fluoropyridin-3-yl)-1-(4-((5-(1-hydroxycyclopropyl)-1H-pyrazol-3-yl)amino)-6,7-dihydro-5H-cyclopenta[d]pyrimidin-2-yl)pyrrolidine-2-carboxamide;
(S)—N-(6-fluoropyridin-3-yl)-1-(4-((5-(1-hydroxycyclopropyl)-1H-pyrazol-3-yl)amino)-6,7-dihydro-5H-cyclopenta[d]pyrimidin-2-yl)pyrrolidine-2-carboxamide;
(2R,4R)—N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;
(2S,4S)—N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;
(2R,4S)—N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;
(2S,4R)—N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;
(R)-2-((2-(2-((6-fluoropyridin-3-yl)carbamoyl)pyrrolidin-1-yl)-6,7-dihydro-5H-cyclopenta[d]pyrimidin-4-yl)amino)thiazole-5-carboxamide;
(S)-2-((2-(2-((6-fluoropyridin-3-yl)carbamoyl)pyrrolidin-1-yl)-6,7-dihydro-5H-cyclopenta[d]pyrimidin-4-yl)amino)thiazole-5-carboxamide;
(R)—N-(6-fluoropyridin-3-yl)-1-(4-((2-isopropyl-1H-imidazol-5-yl)amino)-6,7-dihydro-5H-cyclopenta[d]pyrimidin-2-yl)pyrrolidine-2-carboxamide;
(S)—N-(6-fluoropyridin-3-yl)-1-(4-((2-isopropyl-1H-imidazol-5-yl)amino)-6,7-dihydro-5H-cyclopenta[d]pyrimidin-2-yl)pyrrolidine-2-carboxamide;
(R)—N-(6-fluoropyridin-3-yl)-1-(4-((5-isopropyl-1H-pyrazol-3-yl)amino)-5,5-dimethyl-6,7-dihydro-5H-cyclopenta[d]pyrimidin-2-yl)pyrrolidine-2-carboxamide;
(S)—N-(6-fluoropyridin-3-yl)-1-(4-((5-isopropyl-1H-pyrazol-3-yl)amino)-5,5-dimethyl-6,7-dihydro-5H-cyclopenta[d]pyrimidin-2-yl)pyrrolidine-2-carboxamide;
(R)—N-(6-fluoropyridin-3-yl)-1-(4-((5-isopropyl-1H-pyrazol-3-yl)amino)-7,7-dimethyl-6,7-dihydro-5H-cyclopenta[d]pyrimidin-2-yl)pyrrolidine-2-carboxamide;
(S)—N-(6-fluoropyridin-3-yl)-1-(4-((5-isopropyl-1H-pyrazol-3-yl)amino)-7,7-dimethyl-6,7-dihydro-5H-cyclopenta[d]pyrimidin-2-yl)pyrrolidine-2-carboxamide;

(R)—N-(6-fluoropyridin-3-yl)-1-(4-((5-isopropyl-1H-pyrazol-3-yl)amino)-5,7-dihydrospiro[cyclopenta[d]pyrimidine-6,1'-cyclopropan]-2-yl)pyrrolidine-2-carboxamide;

(S)—N-(6-fluoropyridin-3-yl)-1-(4-((5-isopropyl-1H-pyrazol-3-yl)amino)-5,7-dihydrospiro[cyclopenta[d]pyrimidine-6,1'-cyclopropan]-2-yl)pyrrolidine-2-carboxamide;

(R)—N-(6-fluoropyridin-3-yl)-1-(4-((5-isopropyl-1H-pyrazol-3-yl)amino)-6-oxo-6,7-dihydro-5H-cyclopenta[d]pyrimidin-2-yl)pyrrolidine-2-carboxamide;

(S)—N-(6-fluoropyridin-3-yl)-1-(4-((5-isopropyl-1H-pyrazol-3-yl)amino)-6-oxo-6,7-dihydro-5H-cyclopenta[d]pyrimidin-2-yl)pyrrolidine-2-carboxamide;

(R)—N-(6-fluoropyridin-3-yl)-1-(4-((5-isopropyl-1H-pyrazol-3-yl)amino)-6,6-dimethyl-6,7-dihydro-5H-cyclopenta[d]pyrimidin-2-yl)pyrrolidine-2-carboxamide;

(S)—N-(6-fluoropyridin-3-yl)-1-(4-((5-isopropyl-1H-pyrazol-3-yl)amino)-6,6-dimethyl-6,7-dihydro-5H-cyclopenta[d]pyrimidin-2-yl)pyrrolidine-2-carboxamide;

(R)-1-(6,6-difluoro-4-((5-isopropyl-1H-pyrazol-3-yl)amino)-6,7-dihydro-5H-cyclopenta[d]pyrimidin-2-yl)-N-(6-fluoropyridin-3-yl)pyrrolidine-2-carboxamide;

(S)-1-(6,6-difluoro-4-((5-isopropyl-1H-pyrazol-3-yl)amino)-6,7-dihydro-5H-cyclopenta[d]pyrimidin-2-yl)-N-(6-fluoropyridin-3-yl)pyrrolidine-2-carboxamide;

(R)—N-(6-fluoropyridin-3-yl)-1-(4-((5-isopropyl-1H-pyrazol-3-yl)amino)-5,7-dihydrospiro[cyclopenta[d]pyrimidine-6,2'-oxiran]-2-yl)pyrrolidine-2-carboxamide;

(S)—N-(6-fluoropyridin-3-yl)-1-(4-((5-isopropyl-1H-pyrazol-3-yl)amino)-5,7-dihydrospiro[cyclopenta[d]pyrimidine-6,2'-oxiran]-2-yl)pyrrolidine-2-carboxamide;

(R)—N-(6-fluoropyridin-3-yl)-1-(4-((5-isopropyl-1H-pyrazol-3-yl)amino)-6-thioxo-6,7-dihydro-5H-cyclopenta[d]pyrimidin-2-yl)pyrrolidine-2-carboxamide;

(S)—N-(6-fluoropyridin-3-yl)-1-(4-((5-isopropyl-1H-pyrazol-3-yl)amino)-6-thioxo-6,7-dihydro-5H-cyclopenta[d]pyrimidin-2-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)pyrrolidine-2-carboxamide;

(R)—N-(6-fluoropyridin-3-yl)-1-(4-((5-isopropyl-1H-pyrazol-3-yl)amino)-6,7-dihydro-5H-cyclopenta[d]pyrimidin-2-yl)-N-methylpyrrolidine-2-carboxamide;

(S)—N-(6-fluoropyridin-3-yl)-1-(4-((5-isopropyl-1H-pyrazol-3-yl)amino)-6,7-dihydro-5H-cyclopenta[d]pyrimidin-2-yl)-N-methylpyrrolidine-2-carboxamide;

(R)-1-(4-((5-cyclopropyl-1H-pyrazol-3-yl)amino)-5,6,7,8-tetrahydroquinazolin-2-yl)-N-(thiazol-2-yl)pyrrolidine-2-carboxamide;

(S)-1-(4-((5-cyclopropyl-1H-pyrazol-3-yl)amino)-5,6,7,8-tetrahydroquinazolin-2-yl)-N-(thiazol-2-yl)pyrrolidine-2-carboxamide;

(R)-1-(4-((5-cyclopropyl-1H-pyrazol-3-yl)amino)-6,7,8,9-tetrahydro-5H-cyclohepta[d]pyrimidin-2-yl)-N-(thiazol-2-yl)pyrrolidine-2-carboxamide;

(S)-1-(4-((5-cyclopropyl-1H-pyrazol-3-yl)amino)-6,7,8,9-tetrahydro-5H-cyclohepta[d]pyrimidin-2-yl)-N-(thiazol-2-yl)pyrrolidine-2-carboxamide;

(2R,4R)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl) phosphonic acid;

(2S,4S)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl) phosphonic acid;

(2R,4S)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl) phosphonic acid;

(2S,4R)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl) phosphonic acid;

(2R,4R)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;

(2S,4S)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;

(2R,4S)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;

(2S,4R)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate (R)-2-fluoro-5-(1-(4-((5-isopropyl-1H-pyrazol-3-yl)amino)-6,7-dihydro-5H-cyclopenta[d]pyrimidin-2-yl)pyrrolidine-2-carboxamido)pyridine 1-oxide;

(S)-2-fluoro-5-(1-(4-((5-isopropyl-1H-pyrazol-3-yl)amino)-6,7-dihydro-5H-cyclopenta[d]pyrimidin-2-yl)pyrrolidine-2-carboxamido)pyridine 1-oxide;

(R)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 1-oxide;

(S)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 1-oxide;

(R)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 3-oxide;

(S)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 3-oxide;

(R)—N-(6-hydroxypyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(S)—N-(6-hydroxypyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(R)-1-(4-((5-isopropyl-1H-pyrazol-3-yl)amino)-6,7-dihydro-5H-cyclopenta[d]pyrimidin-2-yl)-N-(6-oxo-1,6-dihydropyridin-3-yl)pyrrolidine-2-carboxamide;

(S)-1-(4-((5-isopropyl-1H-pyrazol-3-yl)amino)-6,7-dihydro-5H-cyclopenta[d]pyrimidin-2-yl)-N-(6-oxo-1,6-dihydropyridin-3-yl)pyrrolidine-2-carboxamide;

(R)-1-((R)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((S)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-((S)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((R)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-((5R,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-((5R,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-((5S,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-((5S,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((5R,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((5R,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((5S,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((5S,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-(4-((5-hydroxy-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-(4-((5-hydroxy-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(pyrimidin-4-yl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(pyrimidin-4-yl)pyrrolidine-2-carboxamide;

(2R,4R)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;

(2R,4S)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;

(2S,4R)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;

(2S,4S)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;

(2R,4R)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

(2R,4S)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

(2S,4R)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

(2S,4S)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide (R)—N-(6-aminopyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(6-aminopyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)-(1-(4-(5-isopropyl-1H-pyrazol-3-ylamino)-6,7-dihydro-5H-cyclopenta[d]pyrimidin-2-yl)pyrrolidin-2-yl)(piperidin-1-yl)methanone;

(S)-(1-(4-(5-isopropyl-1H-pyrazol-3-ylamino)-6,7-dihydro-5H-cyclopenta[d]pyrimidin-2-yl)pyrrolidin-2-yl)(piperidin-1-yl)methanone;

(R)-(1-(4-(5-isopropyl-1H-pyrazol-3-ylamino)-6,7-dihydro-5H-cyclopenta[d]pyrimidin-2-yl)pyrrolidin-2-yl)(morpholino)methanone;

(S)-(1-(4-(5-isopropyl-1H-pyrazol-3-ylamino)-6,7-dihydro-5H-cyclopenta[d]pyrimidin-2-yl)pyrrolidin-2-yl)(morpholino)methanone;

(R)—N-(6-fluoropyridin-3-yl)-1-(4-(5-(2-hydroxypropan-2-yl)-1H-pyrazol-3-ylamino)-6,7-dihydro-5H-cyclopenta[d]pyrimidin-2-yl)pyrrolidine-2-carboxamide;

(S)—N-(6-fluoropyridin-3-yl)-1-(4-(5-(2-hydroxypropan-2-yl)-1H-pyrazol-3-ylamino)-6,7-dihydro-5H-cyclopenta[d]pyrimidin-2-yl)pyrrolidine-2-carboxamide;

(R)-3-(2-(2-(6-fluoropyridin-3-ylcarbamoyl)pyrrolidin-1-yl)-6,7-dihydro-5H-cyclopenta[d]pyrimidin-4-ylamino)-5-isopropyl-1H-pyrazole 2-oxide;

(S)-3-(2-(2-(6-fluoropyridin-3-ylcarbamoyl)pyrrolidin-1-yl)-6,7-dihydro-5H-cyclopenta[d]pyrimidin-4-ylamino)-5-isopropyl-1H-pyrazole 2-oxide;

(R)—N-(6-fluoropyridin-3-yl)-1-(4-(1-hydroxy-5-isopropyl-1H-pyrazol-3-ylamino)-6,7-dihydro-5H-cyclopenta[d]pyrimidin-2-yl)pyrrolidine-2-carboxamide;

(S)—N-(6-fluoropyridin-3-yl)-1-(4-(1-hydroxy-5-isopropyl-1H-pyrazol-3-ylamino)-6,7-dihydro-5H-cyclopenta[d]pyrimidin-2-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(6-(methylthio)pyridin-3-yl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(6-(methylthio)pyridin-3-yl)pyrrolidine-2-carboxamide;

(R)—N-(6-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(6-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-(6-fluoropyridin-3-yl)-1-(4-(5-isopropyl-1H-pyrazol-3-ylamino)-6,7-dihydro-5H-cyclopenta[d]pyrimidin-2-yl)-4-oxopyrrolidine-2-carboxamide;

(S)—N-(6-fluoropyridin-3-yl)-1-(4-(5-isopropyl-1H-pyrazol-3-ylamino)-6,7-dihydro-5H-cyclopenta[d]pyrimidin-2-yl)-4-oxopyrrolidine-2-carboxamide;

(R,R)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R,S)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(S,R)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(S,S)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(R)—N-(2-hydroxyethyl)-1-(4-(5-isopropyl-1H-pyrazol-3-ylamino)-6,7-dihydro-5H-cyclopenta[d]pyrimidin-2-yl)pyrrolidine-2-carboxamide;
(S)—N-(2-hydroxyethyl)-1-(4-(5-isopropyl-1H-pyrazol-3-ylamino)-6,7-dihydro-5H-cyclopenta[d]pyrimidin-2-yl)pyrrolidine-2-carboxamide;
(R)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carbothioamide;
(S)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carbothioamide;
(R)—N-(2-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(S)—N-(2-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(R)—N-(furan-2-ylmethyl)-1-(4-(5-isopropyl-1H-pyrazol-3-ylamino)-6,7-dihydro-5H-cyclopenta[d]pyrimidin-2-yl)pyrrolidine-2-carboxamide;
(S)—N-(furan-2-ylmethyl)-1-(4-(5-isopropyl-1H-pyrazol-3-ylamino)-6,7-dihydro-5H-cyclopenta[d]pyrimidin-2-yl)pyrrolidine-2-carboxamide;
(R)—N-((1H-pyrazol-5-yl)methyl)-1-(4-(5-isopropyl-1H-pyrazol-3-ylamino)-6,7-dihydro-5H-cyclopenta[d]pyrimidin-2-yl)pyrrolidine-2-carboxamide;
(S)—N-((1H-pyrazol-5-yl)methyl)-1-(4-(5-isopropyl-1H-pyrazol-3-ylamino)-6,7-dihydro-5H-cyclopenta[d]pyrimidin-2-yl)pyrrolidine-2-carboxamide;
(R)-1-(4-(5-isopropyl-1H-pyrazol-3-ylamino)-6,7-dihydro-5H-cyclopenta[d]pyrimidin-2-yl)-N-((1-methyl-1H-pyrazol-5-yl)methyl)pyrrolidine-2-carboxamide;
(S)-1-(4-(5-isopropyl-1H-pyrazol-3-ylamino)-6,7-dihydro-5H-cyclopenta[d]pyrimidin-2-yl)-N-((1-methyl-1H-pyrazol-5-yl)methyl)pyrrolidine-2-carboxamide;
(R)-1-(4-(5-isopropyl-1H-pyrazol-3-ylamino)-6,7-dihydro-5H-cyclopenta[d]pyrimidin-2-yl)-N-(oxazol-2-ylmethyl)pyrrolidine-2-carboxamide;
(S)-1-(4-(5-isopropyl-1H-pyrazol-3-ylamino)-6,7-dihydro-5H-cyclopenta[d]pyrimidin-2-yl)-N-(oxazol-2-ylmethyl)pyrrolidine-2-carboxamide;
(R)-1-(4-(5-isopropyl-1H-pyrazol-3-ylamino)-6,7-dihydro-5H-cyclopenta[d]pyrimidin-2-yl)-N-(thiazol-2-ylmethyl)pyrrolidine-2-carboxamide;
(S)-1-(4-(5-isopropyl-1H-pyrazol-3-ylamino)-6,7-dihydro-5H-cyclopenta[d]pyrimidin-2-yl)-N-(thiazol-2-ylmethyl)pyrrolidine-2-carboxamide;
(R,R)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;
(R,S)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;
(S,R)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;
(S,S)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;
(R,R)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;
(R,S)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;
(S,R)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;
(S,S)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;
(R,R)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(R,S)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(S,R)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(S,S)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(R,R)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;
(R,S)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;
(S,R)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;
(S,S)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;
(R,R)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;
(R,S)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;
(S,R)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide; and
(S,S)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;
(R)—N-(2-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(S)—N-(2-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(R)—N-(6-fluoropyridin-3-yl)-1-(4-(5-isopropyl-1H-pyrazol-3-ylamino)-6,7-dihydro-5H-cyclopenta[d]pyrimidin-2-yl)-N-methylpyrrolidine-2-carboxamide; and
(S)—N-(6-fluoropyridin-3-yl)-1-(4-(5-isopropyl-1H-pyrazol-3-ylamino)-6,7-dihydro-5H-cyclopenta[d]pyrimidin-2-yl)-N-methylpyrrolidine-2-carboxamide.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention. For example, in some embodiments, provided is a compound selected from a group consisting of any one or more of Compound Nos. 1-96, such as a group consisting of any one or any two or any three or more of Compound Nos. 1-96, or a salt thereof. A selection of any combination of Compound Nos. 1-96, or salts thereof, is intended the same as if each and every combination were specifically and individually listed. In some embodiments, the compound of Formula I, or a salt thereof, is selected from the group consisting of Compound Nos. 1-96. In some embodiments, the compound of Formula I, or a salt thereof, is selected from the group consisting of Compound Nos. 1-67.

In another variation, the compound of Formula I is a compound of the formula (I-A):

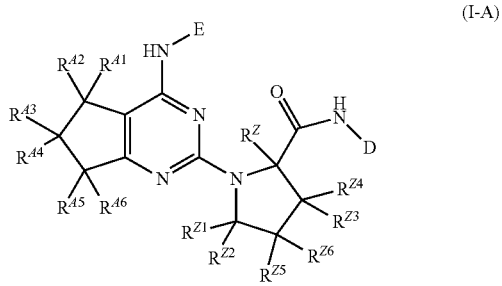

(I-A)

or a salt thereof, where $R^{A1}$, $R^{A2}$, $R^{A3}$, $R^{A4}$, $R^{A5}$, $R^{A6}$, $R^Z$, $R^{Z1}$, $R^{Z2}$, $R^{Z3}$, $R^{Z4}$, $R^{Z5}$, $R^{Z6}$, D and E are as defined for Formula (I). In one variation, each of $R^{A1}$, $R^{A2}$, $R^{A3}$, $R^{A4}$, $R^{A5}$ and $R^{A6}$ is independently hydrogen, substituted or unsubstituted $C_1$-$C_6$ alkyl, halo, substituted or unsubstituted $C_3$-$C_8$ cycloalkyl, substituted or unsubstituted heterocyclyl, or is taken together with a geminal $R^{A(1-6)}$ group and the carbon to which they are attached to form a carbonyl or a thiocarbonyl group. In another variation, each of $R^{Z1}$, $R^{Z2}$, $R^{Z3}$ and $R^{Z4}$ is hydrogen. In another variation, each of $R^{Z5}$ and $R^{Z6}$ is hydrogen. In another variation, $R^{Z5}$ is hydroxyl or —$OR^1$ and $R^{Z6}$ is hydrogen. In another variation, $R^{Z3}$ is hydroxyl and $R^{Z4}$ is hydrogen. In another variation, $R^{Z5}$ is $C_1$-$C_6$ alkoxy and $R^{Z6}$ is hydrogen. In another variation, $R^{Z5}$ is methoxy. In another variation, $R^{Z5}$ is halogen and $R^{Z6}$ is hydrogen. In another variation, $R^{Z5}$ is fluoro. In another variation, each of $R^{Z5}$ and $R^{Z6}$ is substituted or unsubstituted $C_1$-$C_6$ alkyl. In another variation, each of $R^{Z5}$ and $R^{Z6}$ is methyl. In another variation, $R^{Z5}$ is substituted or unsubstituted heteroaryl and $R^{Z6}$ is hydrogen. In another variation, $R^{Z5}$ is substituted tetrazolyl. In another variation, each of $R^{Z5}$ and $R^{Z6}$ is halogen. In another variation, each of $R^{Z5}$ and $R^{Z6}$ is fluoro. In another variation, $R^{Z5}$ is —O—$C_1$-$C_6$ alkylene-P(O)(OH)$_2$, and $R^{Z6}$ is hydrogen. In another variation, $R^{Z5}$ is —OC(O)$R^8$ and $R^{Z6}$ is hydrogen. In another variation, $R^Z$ is hydrogen or methyl. In another variation, D is substituted or unsubstituted pyridyl, substituted or unsubstituted pyrimidyl, or substituted or unsubstituted pyrazinyl. In another variation, D is selected from the group consisting of 6-fluoro-3-pyridyl, 3-pyridyl, pyrimid-5-yl and pyrazin-2-yl. In another variation, D is substituted or unsubstituted $C_1$-$C_6$ alkyl. In another variation, D is methyl. In another variation, D is substituted or unsubstituted piperidin-3-yl. In another variation, D is 1-(2-amino-2-methylpropanoyl)piperidin-3-yl. In another variation, D is 1-isopropylpiperidin-3-yl. In another variation, D is substituted or unsubstituted thiazolyl. In another variation, D is substituted or unsubstituted thiadiazolyl. In another variation, D is substituted or unsubstituted pyrrolidin-3-yl. In another variation, E is substituted or unsubstituted pyrazolyl, substituted or unsubstituted isoxazolyl, substituted or unsubstituted imidazolyl, substituted or unsubstituted oxazole, or substituted or unsubstituted thiazole. In another variation, E is selected from the group consisting of 5-cyclopropylpyrazol-3-yl, 5-cyclopentylpyrazol-3-yl, 5-(isopropyl)pyrazol-3-yl, 3-cyclopropylpyrazol-5-yl, 3-cyclopentylpyrazol-5-yl, 3-(isopropyl)pyrazol-5-yl, and 3-(isopropyl)isoxazol-5-yl.

Further provided is a pharmaceutical composition comprising a compound of Formula I or any variations described herein, or a salt thereof, and a pharmaceutically acceptable carrier.

Further provided is a method of treating cancer comprising administering to an individual in need thereof a therapeutically effective amount of a compound of Formula I or any variations described herein, or a pharmaceutically acceptable salt thereof.

Further provided is use of a compound of Formula I or any variations described herein, or a salt thereof, in the manufacturing of a medicament for the treatment of cancer.

Also provided is a kit comprising a compound of Formula I or any variations described herein, or a pharmaceutically acceptable salt thereof.

BRIEF DESCRIPTION OF THE DRAWINGS

FIG. 1 shown reduction in tumor burden in a COLO205 xenograft model of human colon cancer using Compound 8b. The term "compound' in some instances are abbreviated as "cpd" or "cmpd".

FIG. 2 shows reduction in tumor burden in an MCF7 xenograft model of human breast cancer using Compound 8b.

FIG. 3 shows the effect of Compound 8b on body weight in a COLO205 xenograft model of human colon cancer.

FIG. 4 shows the effect of Compound 8b on body weight in an MCF7 xenograft model of human breast cancer.

DETAILED DESCRIPTION OF THE INVENTION

Definition

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, linear (i.e. unbranched) or branched univalent hydrocarbon structures and combinations thereof, which may be fully saturated, mono- or polyunsaturated, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 8 carbon atoms (a "$C_1$-$C_8$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of saturated alkyl group include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. "Alkenyl" refers to an unsaturated hydrocarbon group having at least one site of olefinic unsaturation (i.e., having at least one moiety of the formula C=C) and preferably having from 2 to 10 carbon atoms (a "$C_2$-$C_{10}$ alkenyl") and more preferably 2 to 6 carbon atoms (a "$C_2$-$C_6$ alkenyl") and the like. "Alkynyl" refers to an unsaturated hydrocarbon group having at least one site of acetylenic unsaturation (i.e., having at least one moiety of the formula C≡C) and preferably having from 2 to 10 carbon atoms (a "$C_2$-$C_{10}$ alkynyl") and more preferably 2 to 6 carbon atoms (a "$C_2$-$C_6$ alkynyl") and the like.

"Substituted alkyl", "substituted alkenyl" and "substituted alkynyl" refer to an alkyl, alkenyl or alkynyl group, respectively, having from 1 to 5 substituents including, but not limited to, substituents such as alkoxy, substituted alkoxy, cycloalkoxy, substituted cycloalkoxy, aryloxy, substituted aryloxy, acyl, acyloxy, carbonylalkoxy, acylamino, aminoacyl, aminocarbonylamino, aminocarbonyloxy, cycloalkyl, substituted cycloalkyl, aryl, substituted aryl, heteroaryl, substituted heteroaryl, substituted or unsubstituted heterocyclyl, amino, substituted amino, cyano, halo, hydroxy, nitro, carboxy, thiol, thioalkyl, aminosulfonyl, sulfonylamino, sulfonyl, oxo, carbonylalkylenealkoxy and the like.

"Alkylene" as used herein refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—), and the like.

"Cycloalkyl" as used herein refers to and includes cyclic univalent hydrocarbon structures, which may be fully saturated, mono- or polyunsaturated, having the number of carbon atoms designated (i.e., $C_1$-$C_{10}$ means one to ten carbon atoms). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 12 annular carbon atoms. A more preferred cycloalkyl is a cyclic hydrocarbon having from 3 to 8 annular carbon atoms (a "$C_3$-$C_8$ cycloalkyl"), or having 3 to 6 carbon atoms (a "$C_3$-$C_6$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like. "Cycloalkenyl" refers to an unsaturated cycloalkyl group having at least one site of olefinic unsaturation (i.e., having at least one moiety of the formula C=C), which can consist of one ring, such as cyclohexyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl and the like.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" as used herein refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Heterocycle", "heterocyclic", or "heterocyclyl" as used herein refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic is connected to the parent structure at a non-aromatic ring position.

"Substituted cycloalkyl", "substituted aryl", "substituted heteroaryl", and "substituted heterocyclyl" as used herein respectively refer to a cycloalkyl group, an aryl group, a heteroaryl group, and a heterocyclyl group having 1 to 5 substituents including, but not limited to, groups such as alkoxy, substituted alkoxy, cycloalkoxy, substituted cycloalkoxy, aryloxy, substituted aryloxy, acyl, acyloxy, carbonylalkoxy, acylamino, aminoacyl, aminocarbonylamino, aminocarbonyloxy, amino, substituted amino, cyano, halo, hydroxy, nitro, carboxy, thiol, thioalkyl, substituted or unsubstituted alkyl, substituted or unsubstituted cycloalkyl, substituted or unsubstituted heterocyclyl, aryl, substituted aryl, heteroaryl, substituted heteroaryl, aminosulfonyl, sulfonylamino, sulfonyl, oxo, carbonylalkylenealkoxy and the like.

"Alkoxy" as used herein refers to the group "alkyl-O—", which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. Similarly, "cycloalkoxy" refers to the group "cycloalkyl-O—" and "aryloxy" refers to the group "aryl-O—". "Substituted alkoxy" refers to the group "substituted alkyl-O—". "Substituted cycloalkoxy" refers to the group "substituted cycloalkyl-O—". "Substituted aryloxy" refers to the group "substituted aryl-O—".

"Acyl" as used herein refers to the groups —C(O)-alkyl, —C(O)-substituted alkyl, —C(O)-cycloalkyl, —C(O)-substituted cycloalkyl, —C(O)-aryl, C(O)-substituted aryl, —C(O)-heteroaryl, —C(O)-substituted heteroaryl, —C(O)-heterocyclyl or —C(O)-substituted heterocyclyl.

"Acyloxy" as used herein refers to the groups —OC(O)-alkyl, —OC(O)-substituted alkyl, —OC(O)-cycloalkyl, —OC(O)-substituted cycloalkyl, —OC(O)-aryl, —OC(O)-substituted aryl, —OC(O)-heteroaryl, —OC(O)-substituted heteroaryl, —OC(O)-heterocyclyl or —OC(O)-substituted heterocyclyl.

"Carbonylalkoxy" as used herein refers to the groups —C(O)O-alkyl, —C(O)O-substituted alkyl, 13 C(O)O-cycloalkyl, —C(O)O-substituted cycloalkyl, —C(O)O-aryl, —C(O)O-substituted aryl, —C(O)O-heteroaryl, —C(O)O-substituted heteroaryl, —C(O)O-heterocyclyl or —C(O)O-substituted heterocyclyl.

"Substituted amino" as used herein refers to the group —$NR_aR_b$, where (a) each $R_a$ and $R_b$ group is independently selected from the group consisting of hydrogen, alkyl, substituted alkyl, cycloalkyl, substituted cycloalkyl, aryl, substituted aryl, heteroaryl, substituted heteroaryl, heterocyclyl, substituted heterocyclyl, provided that both $R_a$ and $R_b$ groups are not hydrogen, or (b) $R_a$ and $R_b$ are taken together with the nitrogen atom to which they are attached to form a heterocyclic ring. "Unsubstituted amino" as used herein refers to the group $NH_2$.

"Acylamino" as used herein refers to the group —C(O)$NR_aR_b$ where $R_a$ and $R_b$ are independently selected from the group consisting of hydrogen, alkyl, substituted alkyl, cycloalkyl, substituted cycloalkyl, aryl, substituted aryl, heteroaryl, substituted heteroaryl, heterocyclyl, substituted heterocyclyl, or $R_a$ and $R_b$ are taken together with the nitrogen atom to which they are attached to form a heterocyclic ring.

"Aminoacyl" as used herein refers to the group —$NR_aC$(O)$R_b$ where each $R_a$ and $R_b$ group is independently selected from the group consisting of hydrogen, alkyl, substituted alkyl, cycloalkyl, substituted cycloalkyl, aryl, substituted aryl, heteroaryl, substituted heteroaryl, heterocyclyl, substituted heterocyclyl. Preferably, $R_a$ is hydrogen or alkyl.

"Sulfonyl" as used herein refers to the groups —$SO_2$-alkyl, —$SO_2$-substituted alkyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclyl or —$SO_2$-substituted heterocyclyl.

"Sulfonylamino" as used herein refers to the group —$SO_2N(R_a)R_b$ where each $R_a$ and $R_b$ group is independently selected from the group consisting of hydrogen, alkyl, substituted alkyl, cycloalkyl, substituted cycloalkyl, aryl, substituted aryl, heteroaryl, substituted heteroaryl, heterocyclyl, substituted heterocyclyl.

"Aminosulfonyl" as used herein refers to the group —$NR_aSO_2R_b$ where the $R_a$ group is selected from the group consisting of hydrogen, alkyl, substituted alkyl, cycloalkyl, substituted cycloalkyl, aryl, substituted aryl, heteroaryl, substituted heteroaryl, heterocyclyl, substituted heterocyclyl, and the $R_b$ group is selected from the group consisting of alkyl, substituted alkyl, cycloalkyl, substituted cycloalkyl, aryl, substituted aryl, heteroaryl, substituted heteroaryl, heterocyclyl, substituted heterocyclyl.

"Aminocarbonylalkoxy" as used herein refers to the group —$NR_aC(O)OR_b$ where each $R_a$ and $R_b$ group is independently selected from the group consisting of hydrogen, alkyl, substituted alkyl, cycloalkyl, substituted cycloalkyl, aryl, substituted aryl, heteroaryl, substituted heteroaryl, heterocyclyl, substituted heterocyclyl.

"Carbonylalkylenealkoxy" as used herein refers to the group —C(=O)—$(CH_2)_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Thiocarbonyl" refers to the group C=S.

"Cyano" refers to the group —CN.

"Oxo" refers to the moiety =O.

"Nitro" refers to the group —$NO_2$.

"Thiol" as used herein when referring to a substituent refers to the groups —SH.

"Thioalkyl" refers to the groups —S-alkyl.

"Geminal" refers to the relationship between two moieties that are attached to the same atom. For example, in the residue —$CH_2$—$CHR^1R^2$, $R^1$ and $R^2$ are geminal and $R^1$ may be referred to as a geminal R group to $R^2$.

"Vicinal" refers to the relationship between two moieties that are attached to adjacent atoms. For example, in the residue $CHR^1$—$CH_2R^2$, $R^1$ and $R^2$ are vicinal and $R^1$ may be referred to as a vicinal R group to $R^2$.

Unless clearly indicated otherwise, "an individual" as used herein intends a mammal, including but not limited to a primate, human, bovine, horse, feline, canine, or rodent.

As used herein a receptor "modulator," such as an IGF-IR modulator, encompasses both a receptor antagonist and a receptor agonist (e.g., an "IGF-IR modulator" encompasses both an IGF-IR receptor antagonist and an IGF-IR receptor agonist). In some aspects, the receptor modulator binds to or inhibits binding of a ligand to the receptor and/or reduces or eliminates or increases or enhances or mimics an activity of the receptor in a reversible or irreversible manner. In some aspects, the receptor modulator inhibits binding of a ligand to the receptor by at least about or by about any one of 10%, 20%, 30%, 40%, 50%, 60%, 70%, 80%, 90%, 95% or 100% as determined by an assay described herein. In some aspects, the receptor modulator reduces an activity of the receptor by at least about or about any of 10%, 20%, 30%, 40%, 50%, 60%, 70%, 80%, 90%, 95% or 100% as compared to the corresponding activity in the same subject prior to treatment with the receptor modulator or compared to the corresponding activity in other subjects not receiving the receptor modulator. In some aspects, a receptor modulator enhances an activity of the receptor by at least about or by about any of 10%, 20%, 30%, 40%, 50%, 60%, 70%, 80%, 90%, 95% or 100 or 200% or 300% or 400% or 500% or more as compared to the corresponding activity in the same subject prior to treatment with the receptor modulator or compared to the corresponding activity in other subjects not receiving the receptor modulator. In some aspects, the receptor modulator is capable of binding to the active site of the receptor (e.g., a binding site for a ligand). In some embodiments, the receptor modulator is capable of binding to an allosteric site of the receptor.

As used herein, "treatment" or "treating" is an approach for obtaining beneficial or desired results including clinical results. For purposes of this invention, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread (e.g., metastasis) of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. Also encompassed by "treatment" is a reduction of pathological consequence of cancer. The methods of the invention contemplate any one or more of these aspects of treatment.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of subjects. Cancer development can be detectable using standard methods, such as routine physical exams, mammography, imaging, or biopsy. Development may also refer to disease progression that may be initially undetectable and includes occurrence, recurrence, and onset.

As used herein, an "at risk" individual is an individual who is at risk of developing cancer. An individual "at risk" may or may not have detectable disease, and may or may not have displayed detectable disease prior to the treatment methods described herein. "At risk" denotes that an individual has one or more so-called risk factors, which are measurable parameters that correlate with development of cancer, which are described herein. An individual having one or more of these risk factors has a higher probability of developing cancer than an individual without these risk factor(s).

As used herein, by "combination therapy" is meant a therapy that includes two or more different compounds. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances.

As used herein, the term "effective amount" intends such amount of a compound of the invention which in combination with its parameters of efficacy and toxicity, should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds. In various embodiments, an effective amount of the composition or therapy may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

As is understood in the art, an "effective amount" may be in one or more doses, i.e., a single dose or multiple doses may be required to achieve the desired treatment endpoint. An effective amount may be considered in the context of administering one or more therapeutic agents, and a compound, or pharmaceutically acceptable salt thereof, may be considered to be given in an effective amount if, in conjunction with one or more other agents, a desirable or beneficial result may be or is achieved.

A "therapeutically effective amount" refers to an amount of a compound or salt thereof sufficient to produce a desired therapeutic outcome (e.g., reducing the severity or duration of, stabilizing the severity of, or eliminating one or more symptoms of cancer). For therapeutic use, beneficial or desired results include, e.g., decreasing one or more symptoms resulting from the disease (biochemical, histologic and/or behavioral), including its complications and intermediate pathological phenotypes presenting during development of the disease, increasing the quality of life of those suffering from the disease, decreasing the dose of other medications required to treat the disease, enhancing effect of another medication, delaying the progression of the disease, and/or prolonging survival of patients.

A "prophylactically effective amount" refers to an amount of a compound, or pharmaceutically acceptable salt thereof, sufficient to prevent or reduce the severity of one or more future symptoms of cancer when administered to an individual who is susceptible and/or who may develop cancer. For prophylactic use, beneficial or desired results include, e.g., results such as eliminating or reducing the risk, lessening the severity of future disease, or delaying the onset of the disease (e.g., delaying biochemical, histologic and/or behavioral symptoms of the disease, its complications, and intermediate pathological phenotypes presenting during future development of the disease).

It is understood that an effective amount of a compound or pharmaceutically acceptable salt thereof, including a prophylactically effective amount, may be given to an individual in the adjuvant setting, which refers to a clinical setting in which an individual has had a history of cancer, and generally (but not necessarily) has been responsive to therapy, which includes, but is not limited to, surgery (e.g., surgical resection), radiotherapy, and chemotherapy. However, because of their history of the cancer, these individuals are considered at risk of developing cancer. Treatment or administration in the "adjuvant setting" refers to a subsequent mode of treatment.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Compounds of the Invention

Compounds according to the invention are detailed herein, including in the Brief Summary of the Invention and the appended claims. The invention includes the use of all of the compounds described herein, including any and all stereoisomers, including geometric isomers (cis/trans), salts (including pharmaceutically acceptable salts) and solvates of the compounds described herein, as well as methods of making such compounds.

In one aspect, provided is a compound of the formula (I):

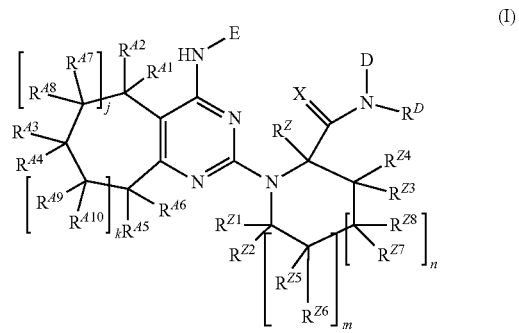

(I)

or a salt thereof, wherein:

D is hydrogen, substituted or unsubstituted $C_1$-$C_6$ alkyl, substituted or unsubstituted aryl, substituted or unsubstituted heteroaryl, substituted or unsubstituted $C_3$-$C_8$ cycloalkyl, substituted or unsubstituted heterocyclyl, or is taken together with $R^D$ and the nitrogen to which they are attached to form a substituted or unsubstituted heterocyclyl;

E is substituted or unsubstituted heteroaryl;

each j, k, m, and n is independently 0 or 1;

each $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ where present, is independently hydrogen, substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —OC(O)$R^8$, —$C(O)R^9$, substituted or unsubstituted $C_3$-$C_8$ cycloalkyl, substituted or unsubstituted heterocyclyl, substituted or unsubstituted aryl, substituted or unsubstituted heteroaryl, or is taken together with a geminal $R^{A(1-10)}$ group and the carbon to which they are attached to form carbonyl, thiocarbonyl, a $C_3$-$C_6$ cycloalkyl, or a heterocyclyl;

$R^D$ is hydrogen, substituted or unsubstituted $C_1$-$C_6$ alkyl, or taken together with D and the nitrogen to which they are attached to form a substituted or unsubstituted heterocyclyl;

X is O or S;

$R^Z$ is hydrogen, or substituted or unsubstituted $C_1$-$C_6$ alkyl;

each $R^{Z1}$ and $R^{Z2}$ is independently hydrogen, or substituted or unsubstituted $C_1$-$C_6$ alkyl, or $R^{Z1}$ and $R^{Z2}$ are taken together with the carbon to which they are attached to form a carbonyl or a $C_3$-$C_6$ cycloalkyl;

each $R^{Z3}$, $R^{Z4}$, $R^{Z5}$, $R^{Z6}$, $R^{Z7}$ and $R^{Z8}$, where present, is independently hydrogen, substituted or unsubstituted $C_1$-$C_6$ alkyl, halo, hydroxy, —$OR^1$, —O—$C_1$-$C_6$ alkylene-P(O)(OH)$_2$, —SH, —$S(O)_pR^2$, —$NR^3R^4$, —$C(O)NR^5R^6$, —$C(O)OR^7$, —OC(O)$R^8$, —$C(O)R^9$, substituted or unsubstituted $C_3$-$C_8$ cycloalkyl, substituted or unsubstituted heterocyclyl, substituted or unsubstituted aryl, substituted or unsubstituted heteroaryl, or is taken together with a geminal $R^{Z(3-8)}$ group and the carbon to which they are attached to form carbonyl, thiocarbonyl or a $C_3$-$C_6$ cycloalkyl;

each p is independently 0, 1 or 2;

each $R^1$ is independently a substituted or unsubstituted $C_1$-$C_6$ alkyl, substituted or unsubstituted $C_3$-$C_8$ cycloalkyl, or substituted or unsubstituted aryl;

each $R^2$ is independently a substituted or unsubstituted $C_1$-$C_6$ alkyl, substituted or unsubstituted $C_3$-$C_8$ cycloalkyl, substituted or unsubstituted aryl or hydroxyl;

each $R^3$, $R^4$, $R^5$, $R^6$ and $R^7$ is independently hydrogen, substituted or unsubstituted $C_1$-$C_6$ alkyl, or substituted or unsubstituted $C_3$-$C_8$ cycloalkyl; and each $R^8$ and $R^9$ is independently hydrogen, substituted or unsubstituted $C_1$-$C_6$ alkyl, substituted or unsubstituted $C_3$-$C_8$ cycloalkyl, substituted or unsubstituted heterocyclyl, substituted or unsubstituted aryl, or substituted or unsubstituted heteroaryl.

In some embodiments, the compound is of the formula (I), or a salt thereof, and j and k are each 0. In other embodiments, the compound is of the formula (I), or a salt thereof, and j is 1 and k is 0. In other embodiments, the compound is of the formula (I), or a salt thereof, and j and k are each 1.

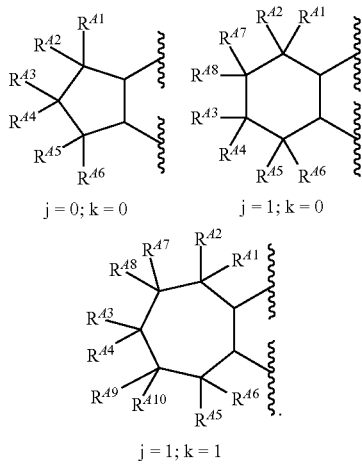

In some of these embodiments, each $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$, where present, is hydrogen. In some of these embodiments, at least one of $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$, where present, is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —$OC(O)R^8$, —$C(O)R^9$, substituted or unsubstituted $C_3$-$C_8$ cycloalkyl, substituted or unsubstituted heterocyclyl, substituted or unsubstituted aryl, or substituted or unsubstituted heteroaryl, or is taken together with a geminal $R^{A(1-10)}$ group and the carbon to which they are attached to form carbonyl, thiocarbonyl, a $C_3$-$C_6$ cycloalkyl, or a heterocyclyl. In some of these embodiments, one of $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$, where present, is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —$OC(O)R^8$, —$C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are hydrogen. In some of these embodiments, two of $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$, where present, are independently substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —$OC(O)R^8$, —$C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are each hydrogen. In some of these embodiments, two geminal $R^{A(1-10)}$ groups of $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$, where present, are taken together with the carbon to which they are attached to form carbonyl, thiocarbonyl, a $C_3$-$C_6$ cycloalkyl, or a heterocyclyl; and the others are each hydrogen. In some variations, $R^{A1}$ and $R^{A2}$ are each $C_1$-$C_6$ alkyl (e.g., methyl), halo (e.g. fluoro), or are taken together with the carbon to which they are attached to form carbonyl, thiocarbonyl, a $C_3$-$C_6$ cycloalkyl (e.g., cyclopropyl), or a heterocyclyl (e.g., oxirane). In some variations, $R^{A3}$ and $R^{A4}$ are each $C_1$-$C_6$ alkyl (e.g., methyl), halo (e.g. fluoro), or are taken together with the carbon to which they are attached to form carbonyl, thiocarbonyl, a $C_3$-$C_6$ cycloalkyl (e.g., cyclopropyl), or a heterocyclyl (e.g., oxirane). In some variations, $R^{A5}$ and $R^{A6}$ are each $C_1$-$C_6$ alkyl (e.g., methyl), halo (e.g. fluoro), or are taken together with the carbon to which they are attached to form carbonyl, thiocarbonyl, a $C_3$-$C_6$ cycloalkyl (e.g., cyclopropyl), or a heterocyclyl (e.g., oxirane).

In some embodiments, the compound is of the formula (I), or a salt thereof, where j and k are each 0:

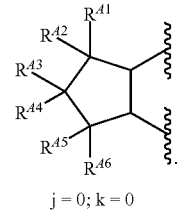

In some of these embodiments, each $R^{A1}$, $R^{A2}$, $R^{A3}$, $R^{A4}$, $R^{A5}$ and $R^{A6}$ is hydrogen. In some of these embodiments, at least one of $R^{A1}$, $R^{A2}$, $R^{A3}$, $R^{A4}$, $R^{A5}$ and $R^{A6}$ is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —$OC(O)R^8$, —$C(O)R^9$, substituted or unsubstituted $C_3$-$C_8$ cycloalkyl, substituted or unsubstituted heterocyclyl, substituted or unsubstituted aryl, substituted or unsubstituted heteroaryl, or is taken together with a geminal $R^{A(1-6)}$ group and the carbon to which they are attached to form carbonyl, thiocarbonyl, a $C_3$-$C_6$ cycloalkyl, or a heterocyclyl. In some of these embodiments, one of $R^{A1}$, $R^{A2}$, $R^{A3}$, $R^{A4}$, $R^{A5}$ and $R^{A6}$ is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —$OC(O)R^8$, —$C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are hydrogen. In some of these embodiments, two of $R^{A1}$, $R^{A2}$, $R^{A3}$, $R^{A4}$, $R^{A5}$ and $R^{A6}$ are independently substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —$OC(O)R^8$, —$C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are each hydrogen. In some of these embodiments, two geminal $R^{A(1-6)}$ groups of $R^{A1}$, $R^{A2}$, $R^{A3}$, $R^{A4}$, $R^{A5}$ and $R^{A6}$ are taken together with the carbon to which they are attached to form carbonyl, thiocarbonyl, a $C_3$-$C_6$ cycloalkyl, or a heterocyclyl; and the others are each hydrogen. In some variations, $R^{A1}$ and $R^{A2}$ are each $C_1$-$C_6$ alkyl (e.g., methyl), halo (e.g. fluoro), or are taken together with the carbon to which they are attached to form carbonyl, thiocarbonyl, a $C_3$-$C_6$ cycloalkyl (e.g., cyclopropyl), or a heterocyclyl (e.g., oxirane). In some variations, $R^{A3}$ and $R^{A4}$ are each $C_1$-$C_6$ alkyl (e.g., methyl), halo (e.g. fluoro), or are taken together with the carbon to which they are attached to form carbonyl, thiocarbonyl, a $C_3$-$C_6$ cycloalkyl (e.g., cyclopropyl), or a heterocyclyl (e.g., oxirane). In some variations, $R^{A5}$ and $R^{A6}$ are each $C_1$-$C_6$ alkyl (e.g., methyl), halo (e.g. fluoro), or are taken together with the carbon to which they are attached to form carbonyl, thiocarbonyl, a $C_3$-$C_6$ cycloalkyl (e.g., cyclopropyl), or a heterocyclyl (e.g., oxirane).

In some embodiments, the compound is of the formula (I), or a salt thereof, where j is 1 and k is 0:

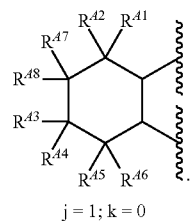

j = 1; k = 0

In some of these embodiments, each $R^{A1}$, $R^{A2}$, $R^{A3}$, $R^{A4}$, $R^{A5}$, $R^{A6}$, $R^{A7}$ and $R^{A8}$ is hydrogen. In some of these embodiments, at least one of $R^{A1}$, $R^{A2}$, $R^{A3}$, $R^{A4}$, $R^{A5}$, $R^{A6}$, $R^{A7}$ and $R^{A8}$ is substituted or unsubstituted $C_1$-$C_6$ alkyl, halo, hydroxy, $-OR^1$, $-SH$, $-S(O)_pR^2$, $-NR^3R^4$, $-C(O)NR^5R^6$, $-C(O)OR^7$, $-OC(O)R^8$, $-C(O)R^9$, substituted or unsubstituted $C_3$-$C_8$ cycloalkyl, substituted or unsubstituted heterocyclyl, substituted or unsubstituted aryl, substituted or unsubstituted heteroaryl, or is taken together with a geminal $R^{A(1-8)}$ group and the carbon to which they are attached to form carbonyl, thiocarbonyl, a $C_3$-$C_6$ cycloalkyl, or a heterocyclyl. In some of these embodiments, one of $R^{A1}$, $R^{A2}$, $R^{A3}$, $R^{A4}$, $R^{A5}$, $R^{A6}$, $R^{A7}$ and $R^{A8}$ is substituted or unsubstituted $C_1$-$C_6$ alkyl, halo, hydroxy, $-OR^1$, $-SH$, $-S(O)_pR^2$, $-NR^3R^4$, $-C(O)NR^5R^6$, $-C(O)OR^7$, $-OC(O)R^8$, $-C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are hydrogen. In some of these embodiments, two of $R^{A1}$, $R^{A2}$, $R^{A3}$, $R^{A4}$, $R^{A5}$, $R^{A6}$, $R^{A7}$ and $R^{A8}$ are independently substituted or unsubstituted $C_1$-$C_6$ alkyl, halo, hydroxy, $-OR^1$, $-SH$, $-S(O)_pR^2$, $-NR^3R^4$, $-C(O)NR^5R^6$, $-C(O)OR^7$, $-OC(O)R^8$, $-C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are each hydrogen. In some of these embodiments, two geminal $R^{A(1-8)}$ groups of $R^{A1}$, $R^{A2}$, $R^{A3}$, $R^{A4}$, $R^{A5}$, $R^{A6}$, $R^{A7}$ and $R^{A8}$ are taken together with the carbon to which they are attached to form carbonyl, thiocarbonyl, a $C_3$-$C_6$ cycloalkyl, or a heterocyclyl; and the others are each hydrogen.

In some embodiments, the compound is of the formula (I), or a salt thereof, where j and k are each 1:

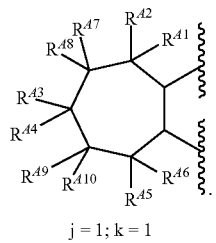

j = 1; k = 1

In some of these embodiments, each $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ is hydrogen. In some of these embodiments, at least one of $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ is substituted or unsubstituted $C_1$-$C_6$ alkyl, halo, hydroxy, $-OR^1$, $-SH$, $-S(O)_pR^2$, $-NR^3R^4$, $-C(O)NR^5R^6$, $-C(O)OR^7$, $-OC(O)R^8$, $-C(O)R^9$, substituted or unsubstituted $C_3$-$C_8$ cycloalkyl, substituted or unsubstituted heterocyclyl, substituted or unsubstituted aryl, substituted or unsubstituted heteroaryl, or is taken together with a geminal $R^{A(1-10)}$ group and the carbon to which they are attached to form carbonyl, thiocarbonyl, a $C_3$-$C_6$ cycloalkyl, or a heterocyclyl. In some of these embodiments, one of $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ is substituted or unsubstituted $C_1$-$C_6$ alkyl, halo, hydroxy, $-OR^1$, $-SH$, $-S(O)_pR^2$, $-NR^3R^4$, $-C(O)NR^5R^6$, $-C(O)OR^7$, $-OC(O)R^8$, $-C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are hydrogen. In some of these embodiments, two of $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ are independently substituted or unsubstituted $C_1$-$C_6$ alkyl, halo, hydroxy, $-OR^1$, $-SH$, $-S(O)_pR^2$, $-NR^3R^4$, $-C(O)NR^5R^6$, $-C(O)OR^7$, $-OC(O)R^8$, $-C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are each hydrogen. In some of these embodiments, two geminal $R^{A(1-10)}$ groups of $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ are taken together with the carbon to which they are attached to form carbonyl, thiocarbonyl, a $C_3$-$C_6$ cycloalkyl, or a heterocyclyl; and the others are each hydrogen.

It is intended and understood that each and every variation of j, k, $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$, where present, described for the formula (I) may be combined with each and every variation of j, k, $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$, where present, and/or each and every variation of m, n, $R^Z$, $R^{Z1}$, $R^{Z2}$, $R^{Z3}$, $R^{Z4}$, $R^{Z5}$, $R^{Z6}$, $R^{Z7}$ and $R^{Z8}$, where present, and/or each and every variation of X, $R^D$, D and E described for the formula (I) as if each and every combination is individually described.

In some embodiments, the compound is of the formula (I), or a salt thereof, and m and n are each 1. In some embodiments, the compound is of the formula (I), or a salt thereof, and m is 1 and n is 0. In some embodiments, the compound is of the formula (I), or a salt thereof, and m and n are each 0.

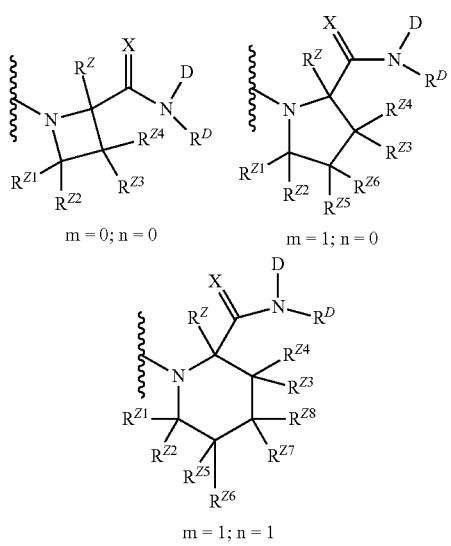

m = 0; n = 0     m = 1; n = 0 m = 1; n = 1

In some of these embodiments, $R^Z$ is hydrogen. In some of these embodiments, $R^Z$ is substituted or unsubstituted $C_1$-$C_6$ alkyl. In one variation, $R^Z$ is unsubstituted $C_1$-$C_6$ alkyl (e.g., methyl). In some of these embodiments, each $R^{Z1}$ and $R^{Z2}$ is hydrogen. In one variation, each $R^{Z3}$, $R^{Z4}$, $R^{Z5}$, $R^{Z6}$, $R^{Z7}$ and $R^{Z8}$, where present, is hydrogen. In some of these embodiments, $R^{Z1}$ and $R^{Z2}$ are independently hydrogen, substituted or unsubstituted $C_1$-$C_6$ alkyl, or taken together with the carbon to which they are attached to form a carbonyl or a $C_3$-$C_6$ cycloalkyl. In some of these embodiments, one of $R^{Z1}$ and $R^{Z2}$ is substituted or unsubstituted $C_1$-$C_6$ alkyl, or taken together with the carbon to which they are attached to form a carbonyl or a $C_3$-$C_6$ cycloalkyl. In some of these embodiments, each $R^{Z3}$, $R^{Z4}$, $R^{Z5}$, $R^{Z6}$, $R^{Z7}$ and $R^{Z8}$, where present, is hydrogen. In some of these embodiments, at least one of $R^{Z3}$, $R^{Z4}$, $R^{Z5}$, $R^{Z6}$, $R^{Z7}$ and $R^{Z8}$, where present, is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —OC(O)$R^8$, —$C(O)R^9$, substituted or unsubstituted $C_3$-$C_8$ cycloalkyl, substituted or unsubstituted heterocyclyl, substituted or unsubstituted aryl, substituted or unsubstituted heteroaryl, or is taken together with a geminal $R^{Z(3-8)}$ group and the carbon to which they are attached to form carbonyl, thiocarbonyl or a $C_3$-$C_6$ cycloalkyl. In some of these embodiments, one of $R^{Z3}$, $R^{Z4}$, $R^{Z5}$, $R^{Z6}$, $R^{Z7}$ and $R^{Z8}$, where present, is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —$OC(O)R^8$, —$C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are hydrogen. In some of these embodiments, two geminal $R^{Z(3-8)}$ groups of $R^{Z3}$, $R^{Z4}$, $R^{Z5}$, $R^{Z6}$, $R^{Z7}$ and $R^{Z8}$, where present, are taken together with the carbon to which they are attached to form carbonyl, thiocarbonyl or a $C_3$-$C_6$ cycloalkyl; and the others are each hydrogen. In some of these embodiments, at least one of $R^{Z3}$, $R^{Z4}$, $R^{Z5}$, $R^{Z6}$, $R^{Z7}$ and $R^{Z8}$, where present, is substituted or unsubstituted $C_1$-$C_6$ alkyl, halo, hydroxy, —$OR^1$, substituted or unsubstituted $C_3$-$C_8$ cycloalkyl, substituted or unsubstituted heterocyclyl, substituted or unsubstituted aryl, substituted or unsubstituted heteroaryl. In some of these embodiments, one of $R^{Z3}$, $R^{Z4}$, $R^{Z5}$, $R^{Z6}$, $R^{Z7}$ and $R^{Z8}$, where present, is halo (e.g., fluoro), hydroxy, —$OR^1$ (e.g., $OCH_3$), or substituted or unsubstituted heteroaryl (e.g., 5-methyl-2H-tetrazol-2-yl); and the others are hydrogen. In some of these embodiments, $R^{Z3}$ and $R^{Z4}$ are each $C_1$-$C_6$ alkyl (e.g., methyl) or halo (e.g., fluoro), or taken together with the carbon to which they are attached to form carbonyl, thiocarbonyl or a $C_3$-$C_6$ cycloalkyl. In some of these embodiments, $R^{Z5}$ and $R^{Z6}$ are each $C_1$-$C_6$ alkyl (e.g., methyl) or halo (e.g., fluoro), or taken together with the carbon to which they are attached to form carbonyl, thiocarbonyl or a $C_3$-$C_6$ cycloalkyl. In some of these embodiments, one of $R^{Z3}$, $R^{Z4}$, $R^{Z5}$, $R^{Z6}$, $R^{Z7}$ and $R^{Z8}$, where present, is a prodrug moiety of the formula —O—$C_1$-$C_6$ alkylene-P(O)(OH)$_2$ (e.g., —$OCH_2$P(O)(OH)$_2$), or —OC(O)$R^8$ where $R^8$ is $C_1$-$C_6$ alkyl (e.g., isopropyl).

In some embodiments, the compound is of the formula (I), or a salt thereof, where m and n are each 0:

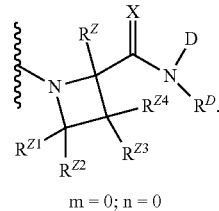

m = 0; n = 0

In some of these embodiments, each $R^{Z1}$ and $R^{Z2}$ is hydrogen. In one variation, $R^{Z1}$, $R^{Z2}$, $R^{Z3}$ and $R^{Z4}$ are each hydrogen. In some of these embodiments, $R^{Z1}$ and $R^{Z2}$ are independently hydrogen, substituted or unsubstituted $C_1$-$C_6$ alkyl, or taken together with the carbon to which they are attached to form a carbonyl or a $C_3$-$C_6$ cycloalkyl. In some of these embodiments, one of $R^{Z1}$ and $R^{Z2}$ is substituted or unsubstituted $C_1$-$C_6$ alkyl, or taken together with the carbon to which they are attached to form a carbonyl or a $C_3$-$C_6$ cycloalkyl. In some of these embodiments, each $R^{Z3}$ and $R^{Z4}$ is hydrogen. In some of these embodiments, one of $R^{Z3}$ and $R^{Z4}$ is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —OC(O)$R^8$, —$C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the other is hydrogen. In some of these embodiments, $R^{Z3}$ and $R^{Z4}$ are taken together with the carbon to which they are attached to form carbonyl, thiocarbonyl or a $C_3$-$C_6$ cycloalkyl. In some of these embodiments, at least one of $R^{Z3}$ and $R^{Z4}$ is substituted or unsubstituted $C_1$-$C_6$ alkyl, halo, hydroxy, —$OR^1$, substituted or unsubstituted $C_3$-$C_8$ cycloalkyl, substituted or unsubstituted heterocyclyl, substituted or unsubstituted aryl, substituted or unsubstituted heteroaryl.

In some embodiments, the compound is of the formula (I), or a salt thereof, where m is 1 and n is 0:

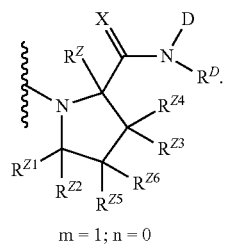

m = 1; n = 0

In some of these embodiments, each $R^{Z1}$ and $R^{Z2}$ is hydrogen. In one variation, $R^{Z1}$, $R^{Z2}$, $R^{Z3}$, $R^{Z4}$, $R^{Z5}$ and $R^{Z6}$ are each hydrogen. In some of these embodiments, $R^{Z1}$ and $R^{Z2}$ are independently hydrogen, substituted or unsubstituted $C_1$-$C_6$ alkyl, or taken together with the carbon to which they are attached to form a carbonyl or a $C_3$-$C_6$ cycloalkyl. In some of these embodiments, one of $R^{Z1}$ and $R^{Z2}$ is substituted or unsubstituted $C_1$-$C_6$ alkyl, or taken together with the carbon to which they are attached to form a carbonyl or a $C_3$-$C_6$ cycloalkyl. In some of these embodiments, each $R^{Z3}$, $R^{Z4}$, $R^{Z5}$ and $R^{Z6}$ is hydrogen. In some of these embodiments, at least one of $R^{Z3}$, $R^{Z4}$, $R^{Z5}$ and $R^{Z6}$ is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —OC(O)$R^8$, —$C(O)R^9$, substituted or unsubstituted $C_3$-$C_8$ cycloalkyl, substituted or unsubstituted heterocyclyl, substituted or unsubstituted aryl, substituted or unsubstituted heteroaryl, or is taken together with a geminal $R^{Z(3-6)}$ group and the carbon to which they are attached to form carbonyl, thiocarbonyl or a $C_3$-$C_6$ cycloalkyl. In some of these embodiments, one of $R^{Z3}$, $R^{Z4}$, $R^{Z5}$ and $R^{Z6}$ is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —$OC(O)R^8$, —$C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are hydrogen. In some of these embodiments, two geminal $R^{Z(3-6)}$ groups of $R^{Z3}$, $R^{Z4}$, $R^{Z5}$ and $R^{Z6}$ are taken together with the carbon to which they are attached to form carbonyl, thiocarbonyl or a $C_3$-$C_6$ cycloalkyl; and the others are each hydrogen. In some of these embodiments, at least one of $R^{Z3}$, $R^{Z4}$, $R^{Z5}$ and $R^{Z6}$ is substituted or unsubstituted $C_1$-$C_6$ alkyl, halo, hydroxy, —$OR^1$, substituted or unsubstituted $C_3$-$C_8$ cycloalkyl, substituted or unsubstituted heterocyclyl, substituted or unsubstituted aryl, substituted or unsubstituted heteroaryl. In some of these embodiments, one of $R^{Z3}$, $R^{Z4}$, $R^{Z5}$ and $R^{Z6}$ is halo (e.g., fluoro), hydroxy, —$OR^1$ (e.g., $OCH_3$), or substituted or unsubstituted heteroaryl (e.g., 5-methyl-2H-tetrazol-2-yl); and the others are hydrogen. In some of these embodiments, $R^{Z3}$ and $R^{Z4}$ are each $C_1$-$C_6$ alkyl (e.g., methyl) or halo (e.g., fluoro), or taken together with the carbon to which they are attached to form carbonyl, thiocarbonyl or a $C_3$-$C_6$ cycloalkyl. In some of these embodiments, $R^{Z5}$ and $R^{Z6}$ are each $C_1$-$C_6$ alkyl (e.g., methyl) or halo (e.g., fluoro), or taken together with the carbon to which they are attached to form carbonyl, thiocarbonyl or a $C_3$-$C_6$ cycloalkyl. In some of these embodiments, one of $R^{Z3}$, $R^{Z4}$, $R^{Z5}$ and $R^{Z6}$ is a prodrug moiety of the formula —O—$C_1$-$C_6$ alkylene-$P(O)(OH)_2$ (e.g., —$OCH_2P(O)(OH)_2$), or —$OC(O)R^8$ where $R^8$ is $C_1$-$C_6$ alkyl (e.g., isopropyl).

In some embodiments, the compound is of the formula (I), or a salt thereof, where m and n are each 1:

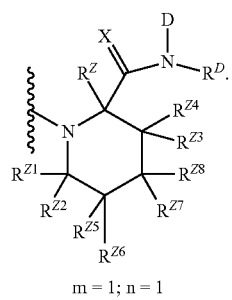

m = 1; n = 1

In some of these embodiments, each $R^{Z1}$ and $R^{Z2}$ is hydrogen. In one variation, each $R^{Z3}$, $R^{Z4}$, $R^{Z5}$, $R^{Z6}$, $R^{Z7}$ and $R^{Z8}$ is hydrogen. In some of these embodiments, $R^{Z1}$ and $R^{Z2}$ are independently hydrogen, substituted or unsubstituted $C_1$-$C_6$ alkyl, or taken together with the carbon to which they are attached to form a carbonyl or a $C_3$-$C_6$ cycloalkyl. In some of these embodiments, one of $R^{Z1}$ and $R^{Z2}$ is substituted or unsubstituted $C_1$-$C_6$ alkyl, or taken together with the carbon to which they are attached to form a carbonyl or a $C_3$-$C_6$ cycloalkyl. In some of these embodiments, each $R^{Z3}$, $R^{Z4}$, $R^{Z5}$, $R^{Z6}$, $R^{Z7}$ and $R^{Z8}$ is hydrogen. In some of these embodiments, at least one of $R^{Z3}$, $R^{Z4}$, $R^{Z5}$, $R^{Z6}$, $R^{Z7}$ and $R^{Z8}$ is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —$OC(O)R^8$, —$C(O)R^9$, substituted or unsubstituted $C_3$-$C_8$ cycloalkyl, substituted or unsubstituted heterocyclyl, substituted or unsubstituted aryl, substituted or unsubstituted heteroaryl, or is taken together with a geminal $R^{Z(3-8)}$ group and the carbon to which they are attached to form carbonyl, thiocarbonyl or a $C_3$-$C_6$ cycloalkyl. In some of these embodiments, one of $R^{Z3}$, $R^{Z4}$, $R^{Z5}$, $R^{Z6}$, $R^{Z7}$ and $R^{Z8}$ is substituted or unsubstituted $C_1$-$C_6$ alkyl, halo, hydroxy, —$OR^1$, —SH, —$S(O)_pR^2$, —$NR^3R^4$, —$C(O)NR^5R^6$, —$C(O)OR^7$, —$OC(O)R^8$, —$C(O)R^9$, substituted or unsubstituted $C_3$-$C_8$ cycloalkyl, substituted or unsubstituted heterocyclyl, substituted or unsubstituted aryl, or substituted or unsubstituted heteroaryl; and the others are hydrogen. In some of these embodiments, two geminal $R^{Z(3-8)}$ groups of $R^{Z3}$, $R^{Z4}$, $R^{Z5}$, $R^{Z6}$, $R^{Z7}$ and $R^{Z8}$ are taken together with the carbon to which they are attached to form carbonyl, thiocarbonyl or a $C_3$-$C_6$ cycloalkyl; and the others are each hydrogen. In some of these embodiments, at least one of $R^{Z3}$, $R^{Z4}$, $R^{Z5}$, $R^{Z6}$, $R^{Z7}$ and $R^{Z8}$ is substituted or unsubstituted $C_1$-$C_6$ alkyl, halo, hydroxy, —$OR^1$, substituted or unsubstituted $C_3$-$C_8$ cycloalkyl, substituted or unsubstituted heterocyclyl, substituted or unsubstituted aryl, substituted or unsubstituted heteroaryl.

In some embodiments, each $R^{41}$, $R^{42}$, $R^{43}$, $R^{44}$, $R^{45}$, $R^{46}$, $R^{47}$, $R^{48}$, $R^{49}$ and $R^{410}$, where present, is independently hydrogen, methyl, fluoro, hydroxyl, or taken together with a geminal $R^{4(1-10)}$ group and the carbon to which they are attached to form a moiety of the structure:

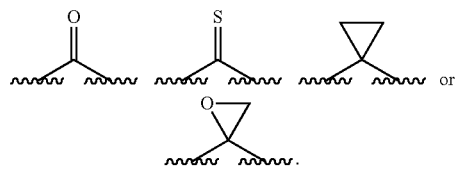

In some embodiments, each $R^{Z3}$, $R^{Z4}$, $R^{Z5}$, $R^{Z6}$, $R^{Z7}$ and $R^{Z8}$, where present, is independently

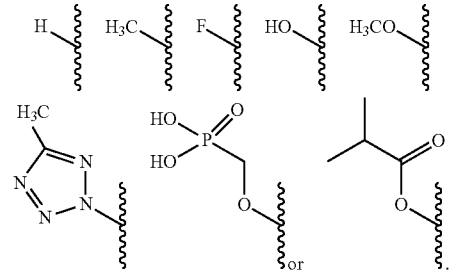

In some embodiments, at least one of $R^{Z3}$, $R^{Z4}$, $R^{Z5}$, $R^{Z6}$, $R^{Z7}$ and $R^{Z8}$ is taken together with a geminal $R^{Z(3-8)}$ group and the carbon to which they are attached to form a carbonyl moiety. In some embodiments, $R^{Z3}$ and $R^{Z4}$ are taken together with the carbon to which they are attached to form a carbonyl moiety. In some embodiments, $R^{Z5}$ and $R^{Z6}$, where present, are taken together with the carbon to which they are attached to form a carbonyl moiety. In some embodiments, $R^{Z7}$ and $R^{Z8}$, where present, are taken together with the carbon to which they are attached to form a carbonyl moiety.

In some embodiments, the compound is of the formula (I), or a salt thereof, where $R^Z$ is hydrogen, or substituted or unsubstituted $C_1$-$C_6$ alkyl. In one variation, $R^Z$ is hydrogen. In another variation, $R^Z$ is substituted or unsubstituted $C_1$-$C_6$ alkyl. In one such variation, $R^Z$ is unsubstituted $C_1$-$C_6$ alkyl (e.g., methyl).

It is intended and understood that each and every variation of m, n, $R^Z$, $R^{Z1}$, $R^{Z2}$, $R^{Z3}$, $R^{Z4}$, $R^{Z5}$, $R^{Z6}$, $R^{Z7}$ and $R^{Z8}$, where present, described for the formula (I) may be combined with each and every variation of j, k, $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$, where present, and/or each and every variation of X, $R^D$, D and E described for the formula (I) as if each and every combination is individually described. For example, in some embodiments, provided is a compound of the formula (I), or a salt thereof, where each j and k is 0, $R^{A1}$, $R^{A2}$, $R^{A3}$, $R^{A4}$, $R^{A5}$ and $R^{A6}$ are as described herein, m is 1, n is 0, and $R^Z$, $R^{Z1}$, $R^{Z2}$, $R^{Z3}$, $R^{Z4}$, $R^{Z5}$ and $R^{Z6}$ are as described herein. In one variation, j and k are each 0, $R^{A1}$, $R^{A2}$, $R^{A3}$, $R^{A4}$, $R^{A5}$ and $R^{A6}$ are each hydrogen, m is 1, n is 0, and $R^Z$, $R^{Z1}$, $R^{Z2}$, $R^{Z3}$, $R^{Z4}$, $R^{Z5}$ and $R^{Z6}$ are each hydrogen.

In some embodiments, the compound is of the formula (I), or a salt thereof, where X is O. In some embodiments, the compound is of the formula (I), or a salt thereof, where X is S. In some of these embodiments, $R^D$ is hydrogen. In some of these embodiments, $R^D$ is substituted or unsubstituted $C_1$-$C_6$ alkyl. In one variation, X is O and $R^D$ is hydrogen. In another variation, X is S and $R^D$ is hydrogen. In another variation, X is O and $R^D$ is unsubstituted $C_1$-$C_6$ alkyl (e.g., methyl). In some of these embodiments, D is hydrogen. In some of these embodiments, D is substituted or unsubstituted $C_1$-$C_6$ alkyl. In some of these embodiments, D is substituted or unsubstituted aryl, substituted or unsubstituted heteroaryl, substituted or unsubstituted $C_3$-$C_8$ cycloalkyl, or substituted or unsubstituted heterocyclyl. In some of these embodiments, D and $R^D$ are independently H or substituted or unsubstituted $C_1$-$C_6$ alkyl (e.g., methyl). In some of these embodiments, D and $R^D$ are taken together with the nitrogen to which they are attached to form a substituted or unsubstituted heterocyclyl (e.g., 3-methylazetidin-1-yl, 3-aminoazetidin-1-yl, morpholin-4-yl, and piperidin-1-yl).

In some embodiments, the compound is of the formula (I), or a salt thereof, where D is substituted or unsubstituted aryl, substituted or unsubstituted heteroaryl, substituted or unsubstituted $C_3$-$C_8$ cycloalkyl, or substituted or unsubstituted heterocyclyl. In some of these embodiments, D is substituted or unsubstituted aryl (e.g., phenyl). In some of these embodiments, D is substituted or unsubstituted $C_3$-$C_8$ cycloalkyl. In some of these embodiments, D is substituted or unsubstituted heterocyclyl, such as substituted or unsubstituted pyrrolidin-3-yl, piperidin-4-yl or piperidin-3-yl (e.g., 1-(isopropyl)piperidin-3-yl and 1-(2-amino-2-methylpropanoyl)piperidin-3-yl). In some of these embodiments, D is substituted or unsubstituted heteroaryl. In some variations, D is a substituted or unsubstituted 5-membered heteroaryl, such as substituted or unsubstituted thiazolyl (e.g., thiazole-2-yl and 5-chlorothiazol-2-yl) or substituted or unsubstituted thiadiazolyl (e.g., 1,2,4-thiadiazol-5-yl). In some variations, D is a substituted or unsubstituted 6-membered heteroaryl which contains at least one annular nitrogen atom. In some variations, D is a 6-membered heteroaryl containing one annular nitrogen atom. In some variations, D is a substituted pyridyl, such as a halo-substituted pyridyl (e.g., 6-fluoro-3-pyridyl). In some variations, D is an unsubstituted pyridyl (e.g., 3-pyridyl). In some variations, D is a 6-membered heteroaryl containing two annular nitrogen atoms. In some variations, D is a substituted or unsubstituted pyrimidyl (e.g., pyrimid-5-yl). In some variations, D is a substituted or unsubstituted pyrazinyl (e.g., pyrazin-2-yl).

In some embodiments, the compound is of the formula (I), or a salt thereof, where D is substituted or unsubstituted $C_1$-$C_6$ alkyl. In some of these embodiments, D is unsubstituted $C_1$-$C_6$ alkyl (e.g., methyl). In some of these embodiments, D is substituted $C_1$-$C_6$ alkyl. In some variations, D is $C_1$-$C_6$ alkyl (e.g., methyl) substituted with substituted or unsubstituted aryl, substituted or unsubstituted heteroaryl, substituted or unsubstituted $C_3$-$C_8$ cycloalkyl, or substituted or unsubstituted heterocyclyl. In some variations D is $C_1$-$C_6$ alkyl (e.g., methyl) substituted with substituted or unsubstituted heteroaryl, such as substituted or unsubstituted oxazolyl (e.g., oxazol-2-yl), substituted or unsubstituted pyrazolyl (e.g., pyrazol-5-yl or 1-methylpyrazol-5-yl), substituted or unsubstituted furanyl (e.g., furan-2-yl), or substituted or unsubstituted thiazolyl (e.g., thiazol-2-yl).

It is intended and understood that each and every variation of X, $R^D$ and D described for the formula (I) may be combined with each and every variation of j, k, $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ where present, and/or each and every variation of m, n, $R^Z$, $R^{Z1}$, $R^{Z2}$, $R^{Z3}$, $R^{Z4}$, $R^{Z5}$, $R^{Z6}$, $R^{Z7}$ and $R^{Z8}$, where present, described for the formula (I) as if each and every combinations individually described. For example, in some embodiments, provided is a compound of the formula (I), or a salt thereof, where each j and k is 0, $R^{A1}$, $R^{A2}$, $R^{A3}$, $R^{A4}$, $R^{A5}$ and $R^{A6}$ are as described herein, m is 1, n is 0, and $R^Z$, $R^{Z1}$, $R^{Z2}$, $R^{Z3}$, $R^{Z4}$, $R^{Z5}$ and $R^{Z6}$ are as described herein, X is O, $R^D$ is hydrogen, and D is as described herein. In one variation, j and k are each 0, $R^{A1}$, $R^{A2}$, $R^{A3}$, $R^{A4}$, $R^{A5}$ and $R^{A6}$ are each hydrogen, m is 1, n is 0, $R^Z$, $R^{Z1}$, $R^{Z2}$, $R^{Z3}$, $R^{Z4}$, $R^{Z5}$ and $R^{Z6}$ are each hydrogen, X is O, $R^D$ is hydrogen, and D is substituted pyridyl, such as a halo-substituted pyridyl (e.g., 6-fluoro-3-pyridyl).

In some embodiments, D is:

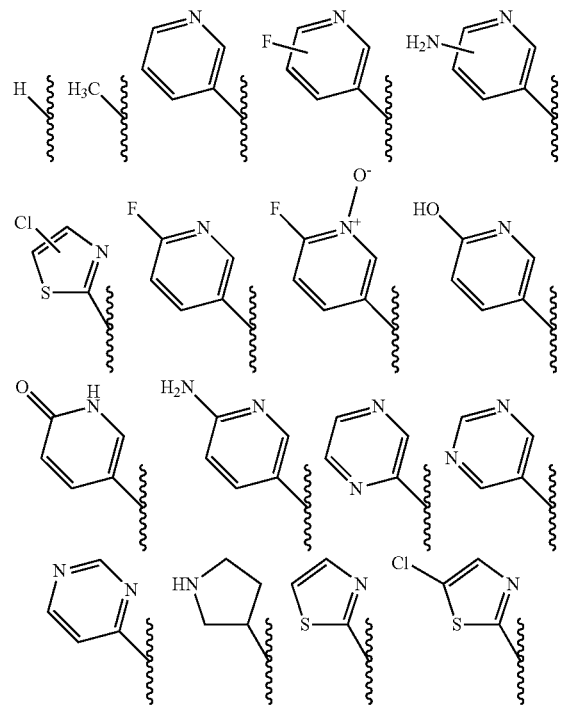

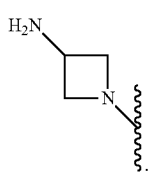

or taken together with $R^D$ and the nitrogen to which they are attached to form:

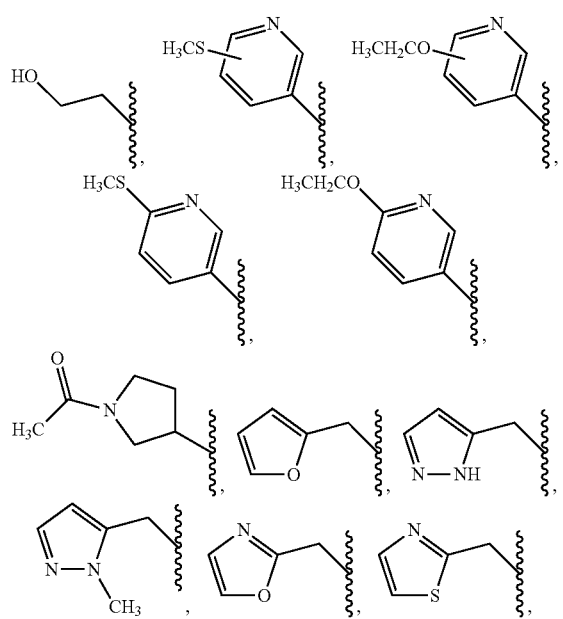

In some embodiments, D is:

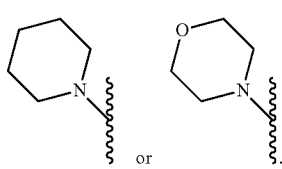 [SMILES: *N1CCCCC1 ; *N1CCOCC1]

or taken together with $R^D$ and the nitrogen to which they are attached to form:

In some embodiments, the compound is of the formula (I), or a salt thereof, where E is substituted or unsubstituted heteroaryl. In some of these embodiments, E is a substituted or unsubstituted 5-membered heteroaryl containing two annular nitrogen atoms. In some variations, E is substituted or unsubstituted pyrazolyl. In some variations, E is a 5-substituted pyrazol-3-yl, such as a 5-cycloalkyl-pyrazol-3-yl (e.g., 5-(cyclopropyl)pyrazol-3-yl, 5-(1-methylcyclopropyl)pyrazol-3-yl, 5-(1-hydroxycyclopropyl)pyrazol-3-yl and 5-cyclopentylpyrazol-3-yl), a 5-alkyl-pyrazol-3-yl (e.g., 5-(isopropyl)pyrazol-3-yl), or 5-carbamoylpyrazol-3-yl; or a 3-substituted pyrazol-5-yl, such as a 3-cycloalkyl-pyrazol-5-yl (e.g., 3-(cyclopropyl)pyrazol-5-yl, 3-(1-methylcyclopropyl)pyrazol-5-yl, 3-(1-hydroxycyclopropyl)pyrazol-5-yl and 3-cyclopentylpyrazol-5-yl), a 3-alkyl-pyrazol-5-yl (e.g., 3-(isopropyl)pyrazol-5-yl), or 3-carbamoylpyrazol-5-yl. In some variations, E is a 5-substituted pyrazol-3-yl, such as 5-hydroxypyrazol-3-yl, a 5-alkyl-pyrazol-3-yl (e.g. 5-(2-hydroxypropan-2-yl)pyrazol-3-yl or 5-(1-hydroxypropan-2-yl)pyrazol-3-yl) or a 5-cycloalkylpyrazol-3-yl (e.g. 5-(2-hydroxycyclopropyl)pyrazol-3-yl). In some variations, E is a 1- and 5-substituted pyrazol-3-yl (e.g. 1-hydroxy-5-isoproylpyrazol-3-yl). In some variations, E is a pyrazolyl oxide, such as a 5-alkyl-pyrazol-3-yl (e.g. 5-(isopropyl)pyrazol-3-yl 2-oxide). In some variations, E is substituted or unsubstituted imidazolyl, such as a substituted imidazol-4-yl (e.g., 1-(isopropyl)imidazol-4-yl and 2-(isopropyl)imidazol-4-yl) or a substituted imidazol-5-yl (e.g., 2-(isopropyl)imidazol-5-yl). In some variations, E is a substituted 5-membered heteroaryl which contains one annular nitrogen atom and one annular oxygen atom. In some variations, E is a substituted or unsubstituted oxazolyl (e.g., 5-carbamoyloxzazol-2-yl) or a substituted or unsubstituted isoxazolyl (e.g., 3-(isopropyl)isoxazol-5-yl). In some variations, E is a substituted 5-membered heteroaryl which contains one annular nitrogen atom and one annular sulfur atom. In some variations, E is a substituted or unsubstituted thiazolyl (e.g., 5-carbamoylthiazol-2-yl).

In some embodiments, E is:

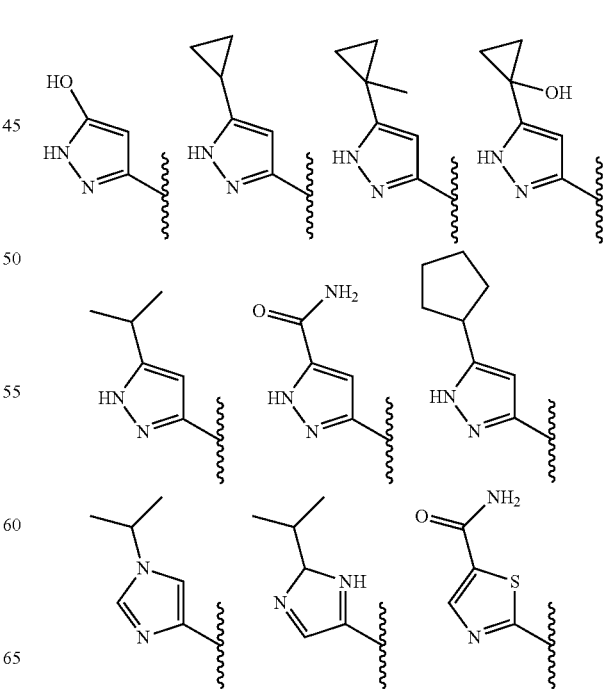

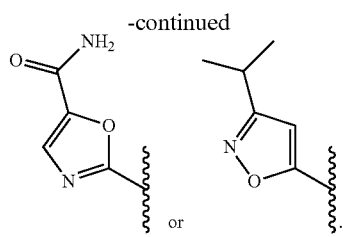

or

In some embodiments, E is:

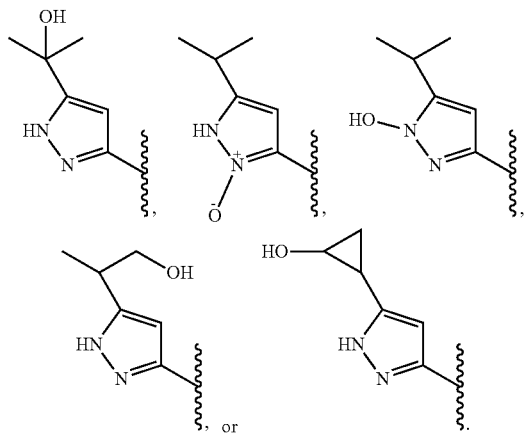

, or

.

It is intended and understood that each and every variation of E described for the formula (I) may be combined with each and every variation of j, k, $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ where present, and/or each and every variation of m, n, $R^Z$, $R^{Z1}$, $R^{Z2}$, $R^{Z3}$, $R^{Z4}$, $R^{Z5}$, $R^{Z6}$, $R^{Z7}$ and $R^{Z8}$, where present, and/or each and every variation of X, $R^D$ and D described for the formula (I) as if each and every combination is individually described. For example, in some embodiments, provided is a compound of the formula (I), or a salt thereof, where each j and k is 0, $R^{A1}$, $R^{A2}$, $R^{A3}$, $R^{A4}$, $R^{A5}$ and $R^{A6}$ are as described herein, m is 1, n is 0, and $R^Z$, $R^{Z1}$, $R^{Z2}$, $R^{Z3}$, $R^{Z4}$, $R^{Z5}$ and $R^{Z6}$ are as described herein, X is O, $R^D$ is hydrogen, and D is as described herein. In one variation, j and k are each 0, $R^{A1}$, $R^{A2}$, $R^{A3}$, $R^{A4}$, $R^{A5}$ and $R^{A6}$ are each hydrogen, m is 1, n is 0, $R^Z$, $R^{Z1}$, $R^{Z2}$, $R^{Z3}$, $R^{Z4}$, $R^{Z5}$ and $R^{Z6}$ are each hydrogen, X is O, $R^D$ is hydrogen, D is substituted pyridyl, such as a halo-substituted pyridyl (e.g., 6-fluoro-3-pyridyl), and E is substituted pyrazolyl (e.g., 5-(cyclopropyl)pyrazol-3-yl or 5-(isopropyl)pyrazol-3-yl).

In one embodiment, provided is a compound of the formula (I-A):

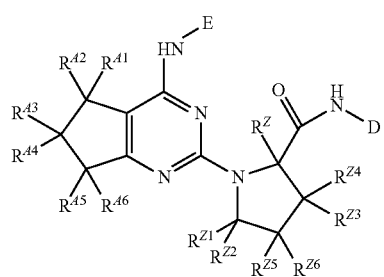

(I-A)

or a salt thereof, where D, E, $R^{A1}$, $R^{A2}$, $R^{A3}$, $R^{A4}$, $R^{A5}$, $R^{A6}$, $R^Z$, $R^{Z1}$, $R^{Z2}$, $R^{Z3}$, $R^{Z4}$, $R^{Z5}$, $R^{Z6}$, p, $R^1$, $R^2$, $R^3$, $R^4$, $R^5$, $R^6$, $R^7$, $R^8$, and $R^9$ are as described for the formula (I), or any variation thereof. It is intended and understood that each and every variation of D, E, $R^{A1}$, $R^{A2}$, $R^{A3}$, $R^{A4}$, $R^{A5}$, $R^{A6}$, $R^Z$, $R^{Z1}$, $R^{Z2}$, $R^{Z3}$, $R^{Z4}$, $R^{Z5}$ and $R^{Z6}$, and each and every combination thereof described herein for the formula (I) apply to the formula (I-A) as if each and every variation and combination are individually described. For example, in some embodiments, provided is a compound of the formula (I-A), or a salt thereof, where each of $R^{A1}$, $R^{A2}$, $R^{A3}$, $R^{A4}$, $R^{A5}$ and $R^{A6}$ is independently hydrogen, substituted or unsubstituted $C_1$-$C_6$ alkyl, halo, substituted or unsubstituted $C_3$-$C_8$ cycloalkyl or is taken together with a geminal $R^{A(1-6)}$ group and the carbon to which they are attached to form a carbonyl group, $R^Z$ is hydrogen or $C_1$-$C_6$ alkyl (e.g., methyl), each of $R^{Z1}$, $R^{Z2}$, $R^{Z3}$ and $R^{Z4}$ is hydrogen, $R^{Z5}$ and $R^{Z6}$ are independently hydrogen, hydroxyl or —$OR^1$, D is substituted or unsubstituted pyridyl, substituted or unsubstituted pyrimidyl, or substituted or unsubstituted pyrazinyl (e.g., 6-fluoro-3-pyridyl, 3-pyridyl, pyrimid-5-yl and pyrazin-2-yl), and E is substituted or unsubstituted pyrazolyl, substituted or unsubstituted isoxazolyl, or substituted or unsubstituted imidazolyl (e.g., 5-cyclopropylpyrazol-3-yl, 5-cyclopentylpyrazol-3-yl, 5-(isopropyl)pyrazol-3-yl, 3-cyclopropylpyrazol-5-yl, 3-cyclopentylpyrazol-5-yl, 3-(isopropyl)pyrazol-5-yl, and 3-(isopropyl)isoxazol-5-yl). In one variation, $R^{A1}$, $R^{A2}$, $R^{A3}$, $R^{A4}$, $R^{A5}$, $R^{A6}$, $R^Z$, $R^{Z1}$, $R^{Z2}$, $R^{Z3}$, $R^{Z4}$, $R^{Z5}$ and $R^{Z6}$ are each hydrogen, D is substituted pyridyl, such as a halo-substituted pyridyl (e.g., 6-fluoro-3-pyridyl), and E is substituted pyrazolyl (e.g., 5-(cyclopropyl)pyrazol-3-yl or 5-(isopropyl)pyrazol-3-yl).

In some embodiments, provided are compounds of the formulae (IIa), (IIb), (IIc), (IId), (IIe), (IIf), (IIg), (IIh), (IIi), (IIj), (IIk), (IIl), (IIm), (IIn), (IIo), (IIp), (IIq), (IIr), (IIs), (IIt), (IIu), (IIv) and (IIw):

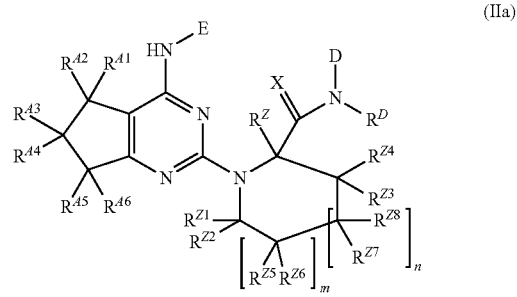

(IIa)

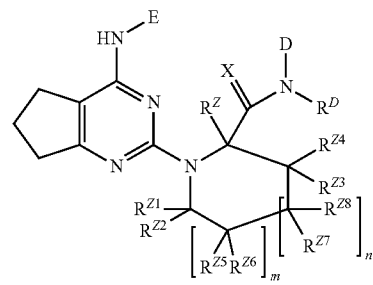

(IIb)

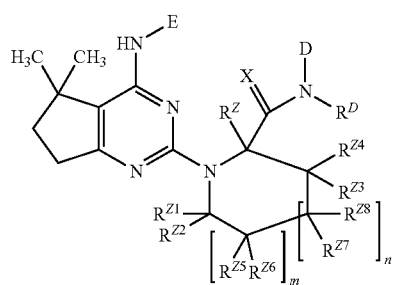
(IIc)
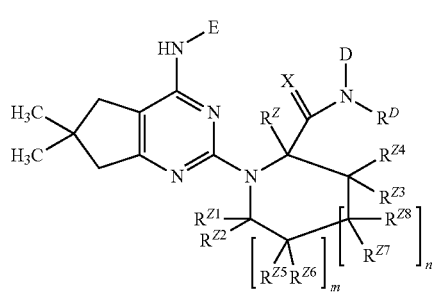
(IId)
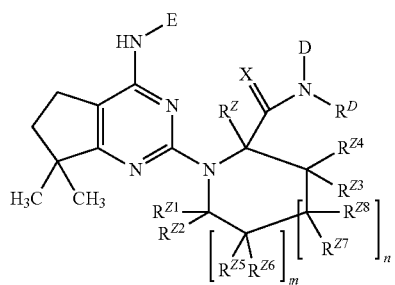
(IIe)
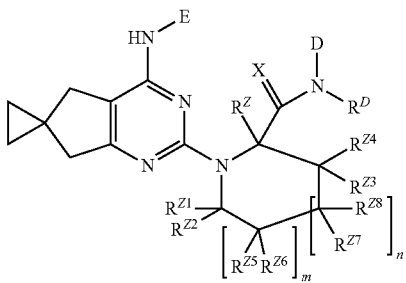
(IIf)
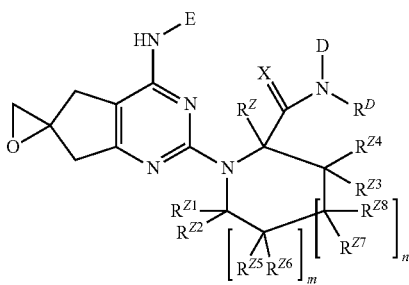
(IIg)
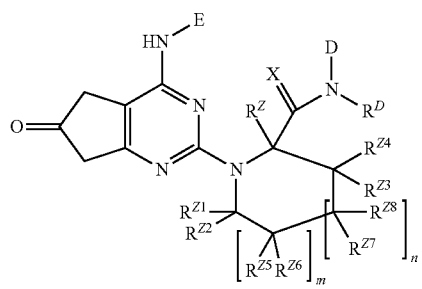
(IIh)
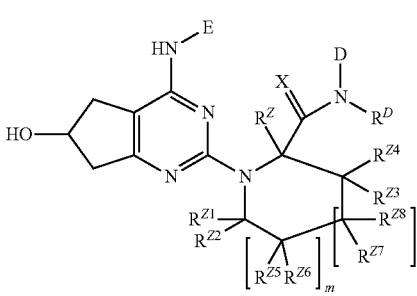
(IIi)
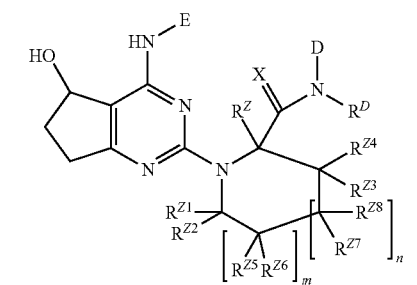
(IIj)
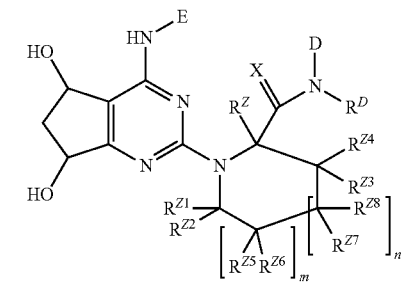
(IIk)
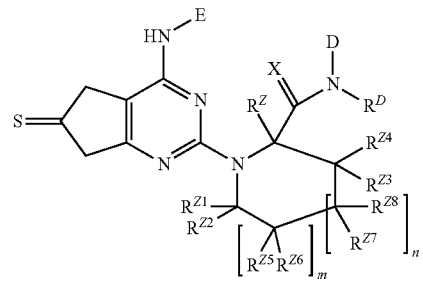
(IIl)

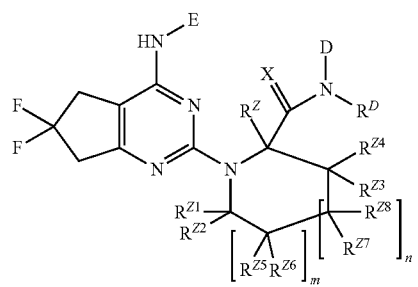 (IIm)
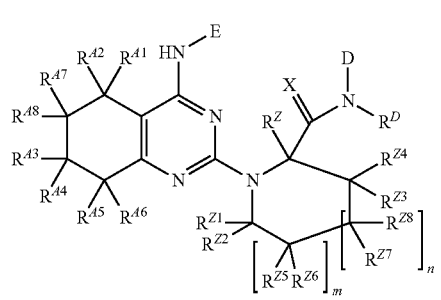 (IIn)
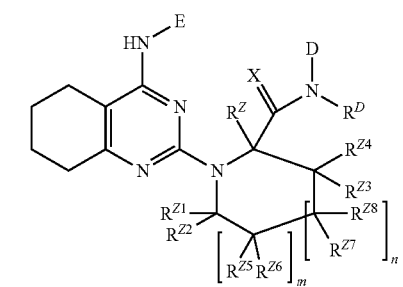 (IIo)
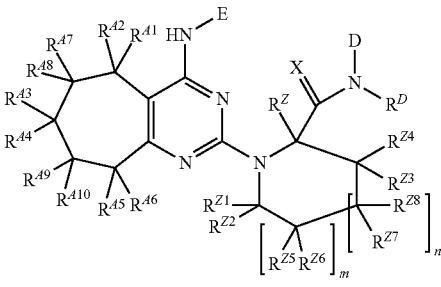 (IIp)
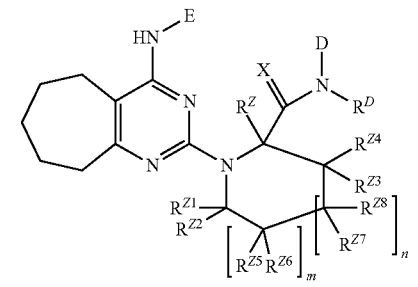 (IIq)
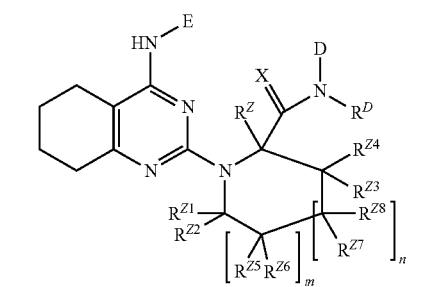 (IIr)
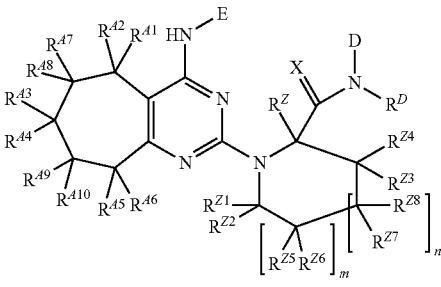 (IIs)
(IIt)
(IIu)
(IIv)

-continued

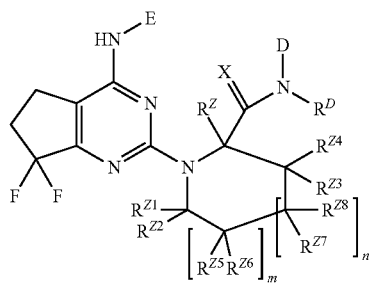
(IIw)

or a salt thereof, where in each of (IIa), (IIb), (IIc), (IId), (IIe), (IIf), (IIg), (IIh), (IIi), (IIj), (IIk), (IIl), (IIm), (IIn), (IIo), (IIp), (IIq), (IIr), (IIs), (IIt), (IIu), (IIv) and (IIw), the substituents D, E, m, n, $R^{A1}$, $R^{A2}$, $R^{A3}$, $R^{A4}$, $R^{A5}$, $R^{A6}$, $R^D$, $R^Z$, X, $R^{Z1}$, $R^{Z2}$, $R^{Z3}$, $R^{Z4}$, $R^{Z5}$, $R^{Z6}$, $R^{Z7}$ $R^{Z8}$, p, $R^1$, $R^2$, $R^3$, $R^4$, $R^5$, $R^6$, $R^7$, $R^8$, and $R^9$ are as described for Formula (I) or any applicable variation thereof. In some variations, X is O and $R^D$ is hydrogen.

In some embodiments, provided are compounds of the formula (IIIa), (IIIb), (IIIc), (IIId), (IIIe), (IIIf), (IIIg), (IIIh), (IIIi), (IIIj), (IIIk), (IIIl), (IIIm), (IIIn), (IIIo), (IIIp), (IIIq), (IIIr), (IIIs), (IIIt), (IIIu), (IIIv) and (IIIw):

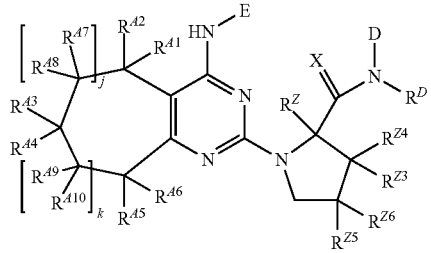
(IIIa)

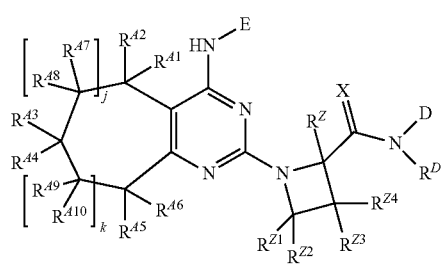
(IIIb)

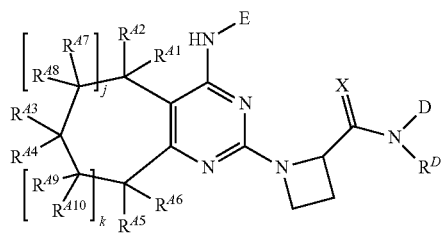
(IIIc)

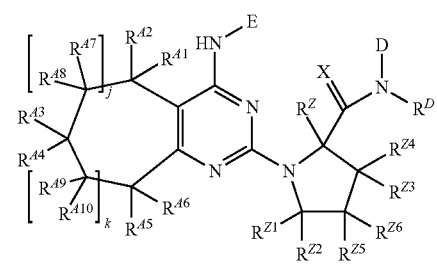
(IIId)

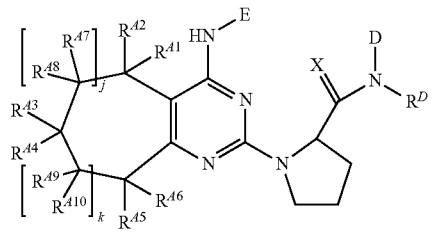
(IIIe)

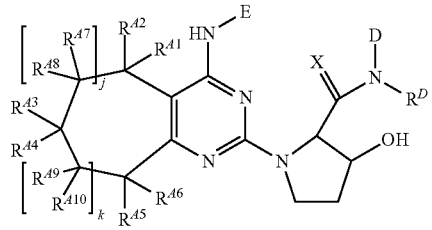
(IIIf)

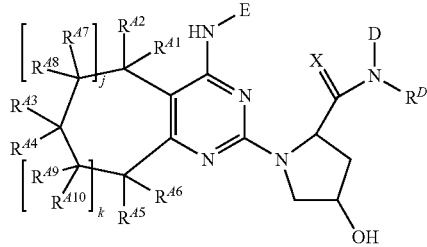
(IIIg)

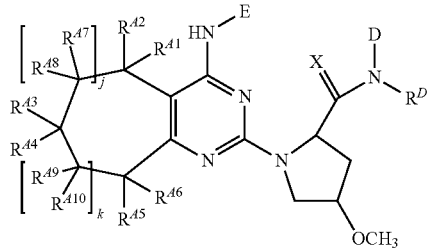
(IIIh)

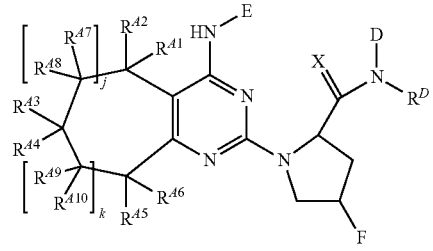
(IIIi)

(IIIj)
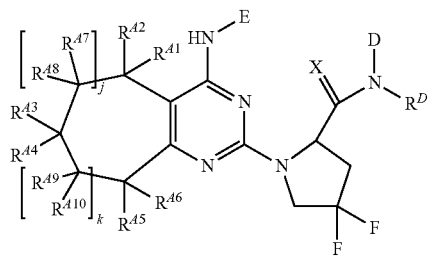
(IIIk)
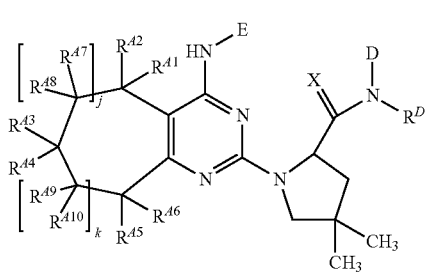
(IIIl)
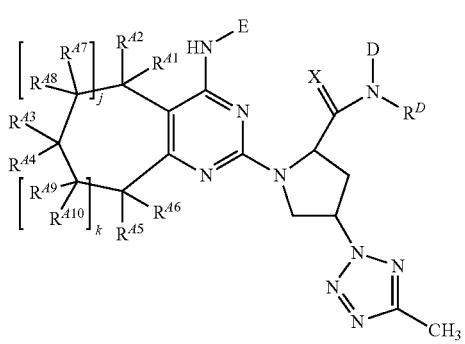
(IIIm)
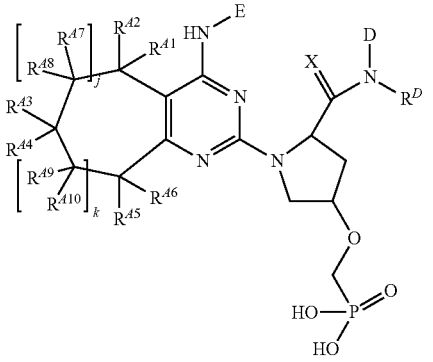
(IIIn)
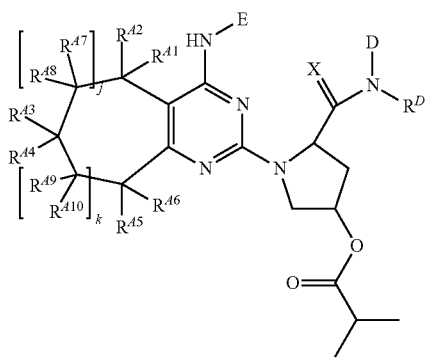
(IIIo)
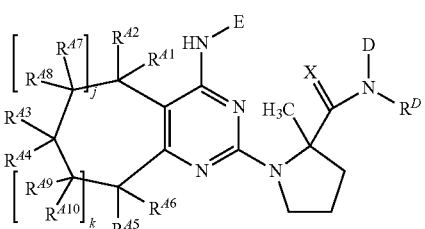
(IIIp)
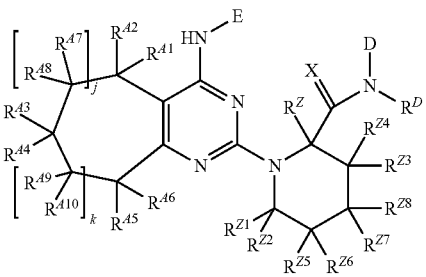
(IIIq)
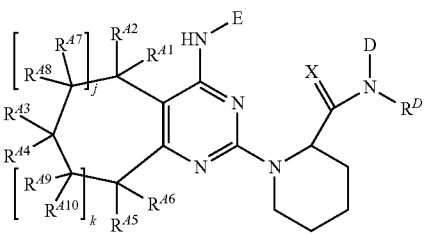
(IIIr)
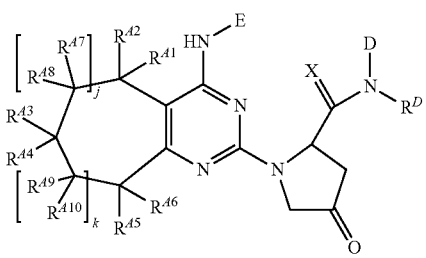
(IIIs)
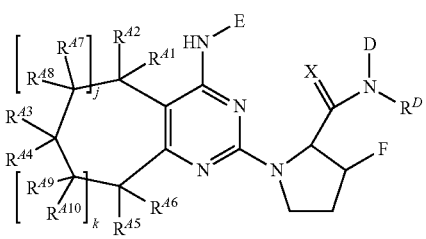
(IIIt)
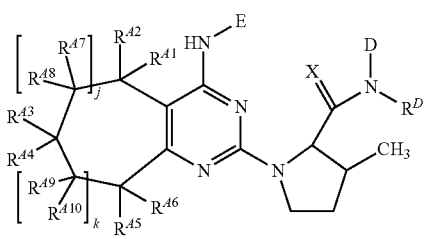

-continued

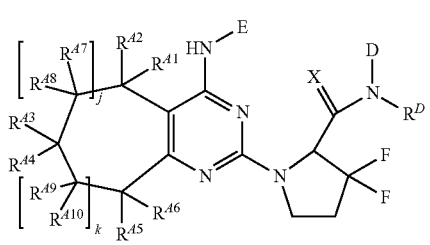
(IIIu)

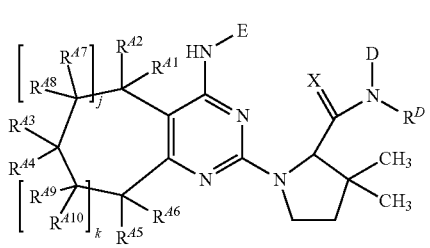
(IIIv)

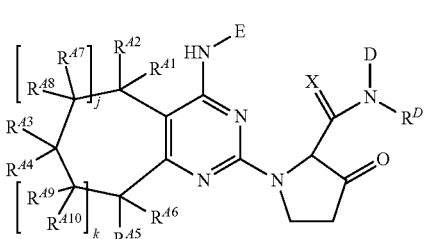
(IIIw)

or a salt thereof, where in each of (IIIa), (IIIb), (IIIc), (IIId), (IIIe), (IIIf), (IIIg), (IIIh), (IIIi), (IIIj), (IIIk), (IIIl), (IIIm), (IIIn), (IIIo), (IIIp), (IIIq), (IIIr), (IIIs), (IIIt), (IIIu), (IIIv) and (IIIw), the substituents D, E, j, k, $R^{A1}$, $R^{A2}$, $R^{A3}$, $R^{A4}$, $R^{A5}$, $R^{A6}$, $R^D$, $R^Z$, X, $R^{Z1}$, $R^{Z2}$, $R^{Z3}$, $R^{Z4}$, $R^{Z5}$, $R^{Z6}$, p, $R^1$, $R^2$, $R^3$, $R^4$, $R^5$, $R^6$, $R^7$, $R^8$, and $R^9$ are as described for Formula (I) or any applicable variation thereof. In some variations, X is O and $R^D$ is hydrogen.

In some embodiments, provided are compounds of the formula (IVa), (IVa'), (IVb), (IVb'), (IVc), (IVc'), (IVd), (IVd'), (IVe), (IVe'), (IVf), (IVf'), (IVf''), (IVf'''), (IVg), (IVg'), (IVg''), (IVg'''), (IVh), (IVh'), (IVh''), (IVh'''), (IVi), (IVi'), (IVi''), (IVi'''), (IVj), (IVj'), (IVk), (IVk'), (IVl), (IVl'), (IVl''), (IVl'''), (IVm), (IVm'), (IVm''), (IVm'''), (IVn), (IVn'), (IVn''), (IVn'''), (IVo), (IVo'), (IVp), (IVp'), (IVq), (IVq'), (IVr), (IVr'), (IVs), (IVs'), (IVs''), (IVs'''), (IVt), (IVt'), (IVt''), (IVt'''), (IVu), (IVu'), (IVv), (IVv'), (IVw), and (IVw'):

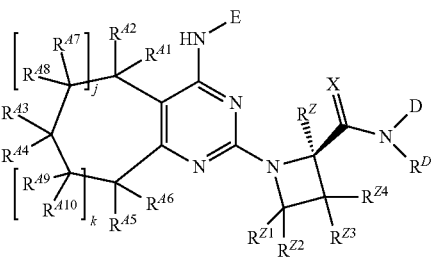
(IVa)

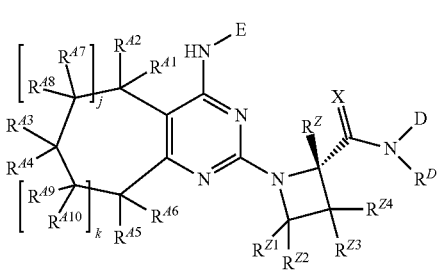
(IVa')

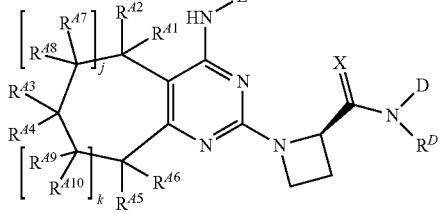
(IVb)

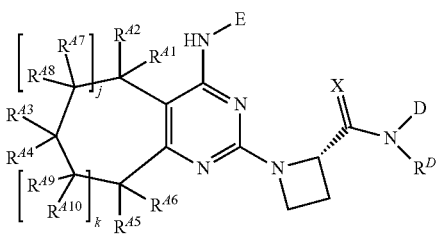
(IVb')

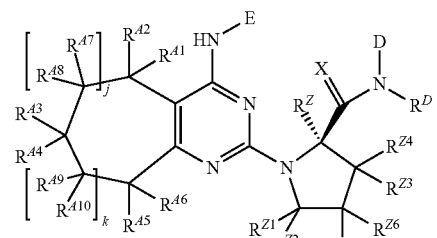
(IVc)

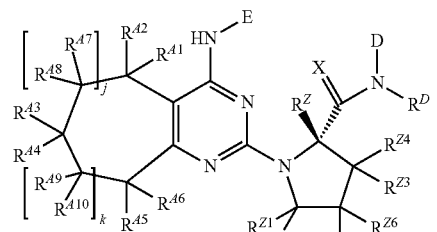
(IVc')

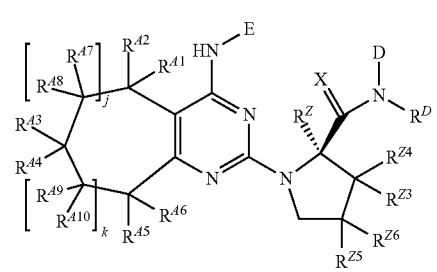
(IVd)

(IVd')
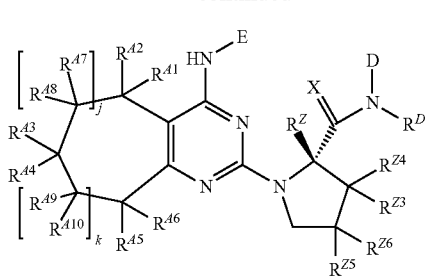
(IVe)
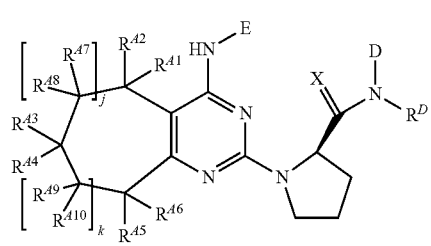
(IVe')
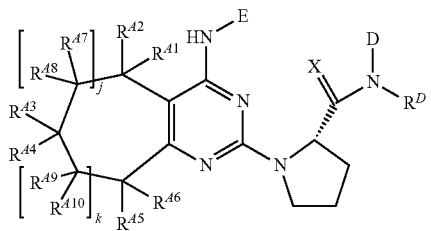
(IVf)
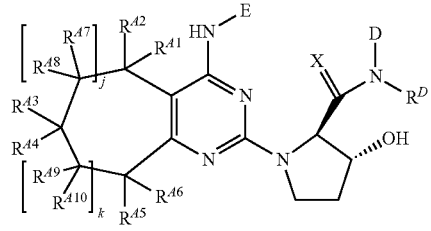
(IVf')
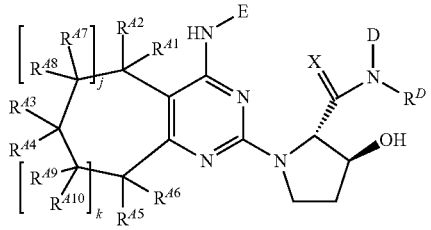
(IVf'')
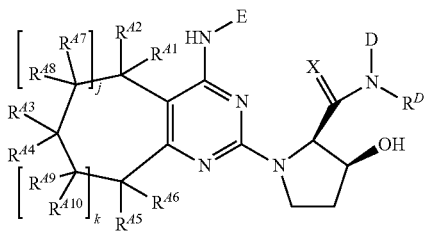
(IVf''')
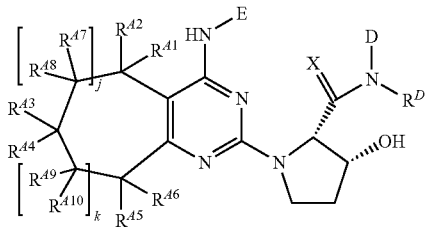
(IVg)
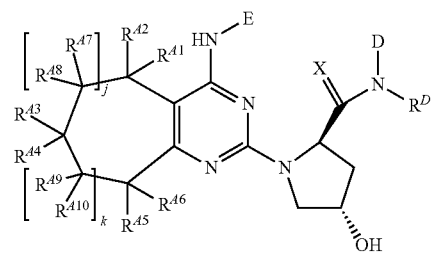
(IVg')
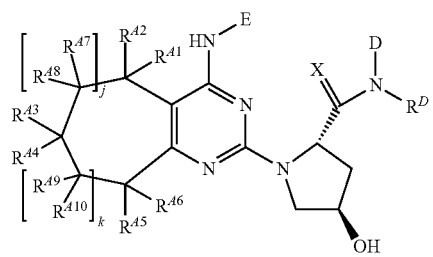
(IVg'')
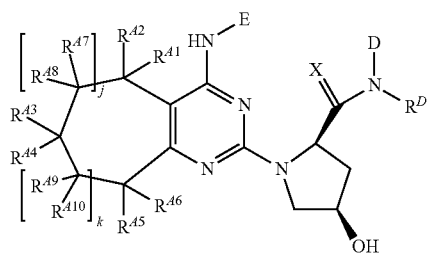
(IVg''')
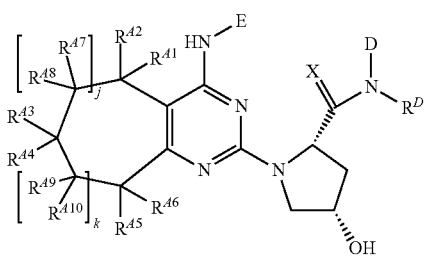
(IVh)
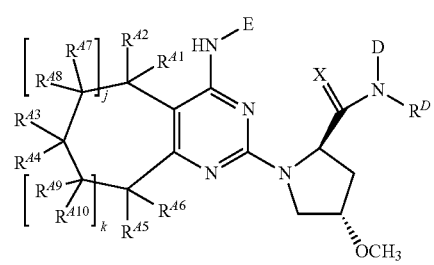

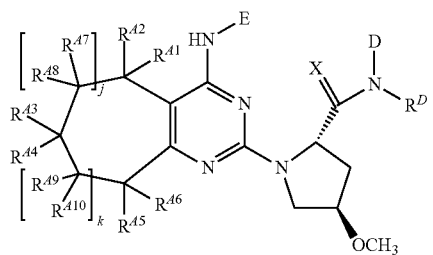
(IVh′)
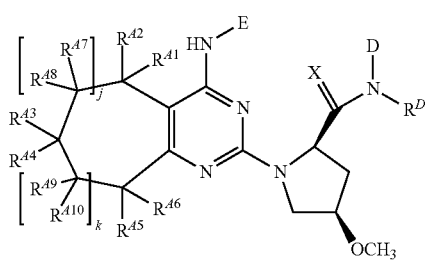
(IVh″)
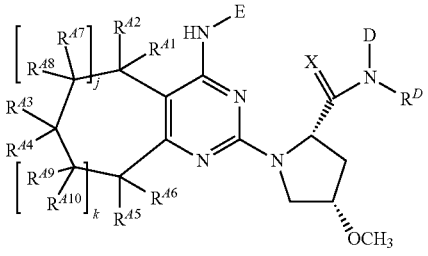
(IVh‴)
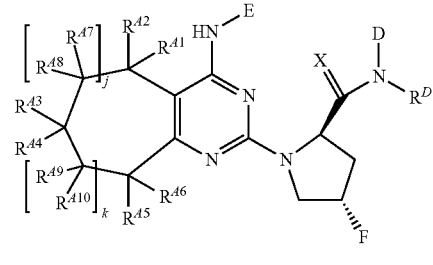
(IVi)
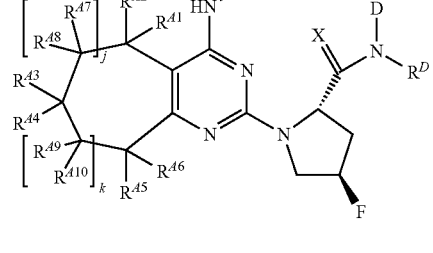
(IVi′)
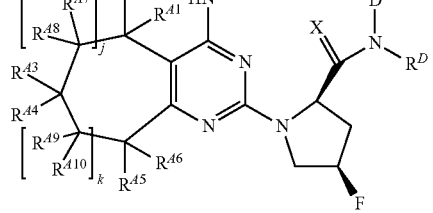
(IVi″)
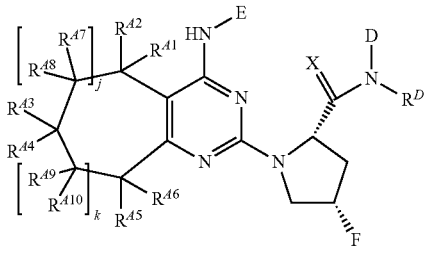
(IVi‴)
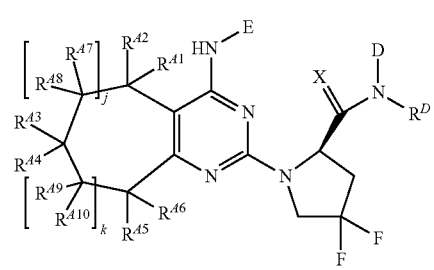
(IVj)
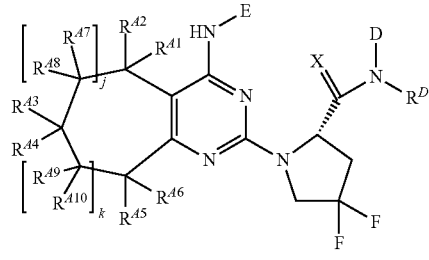
(IVj′)
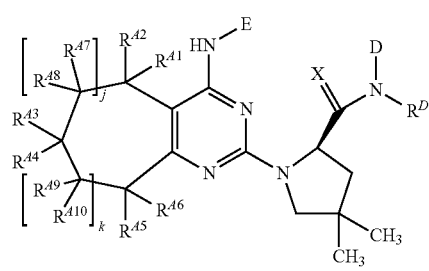
(IVk)
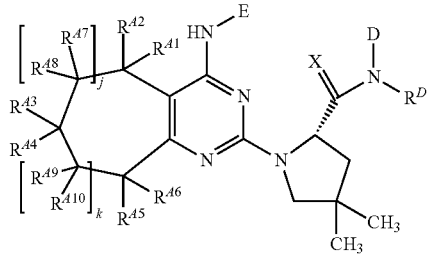
(IVk′)
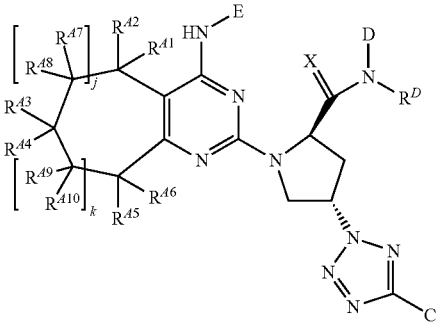
(IVl)

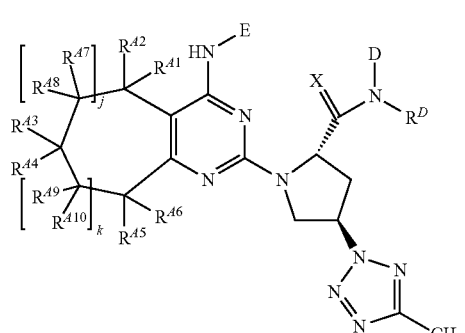 (IVl')
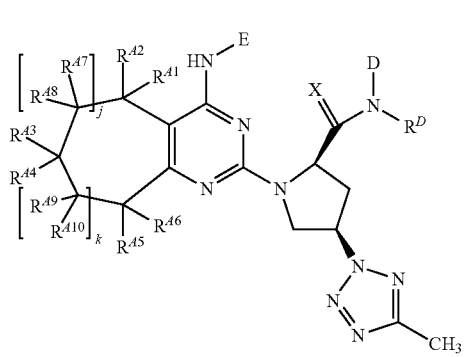 (IVl'')
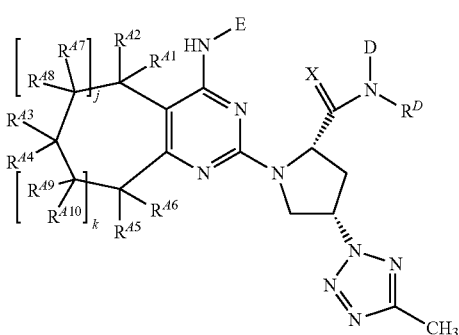 (IVl''')
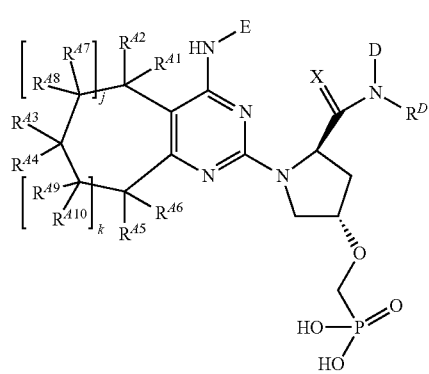 (IVm)
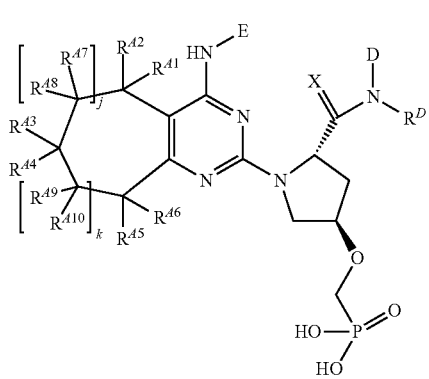 (IVm')
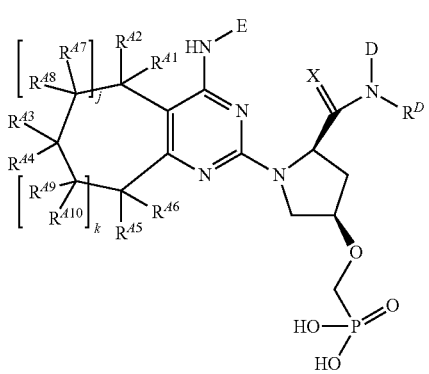 (IVm'')
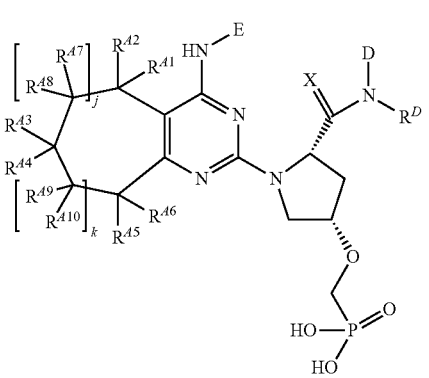 (IVm''')
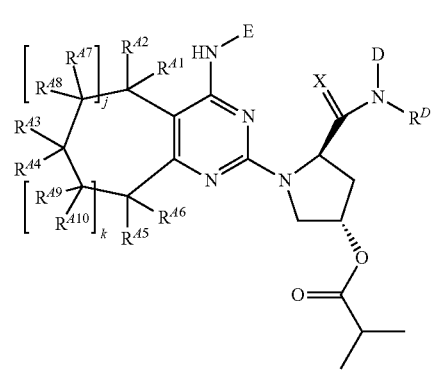 (IVn)

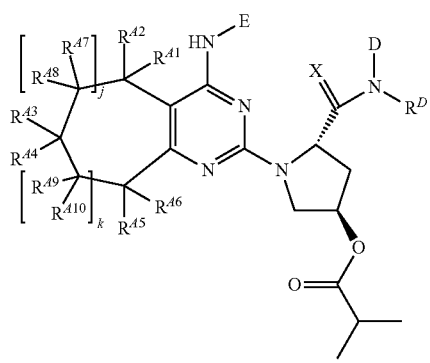
(IVn')
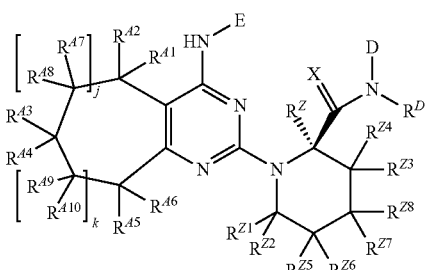
(IVp)
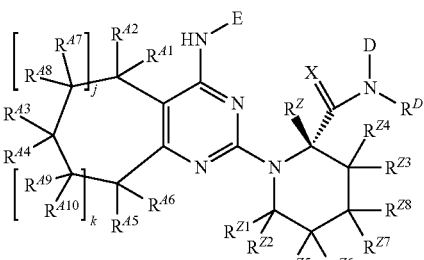
(IVp')
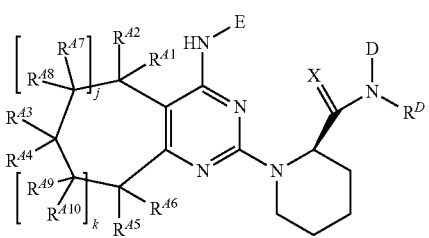
(IVq)
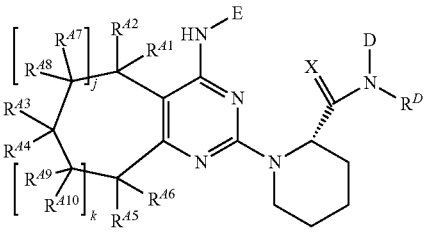
(IVq')
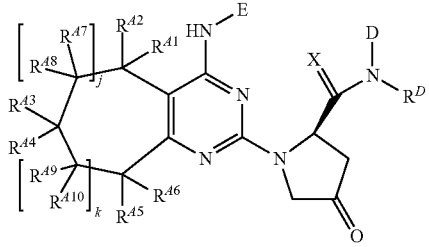
(IVr)
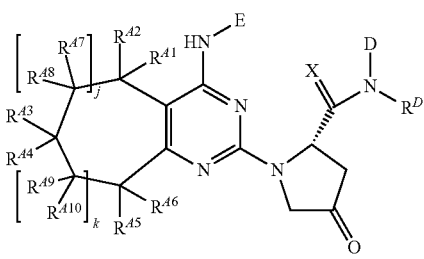
(IVr')

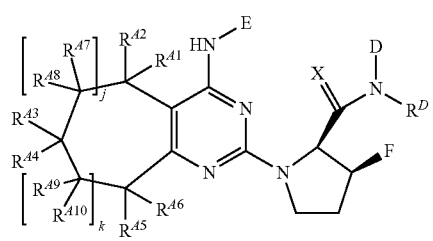 (IVs)
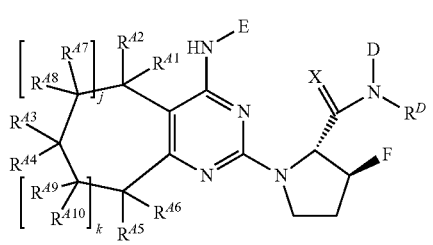 (IVs')
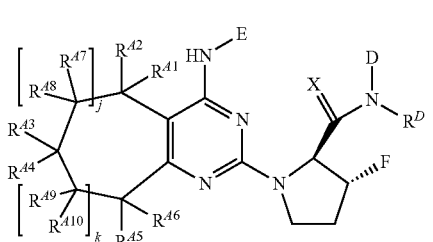 (IVs")
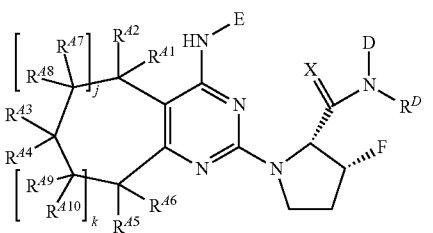 (IVs''')
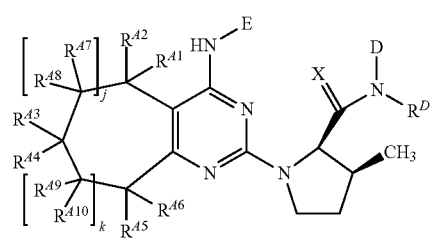 (IVt)
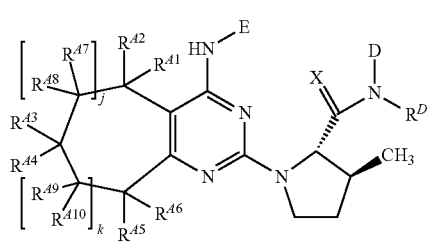 (IVt')
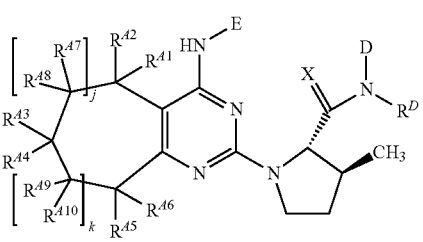 (IVt")
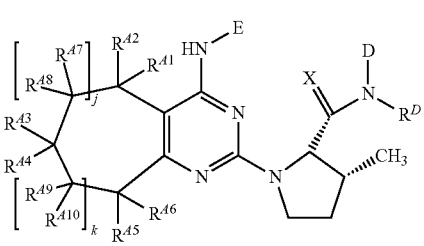 (IVt''')
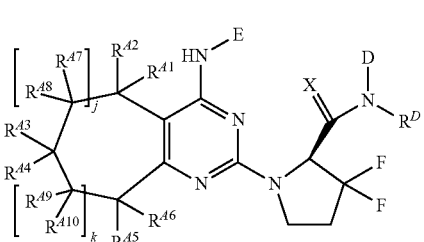 (IVu)
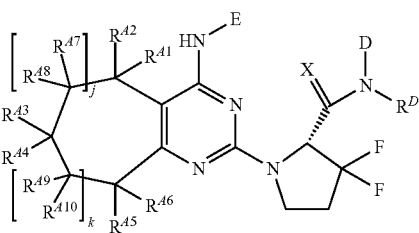 (IVu')
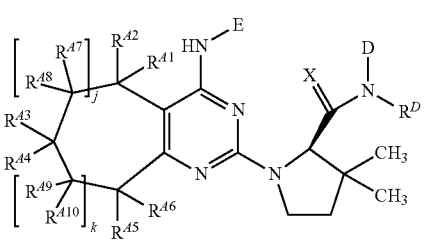 (IVv)
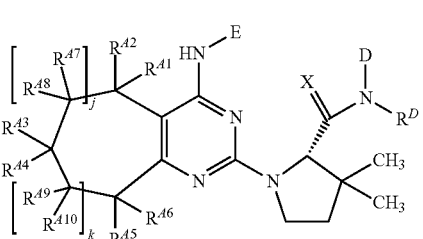 (IVv')

-continued

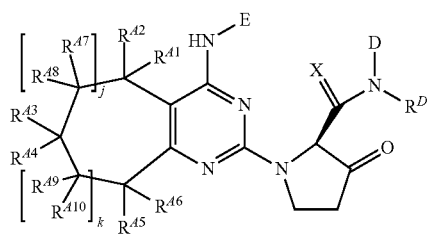
(IVw)

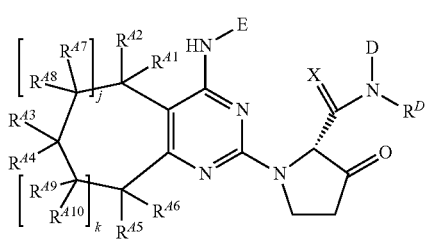
(IVw')

or a salt thereof, where in each of (IVa), (IVa'), (IVb), (IVb'), (IVc), (IVc'), (IVd), (IVd'), (IVe), (IVe'), (IVf), (IVf'), (IVf''), (IVf'''), (IVg), (IVg'), (IVg''), (IVg'''), (IVh), (IVh'), (IVh''), (IVh'''), (IVi), (IVi'), (IVi''), (IVi'''), (IVj), (IVj'), (IVk), (IVk'), (IVl), (IVl'), (IVl''), (IVl'''), (IVm), (IVm'), (IVm''), (IVm'''), (IVn), (IVn'), (IVn''), (IVn'''), (IVo), (IVo'), (IVp), (IVp'), (IVq), (IVq'), (IVr), (IVr'), (IVs), (IVs'), (IVs''), (IVs'''), (IVt), (IVt'), (IVt''), (IVt'''), (IVu), (IVu'), (IVv), (IVv'), (IVw), and (IVw'), the substituents D, E, j, k, $R^{A1}$, $R^{A2}$, $R^{A3}$, $R^{A4}$, $R^{A5}$, $R^{A6}$, $R^D$, $R^Z$, X, $R^{Z1}$, $R^{Z2}$, $R^{Z3}$, $R^{Z4}$, $R^{Z5}$, $R^{Z6}$, p, $R^1$, $R^2$, $R^3$, $R^4$, $R^5$, $R^6$, $R^7$, $R^8$, and $R^9$ are as described for Formula (I) or any applicable variation thereof. In some variations, X is O and $R^D$ is hydrogen.

In some embodiments, provided are compounds of the formula (Va), (Vb), (Vc), (Vd), (Ve), (Vf), (Vg), (Vh), (Vi), (Vj), (Vk), (Vl), (Vm), (Vn), (Vo), (Vp), (Vq), (Vr), (Vs), (Vt), (Vu), (Vv), (Vw), (Vx), (Vy), (Vz), (Vaa), (Vbb), (Vcc), (Vdd), (Vee), (Vff), (Vgg), and (Vhh):

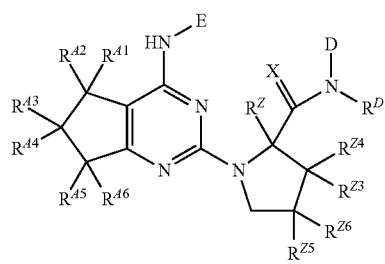
(Va)

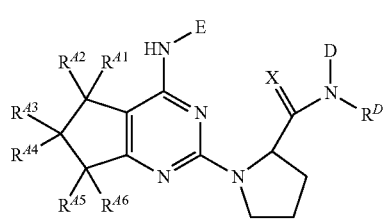
(Vb)

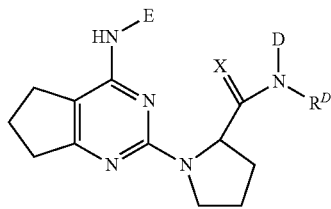
(Vc)

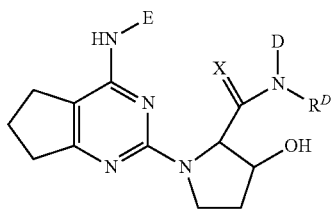
(Vd)

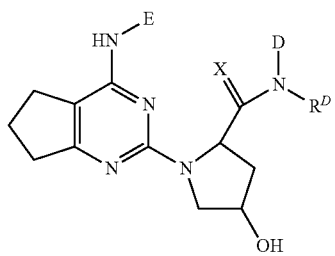
(Ve)

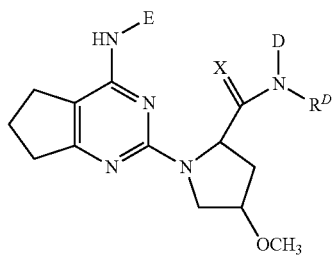
(Vf)

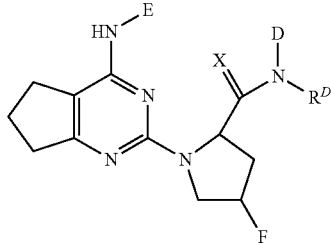
(Vg)

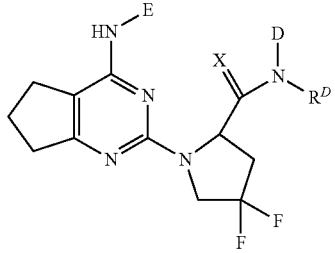
(Vh)

(Vi) 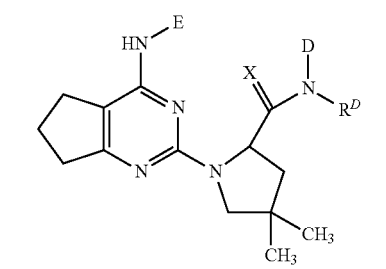
(Vj) 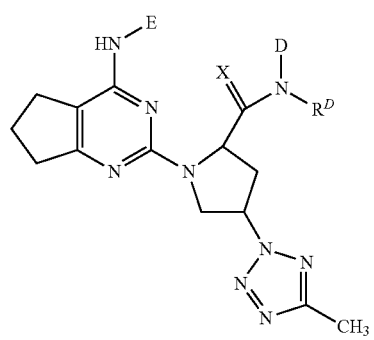
(Vk) 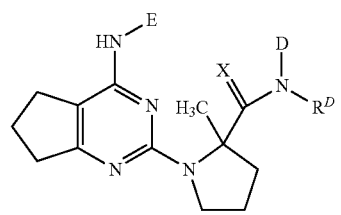
(Vl) 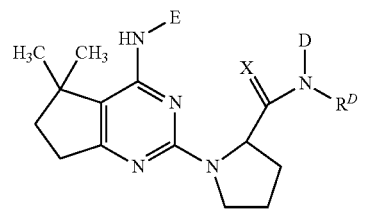
(Vm) 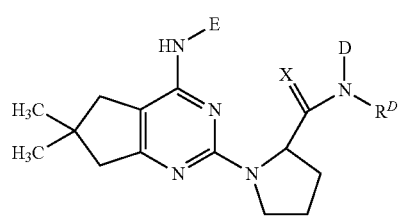
(Vn) 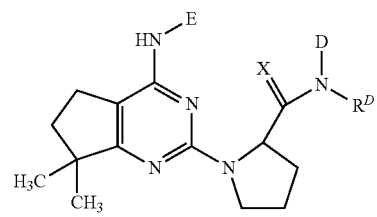
(Vo) 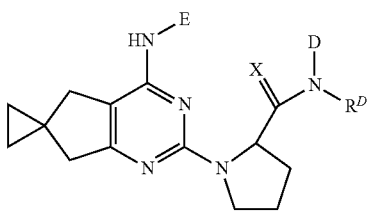
(Vp) 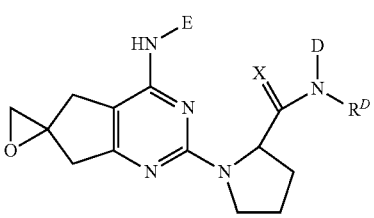
(Vq) 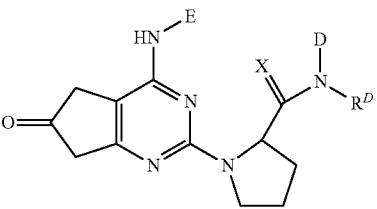
(Vr) 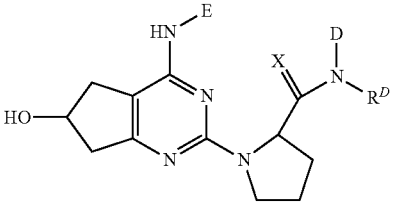
(Vs) 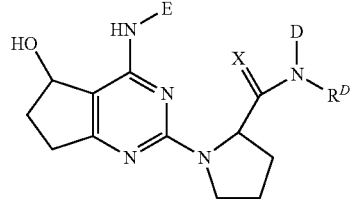
(Vt) 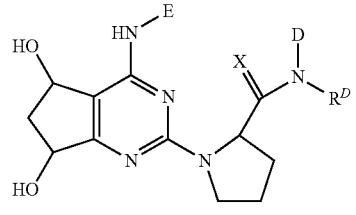
(Vu) 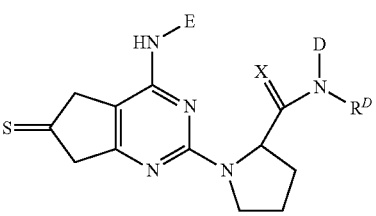

(Vv) 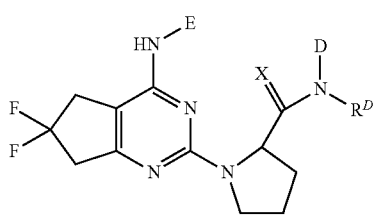
(Vw) 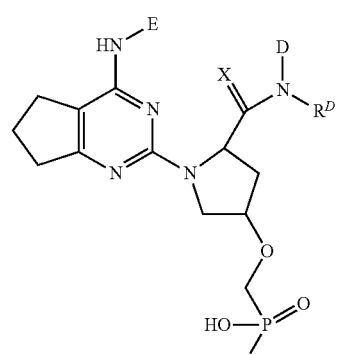
(Vx) 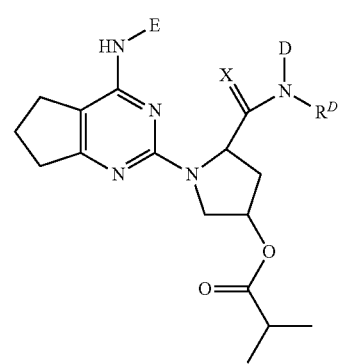
(Vy) 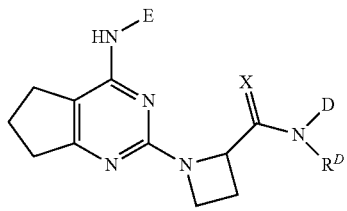
(Vz) 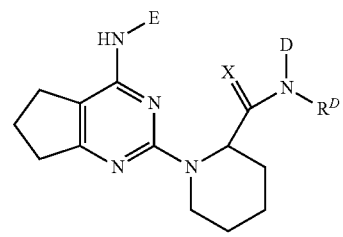
(Vaa) 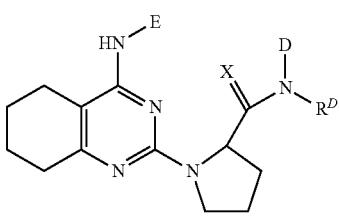
(Vbb) 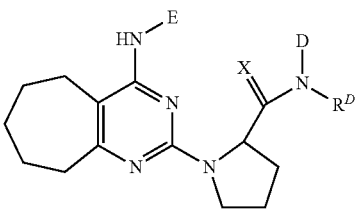
(Vcc) 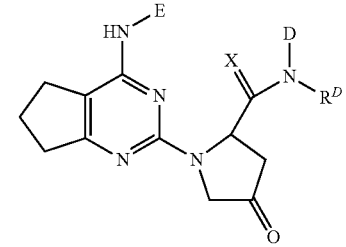
(Vdd) 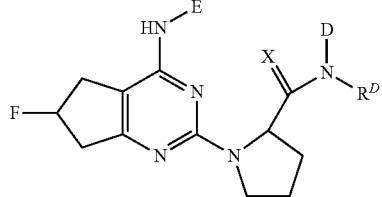
(Vee) 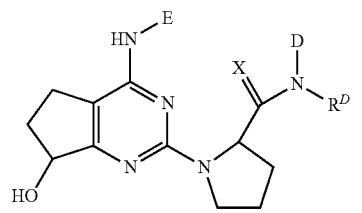
(Vff) 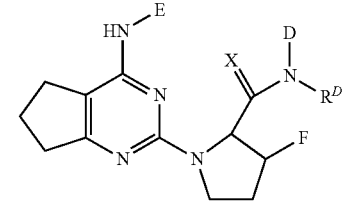
(Vgg) 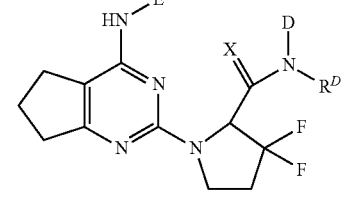
(Vhh) 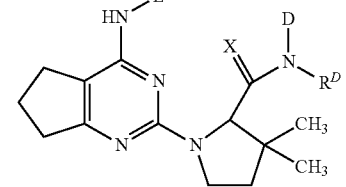
or a salt thereof, where in each of (Va), (Vb), (Vc), (Vd), (Ve), (Vf), (Vg), (Vh), (Vi), (Vj), (Vk), (Vl), (Vm), (Vn), (Vo), (Vp), (Vq), (Vr), (Vs), (Vt), (Vu), (Vv), (Vw), (Vx), (Vy), (Vz), (Vaa), (Vbb), (Vcc), (Vdd), (Vee), (Vff), (Vgg), and (Vhh), the substituents D, E, $R^{A1}$, $R^{A2}$, $R^{A3}$, $R^{A4}$, $R^{A5}$, $R^{A6}$, $R^D$, $R^Z$, X, $R^{Z3}$, $R^{Z4}$, $R^{Z5}$, $R^{Z6}$, p, $R^1$, $R^2$, $R^3$, $R^4$, $R^5$, $R^6$, $R^7$, $R^8$, and $R^9$ are as described for Formula (I) or any applicable variation thereof. In some variations, X is O and $R^D$ is hydrogen.

In another embodiment, provided is a compound of the formula (I-A):

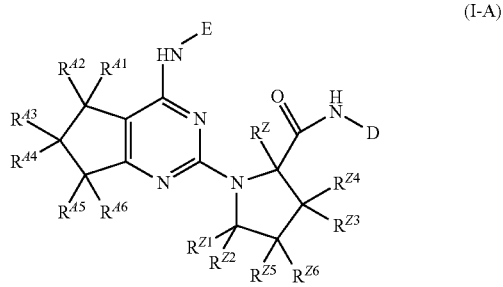

(I-A)

or a salt thereof, where D, E, $R^{A1}$, $R^{A3}$, $R^{A5}$, $R^Z$, $R^{Z1}$, $R^{Z3}$, $R^{Z5}$, p, $R^1$, $R^2$, $R^3$, $R^4$, $R^5$, $R^6$, $R^7$, $R^8$, and $R^9$ are as described for the formula (I), or any applicable variation thereof, provided that one or more of $R^{A2}$, $R^{A4}$, $R^{A6}$, $R^{Z2}$, $R^{Z4}$ and $R^{Z6}$ is hydroxy. In one variation, one of $R^{A2}$, $R^{A4}$ and $R^{A6}$ is hydroxy and the remaining $R^{A2}$, $R^{A4}$, $R^{A6}$, $R^{Z2}$, $R^{Z4}$ and $R^{Z6}$ are other than hydroxy. In one variation, two of $R^{A2}$, $R^{A4}$ and $R^{A6}$ are hydroxy. In one variation, one of $R^{Z2}$, $R^{Z4}$ and $R^{Z6}$ is hydroxy and the remaining $R^{A2}$, $R^{A4}$, $R^{A6}$, $R^{Z2}$, $R^{Z4}$ and $R^{Z6}$ are other than hydroxy. In another variation, two of $R^{Z2}$, $R^{Z4}$ and $R^{Z6}$ are hydroxy. In another variation, at least one of $R^{A2}$, $R^{A4}$ and $R^{A6}$ is hydroxy and at least one of $R^{Z2}$, $R^{Z4}$ and $R^{Z6}$ is hydroxy. In another variation, one of $R^{A2}$, $R^{A4}$ and $R^{A6}$ is hydroxy and one of $R^{Z2}$, $R^{Z4}$ and $R^{Z6}$ is hydroxy.

For In another embodiment, provided is a compound of the formula (I-B):

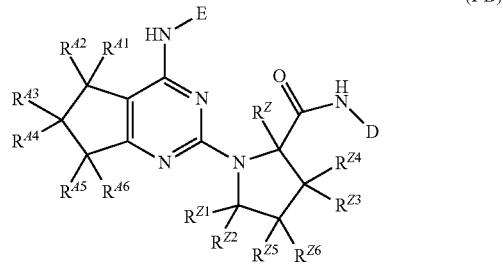

(I-B)

or a salt thereof, where D, E, $R^{A1}$, $R^{A3}$, $R^{A5}$, $R^Z$, $R^{Z1}$, $R^{Z3}$, $R^{Z5}$, p, $R^1$, $R^2$, $R^3$, $R^4$, $R^5$, $R^6$, $R^7$, $R^8$, and $R^9$ are as described for the formula (I), or any applicable variation thereof, provided that one or more of $R^{A2}$, $R^{A4}$, $R^{A6}$, $R^{Z2}$, $R^{Z4}$ and $R^{Z6}$ is hydroxy or —$OR^1$. In one such variation, one or more of $R^{A2}$, $R^{A4}$, $R^{A6}$, $R^{Z2}$, $R^{Z4}$ and $R^{Z6}$ is hydroxy or —$OR^1$ where $R^1$ is an unsubstituted $C_1$-$C_6$ alkyl. In one variation, one of $R^{A2}$, $R^{A4}$ and $R^{A6}$ is hydroxy or —$OR^1$ and the remaining $R^{A2}$, $R^{A4}$, $R^{A6}$, $R^{Z2}$, $R^{Z4}$ and $R^{Z6}$ are other than hydroxy or —$OR^1$. In one variation, two of $R^{A2}$, $R^{A4}$ and $R^{A6}$ are hydroxy or —$OR^1$. In one variation, one of $R^{Z2}$, $R^{Z4}$ and $R^{Z6}$ is hydroxy or —$OR^1$ and the remaining $R^{A2}$, $R^{A4}$, $R^{A6}$, $R^{Z2}$, $R^{Z4}$ and $R^{Z6}$ are other than hydroxy or —$OR^1$. In another variation, two of $R^{Z2}$, $R^{Z4}$ and $R^{Z6}$ are hydroxy or —$OR^1$. In another variation, at least one of $R^{A2}$, $R^{A4}$ and $R^{A6}$ is hydroxy or —$OR^1$ and at least one of $R^{Z2}$, $R^{Z4}$ and $R^{Z6}$ is hydroxy or —$OR^1$. In another variation, one of $R^{A2}$, $R^{A4}$ and $R^{A6}$ is hydroxy or —$OR^1$ and one of $R^{Z2}$, $R^{Z4}$ and $R^{Z6}$ is hydroxy or —$OR^1$. In any variation of formula (I-B), in one aspect, at least one of $R^{A2}$, $R^{A4}$, $R^{A6}$, $R^{Z4}$ and $R^{Z6}$ is hydroxy or —$OR^1$ where $R^1$ is an unsubstituted $C_1$-$C_6$ alkyl.

For compounds bearing one or more chiral centers, each unique stereoisomer has a compound number bearing a suffix "a", "b", etc. As examples, racemic compound 1, bearing one chiral center, can be resolved into its individual enantiomers 1a and 1b.

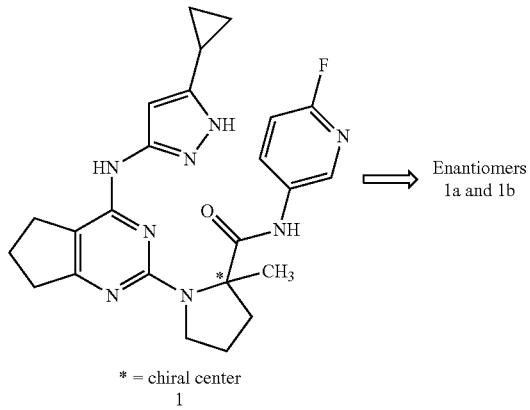 [SMILES: CC1(C(=O)Nc2ccc(F)nc2)CCCN1c1nc2c(c(Nc3cc(C4CC4)[nH]n3)n1)CCC2]

* = chiral center
1

Similarly, racemic compound 10, bearing two chiral centers, can be resolved into its individual diastereomers 10a, 10b, 10c and 10d.

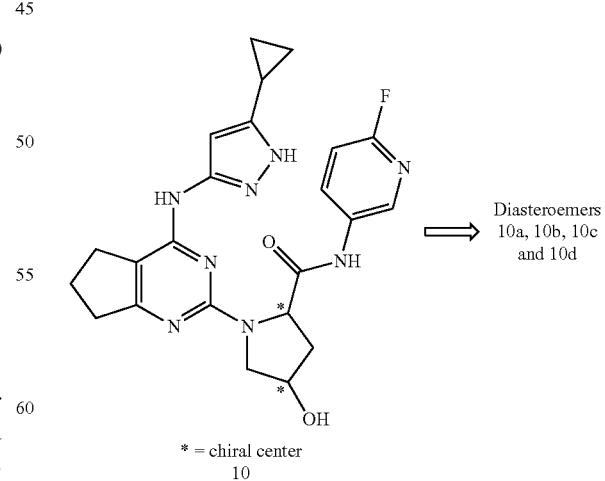

* = chiral center
10

Similarly, racemic compound 22, bearing two chiral centers, can be resolved into its individual diastereomers 22a, 22b, 22c and 22d.

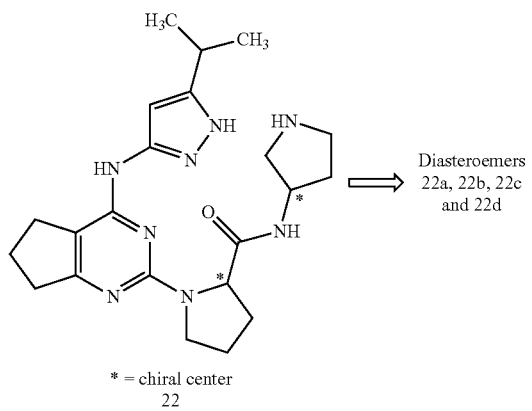 [SMILES: CC(C)c1cc(Nc2nc(N3CCCC3C(=O)NC3CCNC3)nc3c2CCC3)n[nH]1]

* = chiral center
22

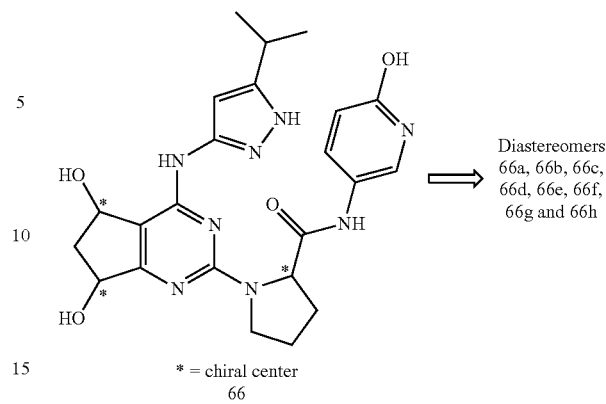

* = chiral center
66

Similarly, racemic compound 66, bearing three chiral centers, can be resolved into its individual diastereomers 66a, 66b, 66c, 66d, 66e, 66f, 66g, and 66h.

Representative compounds of the invention, and their stereoisomers, are listed in Table 1.

TABLE 1

| Compound No. | Structure | Compound Name |
|---|---|---|
| 1 (1a, 1b) | 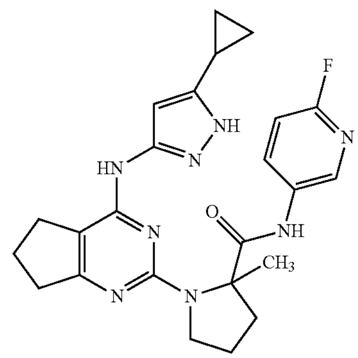 [SMILES: CC1(C(=O)Nc2ccc(F)nc2)CCCN1c1nc2c(c(Nc3cc(C4CC4)[nH]n3)n1)CCC2] | 1-(4-(5-cyclopropyl-1H-pyrazol-3-ylamino)-6,7-dihydro-5H-cyclopenta[d]pyrimidin-2-yl)-N-(6-fluoropyridin-3-yl)-2-methylpyrrolidine-2-carboxamide |
| 2 (2a, 2b) | 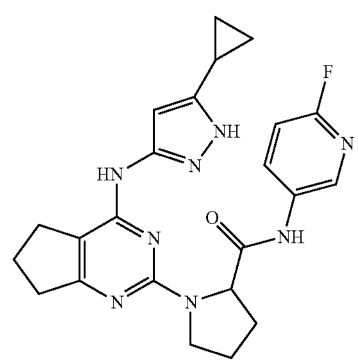 [SMILES: O=C(Nc1ccc(F)nc1)C1CCCN1c1nc2c(c(Nc3cc(C4CC4)[nH]n3)n1)CCC2] | 1-(4-(5-cyclopropyl-1H-pyrazol-3-ylamino)-6,7-dihydro-5H-cyclopenta[d]pyrimidin-2-yl)-N-(6-fluoropyridin-3-yl)pyrrolidine-2-carboxamide |

TABLE 1-continued

| Compound No. | Structure | Compound Name |
|---|---|---|
| 3 (3a, 3b) | 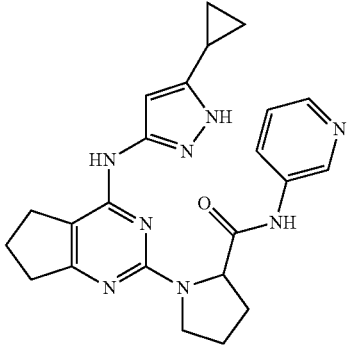 [SMILES: O=C(Nc1cccnc1)C1CCCN1c1nc2c(c(Nc3cc(C4CC4)[nH]n3)n1)CCC2] | 1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide |
| 4 (4a, 4b) | 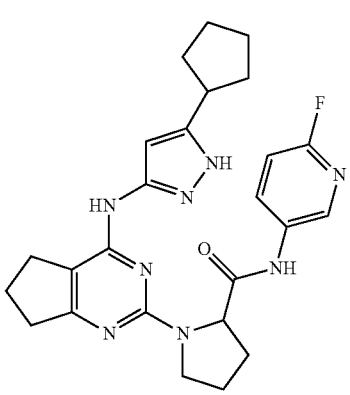 [SMILES: O=C(Nc1ccc(F)nc1)C1CCCN1c1nc2c(c(Nc3cc(C4CCCC4)[nH]n3)n1)CCC2] | 1-(4-(5-cyclopentyl-1H-pyrazol-3-ylamino)-6,7-dihydro-5H-cyclopenta[d]pyrimidin-2-yl)-N-(6-fluoropyridin-3-yl)pyrrolidine-2-carboxamide |
| 5 (5a, 5b) | 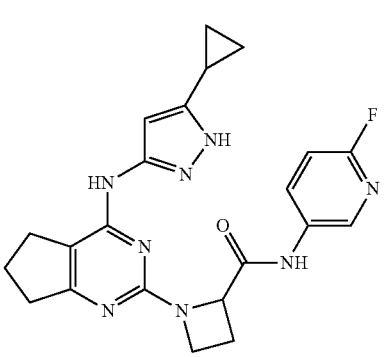 [SMILES: O=C(Nc1ccc(F)nc1)C1CCN1c1nc2c(c(Nc3cc(C4CC4)[nH]n3)n1)CCC2] | 1-(4-(5-cyclopropyl-1H-pyrazol-3-ylamino)-6,7-dihydro-5H-cyclopenta[d]pyrimidin-2-yl)-N-(6-fluoropyridin-3-yl)azetidine-2-carboxamide |
| 6 (6a, 6b) | 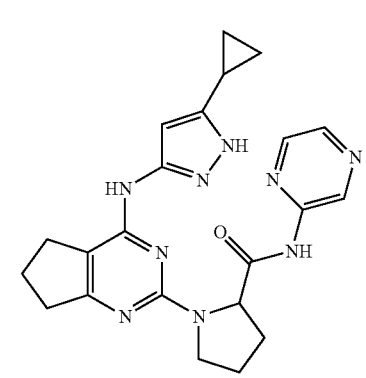 [SMILES: O=C(Nc1cnccn1)C1CCCN1c1nc2c(c(Nc3cc(C4CC4)[nH]n3)n1)CCC2] | 1-(4-(5-cyclopropyl-1H-pyrazol-3-ylamino)-6,7-dihydo-5H-cyclopenta[d]pyrimidin-2-yl)-N-(pyrazin-2-yl)pyrrolidine-2-carboxamide |

TABLE 1-continued

| Compound No. | Structure | Compound Name |
|---|---|---|
| 7 (7a, 7b) | 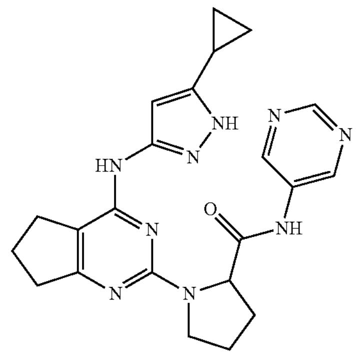 [SMILES: O=C(Nc1cncnc1)C1CCCN1c1nc2c(c(Nc3cc(C4CC4)[nH]n3)n1)CCC2] | 1-(4-(5-cyclopropyl-1H-pyrazol-3-ylamino)-6,7-dihydro-5H-cyclopenta[d]pyrimidin-2-yl)-N-(pyrimidin-5-yl)pyrrolidine-2-carboxamide |
| 8 (8a, 8b) | 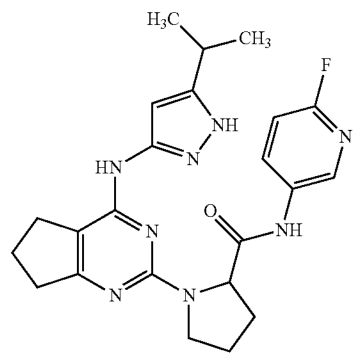 [SMILES: CC(C)c1cc(Nc2nc(N3CCCC3C(=O)Nc3ccc(F)nc3)nc3c2CCC3)n[nH]1] | N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide |
| 9 (9a, 9b) | 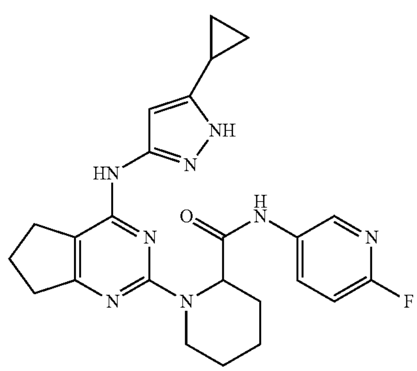 [SMILES: O=C(Nc1ccc(F)nc1)C1CCCCN1c1nc2c(c(Nc3cc(C4CC4)[nH]n3)n1)CCC2] | 1-(4-(5-cyclopropyl-1H-pyrazol-3-ylamino)-6,7-dihydro-5H-cyclopenta[d]pyrimidin-2-yl)-N-(6-fluoropyridin-3-yl)piperidine-2-carboxamide |
| 10 (10a, 10b, 10c, 10d) | 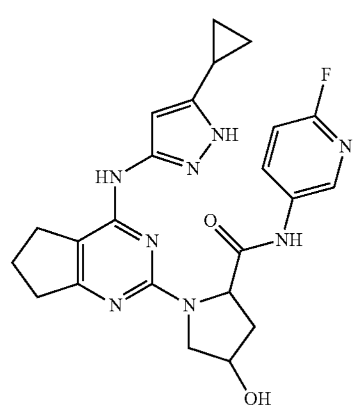 [SMILES: O=C(Nc1ccc(F)nc1)C1CC(O)CN1c1nc2c(c(Nc3cc(C4CC4)[nH]n3)n1)CCC2] | 1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide |

TABLE 1-continued

| Compound No. | Structure | Compound Name |
|---|---|---|
| 11 (11a, 11b, 11c, 11d) | 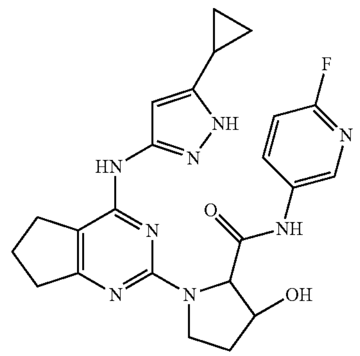 [SMILES: O=C(Nc1ccc(F)nc1)C1C(O)CCN1c1nc2c(c(Nc3cc(C4CC4)[nH]n3)n1)CCC2] | 1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide |
| 12 (12a, 12b) | 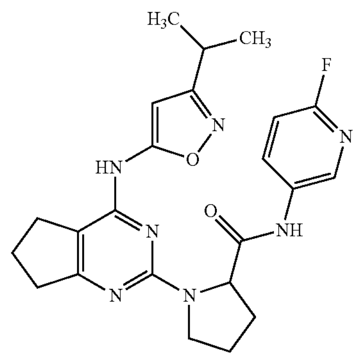 [SMILES: CC(C)c1cc(Nc2nc(N3CCCC3C(=O)Nc3ccc(F)nc3)nc3c2CCC3)on1] | N-(6-fluoropyridin-3-yl)-1-(4-(3-isopropylisoxazol-5-ylamino)-6,7-dihydro-5H-cyclopenta[d]pyrimidin-2-yl)pyrrolidine-2-carboxamide |
| 13 (13a, 13b) | 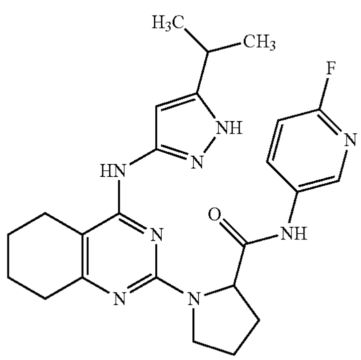 [SMILES: CC(C)c1cc(Nc2nc(N3CCCC3C(=O)Nc3ccc(F)nc3)nc3c2CCCC3)n[nH]1] | N-(6-fluoropyridin-3-yl)-1-(4-(5-isopropyl-1H-pyrazol-3-ylamino)-5,6,7,8-tetrahydroquinazolin-2-yl)pyrrolidine-2-carboxamide |
| 14 (14a, 14b) | 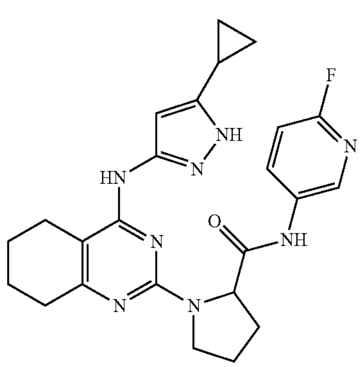 [SMILES: O=C(Nc1ccc(F)nc1)C1CCCN1c1nc2c(c(Nc3cc(C4CC4)[nH]n3)n1)CCCC2] | 1-(4-(5-cyclopropyl-1H-pyrazol-3-ylamino)-5,6,7,8-tetrahydroquinazolin-2-yl)-N-(6-fluoropyridin-3-yl)pyrrolidine-2-carboxamide |

TABLE 1-continued

| Compound No. | Structure | Compound Name |
|---|---|---|
| 15 (15a, 15b) | 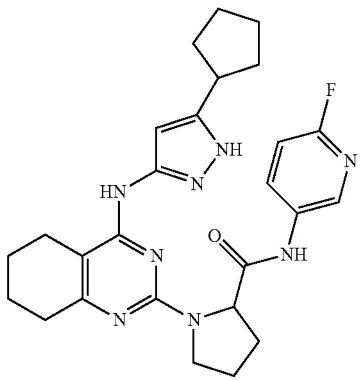 [SMILES: O=C(Nc1ccc(F)nc1)C1CCCN1c1nc2c(c(Nc3cc(C4CCCC4)[nH]n3)n1)CCCC2] | 1-(4-(5-cyclopentyl-1H-pyrazol-3-ylamino)-5,6,7,8-tetrahydroquinazolin-2-yl)-N-(6-fluoropyridin-3-yl)pyrrolidine-2-carboxamide |
| 16 (16a, 16b) | 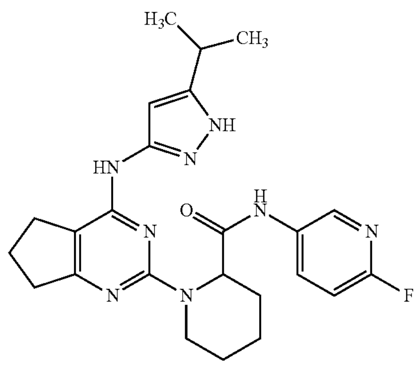 [SMILES: CC(C)c1cc(Nc2nc(N3CCCCC3C(=O)Nc3ccc(F)nc3)nc3c2CCC3)n[nH]1] | N-(6-fluoropyridin-3-yl)-1-(4-(5-isopropyl-1H-pyrazol-3-ylamino)-6,7-dihydro-5H-cyclopenta[d]pyrimidin-2-yl)piperidine-2-carboxamide |
| 17 (17a, 17b) | 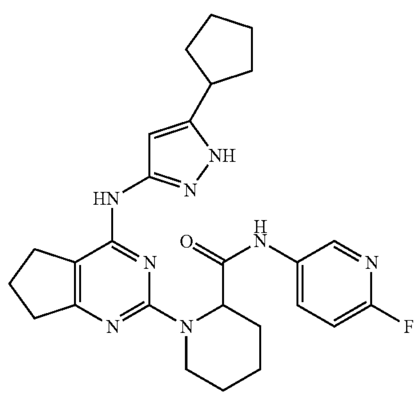 [SMILES: O=C(Nc1ccc(F)nc1)C1CCCCN1c1nc2c(c(Nc3cc(C4CCCC4)[nH]n3)n1)CCC2] | 1-(4-(5-cyclopentyl-1H-pyrazol-3-ylamino)-6,7-dihydro-5H-cyclopenta[d]pyrimidin-2-yl)-N-(6-fluoropyridin-3-yl)piperidine-2-carboxamide |
| 18 (18a, 18b) | 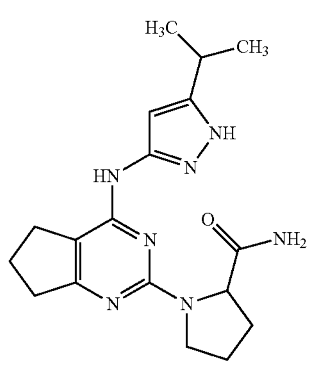 [SMILES: CC(C)c1cc(Nc2nc(N3CCCC3C(N)=O)nc3c2CCC3)n[nH]1] | 1-(4-(5-isopropyl-1H-pyrazol-3-ylamino)-6,7-dihydro-5H-cyclopenta[d]pyrimidin-2-yl)pyrrolidine-2-carboxamide |

TABLE 1-continued

| Compound No. | Structure | Compound Name |
| --- | --- | --- |
| 19 (19a, 19b) | 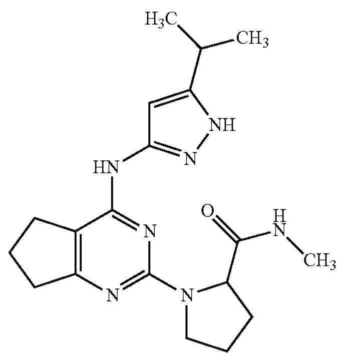 [SMILES: CNC(=O)C1CCCN1c1nc2c(c(Nc3cc(C(C)C)[nH]n3)n1)CCC2] | 1-(4-(5-isopropyl-1H-pyrazol-3-ylamino)-6,7-dihydro-5H-cyclopenta[d]pyrimidin-2-yl)-N-methylpyrrolidine-2-carboxamide |
| 20 (20a, 20b) | 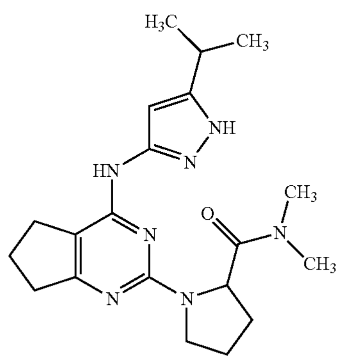 [SMILES: CC(C)c1cc(Nc2nc(N3CCCC3C(=O)N(C)C)nc3c2CCC3)n[nH]1] | 1-(4-(5-isopropyl-1H-pyrazol-3-ylamino)-6,7-dihydro-5H-cyclopenta[d]pyrimidin-2-yl)-N,N-dimethylpyrrolidine-2-carboxamide |
| 21 (21a, 21b, 21c, 21d) | 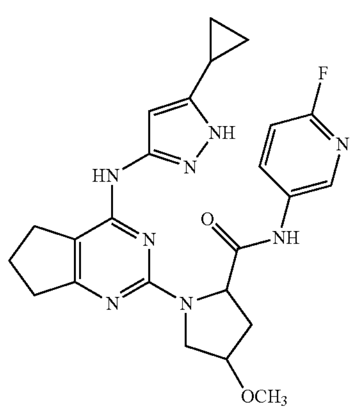 [SMILES: COC1CC(C(=O)Nc2ccc(F)nc2)N(c2nc3c(c(Nc4cc(C5CC5)[nH]n4)n2)CCC3)C1] | 1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide |
| 22 (22a, 22b, 22c, 22d) | 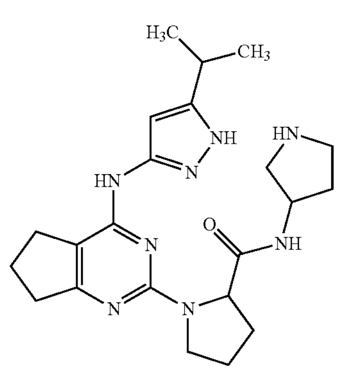 [SMILES: CC(C)c1cc(Nc2nc(N3CCCC3C(=O)NC3CCNC3)nc3c2CCC3)n[nH]1] | 1-(4-(5-isopropyl-1H-pyrazol-3-ylamino)-6,7-dihydro-5H-cyclopenta[d]pyrimidin-2-yl)-N-(pyrrolidin-3-yl)pyrrolidine-2-carboxamide |

TABLE 1-continued

| Compound No. | Structure | Compound Name |
|---|---|---|
| 23 (23a, 23b) | 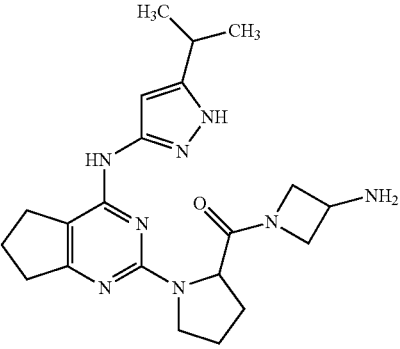 [SMILES: CC(C)c1cc(Nc2nc(N3CCCC3C(=O)N3CC(N)C3)nc3c2CCC3)n[nH]1] | (3-aminoazetidin-1-yl)(1-(4-((5-isopropyl-1H-pyrazol-3-yl)amino)-6,7-dihydro-5H-cyclopenta[d]pyrimidin-2-yl)pyrrolidin-2-yl)methanone |
| 24 (24a, 24b) | 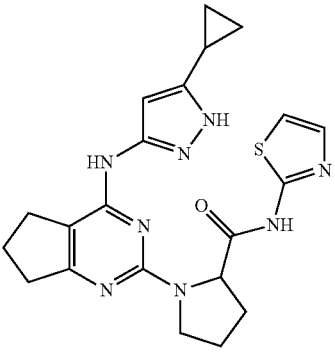 [SMILES: O=C(Nc1nccs1)C1CCCN1c1nc2c(c(Nc3cc(C4CC4)[nH]n3)n1)CCC2] | 1-(4-((5-cyclopropyl-1H-pyrazol-3-yl)amino)-6,7-dihydro-5H-cyclopenta[d]pyrimidin-2-yl)-N-(thiazol-2-yl)pyrrolidine-2-carboxamide |
| 25 (25a, 25b) | 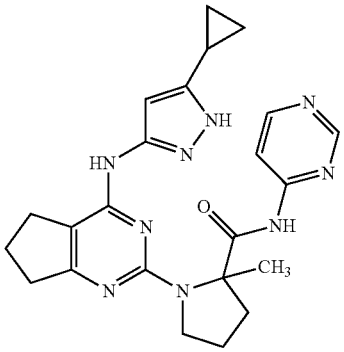 [SMILES: CC1(C(=O)Nc2ccncn2)CCCN1c1nc2c(c(Nc3cc(C4CC4)[nH]n3)n1)CCC2] | 1-(4-((5-cyclopropyl-1H-pyrazol-3-yl)amino)-6,7-dihydro-5H-cyclopenta[d]pyrimidin-2-yl)-2-methyl-N-(pyrimidin-4-yl)pyrrolidine-2-carboxamide |
| 26 (26a, 26b, 26c, 26d) | 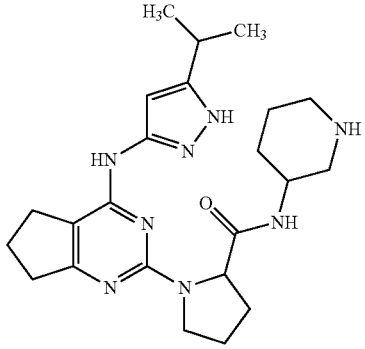 [SMILES: CC(C)c1cc(Nc2nc(N3CCCC3C(=O)NC3CCCNC3)nc3c2CCC3)n[nH]1] | 1-(4-((5-isopropyl-1H-pyrazol-3-yl)amino)-6,7-dihydro-5H-cyclopenta[d]pyrimidin-2-yl)-N-(piperidin-3-yl)pyrrolidine-2-carboxamide |

TABLE 1-continued

| Compound No. | Structure | Compound Name |
| --- | --- | --- |
| 27 (27a, 27b, 27c, 27d) | 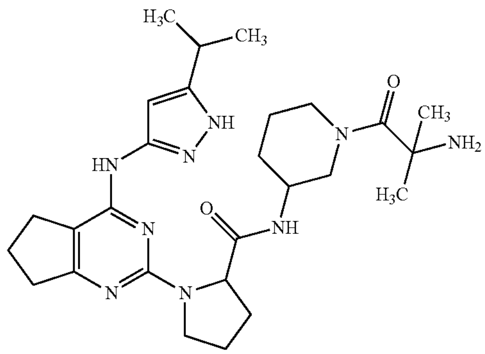 [SMILES: CC(C)c1cc(Nc2nc(N3CCCC3C(=O)NC3CCCN(C(=O)C(C)(C)N)C3)nc3c2CCC3)n[nH]1] | N-(1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide |
| 28 (28a, 28b, 28c, 28d) | 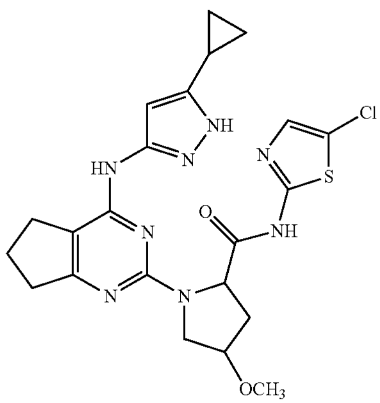 [SMILES: COC1CC(C(=O)Nc2ncc(Cl)s2)N(c2nc3c(c(Nc4cc(C5CC5)[nH]n4)n2)CCC3)C1] | N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide |
| 29 (29a, 29b) | 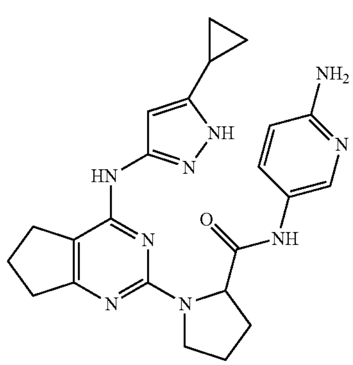 [SMILES: Nc1ccc(NC(=O)C2CCCN2c2nc3c(c(Nc4cc(C5CC5)[nH]n4)n2)CCC3)cn1] | N-(6-aminopyridin-3-yl)-1-(4-((5-cyclopropyl-1H-pyrazol-3-yl)amino)-6,7-dihydro-5H-cyclopenta[d]pyrimidin-2-yl)pyrrolidine-2-carboxamide |
| 30 (30a, 30b, 30c, 30d) | 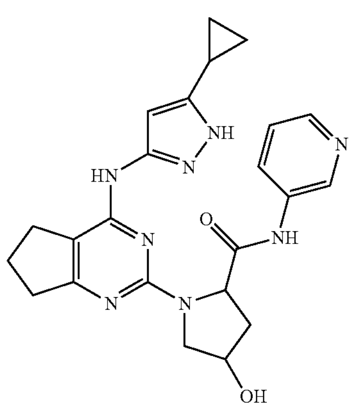 [SMILES: O=C(Nc1cccnc1)C1CC(O)CN1c1nc2c(c(Nc3cc(C4CC4)[nH]n3)n1)CCC2] | 1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide |

TABLE 1-continued

| Compound No. | Structure | Compound Name |
|---|---|---|
| 31 (31a, 31b, 31c, 31d) | 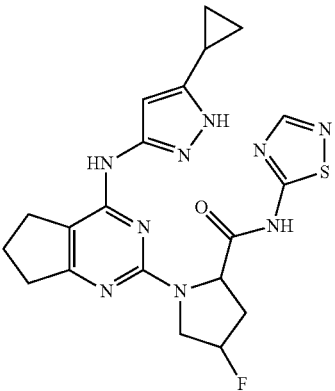 [SMILES: O=C(Nc1ncns1)C1CC(F)CN1c1nc2c(c(Nc3cc(C4CC4)[nH]n3)n1)CCC2] | 1-(4-((5-cyclopropyl-1H-pyrazol-3-ylamino)-6,7-dihydro-5H-cyclopenta[d]pyrimidin-2-yl)-4-fluoro-N-(1,2,4-thiadiazol-5-yl)pyrrolidine-2-carboxamide |
| 32 (32a, 32b) | 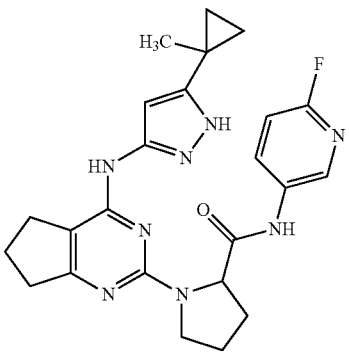 [SMILES: CC1(c2cc(Nc3nc(N4CCCC4C(=O)Nc4ccc(F)nc4)nc4c3CCC4)n[nH]2)CC1] | N-(6-fluoropyridin-3-yl)-1-(4-((5-(1-methylcyclopropyl)-1H-pyrazol-3-yl)amino)-6,7-dihydro-5H-cyclopenta[d]pyrimidin-2-yl)pyrrolidine-2-carboxamide |
| 33 (33a, 33b) | 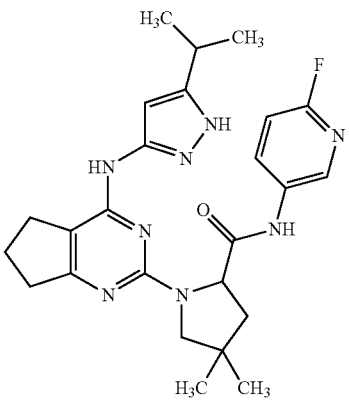 [SMILES: CC(C)c1cc(Nc2nc(N3CC(C)(C)CC3C(=O)Nc3ccc(F)nc3)nc3c2CCC3)n[nH]1] | N-(6-fluoropyridin-3-yl)-1-(4-((5-isopropyl-1H-pyrazol-3-yl)amino)-6,7-dihydro-5H-cyclopenta[d]pyrimidin-2-yl)-4,4-dimethylpyrrolidine-2-carboxamide |
| 34 (34a, 34b, 34c, 34d) | 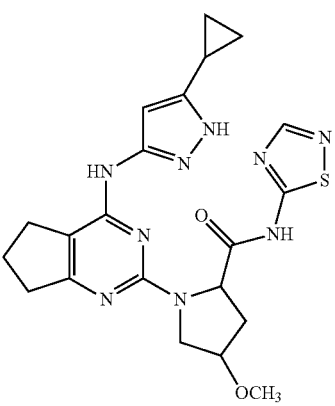 [SMILES: COC1CC(C(=O)Nc2ncns2)N(c2nc3c(c(Nc4cc(C5CC5)[nH]n4)n2)CCC3)C1] | 1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide |

TABLE 1-continued

| Compound No. | Structure | Compound Name |
|---|---|---|
| 35 (35a, 35b, 35c, 35d) | 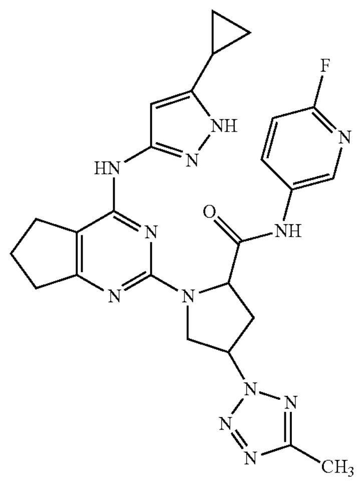 [SMILES: Cc1nnn(C2CC(C(=O)Nc3ccc(F)nc3)N(c3nc4c(c(Nc5cc(C6CC6)[nH]n5)n3)CCC4)C2)n1] | 1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide |
| 36 (36a, 36b, 36c, 36d) | 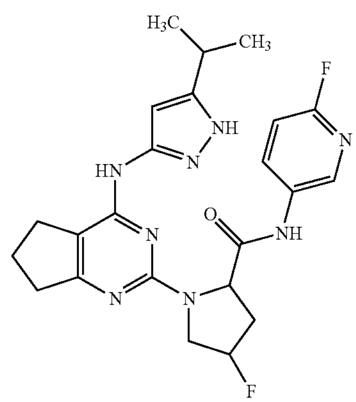 [SMILES: CC(C)c1cc(Nc2nc(N3CC(F)CC3C(=O)Nc3ccc(F)nc3)nc3c2CCC3)n[nH]1] | 4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide |
| 37 (37a, 37b) | 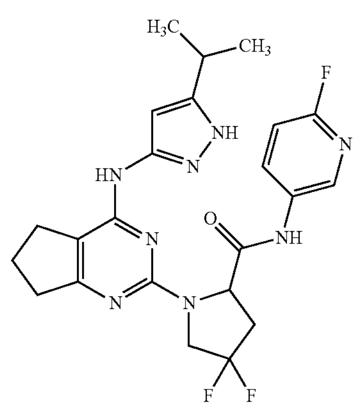 [SMILES: CC(C)c1cc(Nc2nc(N3CC(F)(F)CC3C(=O)Nc3ccc(F)nc3)nc3c2CCC3)n[nH]1] | 4,4-difluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide |

TABLE 1-continued

| Compound No. | Structure | Compound Name |
| --- | --- | --- |
| 38 (38a, 38b) | 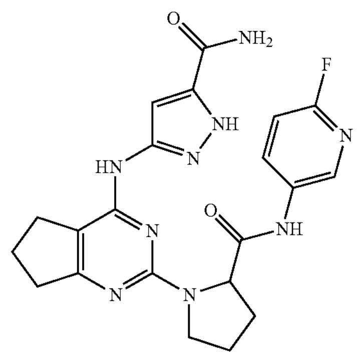 [SMILES: NC(=O)c1cc(Nc2nc(N3CCCC3C(=O)Nc3ccc(F)nc3)nc3c2CCC3)n[nH]1] | 3-((2-(2-((6-fluoropyridin-3-yl)carbamoyl)pyrrolidin-1-yl)-6,7-dihydro-5H-cyclopenta[d]pyrimidin-4-yl)amino)-1H-pyrazole-5-carboxamide |
| 39 (39a, 39b) | 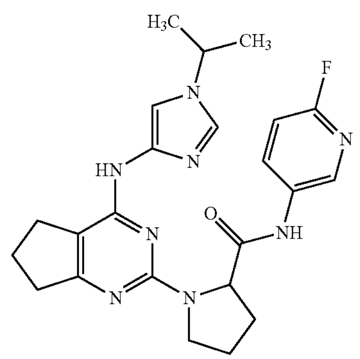 [SMILES: CC(C)n1cnc(Nc2nc(N3CCCC3C(=O)Nc3ccc(F)nc3)nc3c2CCC3)c1] | N-(6-fluoropyridin-3-yl)-1-(4-((1-isopropyl-1H-imidazol-4-yl)amino)-6,7-dihydro-5H-cyclopenta[d]pyrimidin-2-yl)pyrrolidine-2-carboxamide |
| 40 (40a, 40b, 40c, 40d) | 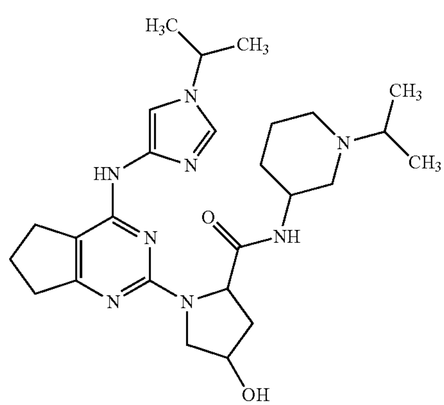 [SMILES: CC(C)N1CCCC(NC(=O)C2CC(O)CN2c2nc3c(c(Nc4cn(C(C)C)cn4)n2)CCC3)C1] | 4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide |
| 41 (41a, 41b) | 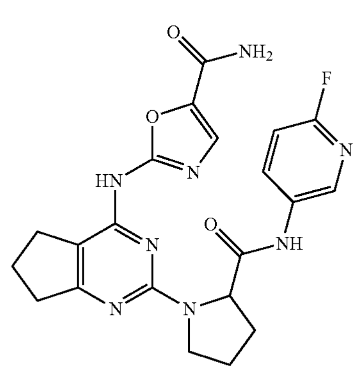 [SMILES: NC(=O)c1cnc(Nc2nc(N3CCCC3C(=O)Nc3ccc(F)nc3)nc3c2CCC3)o1] | 2-((2-(2-((6-fluoropyridin-3-yl)carbamoyl)pyrrolidin-1-yl)-6,7-dihydro-5H-cyclopenta[d]pyrimidin-4-yl)amino)oxazole-5-carboxamide |

TABLE 1-continued

| Compound No. | Structure | Compound Name |
|---|---|---|
| 42 (42a, 42b) | 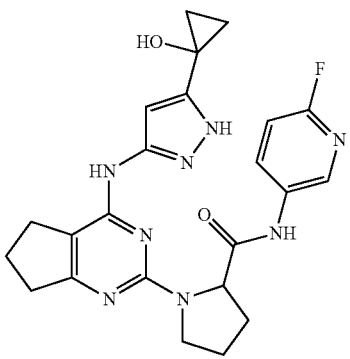 [SMILES: O=C(Nc1ccc(F)nc1)C1CCCN1c1nc2c(c(Nc3cc(C4(O)CC4)[nH]n3)n1)CCC2] | N-(6-fluoropyridin-3-yl)-1-(4-((5-(1-hydroxycyclopropyl)-1H-pyrazol-3-yl)amino)-6,7-dihydro-5H-cyclopenta[d]pyrimidin-2-yl)pyrrolidine-2-carboxamide |
| 43 (43a, 43b, 43c, 43d) | 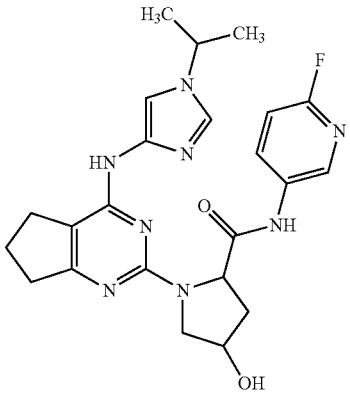 [SMILES: CC(C)n1cnc(Nc2nc(N3CC(O)CC3C(=O)Nc3ccc(F)nc3)nc3c2CCC3)c1] | N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide |
| 44 (44a, 44b) | 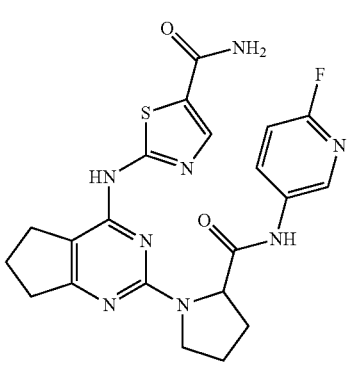 [SMILES: NC(=O)c1cnc(Nc2nc(N3CCCC3C(=O)Nc3ccc(F)nc3)nc3c2CCC3)s1] | 2-((2-(2-((6-fluoropyridin-3-yl)carbamoyl)pyrrolidin-1-yl)-6,7-dihydro-5H-cyclopenta[d]pyrimidin-4-yl)amino)thiazole-5-carboxamide |
| 45 (45a, 45b) | 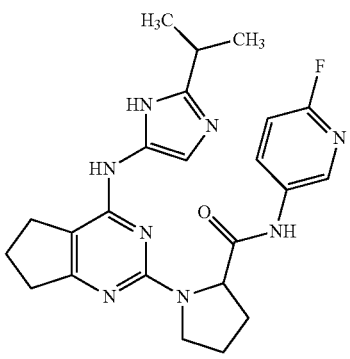 [SMILES: CC(C)c1ncc(Nc2nc(N3CCCC3C(=O)Nc3ccc(F)nc3)nc3c2CCC3)[nH]1] | N-(6-fluoropyridin-3-yl)-1-(4-((2-isopropyl-1H-imidazol-5-yl)amino)-6,7-dihydro-5H-cyclopenta[d]pyrimidin-2-yl)pyrrolidine-2-carboxamide |

TABLE 1-continued

| Compound No. | Structure | Compound Name |
| --- | --- | --- |
| 46 (46a, 46b) | 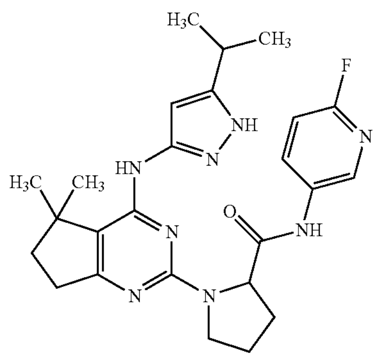 [SMILES: CC(C)c1cc(Nc2nc(N3CCCC3C(=O)Nc3ccc(F)nc3)nc3c2C(C)(C)CC3)n[nH]1] | N-(6-fluoropyridin-3-yl)-1-(4-((5-isopropyl-1H-pyrazol-3-yl)amino)-5,5-dimethyl-6,7-dihydro-5H-cyclopenta[d]pyrimidin-2-yl)pyrrolidine-2-carboxamide |
| 47 (47a, 47b) | 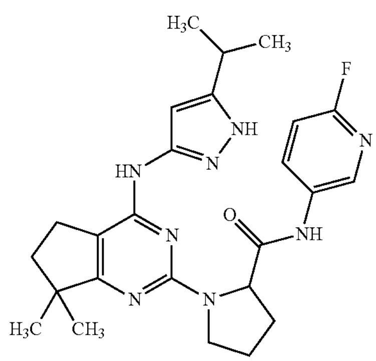 [SMILES: CC(C)c1cc(Nc2nc(N3CCCC3C(=O)Nc3ccc(F)nc3)nc3c2CCC3(C)C)n[nH]1] | N-(6-fluoropyridin-3-yl)-1-(4-((5-isopropyl-1H-pyrazol-3-yl)amino)-7,7-dimethyl-6,7-dihydro-5H-cyclopenta[d]pyrimidin-2-yl)pyrrolidine-2-carboxamide |
| 48 (48a, 48b) | 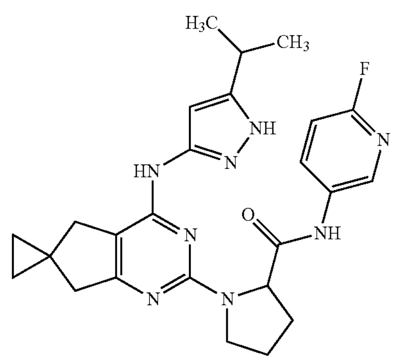 [SMILES: CC(C)c1cc(Nc2nc(N3CCCC3C(=O)Nc3ccc(F)nc3)nc3c2CC2(CC2)C3)n[nH]1] | N-(6-fluoropyridin-3-yl)-1-(4-((5-isopropyl-1H-pyrazol-3-yl)amino)-5,7-dihydrospiro[cyclopenta[d]pyrimidine-6,1'-cyclopropan]-2-yl)pyrrolidine-2-carboxamide |
| 49 (49a, 49b) | 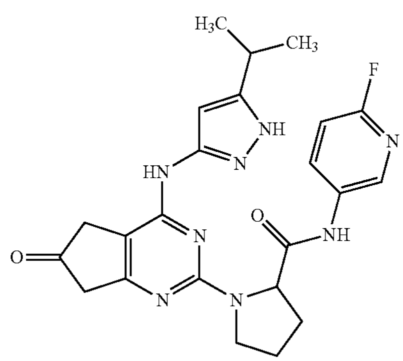 [SMILES: CC(C)c1cc(Nc2nc(N3CCCC3C(=O)Nc3ccc(F)nc3)nc3c2CC(=O)C3)n[nH]1] | N-(6-fluoropyridin-3-yl)-1-(4-((5-isopropyl-1H-pyrazol-3-yl)amino)-6-oxo-6,7-dihydro-5H-cyclopenta[d]pyrimidin-2-yl)pyrrolidine-2-carboxamide |

TABLE 1-continued

| Compound No. | Structure | Compound Name |
|---|---|---|
| 50 (50a, 50b) | 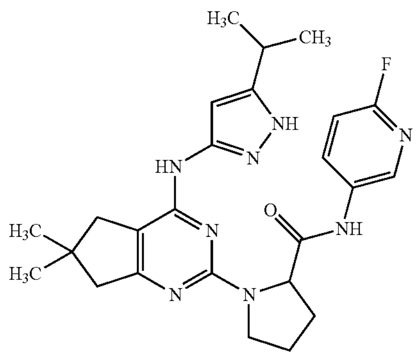 [SMILES: CC(C)c1cc(Nc2nc(N3CCCC3C(=O)Nc3ccc(F)nc3)nc3c2CC(C)(C)C3)n[nH]1] | N-(6-fluoropyridin-3-yl)-1-(4-((5-isopropyl-1H-pyrazol-3-yl)amino)-6,6-dimethyl-6,7-dihydro-5H-cyclopenta[d]pyrimidin-2-yl)pyrrolidine-2-carboxamide |
| 51 (51a, 51b) | 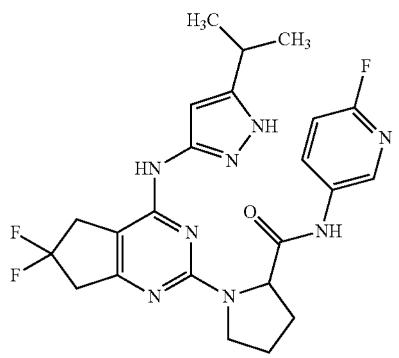 [SMILES: CC(C)c1cc(Nc2nc(N3CCCC3C(=O)Nc3ccc(F)nc3)nc3c2CC(F)(F)C3)n[nH]1] | 1-(6,6-difluoro-4-((5-isopropyl-1H-pyrazol-3-yl)amino)-6,7-dihydro-5H-cyclopenta[d]pyrimidin-2-yl)-N-(6-fluoropyridin-3-yl)pyrrolidine-2-carboxamide |
| 52 (52a, 52b) | 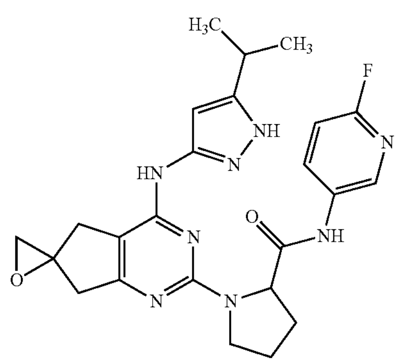 [SMILES: CC(C)c1cc(Nc2nc(N3CCCC3C(=O)Nc3ccc(F)nc3)nc3c2CC2(CO2)C3)n[nH]1] | N-(6-fluoropyridin-3-yl)-1-(4-((5-isopropyl-1H-pyrazol-3-yl)amino)-5,7-dihydrospiro[cyclopenta[d]pyrimidine-6,2'-oxiran]-2-yl)pyrrolidine-2-carboxamide |
| 53 (53a, 53b) | 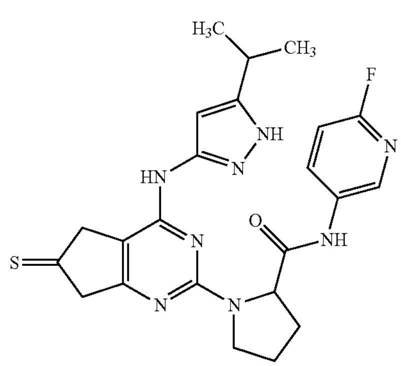 [SMILES: CC(C)c1cc(Nc2nc(N3CCCC3C(=O)Nc3ccc(F)nc3)nc3c2CC(=S)C3)n[nH]1] | N-(6-fluoropyridin-3-yl)-1-(4-((5-isopropyl-1H-pyrazol-3-yl)amino)-6-thioxo-6,7-dihydro-5H-cyclopenta[d]pyrimidin-2-yl)pyrrolidine-2-carboxamide |

TABLE 1-continued

| Compound No. | Structure | Compound Name |
|---|---|---|
| 54 (54a, 54b) | 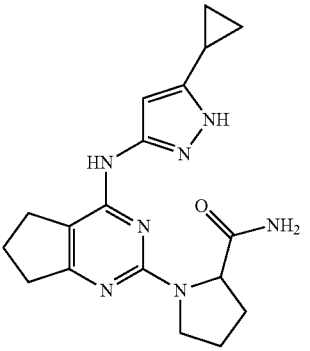 [SMILES: NC(=O)C1CCCN1c1nc2c(c(Nc3cc(C4CC4)[nH]n3)n1)CCC2] | 1-(4-(5-cyclopropyl-1H-pyrazol-3-ylamino)-6,7-dihydro-5H-cyclopenta[d]pyrimidin-2-yl)pyrrolidine-2-carboxamide |
| 55 (55a, 55b) | 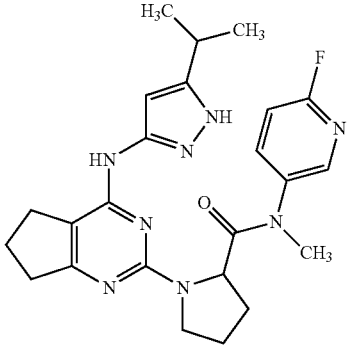 [SMILES: CC(C)c1cc(Nc2nc(N3CCCC3C(=O)N(C)c3ccc(F)nc3)nc3c2CCC3)n[nH]1] | N-(6-fluoropyridin-3-yl)-1-(4-((5-isopropyl-1H-pyrazol-3-yl)amino)-6,7-dihydro-5H-cyclopenta[d]pyrimidin-2-yl)-N-methylpyrrolidine-2-carboxamide |
| 56 (56a, 56b) | 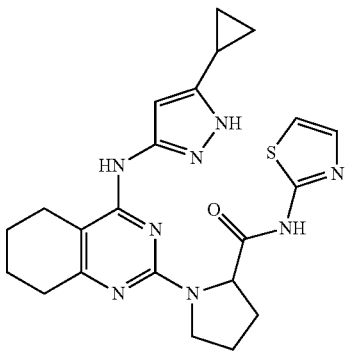 [SMILES: O=C(Nc1nccs1)C1CCCN1c1nc2c(c(Nc3cc(C4CC4)[nH]n3)n1)CCCC2] | 1-(4-((5-cyclopropyl-1H-pyrazol-3-yl)amino)-5,6,7,8-tetrahydroquinazolin-2-yl)-N-(thiazol-2-yl)pyrrolidine-2-carboxamide |
| 57 (57a, 57b) | 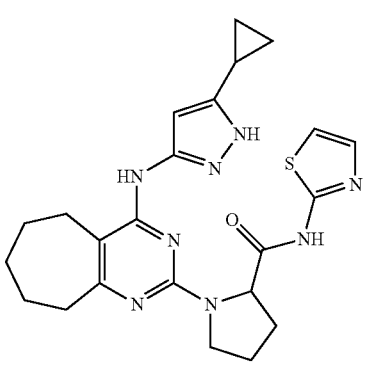 [SMILES: O=C(Nc1nccs1)C1CCCN1c1nc2c(c(Nc3cc(C4CC4)[nH]n3)n1)CCCCC2] | 1-(4-((5-cyclopropyl-1H-pyrazol-3-yl)amino)-6,7,8,9-tetrahydro-5H-cyclohepta[d]pyrimidin-2-yl)-N-(thiazol-2-yl)pyrrolidine-2-carboxamide |

TABLE 1-continued

| Compound No. | Structure | Compound Name |
|---|---|---|
| 58 (58a, 58b, 58c, 58d) | 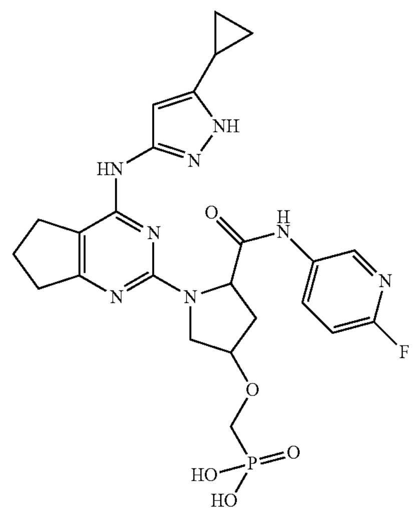 [SMILES: O=C(Nc1ccc(F)nc1)C1CC(OCP(=O)(O)O)CN1c1nc2c(c(Nc3cc(C4CC4)[nH]n3)n1)CCC2] | (((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid |
| 59 (59a, 59b, 59c, 59d) | 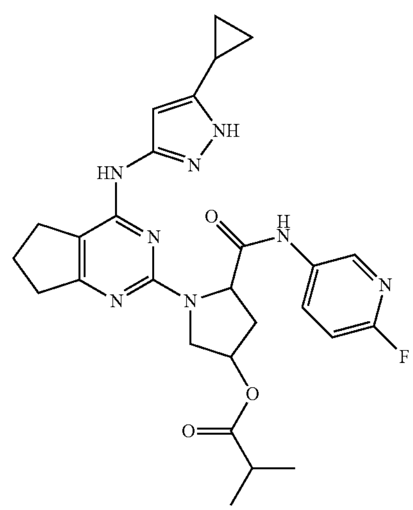 [SMILES: CC(C)C(=O)OC1CC(C(=O)Nc2ccc(F)nc2)N(c2nc3c(c(Nc4cc(C5CC5)[nH]n4)n2)CCC3)C1] | 1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate |
| 60 (60a, 60b) | 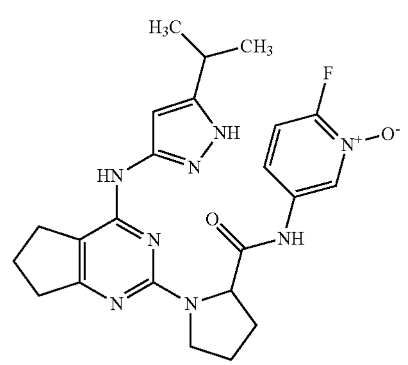 [SMILES: CC(C)c1cc(Nc2nc(N3CCCC3C(=O)Nc3ccc(F)[n+]([O-])c3)nc3c2CCC3)n[nH]1] | 2-fluoro-5-(1-(4-((5-isopropyl-1H-pyrazol-3-yl)amino)-6,7-dihydro-5H-cyclopenta[d]pyrimidin-2-yl)pyrrolidine-2-carboxamido)pyridine 1-oxide |

TABLE 1-continued

| Compound No. | Structure | Compound Name |
|---|---|---|
| 61 (61, 61b) | 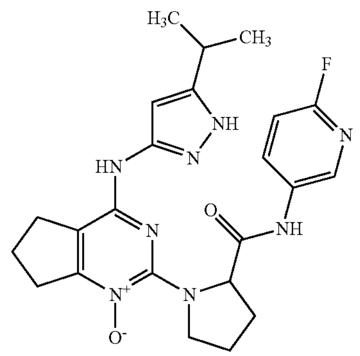 [SMILES: CC(C)c1cc(Nc2nc(N3CCCC3C(=O)Nc3ccc(F)nc3)[n+]([O-])c3c2CCC3)n[nH]1] | 2-(2-((6-fluoropyridin-3-yl)carbamoyl)pyrrolidin-2-yl)-4-((5-isopropyl-1H-pyrazol-3-yl)amino)-6,7-dihydro-5H-cyclopenta[d]pyrimidine 1-oxide |
| 62 (62a, 62b) | 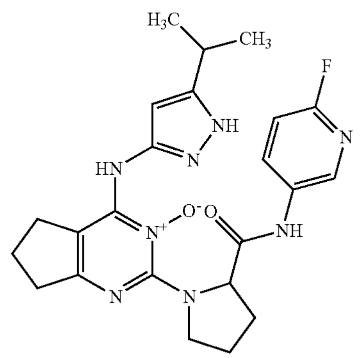 [SMILES: CC(C)c1cc(Nc2c3c(nc(N4CCCC4C(=O)Nc4ccc(F)nc4)[n+]2[O-])CCC3)n[nH]1] | 2-(2-((6-fluoropyridin-3-yl)carbamoyl)pyrrolidin-2-yl)-4-((5-isopropyl-1H-pyrazol-3-yl)amino)-6,7-dihydro-5H-cyclopenta[d]pyrimidine-3-oxide |
| 63 (63a, 63b) | 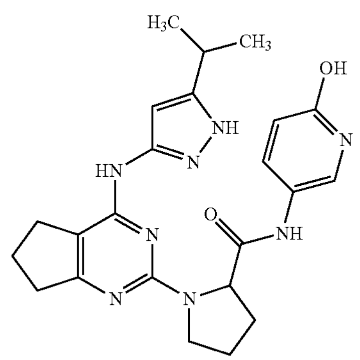 [SMILES: CC(C)c1cc(Nc2nc(N3CCCC3C(=O)Nc3ccc(O)nc3)nc3c2CCC3)n[nH]1] | N-(6-hydroxypyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide |
| 64 (64a, 64b) | 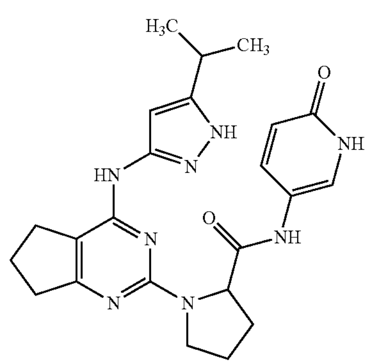 [SMILES: CC(C)c1cc(Nc2nc(N3CCCC3C(=O)Nc3ccc(=O)[nH]c3)nc3c2CCC3)n[nH]1] | 1-(4-((5-isopropyl-1H-pyrazol-3-yl)amino)-6,7-dihydro-5H-cyclopenta[d]pyrimidin-2-yl)-N-(6-oxo-1,6-dihydropyridin-3-yl)pyrrolidine-2-carboxamide |

TABLE 1-continued

| Compound No. | Structure | Compound Name |
|---|---|---|
| 65 (65a, 65b, 65c, 65d) | 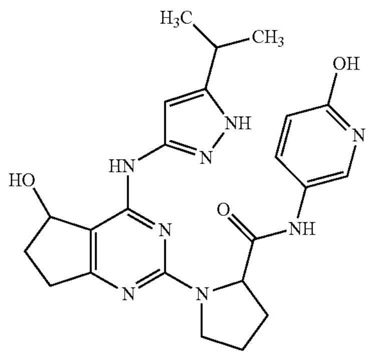 [SMILES: CC(C)c1cc(Nc2nc(N3CCCC3C(=O)Nc3ccc(O)nc3)nc3c2C(O)CC3)n[nH]1] | 1-(5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide |
| 66 (66a, 66b, 66c, 66d, 66e, 66f, 66g, 66h) | 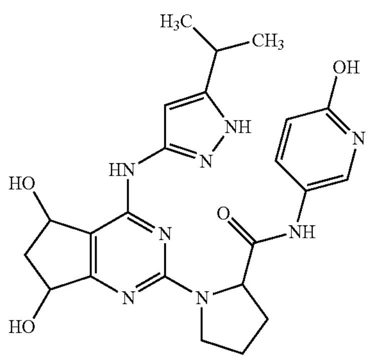 [SMILES: CC(C)c1cc(Nc2nc(N3CCCC3C(=O)Nc3ccc(O)nc3)nc3c2C(O)CC3O)n[nH]1] | 1-(5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide |
| 67 (67a, 67b) | 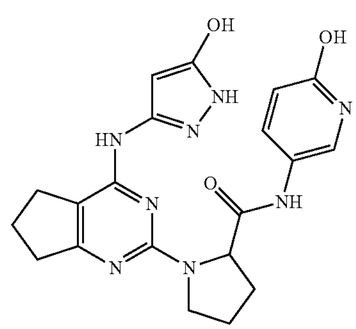 [SMILES: O=C(Nc1ccc(O)nc1)C1CCCN1c1nc2c(c(Nc3cc(O)[nH]n3)n1)CCC2] | 1-(4-((5-hydroxy-1H-pyrazol-3-yl)amino)-6,7-dihydro-5H-cyclopenta[d]pyrimidin-2-yl)-N-(6-hydroxypyridin-3-yl)pyrrolidine-2-carboxamide |
| 68 (68a, 68b) | 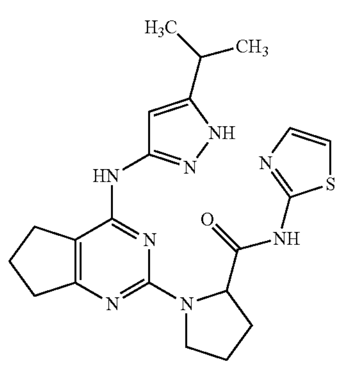 [SMILES: CC(C)c1cc(Nc2nc(N3CCCC3C(=O)Nc3nccs3)nc3c2CCC3)n[nH]1] | 1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide |

TABLE 1-continued

| Compound No. | Structure | Compound Name |
|---|---|---|
| 69 (69a, 69b) | 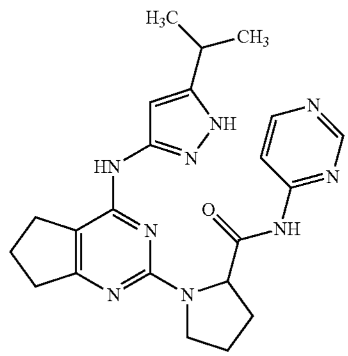 [SMILES: CC(C)c1cc(Nc2nc(N3CCCC3C(=O)Nc3ccncn3)nc3c2CCC3)n[nH]1] | 1-(4-(5-isopropyl-1H-pyrazol-3-ylamino)-6,7-dihydro-5H-cyclopenta[d]pyrimidin-2-yl)-N-(pyrimidin-4-yl)pyrrolidine-2-carboxamide |
| 70 (70a, 70b, 70c, 70d) | 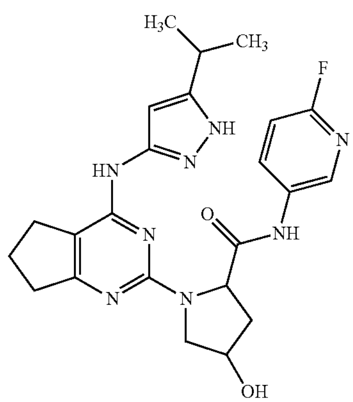 [SMILES: CC(C)c1cc(Nc2nc(N3CC(O)CC3C(=O)Nc3ccc(F)nc3)nc3c2CCC3)n[nH]1] | N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide |
| 71 (71a, 71b, 71c, 71d) | 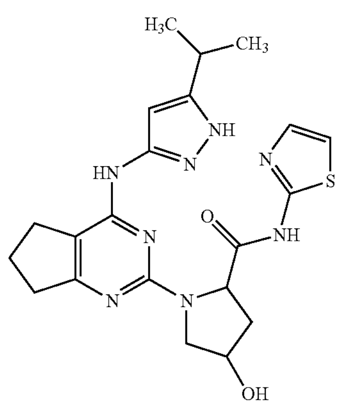 [SMILES: CC(C)c1cc(Nc2nc(N3CC(O)CC3C(=O)Nc3nccs3)nc3c2CCC3)n[nH]1] | 4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide |
| 72 (72a, 72b) | 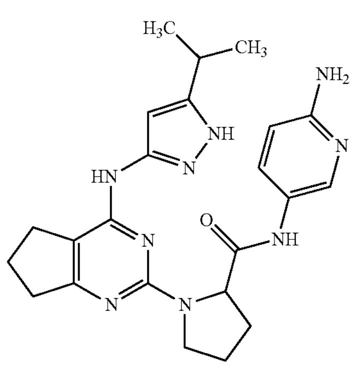 [SMILES: CC(C)c1cc(Nc2nc(N3CCCC3C(=O)Nc3ccc(N)nc3)nc3c2CCC3)n[nH]1] | N-(6-aminopyridin-3-yl)-1-(4-(5-isopropyl-1H-pyrazol-3-ylamino)-6,7-dihydro-5H-cyclopenta[d]pyrimidin-2-yl)pyrrolidine-2-carboxamide |

TABLE 1-continued

| Compound No. | Structure | Compound Name |
| --- | --- | --- |
| 73 (73a, 73b) | 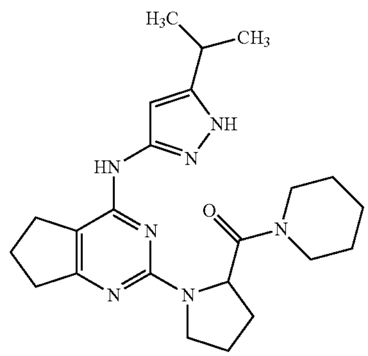 [SMILES: CC(C)c1cc(Nc2nc(N3CCCC3C(=O)N3CCCCC3)nc3c2CCC3)n[nH]1] | (1-(4-(5-isopropyl-1H-pyrazol-3-ylamino)-6,7-dihydro-5H-cyclopenta[d]pyrimidin-2-yl)pyrrolidin-2-yl)(piperidin-1-yl)methanone |
| 74 (74a, 74b) | 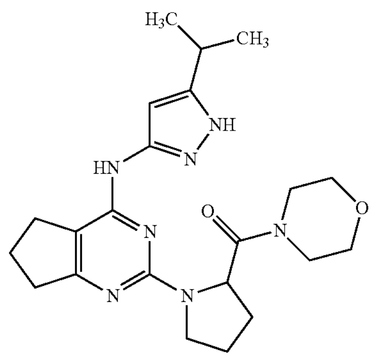 [SMILES: CC(C)c1cc(Nc2nc(N3CCCC3C(=O)N3CCOCC3)nc3c2CCC3)n[nH]1] | (1-(4-(5-isopropyl-1H-pyrazol-3-ylamino)-6,7-dihydro-5H-cyclopenta[d]pyrimidin-2-yl)pyrrolidin-2-yl)(morpholino)methanone |
| 75 (75a, 75b) | 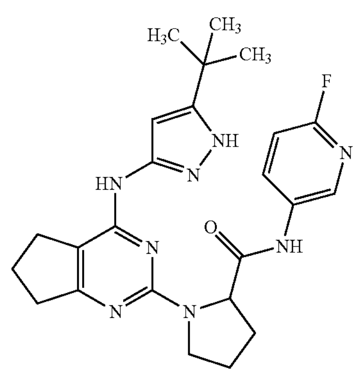 [SMILES: CC(C)(C)c1cc(Nc2nc(N3CCCC3C(=O)Nc3ccc(F)nc3)nc3c2CCC3)n[nH]1] | N-(6-fluoropyridin-3-yl)-1-(4-(5-(2-hydroxypropan-2-yl)-1H-pyrazol-3-ylamino)-6,7-dihydro-5H-cyclopenta[d]pyrimidin-2-yl)pyrrolidine-2-carboxamide |
| 76 (76a, 76b) | 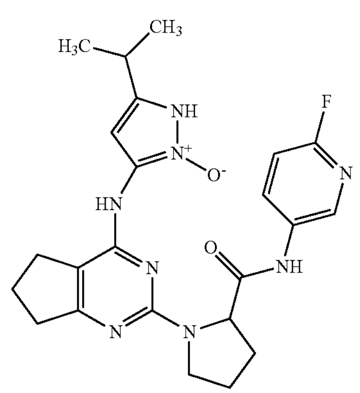 [SMILES: CC(C)c1cc(Nc2nc(N3CCCC3C(=O)Nc3ccc(F)nc3)nc3c2CCC3)[n+]([O-])[nH]1] | 3-(2-(2-(6-fluoropyridin-3-ylcarbamoyl)pyrrolidin-1-yl)-6,7-dihydro-5H-cyclopenta[d]pyrimidin-4-ylamino)-5-isopropyl-1H-pyrazole-2-oxide |

TABLE 1-continued

| Compound No. | Structure | Compound Name |
|---|---|---|
| 77 (77a, 77b) | 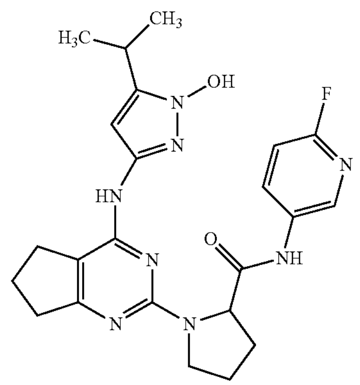 [SMILES: CC(C)c1cc(Nc2nc(N3CCCC3C(=O)Nc3ccc(F)nc3)nc3c2CCC3)nn1O] | N-(6-fluoropyridin-3-yl)-1-(4-(1-hydroxy-5-isopropyl-1H-pyrazol-3-ylamino)-6,7-dihydro-5H-cyclopenta[d]pyrimidin-2-yl)pyrrolidine-2-carboxamide |
| 78 (78a, 78b) | 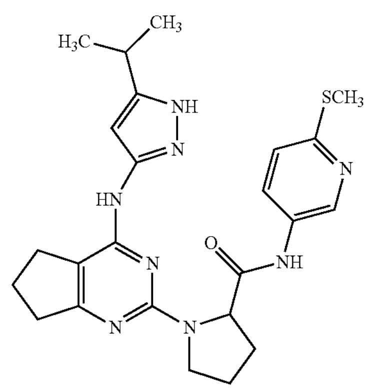 [SMILES: CSc1ccc(NC(=O)C2CCCN2c2nc3c(c(Nc4cc(C(C)C)[nH]n4)n2)CCC3)cn1] | 1-(4-(5-isopropyl-1H-pyrazol-3-ylamino)-6,7-dihydro-5H-cyclopenta[d]pyrimidin-2-yl)-N-(6-(methylthio)pyridin-3-yl)pyrrolidine-2-carboxamide |
| 79 (79a, 79b) | 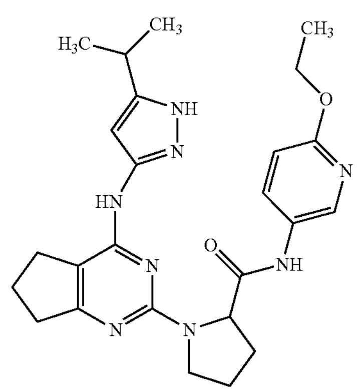 [SMILES: CCOc1ccc(NC(=O)C2CCCN2c2nc3c(c(Nc4cc(C(C)C)[nH]n4)n2)CCC3)cn1] | N-(6-ethoxypyridin-3-yl)-1-(4-(5-isopropyl-1H-pyraozl-3-ylamino)-6,7-dihydro-5H-cyclopenta[d]pyrimidin-2-yl)pyrrolidine-2-carboxamide |

TABLE 1-continued

| Compound No. | Structure | Compound Name |
|---|---|---|
| 80 (80a, 80b) | 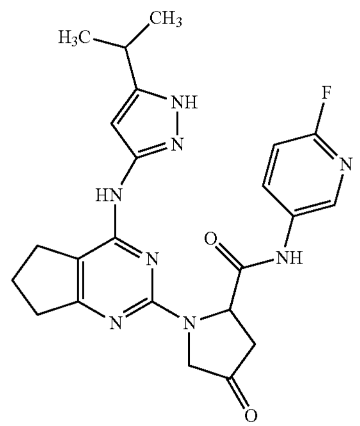 [SMILES: CC(C)c1cc(Nc2nc(N3CC(=O)CC3C(=O)Nc3ccc(F)nc3)nc3c2CCC3)n[nH]1] | N-(6-fluoropyridin-3-yl)-1-(4-(5-isopropyl-1H-pyrazol-3-ylamino)-6,7-dihydro-5H-cyclopenta[d]pyrimidin-2-yl)-4-oxopyrrolidine-2-carboxamide |
| 81 (81a, 81b, 81c, 81d) | 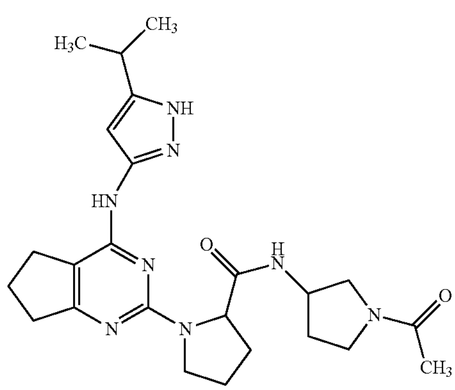 [SMILES: CC(=O)N1CCC(NC(=O)C2CCCN2c2nc3c(c(Nc4cc(C(C)C)[nH]n4)n2)CCC3)C1] | N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide |
| 82 (82a, 82b) | 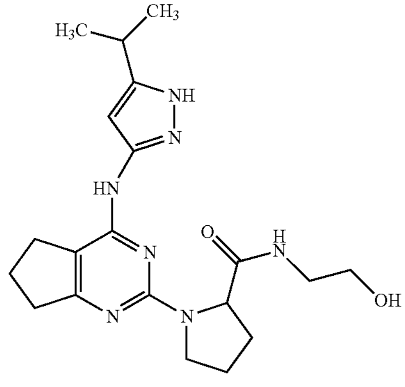 [SMILES: CC(C)c1cc(Nc2nc(N3CCCC3C(=O)NCCO)nc3c2CCC3)n[nH]1] | N-(2-hydroxyethyl)-1-(4-(5-isopropyl-1H-pyrazol-3-ylamino)-6,7-dihydro-5H-cyclopenta[d]pyrimidin-2-yl)pyrrolidine-2-carboxamide |

TABLE 1-continued

| Compound No. | Structure | Compound Name |
|---|---|---|
| 83 (83a, 83b) | 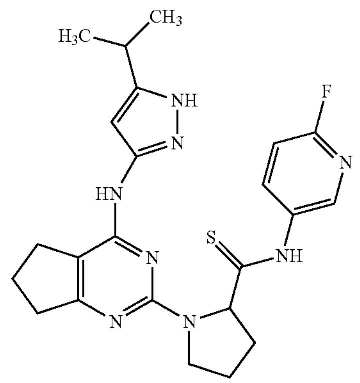 [SMILES: CC(C)c1cc(Nc2nc(N3CCCC3C(=S)Nc3ccc(F)nc3)nc3c2CCC3)n[nH]1] | N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carbothioamide |
| 84 (84a, 84b) | 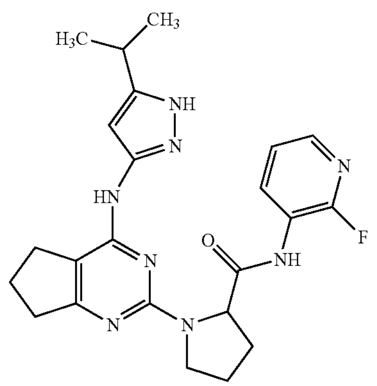 [SMILES: CC(C)c1cc(Nc2nc(N3CCCC3C(=O)Nc3cccnc3F)nc3c2CCC3)n[nH]1] | N-(2-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide |
| 85 (85a, 85b) | 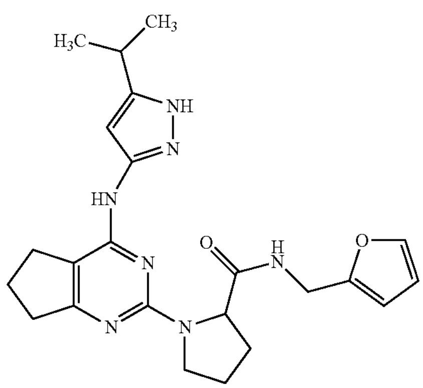 [SMILES: CC(C)c1cc(Nc2nc(N3CCCC3C(=O)NCc3ccco3)nc3c2CCC3)n[nH]1] | N-(furan-2-ylmethyl)-1-(4-(5-isopropyl-1H-pyrazol-3-ylamino)-6,7-dihydro-5H-cyclopenta[d]pyrimidin-2-yl)pyrrolidine-2-carboxamide |
| 86 (86a, 86b) | 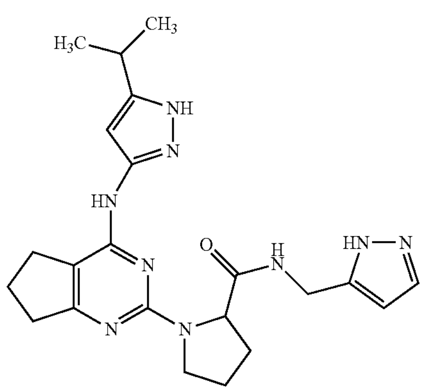 [SMILES: CC(C)c1cc(Nc2nc(N3CCCC3C(=O)NCc3ccn[nH]3)nc3c2CCC3)n[nH]1] | N-((1H-pyrazol-5-yl)methyl)-1-(4-(5-isopropyl-1H-pyrazol-3-ylamino)-6,7-dihydro-5H-cyclopenta[d]pyrimidin-2-yl)pyrrolidine-2-carboxamide |

TABLE 1-continued

| Compound No. | Structure | Compound Name |
|---|---|---|
| 87 (87a, 87b) | 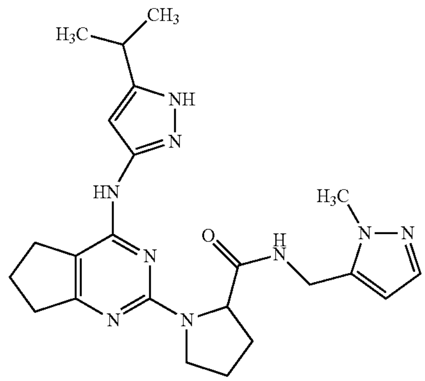 [SMILES: CC(C)c1cc(Nc2nc(N3CCCC3C(=O)NCc3ccnn3C)nc3c2CCC3)n[nH]1] | 1-(4-(5-isopropyl-1H-pyrazol-3-ylamino)-6,7-dihydro-5H-cyclopenta[d]pyrimidin-2-yl)-N-((1-methyl-1H-pyrazol-5-yl)methyl)pyrrolidine-2-carboxamide |
| 88 (88a, 88b) | 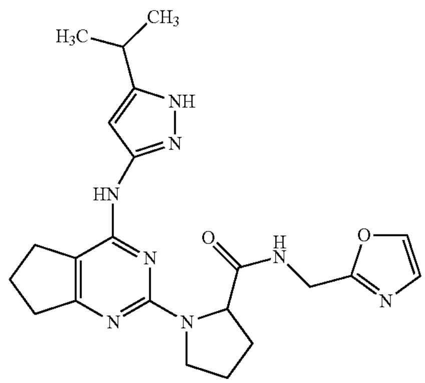 [SMILES: CC(C)c1cc(Nc2nc(N3CCCC3C(=O)NCc3ncco3)nc3c2CCC3)n[nH]1] | 1-(4-(5-isopropyl-1H-pyrazol-3-ylamino)-6,7-dihydro-5H-cyclopenta[d]pyrimidin-2-yl)-N-(oxazol-2-ylmethyl)pyrrolidine-2-carboxamide |
| 89 (89a, 89b) | 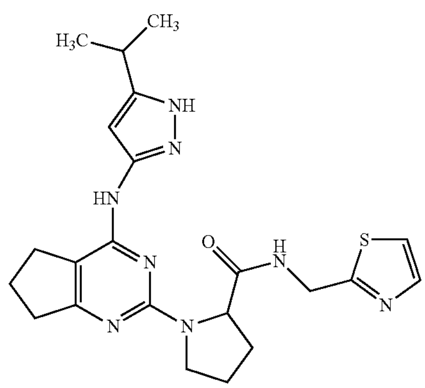 [SMILES: CC(C)c1cc(Nc2nc(N3CCCC3C(=O)NCc3nccs3)nc3c2CCC3)n[nH]1] | 1-(4-(5-isopropyl-1H-pyrazol-3-ylamino)-6,7-dihydro-5H-cyclopenta[d]pyrimidin-2-yl)-N-(thiazol-2-ylmethyl)pyrrolidine-2-carboxamide |
| 90 (90a, 90b, 90c, 90d) | 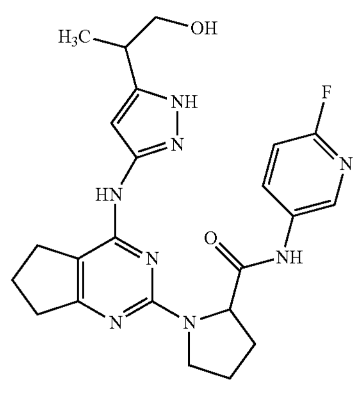 [SMILES: CC(CO)c1cc(Nc2nc(N3CCCC3C(=O)Nc3ccc(F)nc3)nc3c2CCC3)n[nH]1] | N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide |

TABLE 1-continued

| Compound No. | Structure | Compound Name |
|---|---|---|
| 91 (91a, 91b, 91c, 91d) | 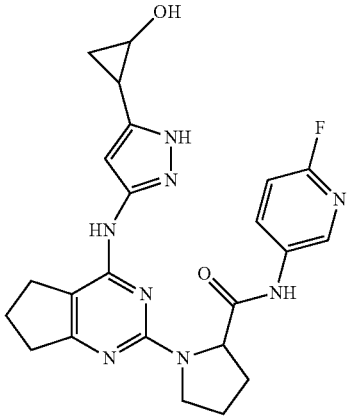 [SMILES: O=C(Nc1ccc(F)nc1)C1CCCN1c1nc2c(c(Nc3cc(C4CC4O)[nH]n3)n1)CCC2] | N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide |
| 92 (92a, 92b, 92c, 92d) | 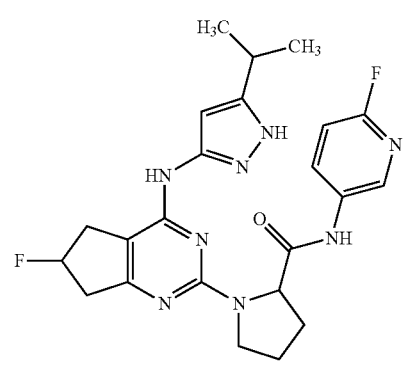 [SMILES: CC(C)c1cc(Nc2nc(N3CCCC3C(=O)Nc3ccc(F)nc3)nc3c2CC(F)C3)n[nH]1] | 1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide |
| 93 (93a, 93b, 93c, 93d) | 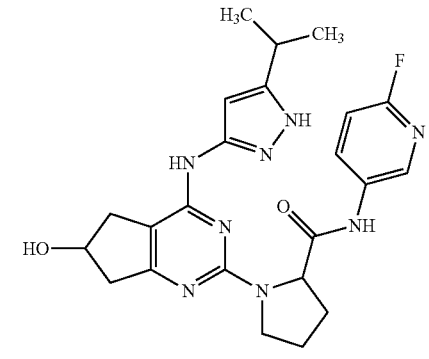 [SMILES: CC(C)c1cc(Nc2nc(N3CCCC3C(=O)Nc3ccc(F)nc3)nc3c2CC(O)C3)n[nH]1] | N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide |
| 94 (94a, 94b, 94c, 94d) | 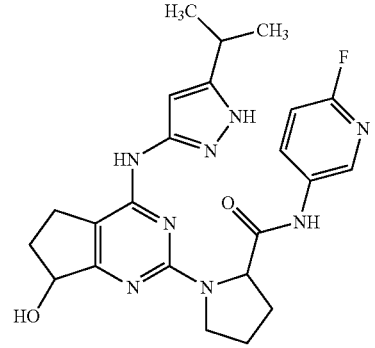 [SMILES: CC(C)c1cc(Nc2nc(N3CCCC3C(=O)Nc3ccc(F)nc3)nc3c2CCC3O)n[nH]1] | N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide |

| Compound No. | Structure | Compound Name |
| --- | --- | --- |
| 95 (95a, 95b) | 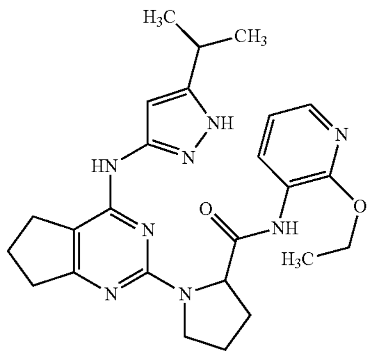 [SMILES: CCOc1ncccc1NC(=O)C1CCCN1c1nc2c(c(Nc3cc(C(C)C)[nH]n3)n1)CCC2] | N-(2-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide |
| 96 (96a, 96b) | 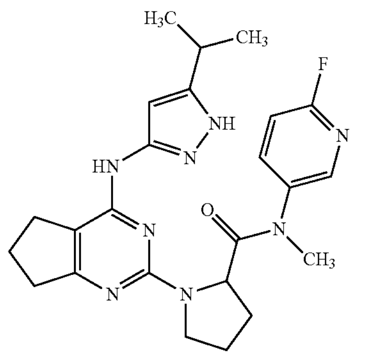 [SMILES: CC(C)c1cc(Nc2nc(N3CCCC3C(=O)N(C)c3ccc(F)nc3)nc3c2CCC3)n[nH]1] | N-(6-fluoropyridin-3-yl)-1-(4-(5-isopropyl-1H-pyrazol-3-ylamino)-6,7-dihydro-5H-cyclopenta[d]pyrimidin-2-yl)-N-methylpyrrolidine-2-carboxamide |

It is understood that the Compound Name listed in Table 1 above refers to the racemic mixture of the compound. However, each of the compounds listed in Table 1 may be resolved into the respective enantiomers and/or diastereomers, if applicable, as shown by the compound number designations a, b, c, d, etc. The compounds of the invention include the following enantiomers and/or diastereomers, if applicable, in its isomerically pure form or in a composition comprising mixtures of compounds of the invention in any ratio, including two or more stereochemical forms, such as in a racemic or non-racemic mixture or a mixture of one or more diastereomers as listed in Table 1 or below:

(R)-1-(4-(5-cyclopropyl-1H-pyrazol-3-ylamino)-6,7-dihydro-5H-cyclopenta[d]pyrimidin-2-yl)-N-(6-fluoropyridin-3-yl)-2-methylpyrrolidine-2-carboxamide;

(S)-1-(4-(5-cyclopropyl-1H-pyrazol-3-ylamino)-6,7-dihydro-5H-cyclopenta[d]pyrimidin-2-yl)-N-(6-fluoropyridin-3-yl)-2-methylpyrrolidine-2-carboxamide;

(R)-1-(4-(5-cyclopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide;

(R)-1-(4-(5-cyclopentyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(S)-1-(4-(5-cyclopentyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)-N-(6-fluoropyridin-3-yl)azetidine-2-carboxamide;

(S)-1-(4-(5-cyclopropyl-1H-pyrazol-3-ylamino)-6,7-dihydro-5H-cyclopenta[d]pyrimidin-2-yl)-N-(6-fluoropyridin-3-yl)azetidine-2-carboxamide;

(R)-1-(4-(5-cyclopropyl-1H-pyrazol-3-ylamino)-6,7-dihydro-5H-cyclopenta[d]pyrimidin-2-yl)-N-(pyrazin-2-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)-N-(pyrazin-2-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)-N-(pyrimidin-5-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)-N-(pyrimidin-5-yl)pyrrolidine-2-carboxamide;

(R)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)-N-(6-fluoropyridin-3-yl)piperidine-2-carboxamide;

(S)-1-(4-(5-cyclopropyl-1H-pyrazol-3-ylamino)-6,7-dihydro-5H-cyclopenta[d]pyrimidin-2-yl)-N-(6-fluoropyridin-3-yl)piperidine-2-carboxamide;

(2R,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;

(2S,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;

(2R,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;

(2S,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;

(2R,3R)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;

(2S,3S)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;

(2R,3S)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;

(2S,3R)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;

(R)—N-(6-fluoropyridin-3-yl)-1-(4-(3-isopropylisoxazol-5-ylamino)-6,7-dihydro-5H-cyclopenta[d]pyrimidin-2-yl)pyrrolidine-2-carboxamide;

(S)—N-(6-fluoropyridin-3-yl)-1-(4-(3-isopropylisoxazol-5-ylamino)-6,7-dihydro-5H-cyclopenta[d]pyrimidin-2-yl)pyrrolidine-2-carboxamide;

(R)—N-(6-fluoropyridin-3-yl)-1-(4-(5-isopropyl-1H-pyrazol-3-ylamino)-5,6,7,8-tetrahydroquinazolin-2-yl)pyrrolidine-2-carboxamide;

(S)—N-(6-fluoropyridin-3-yl)-1-(4-(5-isopropyl-1H-pyrazol-3-ylamino)-5,6,7,8-tetrahydroquinazolin-2-yl)pyrrolidine-2-carboxamide;

(R)-1-(4-(5-cyclopropyl-1H-pyrazol-3-ylamino)-5,6,7,8-tetrahydroquinazolin-2-yl)-N-(6-fluoropyridin-3-yl)pyrrolidine-2-carboxamide;

(S)-1-(4-(5-cyclopropyl-1H-pyrazol-3-ylamino)-5,6,7,8-tetrahydroquinazolin-2-yl)-N-(6-fluoropyridin-3-yl)pyrrolidine-2-carboxamide;

(R)-1-(4-(5-cyclopentyl-1H-pyrazol-3-ylamino)-5,6,7,8-tetrahydroquinazolin-2-yl)-N-(6-fluoropyridin-3-yl)pyrrolidine-2-carboxamide;

(S)-1-(4-(5-cyclopentyl-1H-pyrazol-3-ylamino)-5,6,7,8-tetrahydroquinazolin-2-yl)-N-(6-fluoropyridin-3-yl)pyrrolidine-2-carboxamide;

(R)—N-(6-fluoropyridin-3-yl)-1-(4-(5-isopropyl-1H-pyrazol-3-ylamino)-6,7-dihydro-5H-cyclopenta[d]pyrimidin-2-yl)piperidine-2-carboxamide;

(S)—N-(6-fluoropyridin-3-yl)-1-(4-(5-isopropyl-1H-pyrazol-3-ylamino)-6,7-dihydro-5H-cyclopenta[d]pyrimidin-2-yl)piperidine-2-carboxamide;

(R)-1-(4-(5-cyclopentyl-1H-pyrazol-3-ylamino)-6,7-dihydro-5H-cyclopenta[d]pyrimidin-2-yl)-N-(6-fluoropyridin-3-yl)piperidine-2-carboxamide;

(S)-1-(4-(5-cyclopentyl-1H-pyrazol-3-ylamino)-6,7-dihydro-5H-cyclopenta[d]pyrimidin-2-yl)-N-(6-fluoropyridin-3-yl)piperidine-2-carboxamide;

(R)-1-(4-(5-isopropyl-1H-pyrazol-3-ylamino)-6,7-dihydro-5H-cyclopenta[d]pyrimidin-2-yl)pyrrolidine-2-carboxamide;

(S)-1-(4-(5-isopropyl-1H-pyrazol-3-ylamino)-6,7-dihydro-5H-cyclopenta[d]pyrimidin-2-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-methylpyrrolidine-2-carboxamide;

(S)-1-(4-(5-isopropyl-1H-pyrazol-3-ylamino)-6,7-dihydro-5H-cyclopenta[d]pyrimidin-2-yl)-N-methylpyrrolidine-2-carboxamide;

(R)-1-(4-(5-isopropyl-1H-pyrazol-3-ylamino)-6,7-dihydro-5H-cyclopenta[d]pyrimidin-2-yl)-N,N-dimethylpyrrolidine-2-carboxamide;

(S)-1-(4-(5-isopropyl-1H-pyrazol-3-ylamino)-6,7-dihydro-5H-cyclopenta[d]pyrimidin-2-yl)-N,N-dimethylpyrrolidine-2-carboxamide;

(2R,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;

(2S,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;

(2R,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;

(2S,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;

(R)-1-(4-((5-isopropyl-1H-pyrazol-3-yl)amino)-6,7-dihydro-5H-cyclopenta[d]pyrimidin-2-yl)-N—((R)-pyrrolidin-3-yl)pyrrolidine-2-carboxamide;

(S)-1-(4-((5-isopropyl-1H-pyrazol-3-yl)amino)-6,7-dihydro-5H-cyclopenta[d]pyrimidin-2-yl)-N—((S)-pyrrolidin-3-yl)pyrrolidine-2-carboxamide;

(R)-1-(4-((5-isopropyl-1H-pyrazol-3-yl)amino)-6,7-dihydro-5H-cyclopenta[d]pyrimidin-2-yl)-N—((S)-pyrrolidin-3-yl)pyrrolidine-2-carboxamide;

(S)-1-(4-((5-isopropyl-1H-pyrazol-3-yl)amino)-6,7-dihydro-5H-cyclopenta[d]pyrimidin-2-yl)-N—((R)-pyrrolidin-3-yl)pyrrolidine-2-carboxamide;

(R)-(3-aminoazetidin-1-yl)(1-(4-((5-isopropyl-1H-pyrazol-3-yl)amino)-6,7-dihydro-5H-cyclopenta[d]pyrimidin-2-yl)pyrrolidin-2-yl)methanone;

(S)-(3-aminoazetidin-1-yl)(1-(4-((5-isopropyl-1H-pyrazol-3-yl)amino)-6,7-dihydro-5H-cyclopenta[d]pyrimidin-2-yl)pyrrolidin-2-yl)methanone;

(R)-1-(4-((5-cyclopropyl-1H-pyrazol-3-yl)amino)-6,7-dihydro-5H-cyclopenta[d]pyrimidin-2-yl)-N-(thiazol-2-yl)pyrrolidine-2-carboxamide;

(S)-1-(4-((5-cyclopropyl-1H-pyrazol-3-yl)amino)-6,7-dihydro-5H-cyclopenta[d]pyrimidin-2-yl)-N-(thiazol-2-yl)pyrrolidine-2-carboxamide;

(R)-1-(4-((5-cyclopropyl-1H-pyrazol-3-yl)amino)-6,7-dihydro-5H-cyclopenta[d]pyrimidin-2-yl)-2-methyl-N-(pyrimidin-4-yl)pyrrolidine-2-carboxamide;

(S)-1-(4-((5-cyclopropyl-1H-pyrazol-3-yl)amino)-6,7-dihydro-5H-cyclopenta[d]pyrimidin-2-yl)-2-methyl-N-(pyrimidin-4-yl)pyrrolidine-2-carboxamide;

(R)-1-(4-((5-isopropyl-1H-pyrazol-3-yl)amino)-6,7-dihydro-5H-cyclopenta[d]pyrimidin-2-yl)-N—((R)-piperidin-3-yl)pyrrolidine-2-carboxamide;

(S)-1-(4-((5-isopropyl-1H-pyrazol-3-yl)amino)-6,7-dihydro-5H-cyclopenta[d]pyrimidin-2-yl)-N—((S)-piperidin-3-yl)pyrrolidine-2-carboxamide;

(R)-1-(4-((5-isopropyl-1H-pyrazol-3-yl)amino)-6,7-dihydro-5H-cyclopenta[d]pyrimidin-2-yl)-N—((S)-piperidin-3-yl)pyrrolidine-2-carboxamide;

(S)-1-(4-((5-isopropyl-1H-pyrazol-3-yl)amino)-6,7-dihydro-5H-cyclopenta[d]pyrimidin-2-yl)-N—((R)-piperidin-3-yl)pyrrolidine-2-carboxamide;

(R)—N—((R)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(S)—N—((S)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(R)—N—((S)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(S)—N—((R)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(2R,4R)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;

(2S,4S)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;

(2R,4S)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;

(2S,4R)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;

(R)—N-(6-aminopyridin-3-yl)-1-(4-((5-cyclopropyl-1H-pyrazol-3-yl)amino)-6,7-dihydro-5H-cyclopenta[d]pyrimidin-2-yl)pyrrolidine-2-carboxamide;

(S)—N-(6-aminopyridin-3-yl)-1-(4-((5-cyclopropyl-1H-pyrazol-3-yl)amino)-6,7-dihydro-5H-cyclopenta[d]pyrimidin-2-yl)pyrrolidine-2-carboxamide;

(2R,4R)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2S,4S)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2R,4S)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2S,4R)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2R,4R)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(2S,4S)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(2R,4S)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(2S,4R)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(R)—N-(6-fluoropyridin-3-yl)-1-(4-((5-(1-methylcyclopropyl)-1H-pyrazol-3-yl)amino)-6,7-dihydro-5H-cyclopenta[d]pyrimidin-2-yl)pyrrolidine-2-carboxamide;

(S)—N-(6-fluoropyridin-3-yl)-1-(4-((5-(1-methylcyclopropyl)-1H-pyrazol-3-yl)amino)-6,7-dihydro-5H-cyclopenta[d]pyrimidin-2-yl)pyrrolidine-2-carboxamide;

(R)—N-(6-fluoropyridin-3-yl)-1-(4-((5-isopropyl-1H-pyrazol-3-yl)amino)-6,7-dihydro-5H-cyclopenta[d]pyrimidin-2-yl)-4,4-dimethylpyrrolidine-2-carboxamide (S)—N-(6-fluoropyridin-3-yl)-1-(4-((5-isopropyl-1H-pyrazol-3-yl)amino)-6,7-dihydro-5H-cyclopenta[d]pyrimidin-2-yl)-4,4-dimethylpyrrolidine-2-carboxamide;

(2R,4R)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;

(2S,4S)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;

(2R,4S)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;

(2S,4R)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;

(2R,4R)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;

(2S,4S)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;

(2R,4S)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;

(2S,4R)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;

(2R,4R)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(2S,2S)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(2R,2S)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(2S,4R)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(R)-4,4-difluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(S)-4,4-difluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(R)-3-((2-(2-((6-fluoropyridin-3-yl)carbamoyl)pyrrolidin-1-yl)-6,7-dihydro-5H-cyclopenta[d]pyrimidin-4-yl)amino)-1H-pyrazole-5-carboxamide;

(S)-3-((2-(2-((6-fluoropyridin-3-yl)carbamoyl)pyrrolidin-1-yl)-6,7-dihydro-5H-cyclopenta[d]pyrimidin-4-yl)amino)-1H-pyrazole-5-carboxamide;

(R)—N-(6-fluoropyridin-3-yl)-1-(4-((1-isopropyl-1H-imidazol-4-yl)amino)-6,7-dihydro-5H-cyclopenta[d]pyrimidin-2-yl)pyrrolidine-2-carboxamide;

(S)—N-(6-fluoropyridin-3-yl)-1-(4-((1-isopropyl-1H-imidazol-4-yl)amino)-6,7-dihydro-5H-cyclopenta[d]pyrimidin-2-yl)pyrrolidine-2-carboxamide;

(2R,4R)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;

(2S,4S)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;

(2R,4S)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;

(2S,4R)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;

(R)-2-((2-(2-((6-fluoropyridin-3-yl)carbamoyl)pyrrolidin-1-yl)-6,7-dihydro-5H-cyclopenta[d]pyrimidin-4-yl)amino)oxazole-5-carboxamide;

(S)-2-((2-(2-((6-fluoropyridin-3-yl)carbamoyl)pyrrolidin-1-yl)-6,7-dihydro-5H-cyclopenta[d]pyrimidin-4-yl)amino)oxazole-5-carboxamide;

(R)-N-(6-fluoropyridin-3-yl)-1-(4-((5-(1-hydroxycyclopropyl)-1H-pyrazol-3-yl)amino)-6,7-dihydro-5H-cyclopenta[d]pyrimidin-2-yl)pyrrolidine-2-carboxamide;

(S)-N-(6-fluoropyridin-3-yl)-1-(4-((5-(1-hydroxycyclopropyl)-1H-pyrazol-3-yl)amino)-6,7-dihydro-5H-cyclopenta[d]pyrimidin-2-yl)pyrrolidine-2-carboxamide;

(2R,4R)-N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;

(2S,4S)-N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;

(2R,4S)-N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;

(2S,4R)-N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;

(R)-2-((2-(2-((6-fluoropyridin-3-yl)carbamoyl)pyrrolidin-1-yl)-6,7-dihydro-5H-cyclopenta[d]pyrimidin-4-yl)amino)thiazole-5-carboxamide;

(S)-2-((2-(2-((6-fluoropyridin-3-yl)carbamoyl)pyrrolidin-1-yl)-6,7-dihydro-5H-cyclopenta[d]pyrimidin-4-yl)amino)thiazole-5-carboxamide;

(R)-N-(6-fluoropyridin-3-yl)-1-(4-((2-isopropyl-1H-imidazol-5-yl)amino)-6,7-dihydro-5H-cyclopenta[d]pyrimidin-2-yl)pyrrolidine-2-carboxamide;

(S)-N-(6-fluoropyridin-3-yl)-1-(4-((2-isopropyl-1H-imidazol-5-yl)amino)-6,7-dihydro-5H-cyclopenta[d]pyrimidin-2-yl)pyrrolidine-2-carboxamide;

(R)-N-(6-fluoropyridin-3-yl)-1-(4-((5-isopropyl-1H-pyrazol-3-yl)amino)-5,5-dimethyl-6,7-dihydro-5H-cyclopenta[d]pyrimidin-2-yl)pyrrolidine-2-carboxamide;

(S)-N-(6-fluoropyridin-3-yl)-1-(4-((5-isopropyl-1H-pyrazol-3-yl)amino)-5,5-dimethyl-6,7-dihydro-5H-cyclopenta[d]pyrimidin-2-yl)pyrrolidine-2-carboxamide;

(R)-N-(6-fluoropyridin-3-yl)-1-(4-((5-isopropyl-1H-pyrazol-3-yl)amino)-7,7-dimethyl-6,7-dihydro-5H-cyclopenta[d]pyrimidin-2-yl)pyrrolidine-2-carboxamide;

(S)-N-(6-fluoropyridin-3-yl)-1-(4-((5-isopropyl-1H-pyrazol-3-yl)amino)-7,7-dimethyl-6,7-dihydro-5H-cyclopenta[d]pyrimidin-2-yl)pyrrolidine-2-carboxamide;

(R)-N-(6-fluoropyridin-3-yl)-1-(4-((5-isopropyl-1H-pyrazol-3-yl)amino)-5,7-dihydrospiro[cyclopenta[d]pyrimidine-6,1'-cyclopropan]-2-yl)pyrrolidine-2-carboxamide;

(S)-N-(6-fluoropyridin-3-yl)-1-(4-((5-isopropyl-1H-pyrazol-3-yl)amino)-5,7-dihydrospiro[cyclopenta[d]pyrimidine-6,1'-cyclopropan]-2-yl)pyrrolidine-2-carboxamide;

(R)-N-(6-fluoropyridin-3-yl)-1-(4-((5-isopropyl-1H-pyrazol-3-yl)amino)-6-oxo-6,7-dihydro-5H-cyclopenta[d]pyrimidin-2-yl)pyrrolidine-2-carboxamide;

(S)-N-(6-fluoropyridin-3-yl)-1-(4-((5-isopropyl-1H-pyrazol-3-yl)amino)-6-oxo-6,7-dihydro-5H-cyclopenta[d]pyrimidin-2-yl)pyrrolidine-2-carboxamide;

(R)-N-(6-fluoropyridin-3-yl)-1-(4-((5-isopropyl-1H-pyrazol-3-yl)amino)-6,6-dimethyl-6,7-dihydro-5H-cyclopenta[d]pyrimidin-2-yl)pyrrolidine-2-carboxamide;

(S)-N-(6-fluoropyridin-3-yl)-1-(4-((5-isopropyl-1H-pyrazol-3-yl)amino)-6,6-dimethyl-6,7-dihydro-5H-cyclopenta[d]pyrimidin-2-yl)pyrrolidine-2-carboxamide;

(R)-1-(6,6-difluoro-4-((5-isopropyl-1H-pyrazol-3-yl)amino)-6,7-dihydro-5H-cyclopenta[d]pyrimidin-2-yl)-N-(6-fluoropyridin-3-yl)pyrrolidine-2-carboxamide;

(S)-1-(6,6-difluoro-4-((5-isopropyl-1H-pyrazol-3-yl)amino)-6,7-dihydro-5H-cyclopenta[d]pyrimidin-2-yl)-N-(6-fluoropyridin-3-yl)pyrrolidine-2-carboxamide;

(R)-N-(6-fluoropyridin-3-yl)-1-(4-((5-isopropyl-1H-pyrazol-3-yl)amino)-5,7-dihydrospiro[cyclopenta[d]pyrimidine-6,2'-oxiran]-2-yl)pyrrolidine-2-carboxamide;

(S)-N-(6-fluoropyridin-3-yl)-1-(4-((5-isopropyl-1H-pyrazol-3-yl)amino)-5,7-dihydrospiro[cyclopenta[d]pyrimidine-6,2'-oxiran]-2-yl)pyrrolidine-2-carboxamide;

(R)-N-(6-fluoropyridin-3-yl)-1-(4-((5-isopropyl-1H-pyrazol-3-yl)amino)-6-thioxo-6,7-dihydro-5H-cyclopenta[d]pyrimidin-2-yl)pyrrolidine-2-carboxamide;

(S)-N-(6-fluoropyridin-3-yl)-1-(4-((5-isopropyl-1H-pyrazol-3-yl)amino)-6-thioxo-6,7-dihydro-5H-cyclopenta[d]pyrimidin-2-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)pyrrolidine-2-carboxamide;

(R)-N-(6-fluoropyridin-3-yl)-1-(4-((5-isopropyl-1H-pyrazol-3-yl)amino)-6,7-dihydro-5H-cyclopenta[d]pyrimidin-2-yl)-N-methylpyrrolidine-2-carboxamide;

(S)-N-(6-fluoropyridin-3-yl)-1-(4-((5-isopropyl-1H-pyrazol-3-yl)amino)-6,7-dihydro-5H-cyclopenta[d]pyrimidin-2-yl)-N-methylpyrrolidine-2-carboxamide;

(R)-1-(4-((5-cyclopropyl-1H-pyrazol-3-yl)amino)-5,6,7,8-tetrahydroquinazolin-2-yl)-N-(thiazol-2-yl)pyrrolidine-2-carboxamide;

(S)-1-(4-((5-cyclopropyl-1H-pyrazol-3-yl)amino)-5,6,7,8-tetrahydroquinazolin-2-yl)-N-(thiazol-2-yl)pyrrolidine-2-carboxamide;

(R)-1-(4-((5-cyclopropyl-1H-pyrazol-3-yl)amino)-6,7,8,9-tetrahydro-5H-cyclohepta[d]pyrimidin-2-yl)-N-(thiazol-2-yl)pyrrolidine-2-carboxamide;

(S)-1-(4-((5-cyclopropyl-1H-pyrazol-3-yl)amino)-6,7,8,9-tetrahydro-5H-cyclohepta[d]pyrimidin-2-yl)-N-(thiazol-2-yl)pyrrolidine-2-carboxamide;

(2R,4R)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid;

(2S,4S)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid;

(2R,4S)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid;

(2S,4R)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid;

(2R,4R)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;

(2S,4S)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;
(2R,4S)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;
(2S,4R)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate
(R)-2-fluoro-5-(1-(4-((5-isopropyl-1H-pyrazol-3-yl)amino)-6,7-dihydro-5H-cyclopenta[d]pyrimidin-2-yl)pyrrolidine-2-carboxamido)pyridine 1-oxide;
(S)-2-fluoro-5-(1-(4-((5-isopropyl-1H-pyrazol-3-yl)amino)-6,7-dihydro-5H-cyclopenta[d]pyrimidin-2-yl)pyrrolidine-2-carboxamido)pyridine 1-oxide;
(R)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 1-oxide;
(S)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 1-oxide;
(R)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 3-oxide;
(S)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 3-oxide;
(R)—N-(6-hydroxypyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(S)—N-(6-hydroxypyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(R)-1-(4-((5-isopropyl-1H-pyrazol-3-yl)amino)-6,7-dihydro-5H-cyclopenta[d]pyrimidin-2-yl)-N-(6-oxo-1,6-dihydropyridin-3-yl)pyrrolidine-2-carboxamide;
(S)-1-(4-((5-isopropyl-1H-pyrazol-3-yl)amino)-6,7-dihydro-5H-cyclopenta[d]pyrimidin-2-yl)-N-(6-oxo-1,6-dihydropyridin-3-yl)pyrrolidine-2-carboxamide;
(R)-1-((R)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(S)-1-((S)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(R)-1-((S)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(S)-1-((R)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(R)-1-((5R,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(R)-1-((5R,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(R)-1-((5S,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(R)-1-((5S,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(S)-1-((5R,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(S)-1-((5R,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(S)-1-((5S,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(S)-1-((5S,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(R)-1-(4-((5-hydroxy-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(S)-1-(4-((5-hydroxy-1H-pyrazol-3-yl)amino)-6,7-dihydro-5H-cyclopenta[d]pyrimidin-2-yl)-N-(6-hydroxypyridin-3-yl)pyrrolidine-2-carboxamide;
(R)-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;
(S)-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;
(R)-1-(4-(5-isopropyl-1H-pyrazol-3-ylamino)-6,7-dihydro-5H-cyclopenta[d]pyrimidin-2-yl)-N-(pyrimidin-4-yl)pyrrolidine-2-carboxamide;
(S)-1-(4-(5-isopropyl-1H-pyrazol-3-ylamino)-6,7-dihydro-5H-cyclopenta[d]pyrimidin-2-yl)-N-(pyrimidin-4-yl)pyrrolidine-2-carboxamide;
(2R,4R)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;
(2R,4S)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;
(2S,4R)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;
(2S,4S)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;
(2R,4R)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;
(2R,4S)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;
(2S,4R)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;
(2S,4S)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide
(R)—N-(6-aminopyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(S)—N-(6-aminopyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(R)-(1-(4-(5-isopropyl-1H-pyrazol-3-ylamino)-6,7-dihydro-5H-cyclopenta[d]pyrimidin-2-yl)pyrrolidin-2-yl)(piperidin-1-yl)methanone;

(S)-(1-(4-(5-isopropyl-1H-pyrazol-3-ylamino)-6,7-dihydro-5H-cyclopenta[d]pyrimidin-2-yl)pyrrolidin-2-yl)(piperidin-1-yl)methanone;

(R)-(1-(4-(5-isopropyl-1H-pyrazol-3-ylamino)-6,7-dihydro-5H-cyclopenta[d]pyrimidin-2-yl)pyrrolidin-2-yl)(morpholino)methanone;

(S)-(1-(4-(5-isopropyl-1H-pyrazol-3-ylamino)-6,7-dihydro-5H-cyclopenta[d]pyrimidin-2-yl)pyrrolidin-2-yl)(morpholino)methanone;

(R)—N-(6-fluoropyridin-3-yl)-1-(4-(5-(2-hydroxypropan-2-yl)-1H-pyrazol-3-ylamino)-6,7-dihydro-5H-cyclopenta[d]pyrimidin-2-yl)pyrrolidine-2-carboxamide;

(S)—N-(6-fluoropyridin-3-yl)-1-(4-(5-(2-hydroxypropan-2-yl)-1H-pyrazol-3-ylamino)-6,7-dihydro-5H-cyclopenta[d]pyrimidin-2-yl)pyrrolidine-2-carboxamide;

(R)-3-(2-(2-(6-fluoropyridin-3-ylcarbamoyl)pyrrolidin-1-yl)-6,7-dihydro-5H-cyclopenta[d]pyrimidin-4-ylamino)-5-isopropyl-1H-pyrazole 2-oxide;

(S)-3-(2-(2-(6-fluoropyridin-3-ylcarbamoyl)pyrrolidin-1-yl)-6,7-dihydro-5H-cyclopenta[d]pyrimidin-4-ylamino)-5-isopropyl-1H-pyrazole 2-oxide;

(R)—N-(6-fluoropyridin-3-yl)-1-(4-(1-hydroxy-5-isopropyl-1H-pyrazol-3-ylamino)-6,7-dihydro-5H-cyclopenta[d]pyrimidin-2-yl)pyrrolidine-2-carboxamide;

(S)—N-(6-fluoropyridin-3-yl)-1-(4-(1-hydroxy-5-isopropyl-1H-pyrazol-3-ylamino)-6,7-dihydro-5H-cyclopenta[d]pyrimidin-2-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(6-(methylthio)pyridin-3-yl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(6-(methylthio)pyridin-3-yl)pyrrolidine-2-carboxamide;

(R)—N-(6-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(6-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-(6-fluoropyridin-3-yl)-1-(4-(5-isopropyl-1H-pyrazol-3-ylamino)-6,7-dihydro-5H-cyclopenta[d]pyrimidin-2-yl)-4-oxopyrrolidine-2-carboxamide;

(S)—N-(6-fluoropyridin-3-yl)-1-(4-(5-isopropyl-1H-pyrazol-3-ylamino)-6,7-dihydro-5H-cyclopenta[d]pyrimidin-2-yl)-4-oxopyrrolidine-2-carboxamide;

(R,R)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R,S)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S,R)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S,S)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-(2-hydroxyethyl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(2-hydroxyethyl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carbothioamide;

(S)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carbothioamide;

(R)—N-(2-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(2-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-(furan-2-ylmethyl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(furan-2-ylmethyl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-((1H-pyrazol-5-yl)methyl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-((1H-pyrazol-5-yl)methyl)-1-(4-(5-isopropyl-1H-pyrazol-3-ylamino)-6,7-dihydro-5H-cyclopenta[d]pyrimidin-2-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-((1-methyl-1H-pyrazol-5-yl)methyl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-((1-methyl-1H-pyrazol-5-yl)methyl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(oxazol-2-ylmethyl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(oxazol-2-ylmethyl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(thiazol-2-ylmethyl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(thiazol-2-ylmethyl)pyrrolidine-2-carboxamide;

(R,R)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;

(R,S)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;

(S,R)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;

(S,S)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;

(R,R)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;

(R,S)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;
(S,R)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;
(S,S)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;
(R,R)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(R,S)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(S,R)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(S,S)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(R,R)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;
(R,S)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;
(S,R)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;
(S,S)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;
(R,R)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;
(R,S)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;
(S,R)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;
(S,S)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;
(R)—N-(2-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(S)—N-(2-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide
(R)—N-(6-fluoropyridin-3-yl)-1-(4-(5-isopropyl-1H-pyrazol-3-ylamino)-6,7-dihydro-5H-cyclopenta[d]pyrimidin-2-yl)-N-methylpyrrolidine-2-carboxamide; and
(S)—N-(6-fluoropyridin-3-yl)-1-(4-(5-isopropyl-1H-pyrazol-3-ylamino)-6,7-dihydro-5H-cyclopenta[d]pyrimidin-2-yl)-N-methylpyrrolidine-2-carboxamide.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

General Synthesis of Compounds of Formula (I)

Compounds of Formula (I) can be prepared according to the Scheme below. Appropriately functionalized beta-keto esters can be cyclized with urea to form dihydroxy pyrimidine products which, when subjected to chlorination conditions, yield the dichloropyrimidine derivatives. Treatment with appropriately functionalized amines $E-NH_2$, provide the 4-amino-substituted pyrimidine which, upon reaction with various amino-acid moieties give the 2,4-diaminopyrimidine compound. Conversion of the amino-acid moiety to an ester intermediate with Alkyl-OH reagents is followed by reaction with an amine of the type $DN(R^D)H$, yield compounds of Formula (I).

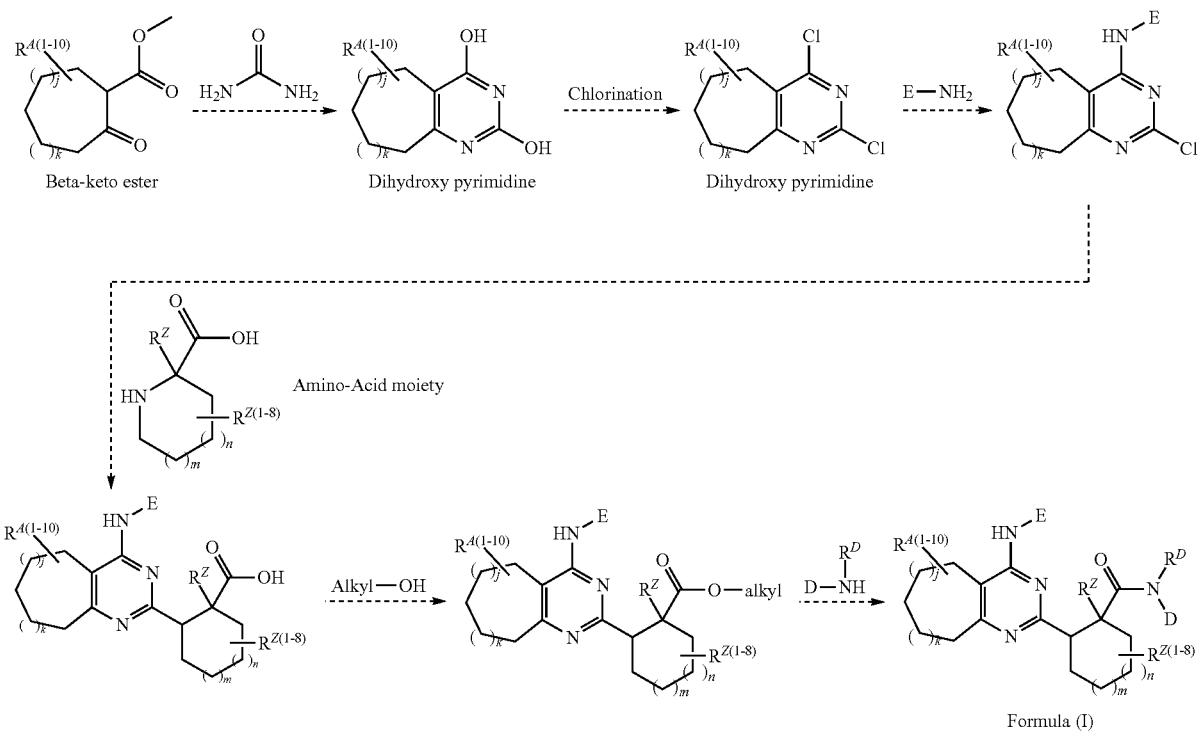

Formula (I)

Beta-keto esters, such as, but not limited to, the following are either available or can be prepared by several routes known to those skilled in the art:

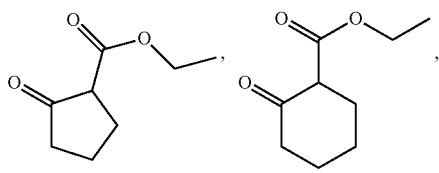

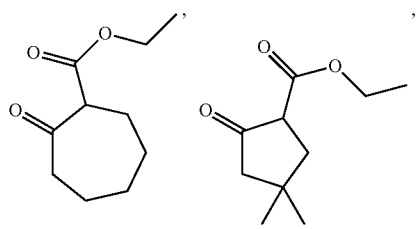

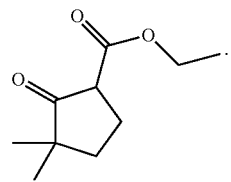

Examples of "E-NH$_2$" such as, but not limited to, the following are either available or can be synthesized by several routes known to those skilled in the art:

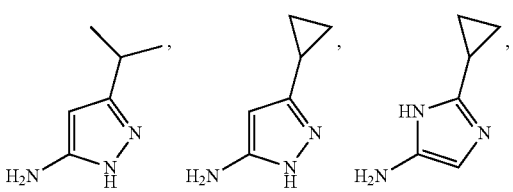

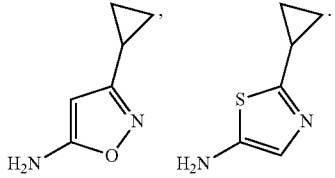

Numerous examples of cyclic amino-acids are available; typical examples discussed herein include, but are not limited to, the following:

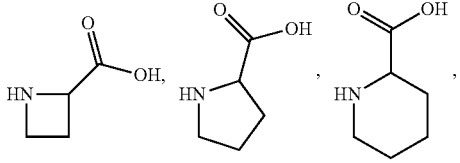

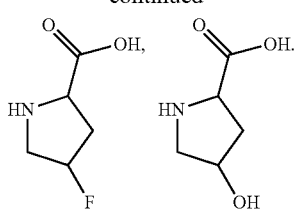
Examples of DN(R^D)H are available; typical examples discussed herein include, but are not limited to, the following:
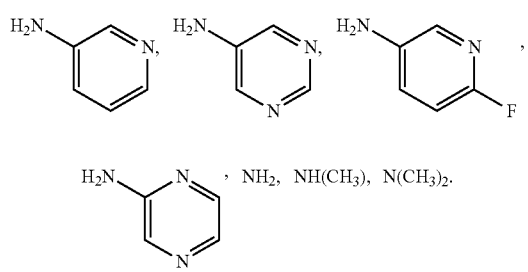
In one embodiment, the synthesis of compounds of Formula (v) is described below.
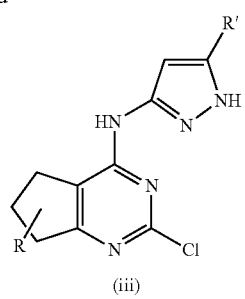
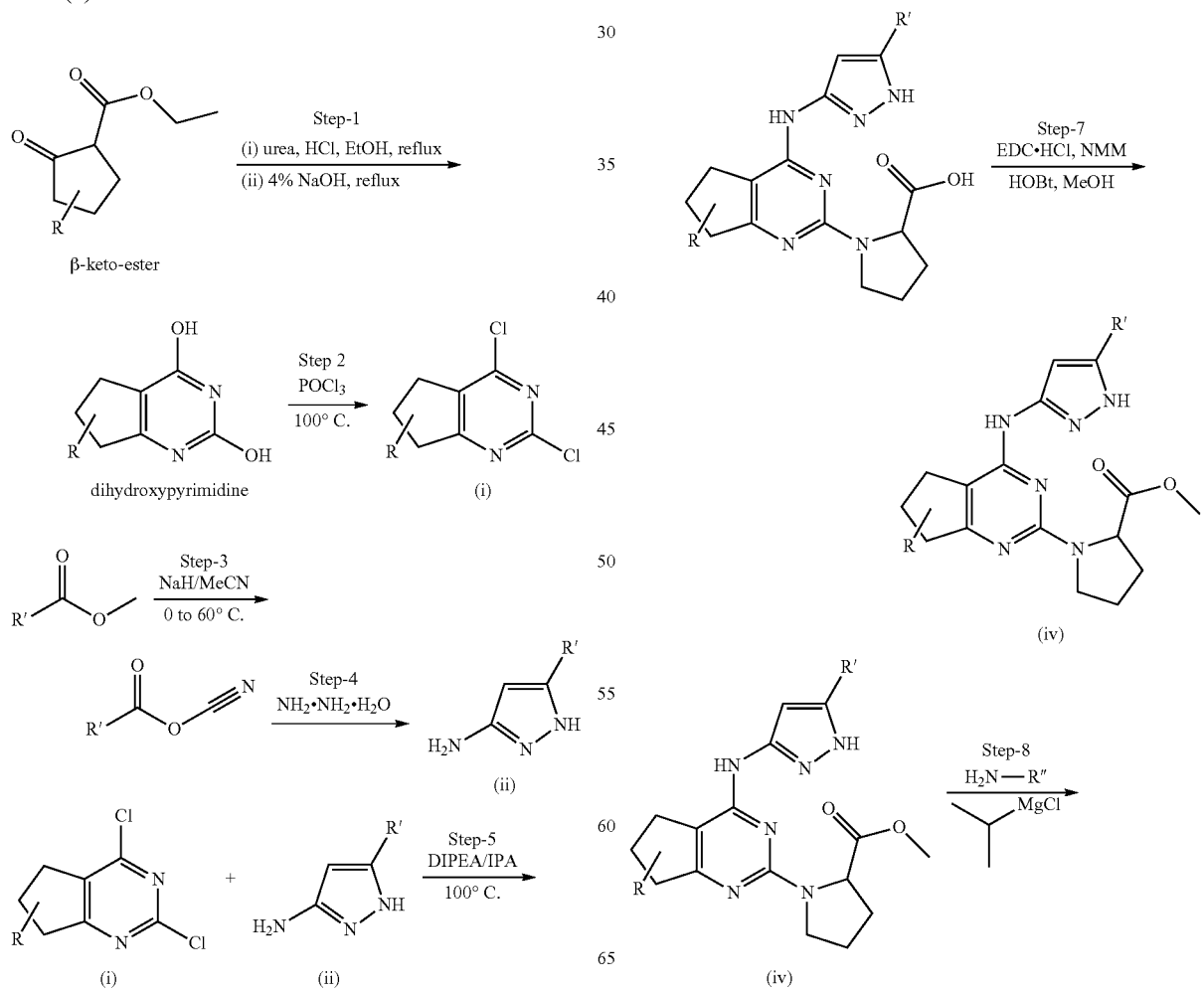

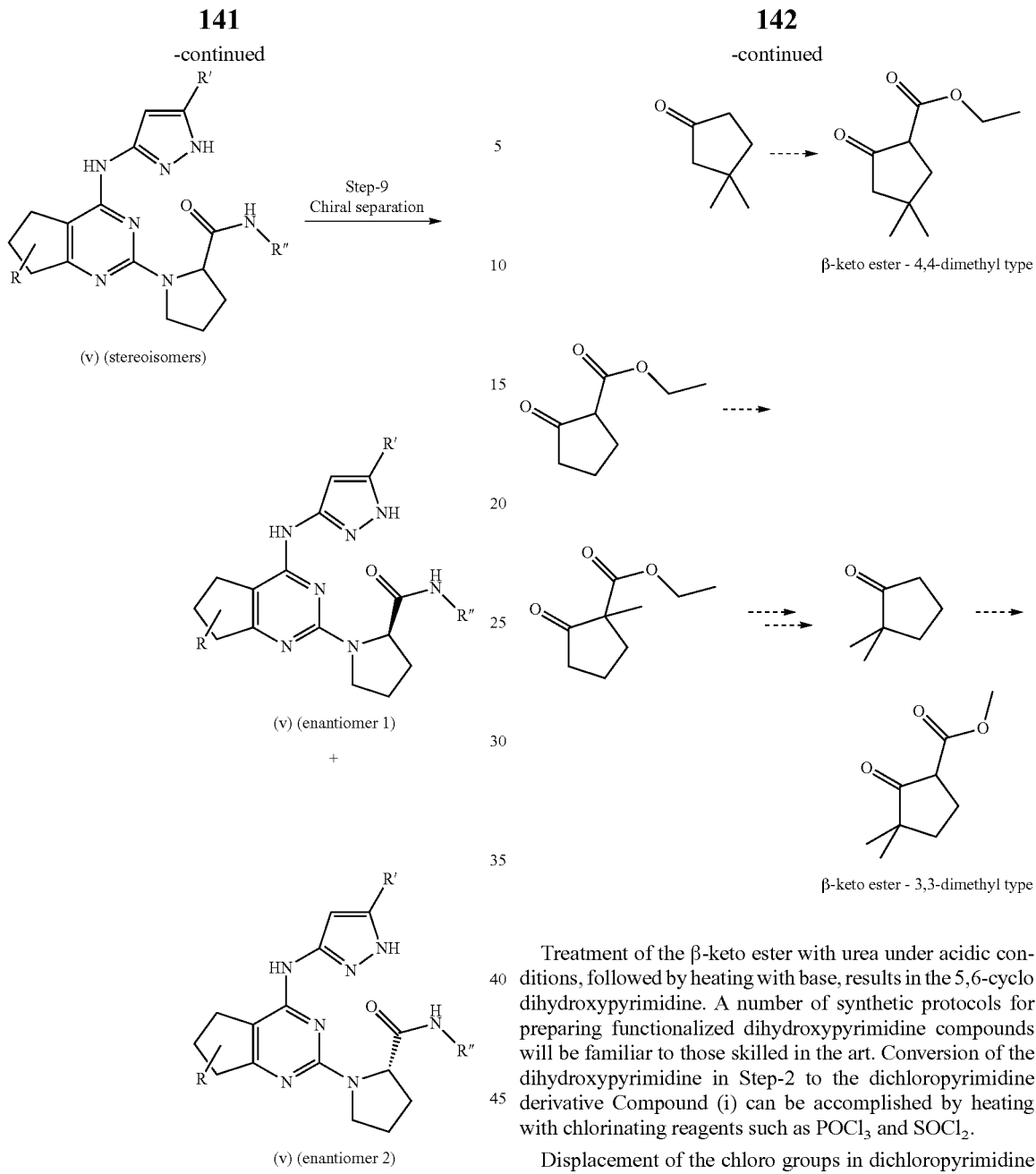

In certain examples of formula (I) provided herein, and as similarly described in the publications presented herein, compounds (i) to (v) can be prepared by the steps as illustrated above.

Step-1 commences with appropriately functionalized cyclic β-keto esters which, if not commercially available, can be prepared according to methods well-known in the art. As examples discussed herein, could be synthesized through routes shown below.

Treatment of the β-keto ester with urea under acidic conditions, followed by heating with base, results in the 5,6-cyclo dihydroxypyrimidine. A number of synthetic protocols for preparing functionalized dihydroxypyrimidine compounds will be familiar to those skilled in the art. Conversion of the dihydroxypyrimidine in Step-2 to the dichloropyrimidine derivative Compound (i) can be accomplished by heating with chlorinating reagents such as $POCl_3$ and $SOCl_2$.

Displacement of the chloro groups in dichloropyrimidine compounds typically proceeds initially at the more labile 4-chloro position, followed by the 2-chloro position. As discussed herein, Compound (i) is treated initially with appropriately functionalized amino compounds such as Compound (ii). Step-3 and Step-4 illustrate the preparation of a functionalized amino pyrazole, by treatment of an ester with acetonitrile under basic conditions, followed by cyclization with hydrazine to give Compound (ii). Some examples of functionalized pyrazoles can include for example:

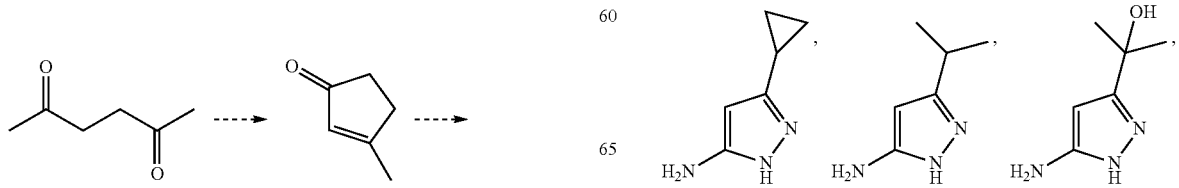

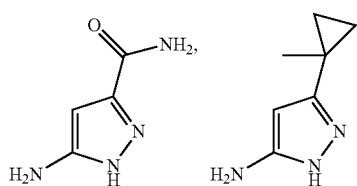

Step-5 indicates that treatment of Compound (i) with Compound (ii) under basic, polar conditions results in the 4-amino-substituted intermediate Compound (iii). A skilled person will be familiar with a range of both basic and acidic means for achieving this substitution. While functionalized pyrazoles have been illustrated above, other functionalized amines can be considered such as amino-imidazoles, amino-thioimidazoles, amino-oxazoles, and the like.

Treatment of Compound (iii) with appropriately functionalized amino compounds such as various amino acids, illustrated here with Proline in Step-6, provides the 2,4-diaminopyrimidine compound, which in Step-7 is converted to the ester Compound (iv), under standard esterification conditions. It is also possible that Step-7 could be by-passed, dependent upon the nature of the remainder of the molecular structure and whether direct conversion of the acid to the amide is achievable synthetically, under standard amino acid coupling conditions with amines to form amides. A number of alternative amino acids such as functionalized Proline compounds of the type illustrated here that are commercially available, could be considered:

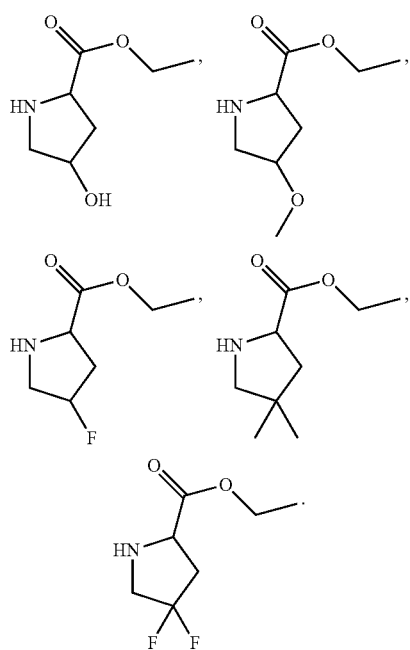

Step-8 completes the synthetic treatment of Compound (iv) with functionalized amines of the type R'''—NH$_2$, typically under basic conditions known in the art for converting esters to amides, resulting in Compound (v). A large number of commercially available amines could be considered for this step, for illustration such as the following:

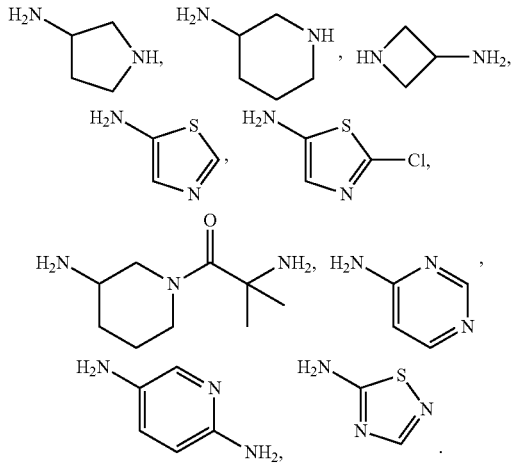

A skilled artisan will appreciate that the use of amino acids bearing a chiral center in Step-6, and discussed in the Examples herein, will result in stereoisomeric products that, dependent upon the appropriate chirality of the reagents and/or the conditions required to complete conversion of the intermediate compounds, will result in either single stereoisomeric products, or mixtures of stereoisomers that may require chiral separation by practical means known in the art. Step-9 indicates the separation of any stereoisomeric mixture of isomers of Compound (v), to yield the desired individual enantiomer or diastereomer, depending on the number of stereocenters present.

In some embodiments, compounds of the formula (I) are synthesized according to Scheme 1, following Steps 1-6 as described below. Thus provided is also a process for making a compound of the formula (I) comprising steps 1-6. In each of 1.1, 1.2, 1.3, 1.4, 1.5, 1.6, 1.7, 1.7a, 1.8, 1.8a, and 1.8b of Scheme 1, the substituents D, E, j, k, m, n, $R^{A1}$, $R^{A2}$, $R^{A3}$, $R^{A4}$, $R^{A5}$, $R^{A6}$, $R^{A7}$, $R^{A8}$, $R^{A9}$, $R^{A10}$, $R^D$, $R^Z$, X, $R^{Z1}$, $R^{Z2}$, $R^{Z3}$, $R^{Z4}$, $R^{Z5}$, $R^{Z6}$, $R^{Z7}$, $R^{Z8}$, p, $R^1$, $R^2$, $R^3$, $R^4$, $R^5$, $R^6$, $R^7$, $R^8$, and $R^9$ are as described for Formula (I) or any applicable variation thereof.

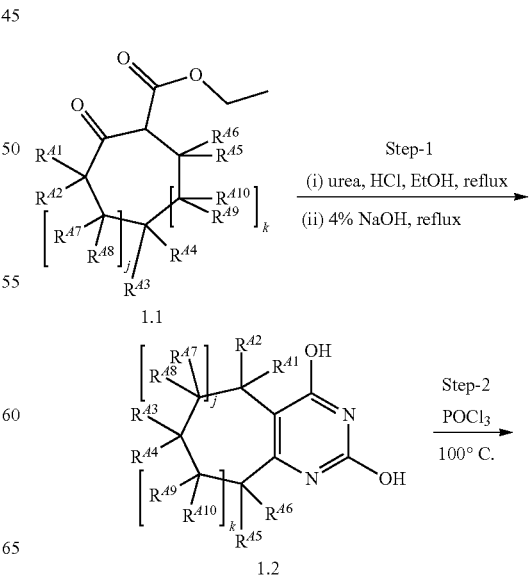

-continued

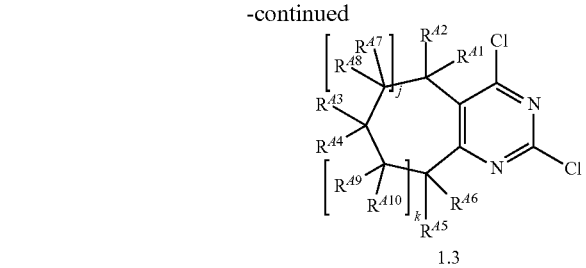

1.3

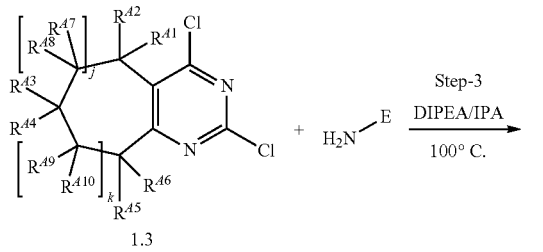

1.3 + H$_2$N—E  $\xrightarrow[\text{100° C.}]{\text{Step-3}\\\text{DIPEA/IPA}}$

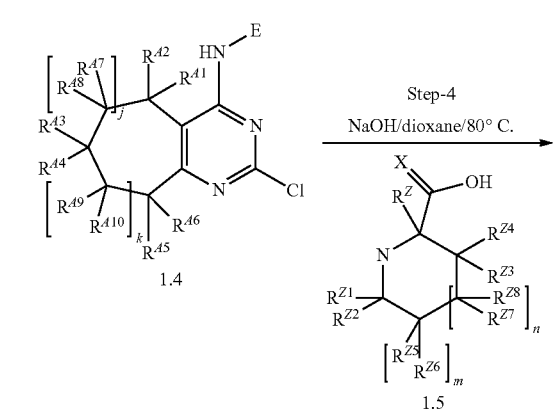

1.4 + <image on right with OH> 1.5  $\xrightarrow[\text{NaOH/dioxane/80° C.}]{\text{Step-4}}$

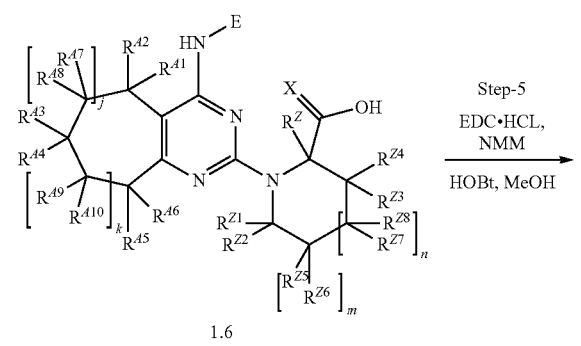

1.6  $\xrightarrow[\text{HOBt, MeOH}]{\text{Step-5}\\\text{EDC·HCL,}\\\text{NMM}}$

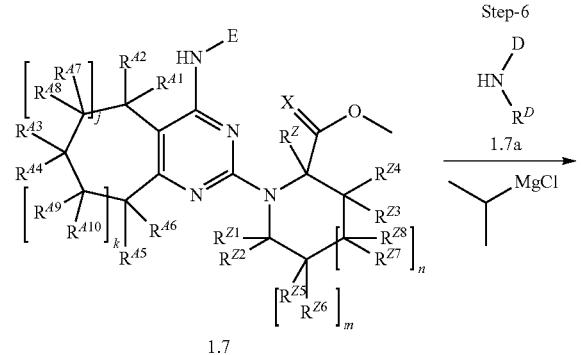

1.7  $\xrightarrow[\text{MgCl}]{\text{Step-6}\\\text{1.7a}}$

-continued

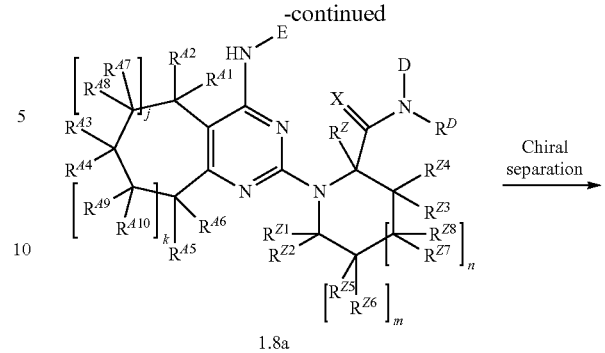

1.8a  $\xrightarrow{\text{Chiral separation}}$ 1.8a
+
1.8b

Step-1: Synthesis of Compound 1.2

Compound 1.1 and urea are combined in a suitable solvent such as EtOH, cooled in an ice-bath, and concentrated HCl is added dropwise. After completion of the addition, the ice bath is removed and the reaction mixture stirred at RT for 30 min. The reaction mixture is then heated to reflux for 5 h. The reaction mixture is cooled to RT, and the EtOH was decanted to give a crystalline solid. The solid is heated to reflux with aqueous 5% NaOH solution for 2 h. The reaction mixture is cooled to RT and the precipitate collected by filtration. The precipitate is washed with water and dried to afford compound 1.2.

Step-2: Synthesis of Compound 1.3

A suspension of compound 1.2 in POCl$_3$ is stirred at 100° C. for 3 h. The reaction mixture is cooled to RT and poured slowly with constant shaking into crushed ice to quench the excess of POCl$_3$. The aqueous layer is extracted with EtOAc. The combined organic layer is washed with water and dried over anhydrous Na$_2$SO$_4$. Removal of EtOAc under reduced pressure affords compound 1.3.

Step-3: Synthesis of Compound 1.4

N,N-diisopropylethyl amine is added to a solution of compound 1.3 in isopropanol followed by addition of compound E-NH$_2$ (5.89 g, 47 mmol). The reaction mixture is heated to reflux at 100° C. for 16 h. The reaction mixture is cooled to RT. The precipitated product is filtered and washed with hexane to afford compound 1.4.

Step-4: Synthesis of Compound 1.6

Compound 1.5 is added to a suspension of compound 1.4 in dioxane followed by 5N NaOH and N,N-diisopropylethyl amine. The reaction mixture is allowed to stir at 80° C. for 16 h. The solvent is removed under reduced pressure and the residue is acidified with 1 N HCl solution to pH 4. The product is suspended in water, filtered, washed with ether and dried to afford compound 1.6.

Step-5: Synthesis of Compound 1.7

To a solution of 1.6 in MeOH (120 mL) is added HOBt.H$_2$O, N-methylmorpholine and EDC.HCl. The reaction mixture is stirred at RT overnight. The MeOH is removed under reduced pressure and the residue is dissolved in EtOAc. The solution is washed with water followed by brine and dried over anhydrous sodium sulfate. Removal of EtOAc under reduced pressure affords compound 1.7.

Step-6: Synthesis of Compound 1.8

To a solution of compound NHDR$^D$ in dry THF is added a 2M solution of isopropylmagnesium chloride in THF dropwise under nitrogen at 0° C. The resultant mixture is stirred at 0° C. for 20 min. To this solution is added a solution of 1.7 in THF (20 mL) dropwise at 0° C. and the reaction mixture is stirred at RT for 2 h. The reaction is quenched with saturated ammonium chloride solution (50 mL). The product is extracted with EtOAc and the organic layer is dried over anhydrous sodium sulfate. Removal of EtOAc under reduced pressure gives a solid residue that is purified by column chromatography on silica gel using a 1-2% MeOH-DCM system as eluent to afford compound 1.8, followed by chiral purification to afford enantiomers 1.8a and 1.8b.

Further Embodiments of the Invention

In one embodiment, the invention relates to Compounds described in Table 1, and uses thereof.

In another embodiment, the invention relates to Compounds 1-59, and stereoisomers thereof, and uses thereof.

The embodiments and variations described herein are suitable for compounds of any formulae detailed herein, where applicable.

Representative examples of compounds detailed herein, including intermediates and final compounds according to the invention are depicted in the tables below. It is understood that in one aspect, any of the compounds may be used in the methods detailed herein, including, where applicable, intermediate compounds that may be isolated and administered to an individual. In some embodiments, embraced are compounds of the formulae 1.1, 1.2, 1.3, 1.4, 1.5, 1.6, 1.7, 1.7a, 1.8, 1.8a, and 1.8b of Scheme 1, where D, E, j, k, m, n, $R^{41}$, $R^{42}$, $R^{43}$, $R^{44}$, $R^{45}$, $R^{46}$, $R^{47}$, $R^{48}$, $R^{49}$, $R^{410}$, $R^D$, $R^Z$, X, $R^{Z1}$, $R^{Z2}$, $R^{Z3}$, $R^{Z4}$, $R^{Z5}$, $R^{Z6}$, $R^{Z7}$, $R^{Z8}$, p, $R^1$, $R^2$, $R^3$, $R^4$, $R^5$, $R^6$, $R^7$, $R^8$, and $R^9$, where applicable, are as described for Formula (I) or any applicable variation thereof.

The compounds depicted herein may be present as salts even if salts are not depicted and it is understood that the invention embraces all salts and solvates of the compounds depicted here, as well as the non-salt and non-solvate form of the compound, as is well understood by the skilled artisan. In some embodiments, the salts of the compounds of the invention are pharmaceutically acceptable salts. Where one or more tertiary amine moiety is present in the compound, the N-oxides are also provided and described. For example, exemplary N-oxide compounds include:

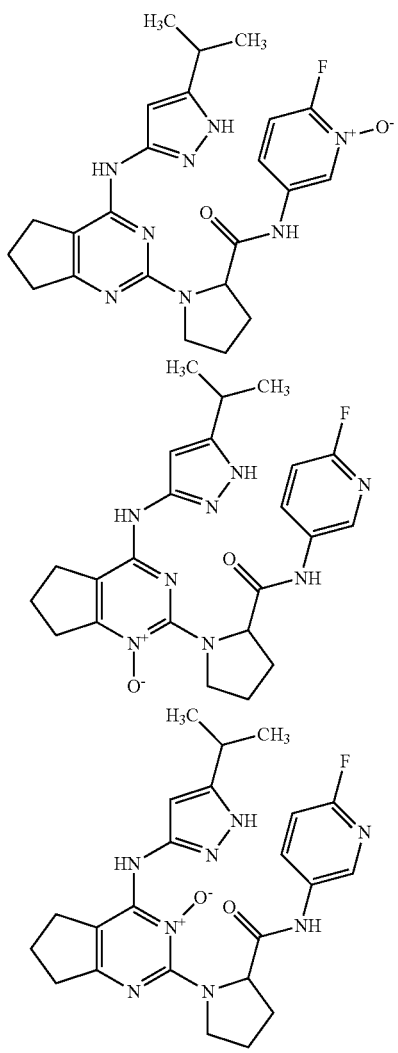

Where tautomeric forms may be present for any of the compounds described herein, each and every tautomeric form is intended even though only one or some of the tautomeric forms may be explicitly depicted. For example, when a 5-cyclopropyl-1H-pyrazol-3-yl moiety is depicted, the corresponding 3-cyclopropyl-1H-pyrazol-5-yl tautomer is also intended. The tautomeric forms specifically depicted may or may not be the predominant forms in solution or when used according to the methods described herein.

The invention also includes any or all of the stereochemical forms, including any enantiomeric or diastereomeric forms of the compounds described. The structure or name is intended to embrace all possible stereoisomers of a compound depicted, and each unique stereoisomer has a compound number bearing a suffix "a", "b", etc. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also includes any or all metabolites of any of the compounds described. The metabolites may include any chemical species generated by a biotransformation of any of the compounds described, such as intermediates and products of metabolism of the compound. In addition to compounds described herein, those skilled in the art would appreciate that typical metabolites of a compound such as, for example, Compound No. 8 could include, but are not limited to, the following:

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a

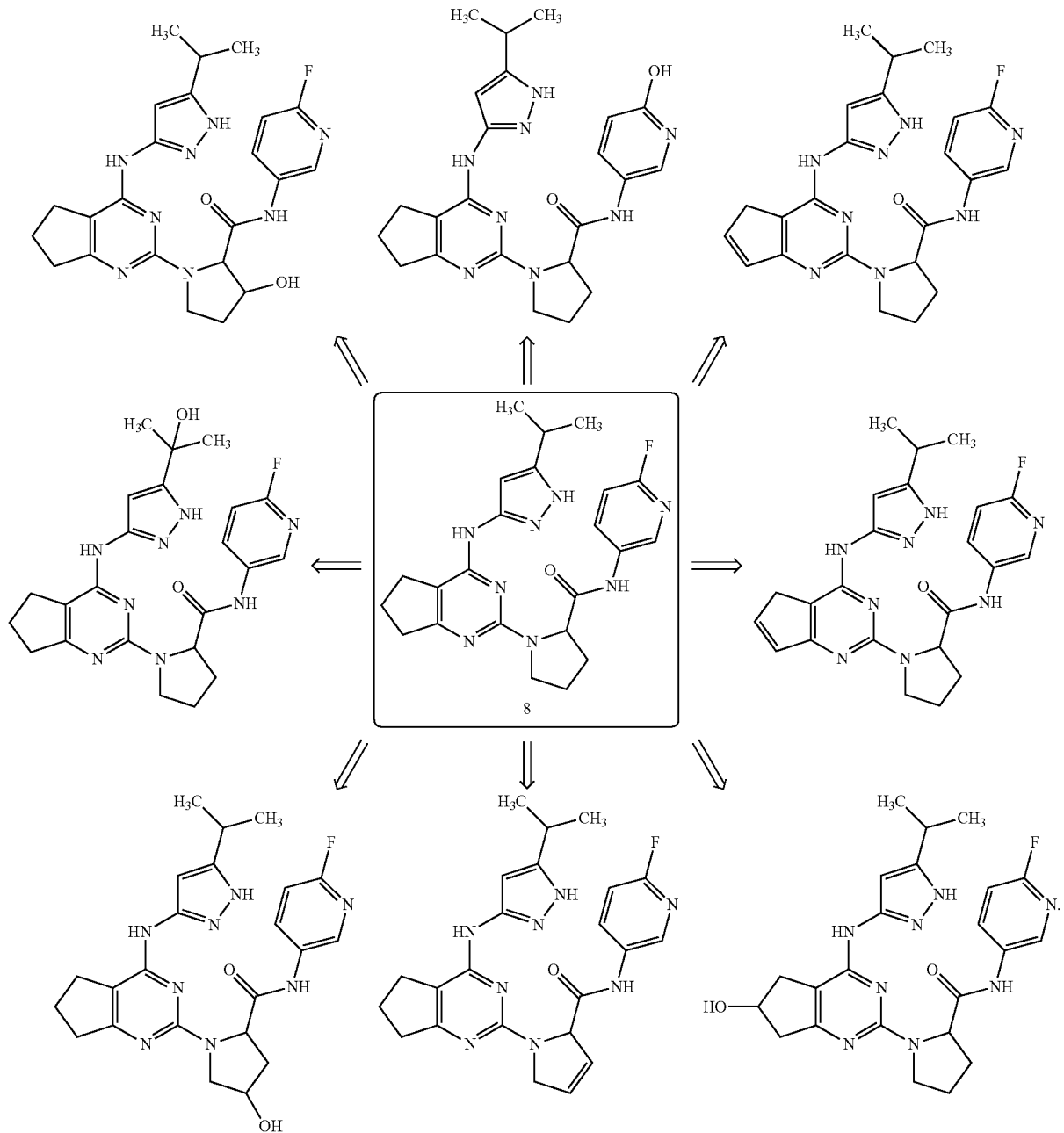

Articles of manufacture comprising a compound of the invention, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

medicament is for use in any of the methods disclosed herein, e.g., for the treatment of cancer.

Pharmaceutical Compositions and Formulations

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. Taking compound 1 as an example, a composition of substantially pure compound 1 intends a composition that contains no more than 35% impurity, wherein the impurity denotes a compound other than compound 1 or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., $20^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound and a pharmaceutically acceptable carrier or excipient. In another variation, a composition of substantially pure compound is provided.

Methods of Use

Compounds and compositions of the invention, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In one aspect, the invention provides a method of inhibiting IGF-IR and/or IR comprising administering to an individual an effective amount of one or more compounds of the invention, or a salt thereof (e.g., a pharmaceutically acceptable salt). In one aspect of the method, a compound of the invention or salt thereof inhibits binding of a ligand to the IGF-IR and/or IR receptor and/or reduces or eliminates or increases or enhances or mimics an activity of the IGF-IR and/or IR receptor in a reversible or irreversible manner. In some aspects, a compound of the invention inhibits binding of a ligand to the IGF-IR and/or IR receptor by at least about or by about any one of 10%, 20%, 30%, 40%, 50%, 60%, 70%, 80%, 90%, 95% or 100% as determined by an assay described herein. In some aspects, a compound of the invention reduces an activity of the IGF-IR and/or IR receptor by at least about or about any of 10%, 20%, 30%, 40%, 50%, 60%, 70%, 80%, 90%, 95% or 100% as compared to the corresponding activity in the same subject prior to treatment with the receptor modulator or compared to the corresponding activity in other subjects not receiving the compound. In one aspect, the individual has or is believed to have a disorder in which IGF-IR and/or IR is implicated. In some embodiments, the compound or salt thereof inhibits IGF-IR. In some embodiments, the compound or salt thereof inhibits IR. In certain embodiments, the compound or salt thereof inhibits both IGF-IR and IR. In certain variations, a compound or composition of the invention is used to treat or prevent an IGF-IR and/or IR related disorder, such as cancer. In one aspect, the method comprises administering to the individual a compound provided herein, or a pharmaceutically acceptable salt thereof, including but not limited to a compound of the invention such as a compound according to any one or more of formulae I; I-A; IIa-IIw; IIIa-IIIw; IVa-IVw; and Va-Vhh; or a compound of Table 1 or an isomer thereof, or a salt (such as a pharmaceutically acceptable salt) of any of the foregoing. In one aspect, the individual is a human in need of cancer treatment.

Unless clearly indicated otherwise, the term "individual" as used herein refers to a mammal, including but not limited to, bovine, horse, feline, rabbit, canine, rodent, or primate (e.g., human). In some embodiments, an individual is a human. In some embodiments, an individual is a non-human primate such as chimpanzees and other apes and monkey species. In some embodiments, an individual is a farm animal such as cattle, horses, sheep, goats and swine; pets such as rabbits, dogs and cats; laboratory animals including rodents, such as rats, mice, and guinea pigs; and the like. The invention may find use in both human medicine and in the veterinary context.

The invention additionally provides methods of inhibiting the phosphorylation of AKT comprising administering to an individual an effective amount of one or more compounds of the invention, or a salt thereof. In some aspects of the method, a compound detailed herein inhibits the phosphorylation of AKT by at least about or by about any one of 10%, 20%, 30%, 40%, 50%, 60%, 70%, 80%, 90%, 95% or 100% as determined by an assay described herein. In some aspects, a compound detailed herein inhibits the phosphorylation of AKT by at least about or about any of 10%, 20%, 30%, 40%, 50%, 60%, 70%, 80%, 90%, 95% or 100% as compared to the corresponding activity in the same subject prior to treatment with the compound or compared to the corresponding activity in other subjects not receiving the compound. In one aspect, the individual has or is believed to have a disorder in which AKT phosphorylation is implicated. In certain variations, inhibiting the phosphorylation of AKT is used to treat or prevent a disorder in which AKT phosphorylation is implicated, such as cancer. In one aspect, the method comprises administering to the individual a compound provided herein, or a pharmaceutically acceptable salt thereof, including but not limited to a compound of the invention such as a compound according to any one or more of formulae I; I-A; IIa-IIw; IIIa-IIIw; IVa-IVw; and Va-Vhh; or a compound of Table 1 or an isomer thereof, or a salt (such as a pharmaceutically acceptable salt) of any of the foregoing.

The invention also provides methods for modulating the activity of a protein kinase comprising administering an effective amount of one or more compounds of the invention, or a salt thereof, to an individual. In one aspect, a method of modulating a protein kinase selected from the kinases of Tables B7-B13 are provided. In some embodiments, the protein kinase comprises one or more protein serine/threonine kinases or one or more protein tyrosine kinases. In some embodiments, the protein kinase comprises one or more protein kinase provided in the accompanying Examples, e.g., one or more protein kinase of Example B3. In some embodiments, the protein tyrosine kinase is selected from the group consisting of IGF-IR, IR, AXL, FAK2, Mer, Met, TrkB, and TrkC. In some embodiments, the protein serine/threonine kinase is selected from the group consisting of AURA, AURB, and AURC. In one aspect, the method comprises administering to the individual a compound provided herein, or a pharmaceutically acceptable salt thereof, including but not limited to a compound of the invention such as a compound according to any one or more of formulae I; I-A; IIa-IIw; IIIa-IIIw; IVa-IVw; and Va-Vhh; or a compound of Table 1 or an isomer thereof, or a salt (such as a pharmaceutically acceptable salt) of any of the foregoing.

The invention additionally provides methods for treating cancer in an individual (e.g., human) comprising administering to the individual an effective amount of a compound of the invention or a pharmaceutically acceptable salt thereof or a composition comprising the compound or salt thereof. In one aspect, the method comprises administering to the individual a compound provided herein, or a pharmaceutically acceptable salt thereof, including but not limited to a compound of the invention such as a compound according to any one or more of formulae I; I-A; IIa-IIw; IIIa-IIIw; IVa-IVw; and Va-Vhh; or a compound of Table 1 or an isomer thereof, or a salt (such as a pharmaceutically acceptable salt) of any of the foregoing. TrkC and the members of the TAM family of receptor tyrosine kinases (AXL, Mer and Met) have been widely implicated in tumorigenesis and progression of several cancers and proposed as therapeutic targets for the treatment of prostate, breast, lung, renal, pancreatic cancers, neuroblastoma, medulloblastoma, head and neck carcinoma and acute myeloid leukemia. In contrast, inhibition of aurora kinase family members AURA, AURB and AURC has been associated with adverse effects like grade 3 neutropenia, a significant drop in the white blood cell count. The invention also provides methods for modulating selectively the activity of protein tyrosine kinase receptors of IGF-IR, IR, AXL, FAK2, Mer, Met, TrkB, and TrkC with lower levels or absence of inhibition of members of Aurora kinase family. The invention also provides methods for preventing, and/or delaying the onset and/or development of cancer in an individual (e.g., human) comprising administering to the individual an effective amount of a compound of the invention or a pharmaceutically acceptable salt thereof or a composition comprising the compound or salt thereof.

In one variation, a method of treating cancer in an individual (e.g., human) is provided comprising administering to the individual an effective amount of a compound of the invention or a pharmaceutically acceptable salt thereof, wherein the cancer is dependent on a kinase signaling pathway (e.g., a signaling pathway of any of the kinases of Tables B7-B13). In one variation, a method of treating cancer in an individual (e.g., human) is provided comprising administering to the individual an effective amount of a compound of the invention or a pharmaceutically acceptable salt thereof, wherein the cancer is dependent on the IGF-IR signaling pathway. In another variation, a method of treating cancer in an individual (e.g., human) is provided comprising administering to the individual an effective amount of a compound of the invention or a pharmaceutically acceptable salt thereof, wherein the cancer is characterized by depending on IGF-IR signaling for survival and/or proliferation. In yet another variation, a method of treating cancer in an individual (e.g., human) is provided comprising administering to the individual an effective amount of a compound of the invention or a pharmaceutically acceptable salt thereof, wherein the cancer cells overexpress IGF-IR as compared to non-cancerous cells, e.g., as compared to non-cancerous cells of the same cell type.

In some embodiments, the amount of the compound or pharmaceutically acceptable salt thereof that is administered to an individual is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the cancer that may be treated is a solid tumor such as sarcomas and carcinomas. In some embodiments, the cancer that may be treated is a liquid tumor such as leukemia. Examples of cancers that may be treated by methods of the invention include, but are not limited to, breast cancer, prostate cancer, ovarian cancer, lung cancer, colon cancer, brain tumors, gastric cancer, liver cancer, thyroid cancer, endometrial cancer, gallbladder cancer, kidney cancer, adrenocortical cancer, sarcoma, skin cancer, head and neck cancer, leukemia, bladder cancer, colorectal cancer, hematopoietic cancer and pancreatic cancer. In some embodiments, the breast cancer is breast carcinoma (ER negative or ER positive), primary breast ductal carcinoma, mammary adenocarcinoma, mammary ductal carcinoma (ER positive, ER negative or HER2 positive), HER2 positive breast cancer, luminal breast cancer or triple negative breast cancer (TNBC). In some embodiments, the breast cancer is unclassified. In some embodiments, the triple negative breast cancer is a basal-like TNBC, a mesenchymal TNBC (mesenchymal or mesenchymal stem-like), an immunomodulatory TNBC, or a luminal androgen receptor TNBC. In some embodiments, the prostate cancer is prostate adenocarcinoma. In some embodiments, the ovarian cancer is ovary adenocarcinoma. In some embodiments, the lung cancer is lung carcinoma, non-small lung carcinoma, adenocarcinoma, mucoepidermoid, anaplastic, large cell, or unclassified. In some embodiments, the colon cancer is colon adenocarcinoma, colon adenocarcinoma from a metastatic site lymph node, metastatic colorectal cancer, or colon carcinoma. In some embodiments, a brain tumor is glioblastoma, astrocytoma, meduloblastoma, meningioma or neuroblastoma. In some embodiments, gastric cancer is stomach cancer. In some embodiments, liver cancer is hepatocellular carcinoma, hepatoblastoma or cholangiocarcinoma. In some embodiments, liver cancer is hepatitis B virus-derived. In some embodiments, liver cancer is virus negative. In some embodiments, thyroid cancer is papillary thyroid carcinoma, follicular thyroid cancer or medullary thyroid cancer. In some embodiments, endometrial cancer is high grade endometroid cancer, uterine papillary serous carcinoma or uterine clear cell carcinoma. In some embodiments, gallbladder cancer is gallbladder adenocarcinoma or squamous cell gallbladder carcinoma. In some embodiments, kidney cancer is renal cell carcinoma or urothelial cell carcinoma. In some embodiments, adrenocortical cancer is adrenal cortical carcinoma. In some embodiments, sarcoma is synovial sarcoma, osteosarcoma, rhabdomiosarcoma, fibrosarcoma or Ewing's sarcoma. In some embodiments, skin cancer is basal cell carcinoma, squamous carcinoma or melanoma. In some embodiments, head and neck cancer is oropharyngeal cancer, nasopharyngeal cancer, laryngeal cancer and cancer of the trachea. In some embodiments, the leukemia is acute promyelocytic leukemia, acute lymphoblastic leukemia, chronic lymphocytic leukemia, chronic myelogenous leukemia, mantle cell lymphoma or multiple myeloma. In some embodiments, the leukemia is acute promyelocytic leukemia, acute lymphoblastic leukemia, chronic lymphocytic leukemia, chronic myelogenous leukemia, mantle cell lymphoma or multiple myeloma.

The invention additionally provides a method for treating a tumor comprising contacting the tumor with an effective amount of one or more compounds of the invention, or a salt thereof. In one aspect of the method, a compound or salt thereof is administered to an individual in need of tumor treatment. Exemplary tumors are derived from carcinomas of the breast, prostate, ovary, lung, or colon. In one aspect, the treatment results in a reduction of the tumor size. In another aspect, the treatment slows or prevents tumor growth and/or metastasis.

The invention further provides methods for treating a hematopoietic malignancy comprising administering an effective amount of one or more compounds of the invention to an individual in need thereof. In some embodiments, the hematopoietic malignancy is acute promyelocytic leukemia.

Any of the methods of treatment provided herein may be used to treat a primary tumor. Any of the methods of treatment provided herein may also be used to treat a metastatic cancer (that is, cancer that has metastasized from the primary tumor). Any of the methods of treatment provided herein may be used to treat cancer at an advanced stage. Any of the methods of treatment provided herein may be used to treat cancer at a locally advanced stage. Any of the methods of treatment provided herein may be used to treat early stage cancer. Any of the methods of treatment provided herein may be used to treat cancer in remission. In some of the embodiments of any of the methods of treatment provided herein, the cancer has reoccurred after remission. In some embodiments of any of the methods of treatment provided herein, the cancer is progressive cancer.

Any of the methods of treatment provided herein may be used to treat an individual (e.g., human) who has been diagnosed with or is suspected of having cancer. In some embodiments, the individual may be a human who exhibits one or more symptoms associated with cancer. In some embodiments, the individual may have advanced disease or a lesser extent of disease, such as low tumor burden. In some embodiments, the individual is at an early stage of a cancer. In some embodiments, the individual is at an advanced stage of cancer. In some of the embodiments of any of the methods of treatment provided herein, the individual may be a human who is genetically or otherwise predisposed (e.g., has one or more so-called risk factors) to developing cancer who has or has not been diagnosed with cancer. In some embodiments, these risk factors include, but are not limited to, age, sex, race, diet, history of previous disease, presence of precursor disease, genetic (e.g., hereditary) considerations, and environmental exposure. In some embodiments, the individuals at risk for cancer include, e.g., those having relatives who have experienced this disease, and those whose risk is determined by analysis of genetic or biochemical markers. In some embodiments, the individual does not have type I diabetes. In some embodiments, the individual does not have type II diabetes with sustained hyperglycemia or type II diabetes with hyperglycemia for prolonged duration (e.g., for several years).

Any of the methods of treatment provided herein may be practiced in an adjuvant setting. In some embodiments, any of the methods of treatment provided herein may be used to treat an individual who has previously been treated for cancer, e.g., with one or more other therapies such as radiation, surgery or chemotherapy. Any of the methods of treatment provided herein may be used to treat an individual who has not previously been treated for cancer. Any of the methods of treatment provided herein may be used to treat an individual at risk for developing cancer, but who has not been diagnosed with cancer. Any of the methods of treatment provided herein may be used as a first line therapy. Any of the methods of treatment provided herein may be used as a second line therapy.

Any of the methods of treatment provided herein in one aspect reduce the severity of one or more symptoms associated with cancer by at least about any of 10%, 20%, 30%, 40%, 50%, 60%, 70%, 80%, 90%, 95% or 100% compared to the corresponding symptom in the same subject prior to treatment or compared to the corresponding symptom in other subjects not receiving a compound or composition of the invention.

Any of the methods of treatment provided herein may be used to treat, stabilize, prevent, and/or delay any type or stage of cancer. In some embodiments, the individual is at least about any of 40, 45, 50, 55, 60, 65, 70, 75, 80, or 85 years old. In some embodiments, one or more symptoms of the cancer are ameliorated or eliminated. In some embodiments, the size of a tumor, the number of cancer cells, or the growth rate of a tumor decreases by at least about any of 10%, 20%, 30%, 40%, 50%, 60%, 70%, 80%, 90%, 95% or 100%. In some embodiments, the cancer is delayed or prevented.

In some embodiments, a compound or composition of the invention may be used to treat or prevent cancer in conjunction with a second therapy useful to reduce one or more side effects associated with administering the compound or composition of the invention. In some embodiments, the second compound for such combination therapy is selected from agents used for the treatment of glucose-related disorders such as Type 2 diabetes mellitus, impaired glucose tolerance, Insulin Resistance Syndrome and hyperglycemia. Examples of such agents include oral antidiabetic compounds from the classes of sulfonylureas, biguanides, thiazolidinediones, alpha-glucosidase inhibitors, meglitinides, other insulin-sensitizing compounds and/or other antidiabetic agents. Particular examples comprise Metformin (N,N-dimethylimidodicarbonimidic diamide), sulfonylureas and the like, or a salt of the forgoing. Testing of glucose concentration levels in an individual receiving a compound of the present invention may be followed by the co-administration of such a second agent (e.g., Metformin) as part of a combination therapy where appropriate (e.g., where the results of a glucose concentration level test in an individual indicate that such combination therapy will be or is expected to be beneficial for the individual).

In some embodiments, the compounds and compositions of the invention may be used to treat or prevent cancer in conjunction with a second therapy useful for cancer treatment. The second therapy includes, but is not limited to, surgery, radiation, and/or chemotherapy.

Dosing and Method of Administration

The dose of a compound administered to an individual (such as a human) may vary with the particular compound or salt thereof, the method of administration, and the particular stage of cancer being treated. The amount should be sufficient to produce a desirable response, such as a therapeutic or prophylactic response against cancer. In some embodiments, the amount of the compound or salt thereof is a therapeutically effective amount. In some embodiments, the amount of the compound or salt thereof is a prophylactically effective amount. In some embodiments, the amount of compound or salt thereof is below the level that induces a toxicological effect (e.g., an effect above a clinically acceptable level of toxicity) or is at a level where a potential side effect can be controlled or tolerated when the composition is administered to the individual.

In some embodiments, the amount of compound or salt thereof is an amount sufficient to inhibit IGR-IR and/or IR, inhibit the phosphorylation of AKT, inhibit cancer cell growth and/or proliferation or increase apoptosis of cancer cells.

The effective amount of the compound may in one aspect be a dose of between about 0.01 and about 100 mg/kg.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intratumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture comprising a compound of the invention or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Kits

The invention further provides kits for carrying out the methods of the invention, which comprises one or more compounds described herein or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or subunit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

EXAMPLES

The following Examples are provided to illustrate but not to limit the invention.

General Protocol for Chiral Preparative HPLC Separation of Racemic Compounds

For chiral separations, samples were dissolved in MeOH and EtOH according to the solubility of sample and filtered through 0.22μ PTFE filters. The columns used were CHIRALPAK-AD; 20*250 mm, 10μ and CHIRALCEL-ODH; 20*250 mm, 5μ. A flow rate of 12 mL/min-17 mL/min was used according to the resolution. Alkanes such as n-Pentane, Hexane and Heptane (40%-95%) and alcohols such as EtOH, Isopropyl alcohol and t-Butanol (5%-60%) were used as mobile phase. In some cases alcohol combinations i.e. (EtOH+MeOH), (EtOH+IPA), (IPA+MeOH), (t-Butanol+MeOH), (t-Butanol+EtOH) were used instead of a single alcohol. Diethyl amine (up to 0.3%) was used as modifier in the mobile phase.

Example H1

General Method for the Chiral HPLC Separation and Characterization of Compounds that are Synthesized Initially as a Mixture of Enantiomers Crude or in some cases partially purified (normal or reverse phase HPLC) mixtures of enantiomers are analyzed by analytical chiral HPLC methods. Once adequate separation is achieved, larger quantities of the mixtures are separated using preparative scale columns. Separation is followed by removal of solvents on a rotary evaporator to accomplish the isolation of the individual single enantiomers. In some cases where appropriate, after removal of solvent, the samples are lyophilized. After isolation, each individual enantiomer is further analyzed by analytical (reverse phase and chiral) HPLC, LCMS and NMR. When final products are converted to salts, final characterization of the compounds is carried out after conversion to the salt for each enantiomer.

Analytical Chiral HPLC of Compounds of the Invention.

Column: Chiralcel OD-H; Column ID: 4.6*250 mm, 5μ. Mobile Phase: Hexane:(EtOH:MeOH 80:20)-93:7. Flow rate: 1 mL/min.

Chiral Preparative Data of Compounds of the Invention.

Column: Chiralcel OD-H. Column ID: 20*250 mm, 5μ. Mobile Phase: Hexane: (EtOH:MeOH 80:20)-95:5. Flow rate: 15 mL/min.

Example H2

General Method for the Chiral HPLC Separation and Characterization of Compounds that are Synthesized Initially as a Mixture of Diastereomers Crude or in some cases partially purified (normal or reverse phase HPLC) mixtures of diastereomers are analyzed by analytical chiral HPLC methods. Once adequate separation is achieved, larger quantities of the mixtures are separated using preparative scale columns. Separation is followed by removal of solvents on a rotary evaporator to accomplish the isolation of the individual single diastereomers. In some cases where appropriate, after removal of solvent, the samples are lyophilized. Once each individual diastereomer is isolated they are further analyzed by analytical (reverse phase and chiral) HPLC, LCMS and NMR. When final products are converted to salts, final characterization of the compounds is carried out after conversion to the salt for each diastereomer.

Analytical Chiral HPLC Data of Compounds of the Invention.

Column: Chiral Pak AD-H. Column ID: 4.6*250 mm, 5μ. Mobile Phase: Hexane (0.2% diethylamine): Isopropanol—93:7. Flow rate: 1 mL/min.

Chiral Preparative Data of Compounds of the Invention.

Column: Chiral PAK-AD-H. Column ID: 20*250 mm, 5μ. Mobile Phase: Hexane (0.2% diethylamine): Isopropanol—93:7. Flow rate: 15 mL/min.

The following abbreviations are used herein: thin layer chromatography (TLC); hour (h); minute (min); second (sec); ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); ethyl acetate (EtOAc); Retention factor (Rf); room temperature (RT).

Compounds detailed herein may be prepared by those of skill in the art by referral to the General Method. Particular examples of the General Method are provided in the Examples below.

Example 1

Preparation of Compound (i)

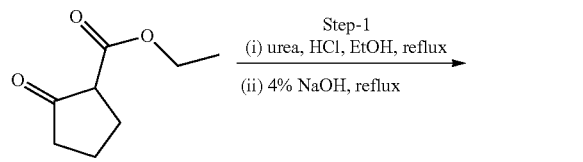

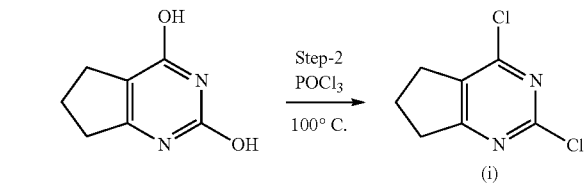

Step-1: Synthesis of 6,7-dihydro-5H-cyclopenta[d]pyrimidine-2,4-diol

To a suspension of ethyl 2-oxocyclopentanecarboxylate (10 mL, 67.2 mmol) and urea (6.07 g, 101 mmol) in EtOH (20 mL), cooled in an ice-bath, was added concentrated HCl (1 mL) dropwise. After completion of addition, the ice bath was removed and the reaction mixture was stirred at RT for 30 min. The reaction mixture was then heated to reflux at 85° C. for 5 h. The reaction mixture was cooled to RT and the EtOH was decanted to give a crystalline solid. The solid was heated to reflux with aqueous 5% NaOH solution (25 mL) for 2 h. The reaction mixture was cooled to RT and the precipitate was collected by filtration. The precipitate was washed with water and dried to afford 6,7-dihydro-5H-cyclopenta[d]pyrimidine-2,4-diol (5.36 g, 52% yield). $^1$H NMR (400 MHz, DMSO-$d_6$) δ (ppm): 1.81-1.97 (m, 2H), 2.38-2.46 (m, 2H), 2.47-2.60 (m, 2H), 10.70 (s, 1H), 11.05 (s, 1H).

Step-2: Synthesis of 2,4-dichloro-6,7-dihydro-5H-cyclopenta[d]pyrimidine, Compound (i)

A suspension of 6,7-dihydro-5H-cyclopenta[d]pyrimidine-2,4-diol (13 g, 85.52 mmol) in POCl$_3$ (100 mL) was stirred at 100° C. for 3 h. The reaction mixture was cooled to RT and poured slowly with constant shaking into crushed ice to quench the excess of POCl$_3$. The aqueous layer was extracted with EtOAc (3×200 mL). The combined organic layer was washed with water (8×300 mL) and dried over anhydrous Na$_2$SO$_4$. Removal of EtOAc under reduced pressure afforded 2,4-dichloro-6,7-dihydro-5H-cyclopenta[d]pyrimidine, Compound (i) (13.0 g, 81% yield). $^1$HNMR (400 MHz, CDCl$_3$) δ (ppm): 2.17-2.25 (m, 2H), 2.93-3.00 (m, 2H), 3.01-3.12 (m, 2H).

Example 2

Preparation of Compound (ii)

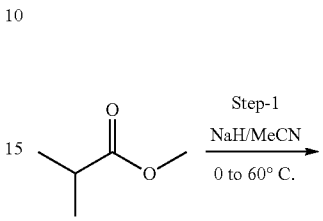

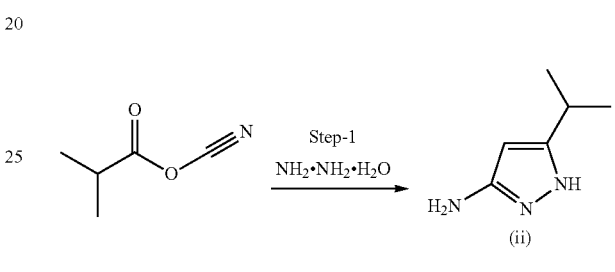

Step-1: Synthesis of 4-methyl-3-oxopentanenitrile

To a suspension of sodium hydride (11.40 g, 284 mmol) in THF (250 mL) was added acetonitrile (11.36 g, 278 mmol) slowly at 0° C. The reaction mixture was allowed to stir at RT for 20 min. The reaction mixture was then cooled to 0° C. and to it was added slowly a solution of methyl isobutyrate (25 g, 245 mmol) in THF (50 mL). The reaction mixture was heated to reflux under nitrogen at 70° C. for 6 h. The solvent was removed under reduced pressure and the reaction mass was treated with 1:1 water-DCM mixture (600 mL). The aqueous layer was acidified with 1N HCl and extracted with DCM (2×400 mL). The organic layer was dried over anhydrous sodium sulfate. Removal of solvent under reduced pressure afforded 4-methyl-3-oxopentanenitrile (15 g, 55% yield). $^1$H NMR (400 MHz, CDCl$_3$) δ (ppm): 1.18 (d, 6H), 2.72-2.84 (m, 1H), 3.51 (s, 2H).

Step-2: Synthesis of 5-isopropyl-1H-pyrazol-3-amine, Compound (ii)

To a solution of 4-methyl-3-oxopentanenitrile (15 g, 135 mmol) in EtOH (150 mL) was added hydrazine hydrate (7.30 g, 146 mmol) slowly at 0° C. The reaction mixture was heated to reflux for 4 h. Removal of EtOH under reduced pressure gave an oily residue that was dissolved in EtOAc (200 mL) and washed with freshly prepared brine (2×50 mL). The organic layer was dried over anhydrous sodium sulfate. Removal of EtOAc gave 5-isopropyl-1H-pyrazol-3-amine, Compound (ii) (10 g, 59% yield). ¹H NMR (400 MHz, CDCl₃) δ (ppm): 1.22 (d, 6H), 2.80-2.92 (m, 1H), 4.80 (brs, 3H), 5.41 (s, 1H).

Example 3

Preparation of Compound (iii)

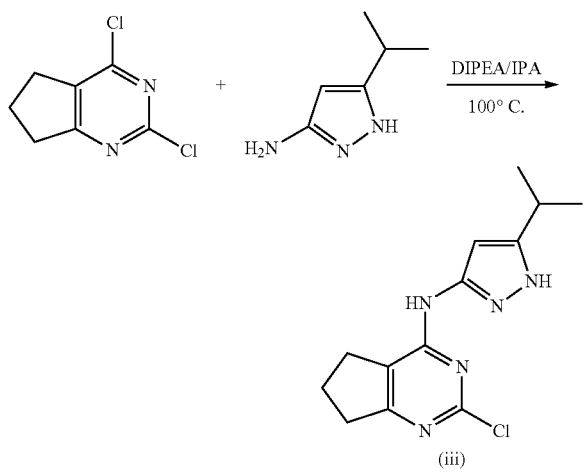

Synthesis of 2-chloro-N-(5-isopropyl-1H-pyrazol-3-yl)-6,7-dihydro-5H-cyclopenta[d]pyrimidin-4-amine, Compound (iii)

To a solution of 2,4-dichloro-6,7-dihydro-5H-cyclopenta[d]pyrimidine, Compound (i) (8 g, 42 mmol) in isopropanol (100 mL) was added N,N-diisopropylethyl amine (8.67 g, 67 mmol) followed by 5-isopropyl-1H-pyrazol-3-amine, Compound (ii) (5.89 g, 47 mmol). The reaction mixture was heated to reflux at 100° C. for 16 h. The reaction mixture was cooled to RT. The precipitated product was filtered and washed with hexane to afford 2-chloro-N-(5-isopropyl-1H-pyrazol-3-yl)-6,7-dihydro-5H-cyclopenta[d]pyrimidin-4-amine, Compound (iii) (5 g, 42%). ¹H NMR (400 MHz, DMSO-d₆) δ (ppm): 1.22 (d, 6H), 1.96-2.07 (m, 2H), 2.70-2.81 (m, 4H), 2.88-3.01 (m, 1H), 6.38 (s, 1H), 9.60 (s, 1H), 12.11 (brs, 1H).

Example 4

Preparation of Compound (iv)

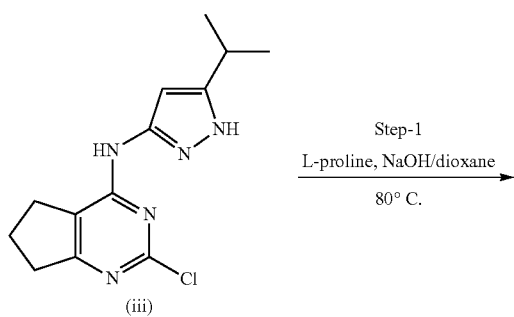

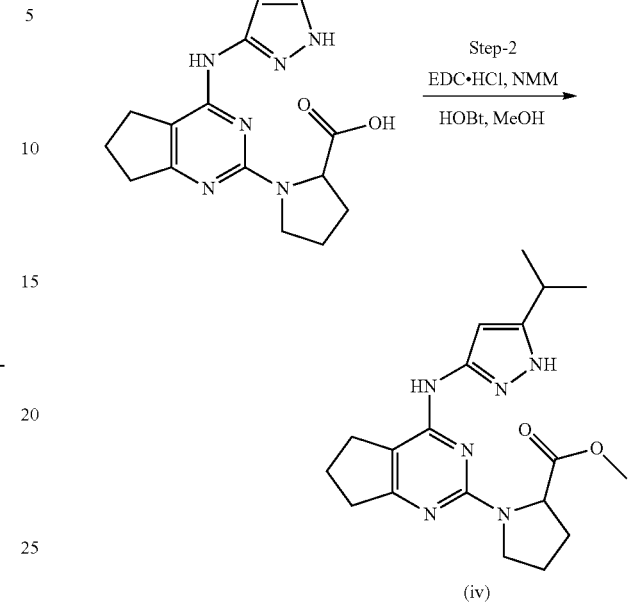

Step-1: Synthesis of 1-(4-(5-isopropyl-1H-pyrazol-3-ylamino)-6,7-dihydro-5H-cyclopenta[d]pyrimidin-2-yl)pyrrolidine-2-carboxylic acid To a suspension of 2-chloro-N-(5-isopropyl-1H-pyrazol-3-yl)-6,7-dihydro-5H-cyclopenta[d]pyrimidin-4-amine, Compound (iii) (5 g, 18 mmol) in dioxane (60 mL) was added L-proline (3.11 g, 27 mmol) followed by 5N NaOH (5.4 mL, 27 mmol) and N,N-diisopropylethyl amine (2.32 g, 18 mmol). The reaction mixture was allowed to stir at 100° C. for 16 h. The solvent was removed under reduced pressure and the residue was acidified with 1 N HCl solution to pH 4. The product was suspended in water (10 mL), filtered, washed with ether and dried to afford 1-(4-(5-isopropyl-1H-pyrazol-3-ylamino)-6,7-dihydro-5H-cyclopenta[d]pyrimidin-2-yl)pyrrolidine-2-carboxylic acid (5 g, 78% yield).

Step-2: Synthesis of methyl 1-(4-(5-isopropyl-1H-pyrazol-3-ylamino)-6,7-dihydro-5H-cyclopenta[d]pyrimidin-2-yl)pyrrolidine-2-carboxylate, Compound (iv)

To a solution of 1-(4-(5-isopropyl-1H-pyrazol-3-ylamino)-6,7-dihydro-5H-cyclopenta[d]pyrimidin-2-yl)pyrrolidine-2-carboxylic acid (5 g, 14 mmol) in MeOH (120 mL) was added HOBt.H₂O (143 mg, 0.94 mmol), N-methylmorpholine (1.42 g, 14 mmol) and EDC.HCl (3.64 g, 19 mmol). The reaction mixture was stirred at RT overnight. The MeOH was removed under reduced pressure and the residue was dissolved in EtOAc (100 mL). The solution was washed with water (2×40 mL) followed by brine (40 mL) and dried over anhydrous sodium sulfate. Removal of EtOAc under reduced pressure afforded methyl 1-(4-(5-isopropyl-1H-pyrazol-3-ylamino)-6,7-dihydro-5H-cyclopenta[d]pyrimidin-2-yl)pyrrolidine-2-carboxylate, Compound (iv) (5 g, 96% yield). ¹H NMR (400 MHz, CDCl₃) δ (ppm): 1.30 (d, 6H), 1.98-2.20 (m, 4H), 2.06-2.37 (m, 1H), 2.60-2.66 (m, 2H), 2.67-2.2.88

(m, 2H), 2.90-3.07 (m, 1H), 3.65-3.79 (m, 1H), 3.70 (s, 3H), 3.80-3.91 (m, 2H), 4.61-4.70 (m, 1H), 6.18 (s, 1H), 6.59 (s, 1H).

Example 5

Preparation of Compound Nos. 1, 1a and 1b

To a solution of (S)-1-(4-(5-cyclopropyl-1H-pyrazol-3-ylamino)-6,7-dihydro-5H-cyclopenta[d]pyrimidin-2-yl)-2-methylpyrrolidine-2-carboxylic acid (1.1 g, 2.99 mmol) in DMF (12 mL) was added 6-fluoropyridin-3-amine (1.7 g, 15.18 mmol), diisopropylethylamine (0.578 g, 4.48 mmol) and HBTU (1.13 g, 2.99 mmol) and the reaction mixture was stirred at RT for 16 h. The reaction mixture was diluted with water (200 mL) and extracted with EtOAc (3×100 mL). The combined organic layer was washed with water (9×200 mL) and dried over anhydrous sodium sulfate. Removal of solvent under reduced pressure gave a crude product which was purified by reverse phase HPLC to afford 50 mg of (S)-1-(4-(5-cyclopropyl-1H-pyrazol-3-ylamino)-6,7-dihydro-5H-cyclopenta[d]pyrimidin-2-yl)-N-(6-fluoropyridin-3-yl)-2-methylpyrrolidine-2-carboxamide. $^1$H NMR (400 MHz, CD$_3$OD, TFA salt) δ (ppm): 0.70-0.80 (m, 2H), 0.89-0.99 (m, 2H), 1.77-1.83 (m, 1H), 1.80 (s, 3H), 2.16-2.30 (m, 5H), 2.38-2.43 (m, 1H), 2.77-2.83 (m, 2H), 2.98-3.05 (m, 2H), 3.78-3.82 (m, 1H), 3.88-3.98 (m, 1H), 6.02 (s, 1H), 6.99 (d, 1H), 7.82-7.90 (m, 1H), 8.18 (s, 1H). The other enantiomer was prepared using the (R) chiral starting material.

Example 6

Preparation of Compound Nos. 2, 2a and 2b

To a solution of 6-fluoropyridin-3-amine (6.09 g, 54.4 mmol) in dry THF (100 mL) was added a 2M solution of isopropylmagnesium chloride (27.2 mL, 54.4 mmol) in THF dropwise under nitrogen at 0° C. The resultant mixture was stirred at 0° C. for 20 min. To this solution was added a solution of methyl 1-(4-(5-cyclopropyl-1H-pyrazol-3-ylamino)-6,7-dihydro-5H-cyclopenta[d]pyrimidin-2-yl)pyrrolidine-2-carboxylate (5 g, 13.5 mmol) in THF (20 mL) dropwise at 0° C. and the reaction mixture was allowed to stir at RT for 2 h. The reaction was quenched with saturated ammonium chloride solution (200 mL). The product was extracted with EtOAc (2×80 mL) and the organic layer was dried over anhydrous sodium sulfate. Removal of EtOAc under reduced pressure gave a solid residue which was purified by column chromatography on silica gel using 2-2.5% MeOH-DCM system as eluent to afford 1-(4-(5-cyclopropyl-1H-pyrazol-3-ylamino)-6,7-dihydro-5H-cyclopenta[d]pyrimidin-2-yl)-N-(6-fluoropyridin-3-yl)pyrrolidine-2-carboxamide (2.85 g, 47% yield) as the racemate. $^1$H NMR (400 MHz, CD$_3$OD, freebase) δ (ppm): 0.56-0.72 (m, 2H), 0.82-0.94 (m, 2H), 1.70-1.82 (m, 1H), 2.00-2.20 (m, 4H), 2.21-2.38 (m, 2H), 2.70-2.77 (m, 2H), 2.78-2.82 (m, 2H), 3.58-3.78 (m, 1H), 3.79-3.81 (m, 1H), 4.70 (dd, 1H), 6.25 (s, 1H), 6.98 (dd, 1H), 7.95 (s, 1H), 8.18 (s, 1H). Separation by chiral HPLC provided enantiomers 2a and 2b.

Example 7

Preparation of Compound Nos. 3, 3a and 3b

To a solution of 1-(4-(5-cyclopropyl-1H-pyrazol-3-ylamino)-6,7-dihydro-5H-cyclopenta[d]pyrimidin-2-yl)pyrrolidine-2-carboxylic acid (200 mg, 0.566 mmol) in DMF (2 mL) was added 3-amino pyridine (265 mg, 2.824 mmol), HATU (257 mg, 0.672 mmol) and DIPEA (0.166 mL, 0.902 mmol). The reaction mixture was allowed to stir at RT for 16 h. The reaction mixture was diluted with water (40 mL) and extracted with EtOAc (2×25 mL). The organic layer was washed with water (8×30 mL) and dried over anhydrous sodium sulfate. Removal of EtOAc under reduced pressure gave a crude product that was purified by reverse phase HPLC to afford 1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide (25 mg) as racemate. The enantiomers were separated by chiral HPLC to afford (R)-1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide (10 mg). $^1$H NMR (400 MHz, CD$_3$OD, freebase) δ (ppm): 0.56-0.70 (m, 2H), 0.78-0.87 (m, 2H), 1.69-1.81 (m, 1H), 2.00-2.19 (m, 4H), 2.21-2.39 (m, 2H), 2.68-2.81 (m, 4H), 3.58-3.72 (m, 1H), 3.78-3.89 (m, 1H), 4.65-4.78 (m, 1H), 6.25 (s, 1H), 7.33 (dd, 1H), 7.94 (s, 1H), 8.22 (d, 1H), 8.60 (s, 1H).

Example 8

Preparation of Compound Nos. 4, 4a and 4b

To a solution of 6-fluoropyridin-3-amine (565 mg, 5.044 mmol) in dry THF (20 mL) was added 2M solution of isopropylmagnesium chloride in THF (2.5 mL, 5.044 mmol) dropwise under nitrogen at 0° C. The resultant mixture was stirred at 0° C. for 20 min. To this solution was added a solution of 1-(4-(3-cyclopentyl-1H-pyrazol-5-ylamino)-6,7-dihydro-5H-cyclopenta[d]pyrimidin-2-yl)pyrrolidine-2-carboxylate (500 mg, 1.262 mmol) in THF (5 mL) dropwise at 0° C. and the reaction mixture was allowed to stir at RT for 2 h. The reaction was quenched with saturated ammonium chloride solution (50 mL). The product was extracted with EtOAc (2×60 mL) and the organic layer was dried over anhydrous sodium sulfate. Removal of EtOAc under reduced pressure afforded an oily residue that was purified by reverse phase HPLC to afford 1-(4-(3-cyclopentyl-1H-pyrazol-5-ylamino)-6,7-dihydro-5H-cyclopenta[d]pyrimidin-2-yl)-N-(6-fluoropyridin-3-yl)pyrrolidine-2-carboxamide as the formate salt (220 mg). $^1$H NMR (400 MHz, CD$_3$OD, formate salt) δ (ppm): 1.41-1.80 (m, 6H), 1.81-2.00 (m, 2H), 2.07-2.21 (m, 4H), 2.22-2.38 (m, 2H), 2.76-2.81 (m, 2H), 2.82-2.97 (m, 3H), 3.59-3.70 (m, 1H), 3.77-3.86 (m, 1H), 4.70-4.80 (m, 1H), 6.27 (brs, 1H), 6.97 (dd, 1H), 7.93-8.02 (m, 1H), 8.18 (s, 1H). Separation by chiral HPLC provided enantiomers 4a and 4b.

Example 9

Preparation of Compound Nos. 5, 5a and 5b

To a solution of (S)-1-(4-(5-cyclopropyl-1H-pyrazol-3-ylamino)-6,7-dihydro-5H-cyclopenta[d]pyrimidin-2-yl)azetidine-2-carboxylic acid (300 mg, 0.909 mmol) in DMF (3 mL) was added 6-fluoropyridin-3-amine (203 mg, 1.818 mmol), HATU (414 mg, 1.091 mmol) and DIPEA (0.26 mL, 1.45 mmol). The reaction mixture was allowed to stir at RT for 16 h. The reaction mixture was diluted with water (40 mL) and extracted with EtOAc (2×25 mL). The organic layer was washed with water (8×30 mL) and dried over anhydrous sodium sulfate. Removal of EtOAc under reduced pressure gave a crude product that was purified by reverse phase HPLC to afford 40 mg of (S)-1-(4-(5-cyclopropyl-1H-pyrazol-3-ylamino)-6,7-dihydro-5H-cyclopenta[d]pyrimidin-2-yl)-N-

(6-fluoropyridin-3-yl)azetidine-2-carboxamide as the formate salt. ¹H NMR (400 MHz, CD₃OD, TFA salt) δ (ppm): 0.40-0.60 (m, 2H), 0.70-0.85 (m, 2H), 1.58-1.70 (m, 1H), 2.20-2.37 (m, 2H), 2.58-2.69 (m, 1H), 2.79-2.97 (m, 3H), 2.98-3.06 (m, 2H), 4.21-4.38 (2H), 5.16 (dd, 1H), 6.16 (s, 1H), 7.05 (dd, 1H), 8.05-8.17 (m, 1H), 8.30 (s, 1H). The other enantiomer was prepared using the (R) chiral starting material.

Example 10

Preparation of Compound Nos. 6, 6a and 6b

To a solution of pyrazin-2-amine (284 mg, 2.99 mmol) in dry THF (12 mL) was added 2M solution of isopropylmagnesium chloride (1.5 mL, 2.99 mmol) in THF dropwise under nitrogen at 0° C. The resultant mixture was stirred at 0° C. for 20 min. To this solution was added a solution of methyl 1-(4-(3-cyclopropyl-1H-pyrazol-5-ylamino)-6,7-dihydro-5H-cyclopenta[d]pyrimidin-2-yl)pyrrolidine-2-carboxylate (200 mg, 0.746 mmol) in THF (2 mL) dropwise at 0° C. and the reaction mixture was allowed to stir at RT for 1.5 h. The reaction was quenched with saturated ammonium chloride solution (20 mL). The product was extracted with EtOAc (2×40 mL) and the organic layer was dried over anhydrous sodium sulfate. Removal of EtOAc under reduced pressure afforded an oily residue that was purified by reverse phase HPLC to afford 1-(4-(3-cyclopropyl-1H-pyrazol-5-ylamino)-6,7-dihydro-5H-cyclopenta[d]pyrimidin-2-yl)-N-(pyrazin-2-yl)pyrrolidine-2-carboxamide (120 mg). ¹H NMR (400 MHz, CD₃OD, freebase) δ (ppm): 0.57-0.67 (m, 2H), 0.78-0.95 (m, 2H), 1.70-1.81 (m, 1H), 2.02-2.18 (m, 4H), 2.25-2.39 (m, 2H), 2.63-2.78 (m, 2H), 2.79-2.85 (m, 2H), 3.60-3.77 (m, 1H), 3.78-3.94 (m, 1H), 4.73-4.81 (m, 1H), 6.25 (s, 1H), 8.26 (d, 1H), 8.30 (s, 1H), 9.31 (s, 1H). Separation by chiral HPLC provided enantiomers 6a and 6b.

Example 11

Preparation of Compound Nos. 7, 7a and 7b

To a solution of 1-(4-(3-cyclopropyl-1H-pyrazol-5-ylamino)-6,7-dihydro-5H-cyclopenta[d]pyrimidin-2-yl)pyrrolidine-2-carboxylic acid (300 mg, 0.847 mmol) in DMF (4 mL) was added pyrimidin-5-amine (201 mg, 2.11 mmol), HATU (386 mg, 1.016 mmol) and DIPEA (0.24 mL, 1.4 mmol). The reaction mixture was allowed to stir at RT for 16 h. The reaction mixture was diluted with water (40 mL) and extracted with EtOAc (2×25 mL). The organic layer was washed with water (8×30 mL) and dried over anhydrous sodium sulfate. Removal of EtOAc under reduced pressure gave a crude product that was purified by reverse phase HPLC to afford 11 mg of 1-(4-(3-cyclopropyl-1H-pyrazol-5-ylamino)-6,7-dihydro-5H-cyclopenta[d]pyrimidin-2-yl)-N-(pyrimidin-5-yl)pyrrolidine-2-carboxamide as free base. ¹H NMR (400 MHz, CD₃OD, formate salt) δ (ppm): 0.58-0.67 (m, 2H), 0.80-0.94 (m, 2H), 1.70-1.78 (m, 1H), 2.09-2.21 (m, 4H), 2.22-2.42 (m, 2H), 2.78-2.81 (m, 2H), 2.82-2.95 (m, 2H), 3.60-2.70 (m, 1H), 3.78-3.88 (m, 1H), 4.78 (dd, 1H), 6.08 (s, 1H), 8.84 (s, 1H), 8.89 (s, 2H). Separation by chiral HPLC provided enantiomers 7a and 7b.

Example 12

Preparation of Compound Nos. 8, 8a and 8b

To a solution of 6-fluoropyridin-3-amine (6.05 g, 13 mmol) in dry THF (100 mL) was added 2M solution of isopropylmagnesium chloride in THF (27 mL, 54 mmol) dropwise under nitrogen at 0° C. The resultant mixture was stirred at 0° C. for 20 min. To this solution was added a solution of methyl 1-(4-(5-isopropyl-1H-pyrazol-3-ylamino)-6,7-dihydro-5H-cyclopenta[d]pyrimidin-2-yl)pyrrolidine-2-carboxylate (5 g, 13 mmol) in THF (20 mL) dropwise at 0° C. and the reaction mixture was allowed to stir at RT for 2 h. The reaction was quenched with saturated ammonium chloride solution (50 mL). The product was extracted with EtOAc (2×40 mL) and the organic layer was dried over anhydrous sodium sulfate. Removal of EtOAc under reduced pressure gave solid residue which was purified by column chromatography on silica gel using 1-2% MeOH-DCM system as eluent followed by chiral purification to afford (S)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide (2.2 g). ¹H NMR (CDCl₃, freebase) δ (ppm): 1.22 (d, 6H), 1.90-2.21 (m, 6H), 2.60-2.70 (m, 1H), 2.72 (t, 2H), 2.88 (t, 2H), 2.81-2.96 (m, 1H), 3.60-3.80 (m, 2H), 4.77 (d, 2H), 6.40 (s, 1H), 6.74 (s, 1H), 6.82 (d, 1H), 7.90 (s, 1H), 8.13 (s, 1H). The other enantiomer was prepared using the (R) chiral starting material.

Example 13

Preparation of Compound Nos. 9, 9a and 9b

To a solution of 6-fluoropyridin-3-amine (586 mg, 5.2 mmol) in dry THF (20 mL) was added 2M solution of isopropylmagnesium chloride in THF (2.6 mL, 5.2 mmol) dropwise under nitrogen at 0° C. The resultant mixture was stirred at 0° C. for 20 min. To this solution was added a solution of methyl 1-(4-(3-cyclopropyl-1H-pyrazol-5-ylamino)-6,7-dihydro-5H-cyclopenta[d]pyrimidin-2-yl)piperidine-2-carboxylate (500 mg, 1.31 mmol) in THF (4 mL) dropwise at 0° C. and the reaction mixture was allowed to stir at RT for 3 h. The reaction was quenched with saturated ammonium chloride solution (40 mL). The product was extracted with EtOAc (2×75 mL) and the organic layer was dried over anhydrous sodium sulfate. Removal of EtOAc under reduced pressure afforded an oily residue that was purified by reverse phase HPLC to afford 1-(4-(3-cyclopropyl-1H-pyrazol-5-ylamino)-6,7-dihydro-5H-cyclopenta[d]pyrimidin-2-yl)-N-(6-fluoropyridin-3-yl)piperidine-2-carboxamide (12 mg). ¹H NMR (400 MHz, CD₃OD, freebase) δ (ppm): 0.58-0.68 (m, 2H), 0.82-0.97 (m, 2H), 1.60-1.90 (m, 6H), 2.10-2.24 (m, 3H), 2.30-2.41 (m, 1H), 2.77-2.81 (m, 2H), 2.81-2.91 (m, 2H), 4.46 (d, 1H), 5.39 (s, 1H), 6.06 (s, 1H), 7.00 (dd, 1H), 8.02-8.12 (m, 1H), 8.27 (s, 1H). Separation by chiral HPLC provided enantiomers 9a and 9b.

Example 14

Preparation of Compound Nos. 10, 10a, 10b, 10c and 10d

To a solution of 1-(4-(3-cyclopropyl-1H-pyrazol-5-ylamino)-6,7-dihydro-5H-cyclopenta[d]pyrimidin-2-yl)-4-hydroxypyrrolidine-2-carboxylic acid (200 mg, 0.54 mmol) in DMF (3 mL) was added 6-fluoropyridin-3-amine (121 mg, 1.08 mmol), HATU (246 mg, 0.648 mmol) and DIPEA (0.16 mL, 0.864 mmol). The reaction mixture was allowed to stir at RT for 16 h. The reaction mixture was diluted with EtOAc (50 mL), washed with water (4×25 mL) and dried over anhydrous sodium sulfate. Removal of EtOAc under reduced pressure gave a crude product that was purified by reverse phase HPLC to afford (2S,4R)-1-(4-(5-cyclopropyl-1H-pyrazol-3- ylamino)-6,7-dihydro-5H-cyclopenta[d]pyrimidin-2-yl)-N-(6-fluoropyridin-3-yl)-4-hydroxypyrrolidine-2-carboxamide (10 mg). Compound No. 10a: $^1$H NMR (400 MHz, CD$_3$OD, freebase) δ (ppm): 0.60-0.68 (m, 2H), 0.80-0.92 (m, 2H), 1.71-1.81 (m, 1H), 1.90-2.01 (m, 1H), 2.03-2.17 (m, 2H), 2.30-2.41 (m, 2H), 2.65-2.83 (m, 4H), 3.75-3.91 (m, 2H), 4.51-4.60 (m, 1H), 6.07 (s, 1H), 6.97 (d, 1H), 7.99 (s, 1H), 8.19 (s, 1H). Compound No. 10b: $^1$H NMR (400 MHz, CD$_3$OD, freebase) δ (ppm): 0.60-0.68 (m, 2H), 0.80-0.92 (m, 2H), 1.71-1.81 (m, 1H), 1.90-2.01 (m, 1H), 2.03-2.17 (m, 2H), 2.30-2.41 (m, 2H), 2.65-2.83 (m, 4H), 3.75-3.91 (m, 2H), 4.51-4.60 (m, 1H), 6.07 (s, 1H), 6.97 (d, 1H), 7.99 (s, 1H), 8.19 (s, 1H). Separation by chiral HPLC provided additional diastereomers 10c and 10d.

Example 15

Preparation of Compound Nos. 11, 11a, 11b, 11c and 11d

To a solution of 6-fluoropyridin-3-amine (292 mg, 2.61 mmol) in dry THF (12 mL) was added 2M solution of isopropylmagnesium chloride in THF (1.3 mL, 2.60 mmol) dropwise under nitrogen at 0° C. The resultant mixture was stirred at 0° C. for 20 min. To this solution was added a solution of (3S)-methyl 1-(4-(5-cyclopropyl-1H-pyrazol-3-ylamino)-6,7-dihydro-5H-cyclopenta[d]pyrimidin-2-yl)-3-hydroxypyrrolidine-2-carboxylate (250 mg, 0.65 mmol) in THF (2 mL) dropwise at 0° C. and the reaction mixture was allowed to stir at RT for 2 h. The reaction was quenched with saturated ammonium chloride solution (50 mL). The product was extracted with EtOAc (2×40 mL) and the organic layer was dried over anhydrous sodium sulfate. Removal of EtOAc under reduced pressure afforded an oily residue that was purified by reverse phase HPLC to afford (2R,3S)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide (10 mg). Compound No. 11a: $^1$H NMR (400 MHz, CD$_3$OD, freebase) δ (ppm): 0.60-0.68 (m, 2H), 0.82-0.96 (m, 2H), 1.77 (brs, 1H), 2.00-2.18 (m, 3H), 2.19-2.30 (m, 1H), 2.70-2.83 (m, 4H), 3.78-3.98 (m, 2H), 4.58-4.77 (m, 2H), 6.28 (brs, 1H), 6.98 (d, 1H), 8.02 (brs, 1H), 8.23 (s, 1H). Compound No. 11b: $^1$H NMR (400 MHz, CD$_3$OD, freebase) δ (ppm): 0.60-0.68 (m, 2H), 0.82-0.96 (m, 2H), 1.77 (brs, 1H), 2.00-2.18 (m, 3H), 2.19-2.30 (m, 1H), 2.70-2.83 (m, 4H), 3.78-3.98 (m, 2H), 4.58-4.77 (m, 2H), 6.28 (brs, 1H), 6.98 (d, 1H), 8.02 (brs, 1H), 8.23 (s, 1H). Separation by chiral HPLC provided additional diastereomers 11c and 11d.

Example 16

Preparation of Compound Nos. 12, 12a and 12b

To a solution of 1-(4-(3-isopropylisoxazol-5-ylamino)-6,7-dihydro-5H-cyclopenta[d]pyrimidin-2-yl)pyrrolidine-2-carboxylic acid (300 mg, 0.840 mmol) in DMF (3 mL) was added 6-fluoropyridin-3-amine (188 mg, 1.680 mmol), HATU (383 mg, 1.008 mmol) and DIPEA (216 mg, 1.68 mmol). The reaction mixture was allowed to stir at RT for 16 h. The reaction mixture was diluted with water (40 mL) and extracted with EtOAc (2×25 mL). The organic layer was washed with water (8×30 mL) and dried over anhydrous sodium sulfate. Removal of EtOAc under reduced pressure gave a crude product that was purified by reverse phase HPLC to afford a racemic mixture (30 mg). The enantiomers were separated by chiral HPLC to afford (R)—N-(6-fluoropyridin-3-yl)-1-(4-(3-isopropylisoxazol-5-ylamino)-6,7-dihydro-5H-cyclopenta[d]pyrimidin-2-yl)pyrrolidine-2-carboxamide (10 mg), and its (S) enantiomer. $^1$H NMR (400 MHz, CD$_3$OD, freebase) δ (ppm): 1.10-1.30 (m, 6H), 2.01-2.18 (m, 4H), 2.20-2.38 (m, 1H), 2.39-2.46 (m, 1H), 2.77-2.90 (m, 5H), 3.60-3.78 (m, 1H), 3.87-3.97 (m, 1H), 4.67 (dd, 1H), 6.25 (brs, 1H), 7.01 (dd, 1H), 8.02-8.12 (m, 1H), 8.31 (s, 1H).

Example 17

Preparation of Compound Nos. 13, 13a and 13b

To a solution of 6-fluoropyridin-3-amine (1.41 g, 12.5 mmol) in THF (30 mL) was added 2M solution of isopropylmagnesium chloride in THF (6.2 mL, 12.4 mmol) dropwise at 0° C. The resultant mixture was stirred at the same temperature for 20 min followed by the dropwise addition of a solution of methyl 1-(4-(5-isopropyl-1H-pyrrol-3-ylamino)-5,6,7,8-tetrahydroquinazolin-2-yl)pyrrolidine-2-carboxylate (1.2 g, 3.12 mmol) in THF (10 mL) at 0° C. The reaction mixture was stirred at RT for 2 h. The progress of reaction was monitored by TLC and LCMS. The reaction mixture was quenched with saturated aqueous NH$_4$Cl (40 mL) and was extracted with EtOAc (3×50 mL). The organic layer was washed with water (50 mL), dried over anhydrous sodium sulfate and concentrated under vacuum to obtain a crude product which was purified by column chromatography on silica (100-200 mesh using 1% MeOH-DCM system as eluent to afford N-(6-fluoropyridin-3-yl)-1-(4-(5-isopropyl-1H-pyrrol-3-ylamino)-5,6,7,8-tetrahydroquinazolin-2-yl)pyrrolidine-2-carboxamide (750 mg) as racemate. The enantiomers were separated by chiral HPLC to afford (R)—N-(6-fluoropyridin-3-yl)-1-(4-(5-isopropyl-1H-pyrazol-3-ylamino)-5,6,7,8 tetrahydroquinazolin-2-yl)pyrrolidine-2-carboxamide (200 mg), and its (S) enantiomer. $^1$H NMR (400 MHz, CDCl$_3$, freebase) δ (ppm): 1.10-1.30 (m, 6H), 1.80-2.20 (m, 7H), 2.35-2.46 (m, 2H), 2.58-2.80 (m, 3H), 2.81-2.99 (m, 1H), 3.58-3.77 (m, 2H), 4.75 (brs, 1H), 6.20 (s, 1H), 6.83 (dd, 1H), 6.95 (s, 1H), 7.91 (s, 1H), 8.18 (s, 1H), 10.80 (brs, 1H).

Example 18

Preparation of Compound Nos. 14, 14a and 14b

To a stirred solution of 6-fluoropyridin-3-amine (2.58 g, 23.01 mmol) in THF (40 mL) was added a 2M solution of isopropylmagnesium chloride in THF (11.5 mL, 23 mmol) at 0° C. After 20 min of stirring, to this was added a solution of methyl 1-(4-(3-cyclopropyl-1H-pyrazol-5-ylamino)-5,6,7,8-tetrahydroquinazolin-2-yl)pyrrolidine-2-carboxylate (2.2 g, 5.75 mmol) in THF (10 mL) at 0° C. The reaction mixture was further stirred at RT for 2 h. After completion of reaction it was quenched with saturated ammonium chloride and the aqueous layer was extracted with EtOAc (3×50 mL). The combined organic layer was treated with brine, dried over Na$_2$SO$_4$ and evaporated under reduced pressure to obtain a crude product, which was purified by column chromatography on 100-200 mesh silica gel using MeOH-DCM (1:10) as eluent to obtain as racemate (0.6 g, 23% yield). The enantiomers were separated by chiral HPLC to afford (R)-1-(4-(5-cyclopropyl-1H-pyrazol-3-ylamino)-5,6,7,8-tetrahydroquinazolin-2-yl)-N-(6-fluoropyridin-3-yl)pyrrolidine-2-carboxamide (130 mg), and its (S) enantiomer. $^1$H NMR (400 MHz, CDCl$_3$, freebase) δ (ppm): 0.60-0.77 (m, 2H), 0.85-0.98 (m, 2H), 1.77-1.90 (m, 6H), 1.91-2.20 (m, 3H), 2.38-2.43 (m, 2H), 2.60-2.80 (m, 3H), 3.59-3.78 (m, 2H), 4.71 (d, 1H), 6.17 (s, 1H), 6.80-6.83 (m, 1H), 6.91 (s, 1H), 7.95 (s, 1H), 8.20 (brs, 1H), 10.90 (brs, 1H).

Example 19

Preparation of Compound Nos. 15, 15a and 15b

To a stirred solution of 6-fluoropyridin-3-amine (1.32 g, 11.77 mmol) in THF (30 mL) was added a 2M solution of isopropylmagnesium chloride in THF (5.9 mL, 11.8 mmol) at 0° C. After 20 min of stirring, to this was added a solution of methyl 1-(4-(3-cyclopentyl-1H-pyrazol-5-ylamino)-5,6,7,8-tetrahydroquinazolin-2-yl)pyrrolidine-2-carboxylate (1.2 g, 2.92 mmol) in THF (10 mL) at 0° C. The reaction mixture was further stirred at RT for 2 h. After completion of reaction it was quenched with saturated ammonium chloride and the aqueous layer was extracted with EtOAc (3×50 mL). The combined organic layer was treated with brine, dried over $Na_2SO_4$ and evaporated under reduced pressure to obtain a crude product, which was purified by column chromatography on 100-200 mesh silica gel using MeOH-DCM (1:10) as eluent to obtain racemic mixture (842 mg, 59% yield). Chiral separation of 200 mg of enantiomeric mixture afforded (R)-1-(4-(5-cyclopentyl-1H-pyrazol-3-ylamino)-5,6,7,8-tetrahydroquinazolin-2-yl)-N-(6-fluoropyridin-3-yl)pyrrolidine-2-carboxamide (50 mg), and its (S) enantiomer. $^1$H NMR (400 MHz, $CDCl_3$, freebase) δ (ppm): 1.42-1.79 (m, 6H), 1.80-2.20 (m, 10H), 2.38-2.43 (m, 2H), 2.60-2.78 (m, 3H), 2.96-3.04 (m, 1H), 3.58-3.70 (m, 2H), 4.72 (d, 1H), 6.42 (s, 1H), 6.78-6.82 (m, 1H), 6.97 (s, 1H), 7.85 (s, 1H), 8.16 (s, 1H), 10.90 (brs, 1H).

Example 20

Preparation of Compound Nos. 16, 16a and 16b

To a stirred solution of 6-fluoropyridin-3-amine (2.4 g, 21.4 mmol) in THF (25 mL) was added a 2M solution of isopropylmagnesium chloride in THF (10.4 mL, 20.8 mmol) at 0° C. After 20 min of stirring, to this was added a solution of methyl 1-(4-(5-isopropyl-1H-pyrazol-3-ylamino)-6,7-dihydro-5H-cyclopenta[d]pyrimidin-2-yl)piperidine-2-carboxylate (2 g, 5.2 mmol) in THF (10 mL) at 0° C. The reaction mixture was further stirred at RT for 2 h. After completion of reaction it was quenched with saturated ammonium chloride and the aqueous layer was extracted with EtOAc (3×50 mL). The combined organic layer was treated with brine, dried over $Na_2SO_4$ and evaporated under reduced pressure to obtain a crude product which was purified by reverse phase HPLC to afford a racemic mixture (100 mg). The enantiomers were separated by chiral HPLC to afford (R)—N-(6-fluoropyridin-3-yl)-1-(4-(5-isopropyl-1H-pyrazol-3-ylamino)-6,7-dihydro-5H-cyclopenta[d]pyrimidin-2-yl)piperidine-2-carboxamide (40 mg), and its (S) enantiomer. $^1$H NMR (400 MHz, $CD_3OD$, freebase) δ (ppm): 1.18-1.25 (m, 6H), 1.27-1.38 (m, 1H), 1.65-1.82 (m, 3H), 2.20-2.34 (m, 2H), 2.41-2.250 (m, 1H), 2.79-2.85 (m, 2H), 2.92-3.00 (m, 1H), 3.00-3.08 (m, 2H), 3.40-3.51 (m, 2H), 4.09-4.17 (m, 1H), 5.38 (s, 1H), 6.21 (s, 1H), 7.00-7.08 (m, 1H), 8.10-8.17 (m, 1H), 8.30 (s, 1H).

Example 21

Preparation of Compound Nos. 17, 17a and 17b

To a stirred solution of 6-fluoropyridin-3-amine (2.3 g, 20.5 mmol) in THF (35 mL) was added a 2M solution of isopropylmagnesium chloride in THF (10.3 mL, 20.6 mmol) at 0° C. After 20 min of stirring, to this was added a solution of methyl 1-(4-(5-cyclopentyl-1H-pyrazol-3-ylamino)-6,7-dihydro-5H-cyclopenta[d]pyrimidin-2-yl)piperidine-2-carboxylate (2.1 g, 5.12 mmol) in THF (10 mL) at 0° C. The reaction mixture was further stirred at RT for 2 h. After completion of reaction it was quenched with saturated ammonium chloride and the aqueous layer was extracted with EtOAc (3×50 mL). The combined organic layer was treated with brine, dried over $Na_2SO_4$ and evaporated under reduced pressure to obtain a crude product which was purified by reverse phase HPLC to afford a racemic mixture (120 mg). The enantiomers were separated by chiral HPLC to afford (R)-1-(4-(5-cyclopentyl-1H-pyrazol-3-ylamino)-6,7-dihydro-5H-cyclopenta[d]pyrimidin-2-yl)-N-(6-fluoropyridin-3-yl)piperidine-2-carboxamide (35 mg), and its (S) enantiomer. $^1$H NMR (400 MHz, $CD_3OD$, freebase) δ (ppm): 1.51-1.81 (m, 10H), 1.95-2.05 (m, 2H), 2.06-2.17 (m, 2H), 2.50-2.32 (m, 1H), 2.25-2.39 (m, 2H), 2.70-2.82 (m, 4H), 2.98-3.05 (m, 1H), 4.61 (brs, 1H), 5.45 (s, 1H), 6.26 (s, 1H), 6.99 (d, 1H), 8.00-8.05 (m 1H), 8.25 (s, 1H).

Example 22

Preparation of Compound Nos. 18, 18a and 18b

To a solution of (R)-methyl 1-(4-(5-isopropyl-1H-pyrazol-3-ylamino)-6,7-dihydro-5H-cyclopenta[d]pyrimidin-2-yl)pyrrolidine-2-carboxylate (500 mg, 1.351 mmol) in THF (10 mL) was added 28% aqueous ammonia (20 mL) and reaction mixture was allowed to stir at 60° C. for 24 h. The progress of reaction was monitored by LCMS. The reaction mixture was diluted with water (100 mL) and extracted with EtOAc (2×100 mL). The organic layer was separated, dried over anhydrous sodium sulfate and concentrated under vacuum to obtain a crude product which was purified by reverse phase HPLC to afford (R)-1-(4-(5-isopropyl-1H-pyrazol-3-ylamino)-6,7-dihydro-5H-cyclopenta[d]pyrimidin-2-yl)pyrrolidine-2-carboxamide (80 mg). $^1$H NMR (400 MHz, $DMSO-d_6$, freebase) δ (ppm): 1.22 (d, 6H), 1.81-2.01 (m, 6H), 2.02-2.18 (m, 1H), 2.59-2.70 (m, 4H), 2.86-2.92 (m, 1H), 3.48 (brs, 1H), 3.67 (brs, 1H), 4.35 (d, 1H), 6.43 (brs, 1H), 6.85 (s, 1H), 7.18 (s, 1H), 8.78 (brs, 1H). The other enantiomer was prepared using the (R) chiral starting material.

Example 23

Preparation of Compound Nos. 19, 19a and 19b

To a solution of 1-(4-(5-isopropyl-1H-pyrazol-3-ylamino)-6,7-dihydro-5H-cyclopenta[d]pyrimidin-2-yl)pyrrolidine-2-carboxylic acid (300 mg, 0.842 mmol) in DMF (5 mL) was added methylamine hydrochloride (284 mg, 4.207 mmol), HATU (320 mg, 0.842 mmol), diisopropylethylamine (163 mg, 1.263 mmol). The reaction mixture was stirred at RT for 16 h. The progress of reaction was monitored by LCMS. The reaction mixture was diluted with water (20 mL) and extracted with EtOAc (3×30 mL). The organic layer was washed with water (8×40 mL) and dried over anhydrous sodium sulfate. Removal of solvent under vacuum gave a crude product which was purified by reverse HPLC to obtain pure 1-(4-(5-isopropyl-1H-pyrazol-3-ylamino)-6,7-dihydro-5H-cyclopenta[d]pyrimidin-2-yl)-N-methylpyrrolidine-2-carboxamide (20 mg) as racemate. The enantiomers were separated by chiral HPLC to afford (R)-1-(4-(5-isopropyl-1H-pyrazol-3-ylamino)-6,7-dihydro-5H-cyclopenta[d]pyrimidin-2-yl)-N-methylpyrrolidine-2-carboxamide (5 mg). $^1$H NMR (400 MHz, CD₃OD, freebase) δ (ppm): 1.30 (d, 6H), 1.95-2.25 (m, 6H), 2.68 (s, 3H), 2.74 (t, 2H), 2.78 (t, 2H), 2.93-3.03 (m, 1H), 3.59 (brs, 1H), 3.80 (brs, 1H), 4.54 (d, 1H), 6.40 (brs, 1H). The other enantiomer was made using the chiral (R) starting material.

Example 24

Preparation of Compound Nos. 20, 20a and 20b

To a solution of 1-(4-(5-isopropyl-1H-pyrazol-3-ylamino)-6,7-dihydro-5H-cyclopenta[d]pyrimidin-2-yl)pyrrolidine-2-carboxylic acid (300 mg, 0.842 mmol) in DMF (5 mL) was added dimethyl amine hydrochloride (343 mg, 4.213 mmol), HATU (320 mg, 0.842 mmol), diisopropylethylamine (163 mg, 1.263 mmol) and the reaction mixture was stirred at RT for 16 h. The progress of reaction was monitored by LCMS. The reaction mixture was diluted with water (20 mL) and extracted with EtOAc (3×30 mL). The organic layer was washed with water (8×40 mL) and dried over anhydrous sodium sulfate. Removal of solvent under reduced pressure gave a crude product which was purified by reverse phase HPLC followed by chiral HPLC to afford (R)-1-(4-(5-isopropyl-1H-pyrazol-3-ylamino)-6,7-dihydro-5H-cyclopenta[d]pyrimidin-2-yl)-N,N-dimethylpyrrolidine-2-carboxamide, and its (S) enantiomer. ¹H NMR (400 MHz, CD₃OD, freebase) δ (ppm): 1.28 (d, 6H), 1.90-2.18 (m, 5H), 2.30-2.42 (m, 1H), 2.62-3.08 (m, 4H), 2.76 (s, 3H), 2.82-2.30 (m, 1H), 2.98 (s, 3H), 3.61-3.91 (m, 2H), 5.01 (d, 1H), 6.00 (brs, 1H).

Example 25

Preparation of Compound Nos. 21, 21a and 21b

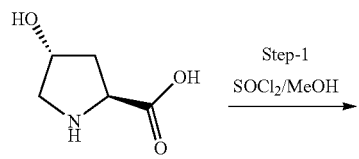

Step-1
SOCl₂/MeOH

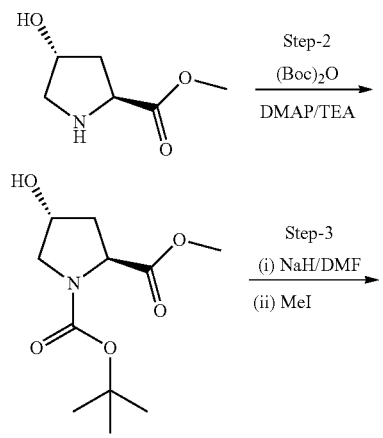

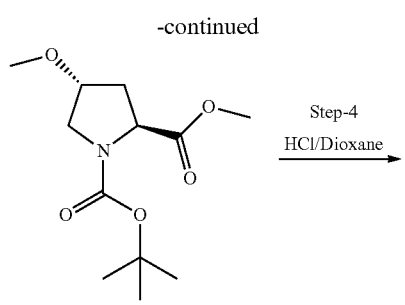

Step-4
HCl/Dioxane

Step-5

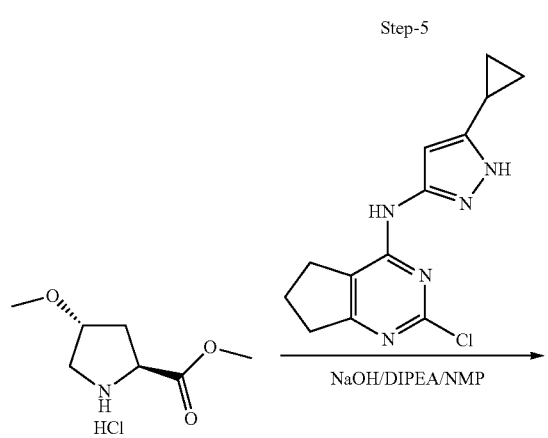

NaOH/DIPEA/NMP

Step-6
EDC·HCl/NMM
HOBt, MeOH

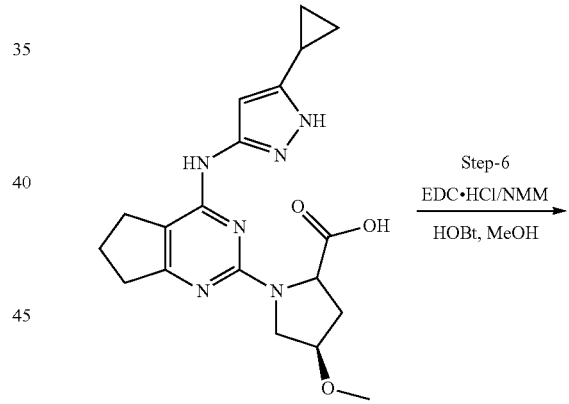

Step-7

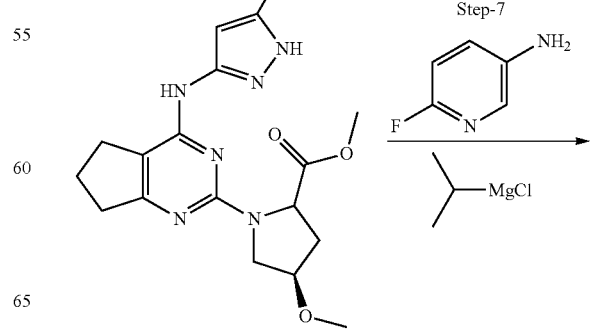

-continued

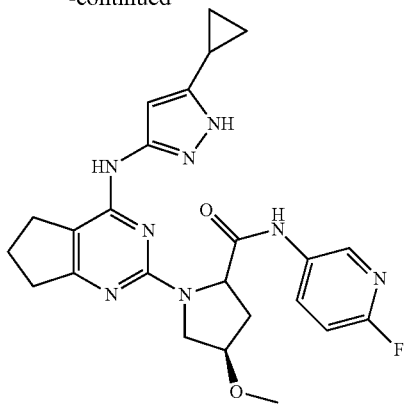

Step-1: Synthesis of (2S,4R)-methyl 4-hydroxypyrrolidine-2-carboxylate

To a suspension of (2S,4R)-4-hydroxypyrrolidine-2-carboxylic acid (15 g, 114.5 mmol) in MeOH (150 mL) was added SOCl$_2$ (17 mL, 229 mmol) dropwise at 0° C. The resultant mixture was allowed to stir at RT overnight. The reaction mixture was concentrated under vacuum, azeotroped with toluene and dried to afford (2S,4R)-methyl 4-hydroxypyrrolidine-2-carboxylate as the HCl salt (20.5 g).

Step-2: Synthesis of (2S,4R)-1-tertbutoxycarbonyl-2-methoxycarbonyl-4-hydroxy pyrrolidine To a suspension of (2S,4R)-methyl 4-hydroxypyrrolidine-2-carboxylate hydrochloride (20.5 g, 113.25 mmol) in DCM was added triethylamine (31.4 mL, 226.5 mmol), DMAP (690 mg, 5.66 mmol) and di-tert-butyl dicarbonate (29.6 g, 135.9 mmol) at 0° C. The reaction mixture was allowed to stir at RT for 3 h. the reaction mixture was washed with water (3×150 mL) followed by saturated NaHCO$_3$ (150 mL) and brine (150 mL). The organic layer was dried over anhydrous sodium sulfate and concentrated under vacuum to afford (2S,4R)-1-tertbutoxycarbonyl-2-methoxycarbonyl-4-hydroxy pyrrolidine as oil (27 g).

Step-3: Synthesis of (2S,4R)-1-tertbutoxycarbonyl-2-methoxycarbonyl-4-methoxy pyrrolidine To a solution of (2S,4R)-1-tertbutoxycarbonyl-2-methoxycarbonyl-4-hydroxy pyrrolidine (10 g, 40.81 mmol) in DMF (60 mL) at 0° C. was added NaH (2.9 g, 122.4 mmol) and the resultant mixture was allowed to stir at the same temperature for 30 min. To this mixture was added MeI (5.08 mL, 81.63 mmol) dropwise at 0° C. and the reaction mixture was allowed to stir at RT for 2 h. The reaction mixture was poured onto ice-cold water (200 mL) and extracted with EtOAc (250 mL). The organic layer was washed with water (8×100 mL) and dried over anhydrous sodium sulfate. Removal of solvent under reduced pressure afforded (2S,4R)-1-tertbutoxycarbonyl-2-methoxycarbonyl-4-methoxy pyrrolidine (9 g) which was used for the next step without further purification.

Step-4: Synthesis of (2S,4R)-methyl 4-methoxypyrrolidine-2-carboxylate hydrochloride A solution of (2S,4R)-1-tertbutoxycarbonyl-2-methoxycarbonyl-4-methoxy pyrrolidine (9 g, 34.74 mmol) in 4 M HCl-dioxane (13 mL) was stirred at RT overnight. The reaction mixture was concentrated to dryness, washed with hexane followed by ether and dried under vacuum to afford (2S,4R)-methyl 4-methoxypyrrolidine-2-carboxylate hydrochloride (6 g).

Step-5: Synthesis of (4R)-1-(4-(5-cyclopropyl-1H-pyrazol-3-ylamino)-6,7-dihydro-5H-cyclopenta[d]pyrimidin-2-yl)-4-methoxypyrrolidine-2-carboxylic acid To a solution of 2-chloro-N-(5-cyclopropyl-1H-pyrazol-3-yl)-6,7-dihydro-5H-cyclopenta[d]pyrimidin-4-amine (5 g, 13.5 mmol) in NMP (20 mL) was added DIPEA (3.6 mL) and 5 N NaOH (4.05 mL) and the resultant mixture was allowed to stir at 135° C. for 20 h. The reaction mixture was diluted with water (100 mL) and extracted with EtOAc (6×80 mL). The aqueous layer was acidified with 1N HCl solution up to pH 4 and extracted with EtOAc (3×60 mL). The organic layer was dried over anhydrous sodium sulfate and concentrated under vacuum to afford (4R)-1-(4-(5-cyclopropyl-1H-pyrazol-3-ylamino)-6,7-dihydro-5H-cyclopenta[d]pyrimidin-2-yl)-4-methoxypyrrolidine-2-carboxylic acid (4.9 g).

Step-6: Synthesis of (4R)-methyl 1-(4-(5-cyclopropyl-1H-pyrazol-3-ylamino)-6,7-dihydro-5H-cyclopenta[d]pyrimidin-2-yl)-4-methoxypyrrolidine-2-carboxylate To a solution of (4R)-1-(4-(5-cyclopropyl-1H-pyrazol-3-ylamino)-6,7-dihydro-5H-cyclopenta[d]pyrimidin-2-yl)-4-methoxypyrrolidine-2-carboxylic acid (3.5 g, 9.11 mmol) in MeOH (20 mL) was added HOBt.H$_2$O (2.27 g, 4.56 mmol), N-methylmorpholine (2 mL, 18.22 mmol) and EDCI.HCl (2.44 g, 12.75 mmol). The reaction mixture was allowed to stir at RT for 1 h. MeOH was removed under reduced pressure and the residue was dissolved in EtOAc (200 mL). The solution was washed with water (10×100 mL) followed by brine (100 mL) and dried over anhydrous sodium sulfate. Removal of EtOAc under reduced pressure afforded (4R)-methyl 1-(4-(5-cyclopropyl-1H-pyrazol-3-ylamino)-6,7-dihydro-5H-cyclopenta[d]pyrimidin-2-yl)-4-methoxypyrrolidine-2-carboxylate (3 g).

Step-7: Synthesis of (4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide To a solution of 6-fluoropyridin-3-amine (1.2 g, 11.30 mmol) in dry THF (20 mL) was added 2M solution of isopropylmagnesium chloride in THF (9.4 mL, 18.8 mmol) dropwise under nitrogen at 0° C. The resultant mixture was stirred at 0° C. for 20 min. To this solution was added a solution of (4R)-methyl 1-(4-(5-cyclopropyl-1H-pyrazol-3-ylamino)-6,7-dihydro-5H-cyclopenta[d]pyrimidin-2-yl)-4-methoxypyrrolidine-2-carboxylate (3 g, 7.53 mmol) in THF (10 mL) dropwise at 0° C. and the reaction mixture was allowed to stir at RT overnight. The reaction was quenched with saturated ammonium chloride solution (50 mL). The product was extracted with EtOAc (2×100 mL) and the organic layer was dried over anhydrous sodium sulfate. Removal of EtOAc under reduced pressure afforded a diastereomeric mixture of Compound 21. The diastereomers were separated by reverse phase followed by chiral HPLC to afford (2R,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide (Compound No. 21a, 208 mg) and (2S,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide (Compound No. 21b, 193 mg). Compound No. 21a: $^1$H NMR (400 MHz, CD$_3$OD, freebase) δ (ppm): 0.60-0.78 (m, 2H), 0.82-0.98 (m, 2H), 1.78-1.82 (m, 1H), 2.08-2.20 (m, 2H), 2.38-2.62 (m, 2H), 2.78-2.91 (m, 4H), 3.40 (s, 3H), 2.70-2.81 (m, 1H), 3.90-4.02 (m, 1H), 4.15-4.21 (m, 1H), 4.72-4.78 (m, 1H), 6.21 (brs, 1H), 7.00 (dd, 1H), 8.00 (brs, 1H), 8.28 (brs, 1H). Compound No. 21b: $^1$H NMR (400 MHz, CD$_3$OD, freebase) δ (ppm): 0.60-0.78 (m, 2H), 0.82-0.98 (m, 2H), 1.78-1.82 (m, 1H), 2.08-2.20 (m, 2H), 2.38-2.62 (m, 2H), 2.78-2.91 (m, 4H), 3.40 (s, 3H), 3.80-4.01 (m, 2H), 4.15-4.21 (m, 1H), 4.72-4.78 (m, 1H), 6.21 (brs, 1H), 7.00 (dd, 1H), 8.00 (brs, 1H), 8.28 (brs, 1H).

Example 26

Preparation of Compound Nos. 22, 22a, 22b, 22c and 22d

To a stirred solution of (3S)-tert-butyl 3-(1-(4-(3-isopropyl-1H-pyrazol-5-ylamino)-6,7-dihydro-5H-cyclopenta[d]pyrimidin-2-yl)pyrrolidine-2-carboxamido)pyrrolidine-1-carboxylate (350 mg, 0.667 mmol) in DCM (3.5 mL) was added TFA (0.15 ml, 2.003 mmol) dropwise under nitrogen atmosphere at 0° C. The resultant mixture was stirred at RT for 16 h. The reaction mixture was concentrated under reduced pressure. The crude obtained was purified by reverse phase HPLC. The stereoisomers obtained were separated by chiral HPLC to afford 21 mg of (R)-1-(4-(3-isopropyl-1H-pyrazol-5-ylamino)-6,7-dihydro-5H-cyclopenta[d]pyrimidin-2-yl)-N—((S)-pyrrolidin-3-yl)pyrrolidine-2-carboxamide. $^1$H NMR (400 MHz, CDCl$_3$) δ (ppm) 1.30 (d, 6H), 1.94-2.15 (m, 6H), 2.60-2.77 (m, 4H), 2.79-3.10 (m, 6H), 3.58-3.66 (m, 1H), 3.70-3.80 (m, 1H), 4.05-4.13 (m, 1H), 4.58 (dd, 1H), 6.38 (s, 1H), 6.79 (s, 1H). The other diastereomers were prepared using appropriate chiral starting materials.

Example 27

Preparation of Compound Nos. 23 to 49, 51 to 54, 56 to 59, 61 to 62, 64 to 67, 75 to 77, 80 to 83, 85 to 94 and Stereoisomers Compound Nos. 23 to 49, 51 to 54, 56 to 59, 61 to 62, 64 to 67, 75 to 77, 80 to 83, 85 to 94, and their individual stereoisomers, can be prepared in a similar fashion according to the General Method, Examples, and publications described herein, and from established synthetic procedures familiar to those skilled in the art.

Example 28

Preparation of Compound Nos. 50, 50a and 50b

To a stirred solution of 5-amino-2-fluoropyridine (79 mg, 0.703 mmol) in dry THF (2 mL) was added isopropyl magnesium chloride 2M in THF (0.43 mL, 0.86 mmol) dropwise under nitrogen atmosphere at 0° C. The resultant mixture was stirred at 0° C. for 30 min. To this was added a solution of (S)-methyl 1-(4-(3-isopropyl-1H-pyrazol-5-ylamino)-6,6-dimethyl-6,7-dihydro-5H-cyclopenta[d]pyrimidin-2-yl)pyrrolidine-2-carboxylate (70 mg, 0.175 mmol) in THF (2 mL) dropwise at 0° C. and the reaction mixture was allowed to stir at RT for 2 h. The reaction mixture was cooled to 0° C. and quenched by saturated ammonium chloride solution (10 mL). The reaction mixture was diluted with water (10 mL) and extracted with EtOAc (2×20 mL). The organic layer was washed with brine (20 mL) and dried over anhydrous sodium sulfate. Removal of EtOAc under vacuum gave a crude oil which was purified by reverse phase HPLC to afford 15 mg of (S)—N-(6-fluoropyridin-3-yl)-1-(4-(3-isopropyl-1H-pyrazol-5-ylamino)-6,6-dimethyl-6,7-dihydro-5H-cyclopenta[d]pyrimidin-2-yl)pyrrolidine-2-carboxamide. $^1$H NMR (400 MHz, CD$_3$OD, freebase) δ (ppm): 1.15-1.25 (m, 6H), 1.20 (s, 6H), 2.02-2.18 (m, 2H), 2.22-2.3.8 (m, 2H), 2.58 (s, 2H), 2.62 (s, 2H), 2.79-2.90 (m, 1H), 3.60-3.70 (m, 1H), 3.78-3.87 (m, 1H), 4.77 (dd, 1H), 6.25 (brs, 1H), 6.99 (dd, 1H), 7.97 (brs, 1H), 8.20 (s, 1H). The other enantiomer was obtained using the chiral (R) starting material.

Example 29

Preparation of Compound Nos. 55, 55a and 55b

To a solution of 6-fluoro-N-methyl-pyridin-3-amine (1.05 g, 8.34 mmol) in THF (15 mL) was added isopropylmagnesium chloride (2M in THF) (4.15 mL, 8.34 mmol) dropwise at 0° C. The reaction mixture was stirred at the same temperature for 30 min. followed by the dropwise addition of solution of ethyl (2S)-1-[4-[(5-isopropyl-1H-pyrazol-3-yl)amino]-6,7-dihydro-5H-cyclopenta[d]pyrimidin-2-yl]pyrrolidine-2-carboxylate (0.8 g, 2.083 mmol) in THF (5 mL) at 0° C. The reaction mixture was stirred at RT for 2 h. The progress of reaction was monitored by LCMS. The reaction mixture was quenched with saturated solution of ammonium chloride (30 mL) and extracted with EtOAc (2×30 mL). The organic layer was washed with water (40 mL) followed by brine (20 mL), dried over anhydrous sodium sulfate and concentrated under vacuum to obtain crude which was purified by reverse phase HPLC to afford (2S)—N-(6-fluoro-3-pyridyl)-1-[4-[(5-isopropyl-1H-pyrazol-3-yl)amino]-6,7-dihydro-5H-cyclopenta[d]pyrimidin-2-yl]-N-methylpyrrolidine-2-carboxamide (190 mg) as solid. $^1$H NMR (400 MHz, CDCl$_3$) δ (ppm): 1.19-1.30 (m, 6H), 1.80-2.30 (m, 6H), 2.58-2.68 (m, 2H), 2.70-2.88 (m, 2H), 2.91-3.00 (m, 1H), 3.28 (s, 3H), 3.61-3.78 (m, 1H), 3.79-3.90 (m, 1H), 4.40 (brs, 1H), 6.18 (s, 1H), 6.66 (s, 1H), 7.00 (brs, 1H), 8.01 (brs, 1H), 8.20 (s, 1H). The other enantiomer was obtained by using the chiral (R) starting material.

Example 30

Preparation of Compound Nos. 60, 60a and 60b

To a solution of (S)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide (200 mg, 0.44 mmol) and urea-hydrogen peroxide (125 mg, 1.33 mmol) in DCM (10 mL) at 0° C. was added trifluoroacetic anhydride (280 mg, 1.33 mmol). The resulting mixture was allowed to stir at RT overnight. The reaction mixture was concentrated under reduced pressure to afford an oily residue that was diluted with saturated sodium bicarbonate solution (10 mL), and the product was extracted with EtOAc (2×25 mL). The combined organic layer was dried over anhydrous sodium sulfate. Removal of EtOAc under reduced pressure gave an oily residue that was purified by reverse phase HPLC to afford 10 mg of (S)-2-fluoro-5-(1-(4-(5-isopropyl-1H-pyrazol-3-ylamino)-6,7-dihydro-5H-cyclopenta[d]pyrimidin-2-yl)pyrrolidine-2-carboxamido)pyridine 1-oxide.

¹HNMR (400 MHz, CD₃OD) δ (ppm): 1.20 (d, 6H), 2.02-2.18 (m, 4H), 2.21-2.36 (m, 2H), 2.75-2.93 (m, 5H), 3.60-3.70 (m, 1H), 3.77-3.84 (m, 1H), 4.77 (dd, 1H), 6.21 (s, 1H), 7.36-7.41 (m, 1H), 7.50 (s, 1H), 8.81-8.89 (m, 1H). The other enantiomer was obtained using chiral (R) starting material.

Example 31

Preparation of Compound Nos. 63, 63a and 63b

To a solution of N-(6-fluoro-3-pyridyl)-1-[4-[(5-isopropyl-1H-pyrazol-3-yl)amino]-6,7-dihydro-5H-cyclopenta[d]pyrimidin-2-yl]pyrrolidine-2-carboxamide (500 mg, 1.111 mmol) in THF (10 mL) was added HCl (1 mL) and reaction mixture was stirred at 60° C. for 16 h. The progress of reaction was monitored by LCMS. The reaction mixture was concentrated under vacuum to obtain crude product which was purified by reverse HPLC to afford N-(6-hydroxy-3-pyridyl)-1-[4-[(5-isopropyl-1H-pyrazol-3-yl)amino]-6,7-dihydro-5H-cyclopenta[d]pyrimidin-2-yl]pyrrolidine-2-carboxamide (249 mg). ¹H NMR (400 MHz, CD₃OD) δ (ppm): 1.17-1.30 (m, 6H), 2.17-2.37 (m, 4H), 2.38-2.50 (m, 1H), 2.79-2.95 (m, 3H), 3.00-3.10 (m, 2H), 3.22-3.38 (m, 2H), 3.58-3.70 (m, 1H), 3.80 (brs, 1H), 4.81 (dd, 1H), 6.22 (s, 1H), 6.68 (d, 1H), 7.60 (d, 1H), 7.98 (s, 1H). Separation by chiral HPLC provides enantiomers 63a and 63b.

Example 32

Preparation of Compound Nos. 68, 68a and 68b

To a solution of thiazol-2-amine (1.08 g, 10.8 mmol) in THF (12 mL) was added isopropyl magnesium chloride (5.4 mL, 10.8 mmol) dropwise at 0° C. The reaction mixture was stirred at the same temperature for 20 min., followed by dropwise addition of solution of methyl (2S)-1-[4-[(5-isopropyl-1H-pyrazol-3-yl)amino]-6,7-dihydro-5H-cyclopenta[d]pyrimidin-2-yl]pyrrolidine-2-carboxylate (1 g, 2.702 mmol) in THF (5 mL). The reaction mixture was stirred at RT for 2 h. The progress of reaction was monitored by LCMS. The reaction mixture was quenched with a saturated solution of ammonium chloride (200 mL) and extracted with EtOAc (2×200 mL). The organic layer was washed with water (2×200 mL) followed by brine (200 mL) and dried over anhydrous sodium sulfate and concentrated under vacuum to obtain a crude product, which was recrystallized in diethyl ether (50 mL) to afford (2S)-1-[4-[(5-isopropyl-1H-pyrazol-3-yl)amino]-6,7-dihydro-5H-cyclopenta[d]pyrimidin-2-yl]-N-thiazol-2-yl-pyrrolidine-2-carboxamide (600 mg). ¹H NMR (400 MHz, CDCl₃) δ (ppm): 1.30 (d, 6H), 2.00-2.22 (m, 5H), 2.50-2.70 (m, 3H), 2.80-3.05 (m, 3H), 3.61-3.80 (m, 2H), 4.85 (d, 1H), 6.28 (brs, 1H), 6.93 (d, 1H), 6.99 (brs, 1H), 7.40 (d, 1H). The other enantiomer is prepared using chiral (R) starting material.

Example 33

Preparation of Compound Nos. 69, 69a and 69b

To a solution of 6-fluoropyridin-3-amine (247 mg, 2.6 mmol) in dry THF (6 mL) was added a 2M solution of isopropylmagnesium chloride (1.3 mL, 2.6 mmol) in THF dropwise under nitrogen at 0° C. The resultant mixture was stirred at 0° C. for 20 minutes. To this solution was added a solution of (S)-ethyl 1-(4-(5-isopropyl-1H-pyrazol-3-ylamino)-6,7-dihydro-5H-cyclopenta[d]pyrimidin-2-yl)pyrrolidine-2-carboxylate (200 mg, 0.52 mmol) in THF (2 mL) dropwise at 0° C. and the reaction mixture was allowed to stir at room temperature for 2 h. The reaction was quenched with saturated ammonium chloride solution (10 mL). The product was extracted with ethyl acetate (3×50 mL). The combined organic layer was washed with water (2×100 mL) and dried over anhydrous sodium sulfate. Removal of ethyl acetate under reduced pressure gave solid residue which was purified by reverse phase HPLC to afford 119 mg of (S)-1-(4-(5-isopropyl-1H-pyrazol-3-ylamino)-6,7-dihydro-5H-cyclopenta[d]pyrimidin-2-yl)-N-(pyrimidin-4-yl)pyrrolidine-2-carboxamide as TFA salt. ¹H NMR (400 MHz, CD₃OD, TFA) δ (ppm): 1.00-1.22 (m, 6H), 2.10-2.39 (m, 5H), 2.40-2.48 (m, 1H), 2.79-2.91 (m, 3H), 2.97-3.10 (m, 2H), 3.60-3.86 (m, 2H), 4.80-4.91 (m, 1H), 6.16 (s, 1H), 8.10 (d, 1H), 8.58 (d, 1H), 8.87. The other enantiomer is prepared using chiral (R) starting material.

Example 34

Preparation of Compound Nos. 70, 70a, 70b, 70c and 70d

To a solution of 6-fluoropyridin-3-amine (4.64 mg, 4.14 mmol) in dry THF (5 mL) was added 2 M solution of isopropylmagnesium chloride (1.98 mL, 3.96 mmol) in THF dropwise under nitrogen at 0° C. The resultant mixture was stirred at 0° C. for 20 min. To this solution was added a solution of (2S,4R)-methyl 4-hydroxy-1-(4-(5-isopropyl-1H-pyrazol-3-ylamino)-6,7-dihydro-5H-cyclopenta[d]pyrimidin-2-yl)pyrrolidine-2-carboxylate (400 mg, 1.04 mmol) in THF (2 mL) dropwise at 0° C. and the reaction mixture was allowed to stir at 25° C. for 4 h. The reaction was quenched with saturated ammonium chloride solution (10 mL) and diluted with water (25 mL). The product was extracted with EtOAc (2×50 mL). The combined organic layer was washed with water (2×100 mL) followed by brine (100 mL) and dried over anhydrous sodium sulfate. Removal of EtOAc under reduced pressure gave an oily residue which was purified by reverse phase HPLC to afford 66 mg of (2S,4R)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide. ¹H NMR (400 MHz, CDCl₃, freebase) δ (ppm): 0.99-1.30 (m, 6H), 2.10-2.30 (m, 4H), 2.65-2.74 (m, 2H), 2.78-2.98 (m, 4H), 3.78-3.05 (m, 1H), 3.91-3.99 (m, 1H), 4.70-4.78 (m, 1H), 4.92-4.98 (m, 1H), 6.34 (s, 1H), 6.77 (s, 1H), 6.82 (dd, 1H), 7.93 (s, 1H), 8.08-8.18 (m, 1H). The other diasteromers are prepared using appropriate chiral starting materials.

Example 35

Preparation of Compound Nos. 71, 71a, 71b, 71c and 71d

To a solution of 6-fluoropyridin-3-amine (415 mg, 4.15 mmol) in dry THF (5 mL) was added a 2M solution of isopropylmagnesium chloride (2.08 mL, 4.16 mmol) in THF dropwise under nitrogen at 0° C. The resultant mixture was stirred at 0° C. for 20 min. To this solution was added a solution of (2S,4R)-methyl 4-hydroxy-1-(4-(5-isopropyl-1H-pyrazol-3-ylamino)-6,7-dihydro-5H-cyclopenta[d]pyrimidin-2-yl)pyrrolidine-2-carboxylate (400 mg, 1.04 mmol) in THF (2 mL) dropwise at 0° C. and the reaction mixture was allowed to stir at 25° C. for 4 h. The reaction was quenched with saturated ammonium chloride solution (10 mL) and diluted with water (25 mL). The product was extracted with EtOAc (2×75 mL). The combined organic layer was washed with water (2×100 mL) followed by brine (100 mL) and dried over anhydrous sodium sulfate. Removal of EtOAc under reduced pressure gave an oily residue which was purified by reverse phase HPLC to afford 95 mg of (2S,4R)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide. $^1$H NMR (400 MHz, CDCl$_3$, freebase) δ (ppm): 1.20-1.39 (m, 6H), 2.05-2.18 (m, 2H), 2.19-2.27 (m, 1H), 2.58-2.78 (m, 3H), 2.79-3.06 (m, 3H), 3.79-3.06 (m 1H), 3.91-4.00 (m, 1H), 4.71-4.78 (m, 1H), 4.98-5.05 (m, 1H), 6.22 (s, 1H), 6.92 (d, 1H), 7.40 (d, 1H). The other diasteromers are prepared using appropriate chiral starting materials.

Example 36

Preparation of Compound Nos. 72, 72a and 72b

To a solution of (S)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide (250 mg, 0.55 mmol) in 1,4-dioxane (5 mL) was added aqueous ammonia (5 mL) and the reaction mixture was allowed to reflux in steel bomb at 130° C. for 18 h. The reaction mixture was concentrated under vacuum to obtain an oily crude product which was purified by reverse phase HPLC to afford 8 mg of (S)—N-(6-aminopyridin-3-yl)-1-(4-(5-isopropyl-1H-pyrazol-3-ylamino)-6,7-dihydro-5H-cyclopenta[d]pyrimidin-2-yl)pyrrolidine-2-carboxamide. $^1$H NMR (400 MHz, CD$_3$OD, freebase) δ (ppm): 1.20 (d, 6H), 2.00-2.20 (m, 4H), 2.75-2.95 (m, 5H), 3.50-3.90 (m, 4H), 4.90-4.98 (m, 1H), 6.40 (s, 1H), 6.50 (d, 1H), 7.40 (s, 1H), 7.90 (s, 1H). The other enantiomer is prepared using the chiral (R) starting material.

Example 37

Preparation of Compound Nos. 73, 73a and 73b

A mixture of 1-(4-(5-isopropyl-1H-pyrazol-3-ylamino)-6,7-dihydro-5H-cyclopenta[d]pyrimidin-2-yl)pyrrolidine-2-carboxylic acid (400 mg, 1.12 mmol), piperidine (143 mg, 1.68 mmol), HATU (512 g, 1.34 mmol) and DIPEA (230 mg, 1.79 mmol) in DMF (4 mL) was allowed to stir at RT overnight. The reaction mixture was diluted with water (50 mL) and extracted with EtOAc (2×50 mL). The combined organic layer was washed with water (8×25 mL) and dried over anhydrous sodium sulfate. Removal of EtOAc gave an oily residue which was purified by reverse phase HPLC followed by chiral HPLC to afford 10 mg of (R)-(1-(4-(5-isopropyl-1H-pyrazol-3-ylamino)-6,7-dihydro-5H-cyclopenta[d]pyrimidin-2-yl)pyrrolidin-2-yl)(piperidin-1-yl)methanone, and its enantiomer. $^1$H NMR (400 MHz, CD$_3$OD, freebase) δ (ppm): 1.30 (d, 6H), 1.40-1.90 (m, 6H), 1.92-2.12 (m, 5H), 2.30-2.42 (m, 1H), 2.65-2.81 (m, 4H), 2.90-3.01 (m, 1H), 3.40-3.90 (m, 6H), 5.00-5.08 (m, 1H), 6.00 (brs, 1H).

Example 38

Preparation of Compound Nos. 74, 74a and 74b

A mixture of 1-(4-(5-isopropyl-1H-pyrazol-3-ylamino)-6,7-dihydro-5H-cyclopenta[d]pyrimidin-2-yl)pyrrolidine-2-carboxylic acid (1 g, 2.8 mmol), morpholine (0.366 g, 4.2 mmol), HATU (1.28 g, 3 mmol) and DIPEA (0.58 g, 4 mmol) in DMF (5 mL) was allowed to stir at RT overnight. The reaction mixture was diluted with water (50 mL) and extracted with EtOAc (2×50 mL). The combined organic layer was washed with water (8×25 mL) and dried over anhydrous sodium sulfate. Removal of EtOAc gave an oily residue which was purified by reverse phase HPLC followed by chiral HPLC to afford 15 mg of (R)-(1-(4-(5-isopropyl-1H-pyrazol-3-ylamino)-6,7-dihydro-5H-cyclopenta[d]pyrimidin-2-yl)pyrrolidin-2-yl)(morpholino)methanone, and its enantiomer. $^1$H NMR (400 MHz, CD$_3$OD, freebase) δ (ppm): 1.29 (d, 6H), 1.92-2.15 (m, 5H), 2.30-2.42 (m, 1H), 2.67-2.81 (m, 4H), 2.90-3.04 (m, 1H), 3.41-3.90 (m, 10H), 4.98-5.08 (m, 1H), 5.85 (brs, 1H).

Example 39

Preparation of Compound Nos. 78, 78a and 78b

A suspension of (R)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide (200 mg, 0.44 mmol) and sodium thiomethoxide (100 mg, 1.42 mmol) in ethanol (2 mL) was heated at 100° C. in a microwave for 1 h. The solvent was removed under reduced pressure and the residue was diluted with EtOAc (50 mL). The solution was washed with saturated sodium bicarbonate solution (20 mL) followed by brine (20 mL), and dried over anhydrous sodium sulfate. Removal of EtOAc under reduced pressure gave an oily residue that was purified by reverse phase HPLC followed by chiral HPLC to afford 10 mg of (R)-1-(4-(5-isopropyl-1H-pyrazol-3-ylamino)-6,7-dihydro-5H-cyclopenta[d]pyrimidin-2-yl)-N-(6-(methylthio)pyridin-3-yl)pyrrolidine-2-carboxamide. $^1$HNMR (400 MHz, CDCl$_3$) δ (ppm): 1.18-1.32 (m, 6H), 1.90-2.20 (m, 5H), 2.51 (s, 3H), 2.60-2.77 (m, 3H), 2.84-2.98 (m, 3H), 3.60-3.79 (m, 2H), 4.78 (d, 1H), 6.40 (s, 1H), 6.70 (s, 1H), 7.08 (d, 1H), 7.98 (brs, 1H), 8.20 (s, 1H). The other enantiomer is prepared using the (S) starting material.

Example 40

Preparation of Compound Nos. 79, 79a and 79b

A suspension of (R)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide (200 mg, 0.44 mmol) and sodium ethoxide (100 mg, 1.42 mmol) in ethanol (2 mL) was heated at 100° C. in a microwave for 1 h. The solvent was removed under reduced pressure and the residue was diluted with EtOAc (50 mL). The solution was washed with saturated sodium bicarbonate solution (20 mL) followed by brine (20 mL) and dried over anhydrous sodium sulfate. Removal of EtOAc under reduced pressure gave an oily residue that was purified by reverse phase HPLC followed by chiral HPLC to afford 4 mg of (R)—N-(6-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide. $^1$HNMR (400 MHz, CDCl$_3$) δ (ppm): 1.18-1.32 (m, 6H), 1.38 (t, 3H), 1.90-2.20 (m, 5H), 2.60-2.77 (m, 3H), 2.84-2.98 (m, 3H), 3.60-3.79 (m, 2H), 4.28 (q, 2H), 4.78 (d, 1H), 6.40 (s, 1H), 6.62 (d, 1H), 6.70 (s, 1H), 7.85 (brs, 1H), 7.79 (s, 1H). The other enantiomer is prepared using the (S) starting material.

Example 41

Preparation of Compound Nos. 84, 84a and 84b

To a stirred solution of 6-fluoropyridin-3-amine (1 g, 8.916 mmol) in dry THF (10 mL) was added isopropyl magnesium chloride 2M in THF (5.2 mL, 10.40 mmol) dropwise under nitrogen atmosphere at 0° C. The resultant mixture was stirred at 0° C. for 30 min. To this was added a solution of methyl (2S)-1-[4-[(3-isopropyl-1H-pyrazol-5-yl)amino]-6,7-dihydro-5H-cyclopenta[d]pyrimidin-2-yl]pyrrolidine-2-carboxylate (1.1 g, 2.972 mmol) in THF (10 mL) dropwise at 0° C. The mixture was stirred at RT for 2 h. The reaction mixture was cooled to 0° C., and quenched with saturated ammonium chloride solution (50 mL). The product was extracted with EtOAc (2×50 mL). The organic layer was washed with brine (50 mL) and dried over anhydrous sodium sulfate. Removal of solvent under reduced pressure gave a crude oily residue that was triturated with ether (3×25 mL) to afford 600 mg of solid product. 50 mg of product was purified by reverse phase HPLC to afford 30 mg of (2S)—N-(2-fluoro-3-pyridyl)-1-[4-[(3-isopropyl-1H-pyrazol-5-yl)amino]-6,7-dihydro-5H-cyclopenta[d]pyrimidin-2-yl]pyrrolidine-2-carboxamide. $^1$HNMR (400 MHz, CDCl$_3$) δ (ppm): 1.28 (d, 6H), 1.90-2.00 (m, 1H), 2.03-2.21 (m, 4H), 2.62-2.78 (m, 3H), 2.80-3.10 (m, 3H), 3.60-3.80 (m, 2H), 4.83 (d, 1H), 6.37 (s, 1H), 6.72 (s, 1H), 7.09-7.18 (m, 1H), 7.78-7.82 (m, 1H), 8.77-8.33 (m, 1H). The other enantiomer is prepared using the (R) chiral starting material.

Example 42

Preparation of Compound Nos. 95, 95a and 95b

To a suspension of (S)—N-(2-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide (25 mg, 0.053 mmol) in ethanol (1 mL) was added Cs$_2$CO$_3$ (26 mg, 0.080 mmol) and the reaction mixture was allowed to stir at 80° C. for 12 h. The reaction mixture was concentrated, diluted with water (20 mL) and extracted with EtOAc (2×20 mL). The combined organic layer was dried over anhydrous sodium sulfate. Removal of EtOAc under reduced pressure gave an oily residue that was purified by reverse phase HPLC to afford 8 mg of (S)—N-(2-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide as the TFA salt. $^1$HNMR (400 MHz, CD$_3$OD) δ (ppm): 1.00-1.17 (m, 6H), 1.27 (t, 3H), 2.08-2.30 (m, 4H), 2.36-2.42 (m, 2H), 2.70-2.90 (m, 3H), 2.92-3.03 (m, 2H), 3.60-3.70 (m, 1H), 3.78-3.88 (m, 1H), 4.37 (q, 2H), 4.85-4.95 (m, 1H), 6.24 (s, 1H), 6.82-6.92 (m, 1H), 7.78-7.93 (m, 1H), 8.10-8.18 (m, 1H). The other enantiomer is prepared using the (R) chiral starting material.

Example 43

Preparation of Compound Nos. 96, 96a and 96b

To a solution of 6-fluoro-N-methylpyridin-3-amine (272 mg, 2.16 mmol) in THF (70 mL) was added isopropyl magnesium chloride solution 2M in THF (1.08 mL, 2.16 mmol) dropwise at 0° C. The mixture was allowed to stir at 0° C. for 20 min. Then, a solution of (R)-methyl 1-(4-(5-isopropyl-1H-pyrazol-3-ylamino)-6,7-dihydro-5H-cyclopenta[d]pyrimidin-2-yl)pyrrolidine-2-carboxylate (200 mg, 0.54 mmol) in THF (3 mL) was added and the reaction mixture was allowed to stir at RT for 2 h. The reaction was quenched with saturated ammonium chloride solution (50 mL) and the mixture was extracted with EtOAc (3×50 mL). The combined organic layer was washed with brine and dried over anhydrous sodium sulfate. Removal of EtOAc under reduced pressure gave an oily residue that was purified by reverse phase HPLC to afford 17 mg of (R)—N-(6-fluoropyridin-3-yl)-1-(4-(5-isopropyl-1H-pyrazol-3-ylamino)-6,7-dihydro-5H-cyclopenta[d]pyrimidin-2-yl)-N-methylpyrrolidine-2-carboxamide. $^1$HNMR (400 MHz, CDCl$_3$) δ (ppm): 1.20-1.35 (m, 6H), 1.79-2.25 (m, 6H), 2.57-2.68 (m, 2H), 2.79-2.82 (m, 2H), 2.91-3.01 (m, 1H), 3.30 (s, 3H), 3.59-3.80 (m, 2H), 4.35-4.45 (m, 1H), 6.16 (s, 1H), 6.90-7.05 (m, 2H), 8.01 (brs, 1H), 8.40 (brs, 1H). The other enantiomer is prepared using the (S) chiral starting material.

Example B1

Western Blot Analysis

Inhibition of Akt phosphorylation induced by IGF-1R was studied by western blot analysis. Human colon carcinoma HT-29 cells were seeded at a density of $8 \times 10^4$ cells/well in a 24-well plate and grown in DME/F12 media containing 10% FBS for 24 h. The cells were then depleted of serum by incubation in DME/F12 media lacking FBS for 24 h. Next, cells were incubated for 2 h with compounds of the invention at concentrations of 0.1, 1, 10, or 100 ng/mL, and control cells were treated with DMSO (vehicle) or 10 ng/mL IGF-1. Cells in all treatment conditions were then treated with 10 ng/mL of IGF-1 for 10 min, followed by removal of media and addition of 200 μL of lysis buffer (Cell Signaling cat.#9803). Lysed cells were centrifuged at 13,000 rpm for 15 min and the protein concentration soluble fraction (supernatant) of each sample was determined using a BCA protein assay (Pierce). Proteins were separated by gel electrophoresis (10% SDS-PAGE, 10 μg protein/well, 100 h), followed by transfer of the proteins to a PVDF membrane (Bio-Rad cat.#162-0177) at 10 V overnight. The membrane was blocked with 5% non-fat dry milk in 1×TBS buffer for 1 h, and then incubated with α-pAKT antibody (1:1000, Cell Signaling cat. #9271) for 3 h. The membrane was washed 3 times with 1×TBS containing 0.01% Tween-20 (10 min/wash), and incubated with α-rabbit secondary antibody (1:10,000, Rockland cat.#611-1322) for 1 h. The membrane was again washed 3 times with 1×TBS containing 0.01% Tween-20 (10 min/wash) and developed using chemiluminescence (Pierce ECL Western Blotting kit cat.#32106).

Western blot quantification of the protein bands was carried out using ImageJ software (v. 1.46), with quantification of actin used as a control whose levels are not affected by the treatments. OSI-906 (3-[8-Amino-1-(2-phenyl-7-quinolyl)imidazo[1,5-a]pyrazin-3-yl]-1-methyl-cyclobutanol) and BMS-754807 ((S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide) were used as controls to detect inhibition of phosphorylation of AKT. Quantitative results of phosphorylated AKT levels normalized to actin levels (pAKT/actin) in samples from cells treated with increasing concentrations of the tested compounds are presented in Table B1. Quantitative results of phosphorylated AKT levels normalized to actin levels (pAKT/actin) in samples from cells treated with 1 nM, 10 nM, or 100 nM of the tested compounds relative to the phosphorylated AKT levels in samples from cells treated with 0.1 nM of the tested compounds are presented in Table B2.

TABLE B1

Levels of phosphorylated AKT in treated cells.

| Compound No. | Vehicle | 0.1 | 1 | 10 | 100 |
|---|---|---|---|---|---|
| OSI-906 | 0.00 | 1.06 | 0.85 | 1.58 | 0.40 |
| BMS-754807 | 0.02 | 1.15 | 1.86 | 0.09 | 0.02 |
| 2 | 0.00 | 1.04 | 0.91 | 0.07 | 0.00 |
| 2a | 0.06 | 1.70 | 1.78 | 1.81 | 1.72 |
| 2b | 0.00 | 1.57 | 0.80 | 0.22 | 0.03 |
| 3a | 0.00 | 2.64 | 1.68 | 1.86 | 2.19 |
| 3b | 0.00 | 2.25 | 1.70 | 0.57 | 0.02 |
| 4 | 0.02 | 1.92 | 1.59 | 1.01 | 0.06 |
| 4a | 0.00 | 2.38 | 1.64 | 1.76 | 1.47 |
| 4b | 0.00 | 1.81 | 1.92 | 1.64 | 0.20 |
| 5 | 0.00 | 2.28 | 0.61 | 0.04 | 0.00 |
| 6 | 0.03 | 1.54 | 0.22 | 0.01 | 0.01 |
| 6a | 0.00 | 1.85 | 1.74 | 1.40 | 1.17 |
| 6b | 0.00 | 0.87 | 0.18 | 0.00 | 0.00 |
| 7 | 0.00 | 1.45 | 2.08 | 1.09 | 1.20 |
| 8a | 0.05 | 1.93 | 2.27 | 1.17 | 1.78 |
| 8b | 0.03 | 1.47 | 0.31 | 0.04 | 0.02 |
| 9 | 0.03 | 0.67 | 0.71 | 0.07 | 0.00 |
| 9a | 0.00 | 1.24 | 1.26 | 0.53 | 0.02 |
| 9b | 0.00 | 1.46 | 1.55 | 1.18 | 0.78 |
| 10a | 0.00 | 2.28 | 0.54 | 0.00 | 0.01 |
| 10b | 0.00 | 2.21 | 2.75 | 1.71 | 1.66 |
| 11a | 0.00 | 1.83 | 1.55 | 1.43 | 1.58 |
| 11b | 0.03 | 1.55 | 1.76 | 1.43 | 0.33 |
| 12a | 0.17 | 4.17 | 3.33 | 2.91 | 4.16 |
| 12b | 0.23 | 3.66 | 3.56 | 4.32 | 2.29 |
| 13a | 0.00 | 0.51 | 0.54 | 0.45 | 0.80 |
| 13b | 0.00 | 0.22 | 0.09 | 0.00 | 0.00 |
| 14a | 0.00 | 0.73 | 0.51 | 0.43 | 0.35 |
| 14b | 0.00 | 0.51 | 0.49 | 0.02 | 0.00 |
| 15a | 0.00 | 0.70 | 0.89 | 0.92 | 0.59 |
| 15b | 0.00 | 0.52 | 0.58 | 0.43 | 0.13 |
| 16a | 0.00 | 0.82 | 0.62 | 0.61 | 0.30 |
| 16b | 0.00 | 0.53 | 0.51 | 0.15 | 0.01 |
| 17a | 0.00 | 0.89 | 1.22 | 1.01 | 1.08 |
| 17b | 0.00 | 0.83 | 0.99 | 0.95 | 1.08 |

TABLE B2

Normalized phosphorylated AKT (relative to actin) levels relative to 0.1 nM compound treatment.

| Compound No. | Vehicle | 0.1 | 1 | 10 | 100 |
|---|---|---|---|---|---|
| OSI-906 | 0.0 | 1.0 | 0.8 | 1.5 | 0.4 |
| BMS-754807 | 0.0 | 1.0 | 1.6 | 0.1 | 0.0 |
| 2 | 0.0 | 1.0 | 0.9 | 0.1 | 0.0 |
| 2a | 0.0 | 1.0 | 1.0 | 1.1 | 1.0 |
| 2b | 0.0 | 1.0 | 0.5 | 0.1 | 0.0 |
| 3a | 0.0 | 1.0 | 0.6 | 0.7 | 0.8 |
| 3b | 0.0 | 1.0 | 0.8 | 0.3 | 0.0 |
| 4 | 0.0 | 1.0 | 0.8 | 0.5 | 0.0 |
| 4a | 0.0 | 1.0 | 0.7 | 0.7 | 0.6 |
| 4b | 0.0 | 1.0 | 1.1 | 0.9 | 0.1 |
| 5 | 0.0 | 1.0 | 0.3 | 0.0 | 0.0 |
| 6 | 0.0 | 1.0 | 0.1 | 0.0 | 0.0 |
| 6a | 0.0 | 1.0 | 0.9 | 0.8 | 0.6 |
| 6b | 0.0 | 1.0 | 0.2 | 0.0 | 0.0 |
| 7 | 0.0 | 1.0 | 1.4 | 0.7 | 0.8 |
| 8a | 0.0 | 1.0 | 1.2 | 0.6 | 0.9 |
| 8b | 0.0 | 1.0 | 0.1 | 0.0 | 0.0 |
| 9 | 0.0 | 1.0 | 1.1 | 0.1 | 0.0 |
| 9a | 0.0 | 1.0 | 1.0 | 0.4 | 0.0 |
| 9b | 0.0 | 1.0 | 1.1 | 0.8 | 0.5 |
| 10a | 0.0 | 1.0 | 0.2 | 0.0 | 0.0 |
| 10b | 0.0 | 1.0 | 1.2 | 0.8 | 0.8 |
| 11a | 0.0 | 1.0 | 0.8 | 0.8 | 0.9 |
| 11b | 0.0 | 1.0 | 1.1 | 0.9 | 0.2 |
| 12a | 0.0 | 1.0 | 0.8 | 0.7 | 1.0 |
| 12b | 0.1 | 1.0 | 1.0 | 1.2 | 0.6 |
| 13a | 0.0 | 1.0 | 1.1 | 0.9 | 1.6 |
| 13b | 0.0 | 1.0 | 0.4 | 0.0 | 0.0 |
| 14a | 0.0 | 1.0 | 0.7 | 0.6 | 0.5 |
| 14b | 0.0 | 1.0 | 0.9 | 0.0 | 0.0 |
| 15a | 0.0 | 1.0 | 1.3 | 1.3 | 0.8 |
| 15b | 0.0 | 1.0 | 1.1 | 0.8 | 0.3 |
| 16a | 0.0 | 1.0 | 0.8 | 0.7 | 0.4 |
| 16b | 0.0 | 1.0 | 1.0 | 0.3 | 0.0 |
| 17a | 0.0 | 1.0 | 1.4 | 1.1 | 1.2 |
| 17b | 0.0 | 1.0 | 1.2 | 1.1 | 1.3 |

| Compound No. | p-AKT relative to levels with 0.1 nM compound | | | | |
|---|---|---|---|---|---|
| | Vehicle | 0.1 nM | 1 nM | 10 nM | 100 nM |
| OSI-906 | 0.0 | 1.0 | 0.8 | 1.5 | 0.4 |
| BMS-754807 | 0.0 | 1.0 | 1.6 | 0.1 | 0.0 |
| 2 | 0.0 | 1.0 | 0.9 | 0.1 | 0.0 |
| 2a | 0.0 | 1.0 | 1.0 | 1.1 | 1.0 |
| 2b | 0.0 | 1.0 | 0.5 | 0.1 | 0.0 |
| 3a | 0.0 | 1.0 | 0.6 | 0.7 | 0.8 |
| 3b | 0.0 | 1.0 | 0.8 | 0.3 | 0.0 |
| 4 | 0.0 | 1.0 | 0.8 | 0.5 | 0.0 |
| 4a | 0.0 | 1.0 | 0.7 | 0.7 | 0.6 |
| 4b | 0.0 | 1.0 | 1.1 | 0.9 | 0.1 |
| 5 | 0.0 | 1.0 | 0.3 | 0.0 | 0.0 |
| 6 | 0.0 | 1.0 | 0.1 | 0.0 | 0.0 |
| 6a | 0.0 | 1.0 | 0.9 | 0.8 | 0.6 |
| 6b | 0.0 | 1.0 | 0.2 | 0.0 | 0.0 |
| 7 | 0.0 | 1.0 | 1.4 | 0.7 | 0.8 |
| 8a | 0.0 | 1.0 | 1.2 | 0.6 | 0.9 |
| 8b | 0.0 | 1.0 | 0.1 | 0.0 | 0.0 |
| 9 | 0.0 | 1.0 | 1.1 | 0.1 | 0.0 |
| 9a | 0.0 | 1.0 | 1.0 | 0.4 | 0.0 |
| 9b | 0.0 | 1.0 | 1.1 | 0.8 | 0.5 |
| 10a | 0.0 | 1.0 | 0.2 | 0.0 | 0.0 |
| 10b | 0.0 | 1.0 | 1.2 | 0.8 | 0.8 |
| 11a | 0.0 | 1.0 | 0.8 | 0.8 | 0.9 |
| 11b | 0.0 | 1.0 | 1.1 | 0.9 | 0.2 |
| 12a | 0.0 | 1.0 | 0.8 | 0.7 | 1.0 |
| 12b | 0.1 | 1.0 | 1.0 | 1.2 | 0.6 |
| 13a | 0.0 | 1.0 | 1.1 | 0.9 | 1.6 |
| 13b | 0.0 | 1.0 | 0.4 | 0.0 | 0.0 |
| 14a | 0.0 | 1.0 | 0.7 | 0.6 | 0.5 |
| 14b | 0.0 | 1.0 | 0.9 | 0.0 | 0.0 |
| 15a | 0.0 | 1.0 | 1.3 | 1.3 | 0.8 |
| 15b | 0.0 | 1.0 | 1.1 | 0.8 | 0.3 |
| 16a | 0.0 | 1.0 | 0.8 | 0.7 | 0.4 |
| 16b | 0.0 | 1.0 | 1.0 | 0.3 | 0.0 |
| 17a | 0.0 | 1.0 | 1.4 | 1.1 | 1.2 |
| 17b | 0.0 | 1.0 | 1.2 | 1.1 | 1.3 |

The compounds of the invention inhibited AKT phosphorylation with varying degrees of efficacy and several proved more effective than either OSI-906 or BMS.

The effects of other derivatives of Cpd. No. 8b on AKT phosphorylation were tested as described above.

| Compound No. | pAKT relative to 0.1 nM compound | | | | |
|---|---|---|---|---|---|
| | Vehicle | 0.1 nM | 1 nM | 10 nM | 100 nM |
| 5 | 0.01 | 1.00 | 0.59 | 0.08 | 0.03 |
| 6b | 0.00 | 1.00 | 0.39 | 0.02 | 0.01 |
| 10a | 0.01 | 1.00 | 0.69 | 0.16 | 0.01 |
| 10d | 0.00 | 1.00 | 0.84 | 0.23 | 0.01 |
| 13b | 0.03 | 1.00 | 0.49 | 0.04 | 0.02 |

Example B2

In Vitro IGF-1R and IR Enzymatic Assays $IC_{50}$ values of the compounds of the invention against IGF-1R and IR were measured in vitro using an ADP-Glo kinase assay Kit (Promega). For the IGF-1R assay, active recombinant IGF-1R (Millipore #14-802) was used at 1 ng/reaction, the substrate IGF-1R tide (Millipore #12-527) was used at 125 μM and ATP was used at 100 μM. For the IR assay, active recombinant IR (Millipore #14-803) as used at 1 ng/reaction, the substrate Ax1 tide (Millipore #12-516) was used at 125 μM and ATP at 50 μM. Kinase reactions in both assays were conducted at 30° C. for 20 min with increasing concentrations of compounds of the invention.

The $IC_{50}$ values of Compound nos. 2b & 8b, and BMS-754807 against IGF-1R and IR are listed in Tables B3 and B4, respectively.

TABLE B3

$IC_{50}$ Values of Compound nos. 2b & 8b, and BMS-754807 against IGF-1R.

| Compound No. | Hill Slope N1 | Hill Slope N2 | $IC_{50}$ (M) N1 | $IC_{50}$ (M) N2 |
|---|---|---|---|---|
| 2b | 1.195 | 1.384 | 7.239E−09 | 5.29E−09 |
| 8b | 1.042 | 1.307 | 3.108E−09 | 5.49E−09 |
| BMS 754807 | 1.176 | 1.123 | 1.673E−08 | 1.91E−08 |

TABLE B4

$IC_{50}$ Values of Compound nos. 2b & 8b, and BMS-754807 against IR.

| Compound No. | Hill Slope N1 | Hill Slope N2 | $IC_{50}$ (M) N1 | $IC_{50}$ (M) N2 |
|---|---|---|---|---|
| 2b | 1.34 | 1.13 | 5.51E−09 | 4.07E−09 |
| 8b | 0.96 | 1.19 | 3.95E−09 | 3.60E−09 |
| BMS 754807 | 1.16 | 1.05 | 2.35E−08 | 2.50E−08 |

The compounds of the invention were screened against activated IGF-1R at a concentration of $3.00 \times 10^{-8}$ M in duplicate. The assay results are presented as the percent inhibition of binding in Table B5.

TABLE B5

Percent Inhibition of Binding against Activated IGF-1R, and selected $IC_{50}$ values.

| Compound No. | % Inh @ 30 nM (N1) | (N2) | Avg | $IC_{50}$ (nM) |
|---|---|---|---|---|
| 2a | −12 | 18 | 3 | |
| 2b | 90 | 88 | 89 | 6.1 |
| 4a | 4 | 17 | 10 | |
| 4b | 22 | 35 | 28 | |
| 5 | | | 66, 79 | 13, 17 |
| 6a | 22 | 33 | 28 | |
| 6b | 93 | 95 | 94 | 6.5 |
| 8a | | | 0 | |
| 8b | 93 | 95 | 94 | 5.1 |
| 9b | 14 | 17 | 16 | |
| 11a | 17 | 10 | 13 | |
| 10a | | | 32 | 33.0 |
| 10b | | | −11 | |
| 10c | | | 15 | |
| 10d | | | 84 | 5.8 |
| 11b | 22 | 11 | 17 | |
| 12a | 19 | 20 | 20 | |
| 12b | 13 | 34 | 24 | |
| 13a | 10 | 34 | 22 | |
| 13b | 82 | 80 | 81 | 17 |
| 14b | 77 | 76 | 77 | 22 |
| 15a | 17 | 20 | 19 | |
| 15b | 32 | 28 | 30 | |
| 16a | 27 | 15 | 21 | |
| 16b | 40 | 40 | 40 | |
| 17a | 12 | 24 | 18 | |
| 17b | 21 | 23 | 22 | |
| 18a | | | 14 | |
| 18b | | | 39 | |
| 19a | | | −3 | |
| 19b | | | 21 | |
| 20a | | | 11 | |
| 20b | | | 9 | |
| 21a | | | 14 | |
| 21b | | | 41 | |
| 50 | | | 35 | |

The compounds of the invention were screened against activated IR at a concentration of $3.00 \times 10^{-8}$ M in duplicate. The assay results are presented as the percent inhibition of binding in Table B6.

TABLE B6

Percent Inhibition of Binding against Activated IR.

| Compound No. | % Inh @ 30 nM (N1) | (N2) | Avg | $IC_{50}$ (nM) |
|---|---|---|---|---|
| 2a | 0 | 10 | 5 | |
| 2b | 92 | 88 | 90 | 5.7 |
| 4a | −14 | −2 | −8 | |
| 4b | 41 | 33 | 37 | |
| 5 | | | 76, 88 | 8.3, 12.0 |
| 6a | −13 | 9 | −2 | |
| 6b | 92 | 91 | 92 | 41.3 |
| 8b | 91 | 89 | 90 | 5.45 |
| 9b | 3 | 9 | 6 | |
| 10a | | | 54 | 33.0 |
| 10d | | | 85 | 7.2 |
| 11a | −17 | −9 | −13 | |
| 11b | −2 | 9 | 3 | |
| 12a | 10 | 8 | 9 | |
| 12b | −14 | −10 | −12 | |
| 13a | 4 | −1 | 2 | |
| 13b | 84 | 80 | 82 | 13 |
| 14b | 82 | 81 | 81 | 16 |
| 15a | −2 | 4 | 1 | |
| 15b | 28 | 31 | 30 | |
| 16a | 1 | −7 | −3 | |
| 16b | 26 | 23 | 25 | |
| 17a | 2 | 5 | 3 | |
| 17b | 2 | 10 | 6 | |
| 18a | | | 3 | |
| 18b | | | 32 | |
| 19a | | | −9 | |
| 19b | | | 9 | |
| 21b | | | 30 | 120.0 |
| 50 | | | 51 | 36.0 |
| 68 | | | | 11.0 |
| 69 | | | | 32.0 |
| 70 | | | | 22.0 |

TABLE B6-continued

Percent Inhibition of Binding against Activated IR.

| Compound No. | % Inh @ 30 nM | | | |
|---|---|---|---|---|
| | (N1) | (N2) | Avg | IC$_{50}$ (nM) |
| 71 | | | | 44.0 |
| 72 | | | | 16.0 |

The binding data of the compounds of the invention to IGF-1R and IR reflect the efficacy of the compounds in inhibiting the phosphorylation of AKT as demonstrated in Example 1.

Example B3

Kinome Analysis

Example B3A

Screening of Compound Nos. 2b & 8b, BMS-754807, and OSI-906 Against a Panel of 192 Kinases A kinase profiling study of compound 8b was conducted by Caliper LifeSciences Services (Hanover, Md.). The compound was tested at concentrations of $1.0 \times 10^{-8}$ and $1.0 \times 10^{-9}$ M in the RapidKinase192™ panel in duplicate. The following kinases were assessed in the panel: ABL; Abl(H396P); Abl (Q252H); Abl(T315I); ABL1(E255K); ABL1(G250E); ABL1(Y253F); AKT1; AKT2; AKT3; ALK; AMPK; AMPK-alpha2/beta1/gamma1; Arg; AurA; AurB; AurC; AXL; BLK; BMX; BRSK1; BRSK2; BTK; CaMK1a; CamK1d; CAMK2; CaMK2a; CAMK4; CaMKII beta; CaMKII gamma; Casein kinase 1g2; CDK1/Cycline B1; CDK2; CDK3; CDK5/p25; CHK1; CHK2; CK1d; CK1-epsilon; CK1g3 (CSNK1G3); CK1-gamma1; CLK2; c-Raf; CSNK1A1; c-TAK1; DAPK1; DCAMKL1; DCAMKL2; DDR2; DYRK1a; DYRK1B; DYRK3; DYRK4; EGFR; EGFR (ErbB1) T790M L858R; EGFR(T790M); EPHA1; EPHA2; EPHA3; EPHA4; EPHA5; EPHA8; EPHB1; EPHB2; EPHB3; EPHB4; Erk1; Erk2; Fer; FES; FGFR1; FGFR1 (V561M); FGFR2; FGFR2(N549H); FGFR3; FGFR3 [K650E]; FGFR4; FGR; FLT1; FLT3; Flt3(D835Y); FLT4; FMS; FRK; FYN; GCK; GSK3-alpha; GSK3b; Hck; HER4; HGK; HIPK1; HIPK2; IGF1R; IKBKE (IKK epsilon); IKK-beta; INSR; IRAK4; ITK; JAK2; KDR; KIT; KIT [T670I]; LCK; LOK; LTK; LYN; LYNB; MAPKAPK2; MAPKAPK3; MARK1; MARK2; MARK4; MELK; Mer; MET; MET M1250T; MINK; MNK1 (MKNK1); MSK1; MSK2; MST1; MST1R; MST2; MST3 (STK24); NEK1; NEK2; NTRK2 (TRKB); NuaK1; p38a; p38alpha/SAPK2a (T106M); p38-beta2; p38-delta; p38-gamma; p70S6K; PAK2; PAK3; PAK4; PAK5 (PAK7); PASK; PDGFR beta; PDGFR_alpha; PDGFRA (D842V); PDGFR-alpha (V561D); PhKg1; PhKg2; PIM1; PIM2; PIM3; PKA; PKC-alpha; PKCb2; PKC-beta1; PKC-delta; PKC-epsilon; PKC-eta; PKC-gamma; PKC-theta; PKCz; PKD1; PKD2; PKD3; PKG1-beta; PKGa; PRAK; PRKCI (PKC-iota); PRKX; PYK2; RET; Ret (V804L); RET; Y791F; ROCK1; ROCK2; ROS(ROS1); RSK1; RSK2; RSK3; RSK4; SGK1; SGK2; SGK3; SRC; SRM (SRMS); SYK; TEC; TRKC (NTRK3); TSSK1; TSSK2; TXK; TYRO3; YES; and ZIPK (DAPK3). The screening was performed using the Caliper EZReader2, a 4-sipper LabChip, and ProfilerPro Kinase Selectivity Assay Kits 1 and 2. The assay measures the conversion of a fluorescent peptide substrate to a phosphorylated product. Briefly, the reaction mixture was introduced through a capillary sipper onto the microfluidic chip, where the substrate and product were electrophoretically separated and detected by laser-induced fluorescence. The time-dependent fluorescence signal indicates the extent of the reaction. The extent of binding was classified into three main groups: Low (39% or lower inhibition), Medium (40 to 59% inhibition) and High (60% or higher inhibition).

For Compound No. 8b, it was found that all binding was Low at both 1 nM and 10 nM concentration, with the exception of the following (+=Low, ++=Med, +++=High) as shown in Table B7.

TABLE B7

Kinase binding of Compound No. 8b.

| Kinase | Average % Inh @ 1 nM | Average % Inh @ 10 nM |
|---|---|---|
| | Compound No. 8b | |
| IGF-1R | + | +++ |
| AXL | + | ++ |
| INSR | ++ | +++ |
| Mer | + | +++ |
| MET | + | ++ |
| NTRK2(TRKB) | +++ | +++ |
| PYK2 | + | ++ |
| ROS (ROS1) | ++ | +++ |
| TRXC(NTRK3) | +++ | +++ |

Kinase profiling studies of Compound no. 2b, BMS-754807, and OSI-906 were also conducted as described above using a single concentration of 1 µM.

For Compound no. 2b, it was found that all binding was Low with the exception of the following (++=Med, +++=High) as shown in Table B8:

TABLE B8

Kinase binding of Compound No. 2b.
Average % Inh @ 1 µM

| Kinase | Compound No. 2b |
|---|---|
| ABL | ++ |
| Abl(H396P) | ++ |
| Abl(Q252H) | ++ |
| Abl(T315I) | +++ |
| ABL1(G250E) | +++ |
| ABL1(Y253F) | ++ |
| ALK | +++ |
| AMPK | +++ |
| AMPK-α2/β1/γ1 | +++ |
| Arg | +++ |
| AurA, B, C | +++ |
| AXL | +++ |
| BLK | +++ |
| BMX | ++ |
| BTK | ++ |
| DCAMKL1 | ++ |
| DCAMKL2 | +++ |
| DDR2 | +++ |
| EPHA1, 2 | +++ |
| EPHA3 | ++ |
| EPHA4 | ++ |
| EPHA5 | +++ |
| EPHB1 | +++ |
| EPHB2 | +++ |
| EPHB4 | ++ |
| Fer | +++ |
| FES | ++ |
| FGFR1 | +++ |
| FGFR1(V561M) | +++ |
| FGFR2 | +++ |
| FGFR2(N549H) | +++ |

TABLE B8-continued

Kinase binding of Compound No. 2b.
Average % Inh @ 1 μM

| Kinase | Compound No. 2b |
| --- | --- |
| FGFR3 | +++ |
| FGFR3(K650E) | +++ |
| FGR | +++ |
| FLT3 | ++ |
| Flt3(D835Y) | +++ |
| FLT4 | ++ |
| FRK | +++ |
| FYN | +++ |
| Hck | +++ |
| IGF1R | +++ |
| INSR | +++ |
| ITK | ++ |
| JAK2 | +++ |
| KDR | ++ |
| LCK | +++ |
| LTK | +++ |
| LYN | +++ |
| LYNB | +++ |
| Mer | +++ |
| MET | +++ |
| MET(M1250T) | +++ |
| MST1, 1R, 2 | +++ |
| NTRK2(TRKB) | +++ |
| NuaK1 | +++ |
| PAK5(PAK7) | ++ |
| PhKg2 | ++ |
| PYK2 | +++ |
| RET | +++ |
| Ret(V804L) | +++ |
| RET(Y791F) | +++ |
| ROS(ROS1) | +++ |
| SRC | +++ |
| TRXC(NTRK3) | +++ |
| TYRO3 | +++ |
| Yes | +++ |

In particular cases of high inhibition at 1 μM, testing was continued at concentrations of 10 nM and 100 nM, with the following results obtained (+=Low, ++=Med, +++=High) as shown in Table B9:

TABLE B9

Kinase binding of Compound No. 2b at 10 nM and 100 nM.
Compound no. 2b

| Kinase | Average % Inh @ 10 nM | Average % Inh @ 100 nM |
| --- | --- | --- |
| Abl(T315I) | + | + |
| ALK | + | + |
| AMPK | + | ++ |
| AMPK-α2/β1/γ1 | + | ++ |
| Arg | + | + |
| AurA | + | +++ |
| AurB | ++ | +++ |
| AurC | +++ | +++ |
| AXL | ++ | +++ |
| BLK | + | + |
| BMX | + | + |
| EPHA1 | + | ++ |
| Fer | + | +++ |
| FGFR1 | + | + |
| FGFR1(V561M) | + | ++ |
| FGFR2 | + | + |
| FGFR2(N549H) | + | + |
| FGR | + | + |
| FYN | + | +++ |
| Hck | + | ++ |
| IGF1R | + | ++ |
| INSR | + | +++ |
| LCK | + | + |
| LYN | + | ++ |
| LYNB | + | ++ |
| Mer | ++ | +++ |
| MET | + | +++ |
| MET M1250T | + | + |
| MST1 | + | ++ |
| MST2 | + | + |
| NTRK(TRKB) | +++ | +++ |
| NuaK1 | + | ++ |
| PYK2 | + | +++ |
| RET | + | ++ |
| Ret(V804L) | + | ++ |
| RET(Y791F) | + | ++ |
| ROS(ROS1) | +++ | +++ |
| SRC | + | +++ |
| TRKC(NTRK3) | +++ | +++ |
| TYRO3 | + | + |
| Yes | + | ++ |

For BMS-754807, it was found that all binding was Low with the exception of the following (++=Med, +++=High) as shown in Table B10:

TABLE B10

Kinase binding of BMS-754807.
Kinase
Average % Inh @ 1 μM

| Kinase | BMS-754807 |
| --- | --- |
| Abl(T315I) | +++ |
| ALK | +++ |
| AMPK | +++ |
| AMPK-α2/β1/γ1 | +++ |
| Arg | ++ |
| AurA, B, C | +++ |
| AXL | +++ |
| BLK | ++ |
| BMX | +++ |
| c-TAK1 | +++ |
| DCAMKL1 | +++ |
| DCAMKL2 | +++ |
| DDR2 | +++ |
| EPHA1, 2 | +++ |
| EPHA4 | ++ |
| EPHA5 | ++ |
| EPHB1 | +++ |
| EPHB2 | ++ |
| EPHB4 | ++ |
| Fer | +++ |
| FES | +++ |
| FGFR1 | +++ |
| FGFR1(V561M) | +++ |
| FGFR2 | +++ |
| FGFR2(N549H) | +++ |
| FGFR3 | +++ |
| FGFR3(K650E) | ++ |
| FGR | +++ |
| FLT3 | ++ |
| Flt3(D835Y) | ++ |
| FRK | ++ |
| FYN | +++ |
| Hck | +++ |
| IGF1R | +++ |
| INSR | +++ |
| ITK | +++ |
| JAK2 | +++ |
| LCK | ++ |
| LTK | ++ |

TABLE B10-continued

Kinase binding of BMS-754807.
Kinase Average % Inh @ 1 µM

| Kinase | BMS-754807 |
|---|---|
| LYN | ++ |
| LYNB | ++ |
| MARK1 | ++ |
| MARK2, 4 | +++ |
| Mer | +++ |
| MET | +++ |
| MET(M1250T) | +++ |
| MST1, 1R, 2 | +++ |
| MST3 | ++ |
| NTRK2(TRKB) | +++ |
| NuaK1 | +++ |
| PAK5(PAK7) | +++ |
| PhKg2 | ++ |
| PYK2 | +++ |
| RET | +++ |
| Ret(V804L) | +++ |
| RET(Y791F) | +++ |
| ROS(ROS1) | +++ |
| SRC | +++ |
| TRXC(NTRK3) | +++ |
| TYRO3 | ++ |
| Yes | ++ |

In particular cases of high inhibition at 1 µM, testing was continued at concentrations of 10 nM and 100 nM, with the following results obtained (+=Low, ++=Med, +++=High) as shown in Table B11:

TABLE B11

Kinase binding of BMS-754807 at 10 nM and 100 nM.
BMS-754807

| Kinase | Average % Inh @ 10 nM | Average % Inh @ 100 nM |
|---|---|---|
| AMPK | + | ++ |
| AMPK-α2/β1/γ1 | + | ++ |
| AurA | +++ | +++ |
| AurB | +++ | +++ |
| AurC | +++ | +++ |
| AXL | + | ++ |
| BMX | + | + |
| DCAMKL1 | + | + |
| DCAMKL2 | + | ++ |
| DDR2 | + | ++ |
| EPHA1 | + | ++ |
| EPHA2 | + | + |
| Fer | + | +++ |
| FES | + | + |
| FGFR1 | + | + |
| FGFR1(V561M) | + | ++ |
| FGFR2 | + | + |
| IGF1R | + | +++ |
| INSR | ++ | +++ |
| Mer | + | ++ |
| MET | + | +++ |
| MET M1250T | + | ++ |
| MST1 | + | + |
| MST1R | + | + |
| NTRK(TRKB) | +++ | +++ |
| PYK2 | + | +++ |
| ROS(ROS1) | +++ | +++ |
| TRKC(NTRK3) | +++ | +++ |

For OSI-906, it was found that all binding was Low with the exception of the following (++=Med, +++=High) as shown in Table B12:

TABLE B12

Kinase binding of OSI-906.

| Kinase | Average % Inh @ 1 µM OSI-906 |
|---|---|
| IGF-1R | +++ |
| INSR | +++ |
| KDR | ++ |

For Compound 8a, an enantiomer of Compound 8b, kinome profiling of 192 kinases was also conducted but it was found that inhibition of all kinases was Low (<20% inhibition).

Compounds 2b and 8b were found to bind with high affinity to only a few kinases, including IGF-1R and IR. The compounds did not bind with high affinity to targets that are known to be associated with adverse downstream effects, such as AURA, AURB and AURC. However, the compounds did bind to targets such as TrkC, Mer, Met and AXL, which may be beneficial because some of these kinases have been implicated in tumorigenesis and cancer progression.

Compound 8b and several derivatives were tested by Caliper LifeSciences Services (Hanover, Md.) against a panel of 11 kinases at three different concentrations, 0.1 µM, 0.01 µM and 0.001 µM. The kinases tested were AurA, AurB, AurC, AXL, FAK2, IGF1R, InsR, Mer, MET, TrkB and TrkC. At 0.1 µM, many of the compounds strongly inhibited most of the kinases. However, at 0.01 µM, only Compounds 5, 6b, 10a and 10d strongly inhibited AXL, FAK2, TrkB and TrkC. These kinases have been reported to be involved in tumorigenesis and cancer progression. These compounds and derivatives could be used to specifically target these four kinases and not target other kinases such as AURA, AURB and AURC, the inhibition of which is associated with adverse effects. At the lowest concentration (0.001 µM) none of the compounds inhibited the kinase more than 40%.

Example B3B

Screening of Compound No. 8b Against Select Panel of 9 Kinases

Kinase assays were performed using the top 9 kinases identified from the panel of 192 kinases against Compound no. 8b. The assays were conducted by Caliper LifeSciences Services (Hanover, Md.) using Compound No. 8b over a range of 8 concentrations from $3.0 \times 10^{-7}$ to $1.0 \times 10^{-10}$ M in duplicate. The assays were conducted using the Caliper LabChip 3000 and a 12-sipper LabChip as described above. The assay results are presented as $IC_{50}$ values in Table B13.

TABLE B13

$IC_{50}$ values of Compound No. 8b and BMS-754807 against select panel of nine kinases.

| Kinase | Compound No. 8b $IC_{50}$ (nM) | BMS-754807 $IC_{50}$ (nM) |
|---|---|---|
| AXL | 9.756 | 74.02 |
| AURA | 131.7 | 29.91 |
| AURB | 74.69 | 57.33 |
| AURC | 41.37 | 2.698 |
| FAK2(PTK2b) | 2.361 | 4.346 |
| Mer | 3.840 | 79.56 |
| Met | 7.743 | 16.07 |
| TrkB | 12.21 | 7.022 |
| TrkC | 3.002 | 3.259 |

ROS1 is a proto-oncogene and is highly expressed in many cancers. The binding of Compound 8b and BMS-754807 was measured by Caliper LifeScience Services (Hanover, Md.) as described above. Compounds were tested over a range of concentrations, from 0.03 nM to 1 and the IC50 was calculated.

| Kinase | Compound No. 8b IC$_{50}$ (nM) | BMS-754807 IC$_{50}$ (nM) |
|---|---|---|
| ROS1 | 15 | 8.91 |

Example B4

Extended Panel Screen Against Non-Kinase Targets

Compound no. 8b was screened against a panel of 72 non-kinase targets shown in Table B14. The experiments were performed by Ricerca Biosciences (Painesville, Ohio) using the LeadProfilingScreen and CYP450 assays. Compound no. 8b was screened at a concentration of 1 µM. No significant hits were identified. The percent inhibition of all non-kinase targets was under 30 percent inhibition, with the compound exhibiting a percent inhibition of under 10 percent inhibition for over 50 of the non-kinase targets tested.

TABLE B14

| Non-Kinase Targets<br>Non-Kinase Targets |
|---|
| CYP$_{450}$ (1A2, 2C19, 2C9, 3D6, 3A4), Adenosine (A$_1$, A$_{2A}$, A$_3$), Adrenergic ($\alpha_{1A}$, $\alpha_{1B}$, $\alpha_{1D}$, $\alpha_{2A}$, $\beta_1$, $\beta_2$), Androgen (Testosterone) AR, Bradykinin (B$_1$, B$_2$), Ca-Channel (L-Type, N-Type), Cannabinoid CB$_1$, Dopamine (D$_1$, D$_{2S}$, D$_3$, D$_{4.2}$), Endothelin (ET$_A$, ET$_B$), Epidermal Growth Factor (EGF), Estrogen ERα, GAB A (A, B1A), Glucocorticoid, Glutamate (Kainate), Glutamate NMDA (Agonist, Glycine, Phencyclidine), Histamine (H$_1$, H$_2$, H$_3$), Imidazoline I$_2$ Central, Interleukin IL-1, Leukotriene CysLT$_1$, Melatonin M$_1$, Muscarinic (M$_1$, M$_2$, M$_3$), Neuropeptide (Y$_1$, Y$_2$), Nicotinic (Acetylcholine, α1), Opiate ($\delta_1$, κ, µ), Phorbol Ester, Platelet Activating Factor, Potassium Channel (K$_{ATP}$, hERG), Prostanoid EP$_4$, Purinergic (P$_{2X}$, P$_{2Y}$), Rolipram, Serotonin (5-HT$_{1A}$, 5-HT$_{2B}$, 5-HT$_3$), Sigma σ$_1$, Tachykinin NK$_1$, Thyroid Hormone, Transporter (Dopamine DAT, GABA, Norepinephrine NET, Serotonin SERT. |

Example B5

Cell Viability Studies

Compound nos. 2b & 8b, OSI-906 and BMS-754807 were screened against a panel of 10 cancer cell lines (BT-20, HCC 1187, LNCaP, MCF-7, MDA MB 175, MDA MB 231, OVCAR-3, T47D, UACC 812, and ZR-75-1). This panel of cell lines includes an ER− breast carcinoma, primary breast ductal carcinoma, prostate adenocarcinoma, mammary adenocarcinoma, mammary ductal carcinoma, mammary ductal carcinoma, ovary adenocarcinoma, ER+ breast carcinoma, ER-HER2+ mammary ductal carcinoma and an ER+ mammary ductal carcinoma, respectively.

This study was conducted by Caliper LifeSciences Services (Hanover, Md.) using the Cell Titer-Glo® assay to determine inhibition of cell proliferation. This assay quantitates the ATP present in order to determine the number of viable cells in culture. Briefly, the compounds were incubated with the cells for 72 h, followed by cell lysis. The resulting luminescent signal is proportional to the amount of ATP present and, therefore, directly proportional to the number of cells present in culture. The compounds were studied over a range of 10 concentrations from $1 \times 10^{-4}$ to $5 \times 10^{-9}$ M in duplicate and IC$_{50}$ values were calculated. The maximum concentration used in the dose range for IC$_{50}$ determination was $1 \times 10^{-6}$ M. Compound No. 8b inhibited proliferation in all cell lines tested.

Compound nos. 2b & 8b, OSI-906, and BMS-754807 were further screened by Caliper LifeSciences against an additional panel of 7 cell lines (A549, COLO 205, HCT-15, HCT-116, HL-60, HT-29, SW-620) using the assay described above. These cell lines are derived from human lung carcinoma, colon adenocarcinoma, colon adenocarcinoma, colon carcinoma, acute promyelocytic leukemia, colon adenocarcinoma, colon adenocarcinoma (from metastatic site lymph node), respectively.

The assay results are presented as calculated IC$_{50}$ values in Table B15. Compound nos. 2b & 8b displayed more potent effects in all cell lines tested than either OSI or BMS.

TABLE B15

IC$_{50}$ values for Compound Nos. 2b & 8b, OSI-906 and BMS-754807 tested in cell viability assays.

| Cell Line | Tissue | Compound No. 2b IC$_{50}$ (µM) | Compound No. 8b IC$_{50}$ (µM) | OSI-906 IC$_{50}$ (µM) | BMS-754807 IC$_{50}$ (µM) |
|---|---|---|---|---|---|
| HT-29 | colon cancer | 0.5 | <0.01 | <100 | <10 |
| HL-60 | promyelocytic leukemia | <10 | 0.01 | <100 | <10 |
| A549 | non-small lung carcinoma | 1 | <10 | 10 | <10 |
| COLO-205 | colon adenocarcinoma | <0.01 | <0.01 | 1 | <1 |
| HCT15 | colon carcinoma | <10 | <10 | <100 | <100 |
| HCT116 | colon carcinoma | 1 | 1 | <100 | 10 |
| HL60 | promyelocytic leukemia | <0.01 | <0.01 | <10 | <10 |
| HT29 | colon adenocarcinoma | <0.01 | <0.01 | <10 | <1 |
| SW-620 | metastatic colorectal cancer | 0.1 | 1 | <100 | 1 |
| BT20 | breast cancer | | <10 | | <100 |
| LNCaP | prostate cancer | | <10 | | <10 |

TABLE B15-continued

IC$_{50}$ values for Compound Nos. 2b & 8b, OSI-906
and BMS-754807 tested in cell viability assays.

| Cell Line | Tissue | Compound No. 2b IC$_{50}$ (µM) | Compound No. 8b IC$_{50}$ (µM) | OSI-906 IC$_{50}$ (µM) | BMS-754807 IC$_{50}$ (µM) |
|---|---|---|---|---|---|
| MCF7 | breast cancer | | <10 | | 0.1 |
| T47D | breast cancer | | <1 | | <10 |
| MDAMB175 | breast cancer | | <10 | | <100 |
| MDAMB231 | breast cancer | | 10 | | <10 |
| OVCAR3 | ovarian cancer | | 1 | | <10 |
| UACC812 | breast cancer | | <10 | | <100 |
| HCC1187 | breast cancer | | <10 | | <10 |
| ZR-75-1 | breast cancer | | <100 | | >100 |

Compounds 2b, 5, 6b and 10a were tested along with derivatives in viability assays as described above by Caliper LifeSciences Systems (Hanover, Md.), in A549, HCT-15, HCT-116, MCF-7, MDA-MB-231, OVCAR3, T47D, COLO205, HT-29, BT-20, HCC1187, HL-60, MDA-MB-175, SW-620, and UACC812 cells. IC$_{50}$ values were calculated as before, and are presented in Table B16.

TABLE B16

IC$_{50}$ values for Compound Nos. 2b 5, 6b and 10a tested in cell viability assays.

| Cell Line | Tissue | Compound No. 2b IC$_{50}$ (µM) | Compound No. 5 IC$_{50}$ (µM) | Compound No. 10a IC$_{50}$ (µM) | Compound No. 6b IC$_{50}$ (µM) |
|---|---|---|---|---|---|
| A549 | non-small lung carcinoma | <1 | <1 | <10 | <1 |
| HCT15 | colon carcinoma | 1 | <10 | <100 | 1 |
| HCT116 | colon carcinoma | 1 | <10 | 10 | <1 |
| MCF7 | breast cancer | 1 | <1 | <1 | <1 |
| MDAMB231 | breast cancer | 1 | <10 | 10 | <1 |
| OVCAR3 | ovarian cancer | <1 | <1 | 1 | <0.1 |
| T47D | breast cancer | 1 | <1 | 1 | <1 |
| COLO205 | colon cancer | <0.1 | 0.1 | <0.1 | <0.1 |
| HT-29 | colon adenocarcinoma | <0.01 | 0.01 | <0.1 | <0.01 |
| BT-20 | breast cancer | 1 | <10 | <10 | 1 |
| HCC-1187 | breast cancer | 0.1 | <1 | <1 | <1 |
| HL60 | promyelocytic leukemia | <1 | <0.1 | 0.1 | <1 |
| LNCaP | Prostate cancer | <1 | 0.1 | <1 | 0.1 |
| MDA-MB-175 | breast cancer | <10 | 1 | <10 | <1 |
| SW-620 | metastatic colorectal cancer | <1 | <1 | <10 | <1 |
| UACC 812 | breast cancer | <10 | <100 | <10 | 1 |

The inhibitory effects of Compound 8a were tested in two cell lines. The proliferation of the breast cancer cell lines MDA-MB-175 and UACC812 did not drop below 68% as compared to the untreated control with any concentration of compound tested (3 µM was the maximum concentration tested).

Analogous studies utilizing pancreatic cancer cell lines such as ASPC-1 and PANC-1 can be performed with compounds of the invention. In one example, Compound 8b gave IC$_{50}$ values of 0.195 uM and 3.663 uM, respectively.

Example B6A

Efficacy in Xenograft Model

To evaluate the efficacy of tumor growth inhibition, the compound 8b was studied using human cancer mouse models. The models are prepared by subcutaneously or orthotopically implanting mice with human cancer cells. When the tumor size of the mice develops (e.g., reaches 100 mm$^3$), the mice are divided into groups for treatment with compound 8b (where different groups receiving the compound 8b may be administered different amounts of the compound 8b) or are provided no compound as a control. The mice are treated (e.g., orally administered a compound of the invention) for a period of time. During the course of the study, the tumor is measured and the weight of the mice is determined. After the treatment period, the mice are sacrificed shortly (e.g. 1 or 2 hours) after the final dose. Blood and tissue are collected for biochemical analysis.

Example B6B

Efficacy in Xenograft Model of Human Colon Cancer

To evaluate the efficacy of tumor growth inhibition, compound 8b was studied using a human colon cancer mouse model. The model is prepared by subcutaneously implanting 50 nude, male 5-6 week old mice with approximately 4×10$^6$ viable human colon cancer COLO-205 cells. When the tumor size reached 100 mm³, the mice were divided into 5 groups (10 mice/group) for treatment with 0, 1, 3, 10, and 15 mg/kg of compound 8b. As detailed in the FIGS. 1 and 3, the 10 and 15 mg/kg group were treated with 3 days of drug holiday and all other groups were treated daily. Tumor volume and mouse body weight were monitored over the 20 day experiment. A Kruskal-Wallis ANOVA test was used to determine statistical significance of tumor volume measurements.

Example B6C

Efficacy in Xenograft Model of Human Breast Cancer

To evaluate the efficacy of tumor growth inhibition, compound 8b was studied using a human breast cancer mouse model. The model was prepared by orthotopic implanting 50 nude, female 5-6 week old mice with approximately 2×10⁶ viable human breast cancer MCF7 cells supplemented with estrogen pellets (1.5 mg 60 day slow release). When the tumor size reached 100 mm³, the mice were divided into 5 groups (10 mice/group) for treatment with 0 and 10 mg/kg/po daily; 10 and 15 mg/kg/po every other day; and 15 mg/kg/po with 2 days on and 2 days off, of compound 8b.

The appropriate amount of compound 8b was sonicated in a PEG-400 solution (80% w/v in case of Example B6B; and 50% w/v in case of Example B6C) to completely dissolve the compound, followed by dropwise addition of the required amount of $H_2O$. The resulting 250 μL dose volume (10 mL/kg) was administered orally to the mouse. During the course of the study, the tumor was measured and the weight of the mice was determined.

At the end of the study, the mice were sacrificed at 2 h (Example B6B) and at 1 h (Example B6C) after the final dose. Blood and tissue were collected for biochemical analysis.

Compound 8b dose-dependently and significantly reduced tumor burden in the COLO205 colon cancer model (FIG. 1) as well as in the MCF7 breast cancer model (FIG. 2). This was well supported by tumor weight and compound 8b exposure levels measured at the end of the each study. Compound 8b dose-dependently reduced body weights of the mice during the initial part of the study but they did recover from their weight loss marginally in the latter part of the study (FIG. 4) or when drug holiday was given (FIGS. 3 and 4).

Any noted weight loss or/and hyperglycemia can be managed by giving a drug holiday and/or treatment with antihyperglycemic drugs (e.g. insulin or metformin or other appropriate antidiabetic drug) as needed.

Analogous studies with compounds of the invention can be performed with further dosing regimens including, for example treatment with test compound at <10 mg/kg such as 5 mg/kg, or >15 mg/kg such as 30 mg/kg, and at varied time points such as daily, every other day, etc. Similarly, activity of compounds of the invention in alternative cell types such as pancreatic cancer AsPC-1 cells can be assessed in similar fashion to those described above.

Example B7

Cell Screens for Cancer Types and Subtypes

Cancer cells are grown according to recommended culture conditions. To evaluate cell viability, cells are plated and allowed to attach overnight. The cell density is adjusted so that the cells will be 70-80% confluent at the end of the assay. After cell attachment, the medium is removed and replaced with fresh medium containing test compound at different concentrations. Test compound is diluted from a DMSO stock such that the final DMSO concentration in the assay is 0.2%. Seventy-two hours after exposing cells to test compound, cell viability is evaluated using a cell viability assay such as CellTiter Glo™ (Promega, Madison, Wis.), and $IC_{50}$ values are determined.

Cancer cell types that may be used in this assay include, without limitation, bladder cancer, breast cancer, colorectal cancer, endometrial cancer, hematopoietic cancer, liver cancer, lung cancer, ovarian cancer, pancreatic cancer, and prostate cancer cells. Breast cancer cell types include, without limitation, HER2 positive breast cancer, luminal breast cancer, triple negative breast cancer (e.g., basal, mesenchymal, mesenchymal stem-like, immunomodulatory, and luminal androgen receptor subtypes), and unclassified breast cancer cells. Liver cancer cell types include, without limitation, hepatitis B virus-derived liver cancer and virus-negative liver cancer cells. Lung cancer cell types include, without limitation, non-small cell lung carcinoma, small cell lung carcinoma, adenocarcinoma, mucoepidermoid, anaplastic, large cell, and unclassified lung cancer cells.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:
1. A compound of the formula (I):

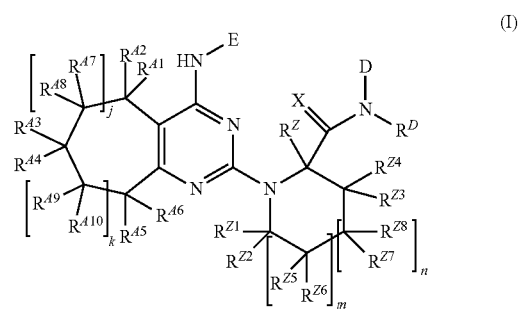

or a salt or N-oxide thereof, wherein:
D is hydrogen; unsubstituted $C_1$-$C_6$ alkyl; $C_1$-$C_6$ alkyl substituted by 1 to 5 substituents independently selected from the group consisting of hydroxy, heteroaryl, and heteroaryl substituted by $C_1$-$C_6$ alkyl; unsubstituted aryl; unsubstituted heteroaryl; heteroaryl substituted by 1 to 5 substituents independently selected from the group consisting of alkoxy, amino, halo, hydroxy and thioalkyl; unsubstituted $C_3$-$C_8$ cycloalkyl; unsubstituted heterocyclyl; or heterocyclyl substituted by 1 to 5 substituents independently selected from unsubstituted acyl, acyl substituted by amino, $C_1$-$C_6$ alkyl and oxo; wherein the heteroaryl of D is selected from the group consisting of pyridyl, pyrimidyl, pyrazinyl, thiazolyl, oxazolyl, pyrazolyl, furanyl and thiadiazolyl, and the heterocyclyl of D is selected from the group consisting of pyrrolidinyl and piperidinyl;
E is unsubstituted 5-membered heteroaryl or 5-membered heteroaryl substituted by 1 to 4 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl;

each j, k, m, and n is independently 0 or 1;

each $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$, where present, is independently hydrogen, unsubstituted $C_1$-$C_6$ alkyl, halo, hydroxy, or taken together with a geminal $R^{A(1-10)}$ group and the carbon to which they are attached to form a carbonyl moiety or a thiocarbonyl moiety;

$R^D$ is hydrogen;

X is O or S;

$R^Z$ is hydrogen, or unsubstituted $C_1$-$C_6$ alkyl;

each $R^{Z1}$ and $R^{Z2}$ is independently hydrogen, or unsubstituted $C_1$-$C_6$ alkyl;

each $R^{Z3}$, $R^{Z4}$, $R^{Z5}$, $R^{Z6}$, $R^{Z7}$ and $R^{Z8}$, where present, is independently hydrogen, unsubstituted $C_1$-$C_6$ alkyl, halo, hydroxy, —$OR^1$, —O—$C_1$-$C_6$ alkylene-P(O)(OH)$_2$, —OC(O)$R^8$, unsubstituted tetrazolyl, tetrazolyl substituted by $C_1$-$C_6$ alkyl, or is taken together with a geminal $R^{Z(3-8)}$ group and the carbon to which they are attached to form a carbonyl moiety;

each $R^1$ is independently unsubstituted $C_1$-$C_6$ alkyl;

each $R^8$ is independently unsubstituted $C_1$-$C_6$ alkyl.

2. The compound of claim 1, or a salt or N-oxide thereof, wherein each of j and k is 0.

3. The compound of claim 2, or a salt or N-oxide thereof, wherein each of $R^{A1}$, $R^{A2}$, $R^{A3}$, $R^{A4}$, $R^{A5}$ and $R^{A6}$ is hydrogen.

4. The compound of claim 2, or a salt or N-oxide thereof, wherein each of $R^{A1}$ and $R^{A2}$ is independently $C_1$-$C_6$ alkyl; and each of $R^{A3}$, $R^{A4}$, $R^{A5}$ and $R^{A6}$ is hydrogen.

5. The compound of claim 4, or a salt or N-oxide thereof, wherein each of $R^{A1}$ and $R^{A2}$ is methyl.

6. The compound of claim 2, or a salt or N-oxide thereof, wherein each of $R^{A3}$ and $R^{A4}$ is independently $C_1$-$C_6$ alkyl; and each of $R^{A1}$, $R^{A2}$, $R^{A5}$ and $R^{A6}$ is hydrogen.

7. The compound of claim 6, or a salt or N-oxide thereof, wherein each of $R^{A3}$ and $R^{A4}$ is methyl.

8. The compound of claim 2, or a salt or N-oxide thereof, wherein each of $R^{A5}$ and $R^{A6}$ is independently $C_1$-$C_6$ alkyl; and each of $R^{A1}$, $R^{A2}$, $R^{A3}$ and $R^{A4}$ is hydrogen.

9. The compound of claim 8, or a salt or N-oxide thereof, wherein each of $R^{A5}$ and $R^{A6}$ is methyl.

10. The compound of claim 2, or a salt or N-oxide thereof, wherein each of $R^{A1}$, $R^{A2}$, $R^{A5}$ and $R^{A6}$ is hydrogen.

11. The compound of claim 2, or a salt or N-oxide thereof, wherein each of $R^{A5}$ and $R^{A6}$ is hydrogen.

12. The compound of claim 2, or a salt or N-oxide thereof, wherein $R^{A3}$ and $R^{A4}$ are taken together with the carbon to which they are attached to form a carbonyl moiety; and each of $R^{A1}$, $R^{A2}$, $R^{A5}$ and $R^{A6}$ is hydrogen.

13. The compound of claim 2, or a salt or N-oxide thereof, wherein $R^{A3}$ and $R^{A4}$ are taken together with the carbon to which they are attached to form a thiocarbonyl moiety; and each of $R^{A1}$, $R^{A2}$, $R^{A5}$ and $R^{A6}$ is hydrogen.

14. The compound of claim 2, or a salt or N-oxide thereof, wherein each of $R^{A3}$ and $R^{A4}$ is independently halogen; and each of $R^{A1}$, $R^{A2}$, $R^{A5}$ and $R^{A6}$ is hydrogen.

15. The compound of claim 14, or a salt or N-oxide thereof, wherein each of $R^{A3}$ and $R^{A4}$ is fluorine.

16. The compound of claim 2, or a salt or N-oxide thereof, wherein $R^{A3}$ is halogen; and each of $R^{A1}$, $R^{A2}$, $R^{A4}$, $R^{A5}$ and $R^{A6}$ is hydrogen.

17. The compound of claim 16, or a salt or N-oxide thereof, wherein $R^{A3}$ is fluorine.

18. The compound of claim 2, or a salt or N-oxide thereof, wherein each of $R^{A1}$, $R^{A2}$, $R^{A3}$, $R^{A4}$, $R^{A5}$ and $R^{A6}$ is independently hydroxy or hydrogen.

19. The compound of claim 18, or a salt or N-oxide thereof, wherein one of $R^{A1}$, $R^{A2}$, $R^{A3}$, $R^{A4}$, $R^{A5}$ and $R^{A6}$ is hydroxy.

20. The compound of claim 18, or a salt or N-oxide thereof, wherein two of $R^{A1}$, $R^{A2}$, $R^{A3}$, $R^{A4}$, $R^{A5}$ and $R^{A6}$ are hydroxy.

21. The compound of claim 1, or a salt or N-oxide thereof, wherein j is 1 and k is 0.

22. The compound of claim 21, or a salt or N-oxide thereof, wherein each of $R^{A1}$, $R^{A2}$, $R^{A3}$, $R^{A4}$, $R^{A5}$, $R^{A6}$, $R^{A7}$ and $R^{A8}$ is hydrogen.

23. The compound of claim 1, or a salt or N-oxide thereof, wherein each of j and k is 1.

24. The compound of claim 23, or a salt or N-oxide thereof, wherein each of $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ is hydrogen.

25. The compound of claim 1, or a salt or N-oxide thereof, wherein each of m and n is 0.

26. The compound of claim 25, or a salt or N-oxide thereof, wherein each of $R^{Z1}$, $R^{Z2}$, $R^{Z3}$ and $R^{Z4}$ is hydrogen.

27. The compound of claim 1, or a salt or N-oxide thereof, wherein m is 1 and n is 0.

28. The compound of claim 27, or a salt or N-oxide thereof, wherein each of $R^{Z1}$, $R^{Z2}$, $R^{Z3}$ and $R^{Z4}$ is hydrogen.

29. The compound of claim 27, or a salt or N-oxide thereof, wherein each of $R^{Z5}$ and $R^{Z6}$ is hydrogen.

30. The compound of claim 27, or a salt or N-oxide thereof, wherein $R^{Z5}$ is hydroxy; and $R^{Z6}$ is hydrogen.

31. The compound of claim 27, or a salt or N-oxide thereof, wherein $R^{Z3}$ is hydroxy; and $R^{Z4}$ is hydrogen.

32. The compound of claim 27, or a salt or N-oxide thereof, wherein $R^{Z5}$ is $OR^1$; and $R^{Z6}$ is hydrogen.

33. The compound of claim 32, or a salt or N-oxide thereof, wherein $R^{Z5}$ is methoxy.

34. The compound of claim 27, or a salt or N-oxide thereof, wherein $R^{Z5}$ is halogen; and $R^{Z6}$ is hydrogen.

35. The compound of claim 34, or a salt or N-oxide thereof, wherein $R^{Z5}$ is fluorine.

36. The compound of claim 27, or a salt or N-oxide thereof, wherein each of $R^{Z5}$ and $R^{Z6}$ is independently unsubstituted $C_1$-$C_6$ alkyl.

37. The compound of claim 36, or a salt or N-oxide thereof, wherein each of $R^{Z5}$ and $R^{Z6}$ is methyl.

38. The compound of claim 27, or a salt or N-oxide thereof, wherein $R^{Z5}$ is unsubstituted tetrazolyl or tetrazolyl substituted by $C_1$-$C_6$ alkyl; and $R^{Z6}$ is hydrogen.

39. The compound of claim 38, or a salt or N-oxide thereof, wherein $R^{Z5}$ is tetrazolyl substituted by $C_1$-$C_6$ alkyl.

40. The compound of claim 27, or a salt or N-oxide thereof, wherein each of $R^{Z5}$ and $R^{Z6}$ is independently halogen.

41. The compound of claim 40, or a salt or N-oxide thereof, wherein each of $R^{Z5}$ and $R^{Z6}$ is fluorine.

42. The compound of claim 27, or a salt or N-oxide thereof, wherein $R^{Z5}$ is —O—$C_1$-$C_6$ alkylene-P(O)(OH)$_2$; and $R^{Z6}$ is hydrogen.

43. The compound of claim 27, or a salt or N-oxide thereof, wherein $R^{Z5}$ is —OC(O)$R^8$; and $R^{Z6}$ is hydrogen.

44. The compound of claim 27, or a salt or N-oxide thereof, wherein $R^{Z5}$ and $R^{Z6}$ are taken together with the carbon to which they are attached to form a carbonyl moiety.

45. The compound of claim 1, or a salt or N-oxide thereof, wherein each of m and n is 1.

46. The compound of claim 45, or a salt or N-oxide thereof, wherein each of $R^{Z3}$, $R^{Z4}$, $R^{Z5}$, $R^{Z6}$, $R^{Z7}$ and $R^{Z8}$ is hydrogen.

47. The compound of claim 1, or a salt or N-oxide thereof, wherein X is O.

48. The compound of claim 1, or a salt or N-oxide thereof, wherein X is S.

49. The compound of claim 1, or a salt or N-oxide thereof, wherein $R^Z$ is hydrogen.

50. The compound of claim 1, or a salt or N-oxide thereof, wherein $R^Z$ is unsubstituted $C_1$-$C_6$ alkyl.

51. The compound of claim 50, or a salt or N-oxide thereof, wherein $R^Z$ is methyl.

52. The compound of claim 1, or a salt or N-oxide thereof, wherein D is hydrogen.

53. The compound of claim 1, or a salt or N-oxide thereof, wherein D is unsubstituted $C_1$-$C_6$ alkyl or $C_1$-$C_6$ alkyl substituted by 1 to 5 substituents independently selected from the group consisting of hydroxy, heteroaryl, and heteroaryl substituted by $C_1$-$C_6$ alkyl.

54. The compound of claim 53, or a salt or N-oxide thereof, wherein D is methyl.

55. The compound of claim 53, or a salt or N-oxide thereof, wherein D is hydroxyethyl.

56. The compound of claim 53, or a salt or N-oxide thereof, wherein D is methyl substituted with unsubstituted oxazolyl, oxazolyl substituted by $C_1$-$C_6$ alkyl, unsubstituted pyrazolyl, pyrazolyl substituted by $C_1$-$C_6$ alkyl, unsubstituted furanyl, furanyl substituted by $C_1$-$C_6$ alkyl, unsubstituted thiazolyl, or thiazolyl substituted by $C_1$-$C_6$ alkyl.

57. The compound of claim 56, or a salt or N-oxide thereof, wherein D is methyl substituted with oxazol-2-yl, pyrazol-5-yl, 1-methylpyrazol-5-yl, furan-2-yl, or thiazol-2-yl.

58. The compound of claim 1, or a salt or N-oxide thereof, wherein D is unsubstituted phenyl.

59. The compound of claim 1, or a salt or N-oxide thereof, wherein D is unsubstituted pyridyl or pyridyl substituted by 1 to 5 substituents independently selected from the group consisting of alkoxy, amino, halo, hydroxy and thioalkyl.

60. The compound of claim 59, or a salt or N-oxide thereof, wherein D is unsubstituted pyridyl.

61. The compound of claim 59, or a salt or N-oxide thereof, wherein D is pyridyl substituted by 1 to 5 substituents independently selected from the group consisting of alkoxy, amino, halo, hydroxy and thioalkyl.

62. The compound of claim 59, or a salt or N-oxide thereof, wherein D is selected from the group consisting of 3-pyridyl and 6-fluoro-3-pyridyl.

63. The compound of claim 59, or a salt or N-oxide thereof, wherein D is selected from the group consisting of 6-hydroxypyridin-3-yl, 6-aminopyridin-3-yl, 6-(methylthio)pyridin-3-yl, and 6-ethoxypyridin-3-yl.

64. The compound of claim 1, or a salt or N-oxide thereof, wherein D is unsubstituted pyrimidyl or pyrimidyl substituted by 1 to 5 substituents independently selected from the group consisting of alkoxy, amino, halo, hydroxy and thioalkyl.

65. The compound of claim 64, or a salt or N-oxide thereof, wherein D is unsubstituted pyrimidyl.

66. The compound of claim 65, or a salt or N-oxide thereof, wherein D is pyrimid-5-yl.

67. The compound of claim 64, or a salt or N-oxide thereof, wherein D is pyrimidyl substituted by 1 to 5 substituents independently selected from the group consisting of alkoxy, amino, halo, hydroxy and thioalkyl.

68. The compound of claim 1, or a salt or N-oxide thereof, wherein D is unsubstituted pyrazinyl or pyrazinyl substituted by 1 to 5 substituents independently selected from the group consisting of alkoxy, amino, halo, hydroxy and thioalkyl.

69. The compound of claim 68, or a salt or N-oxide thereof, wherein D is pyrazin-2-yl.

70. The compound of claim 68, or a salt or N-oxide thereof, wherein D is pyrazinyl substituted by 1 to 5 substituents independently selected from the group consisting of alkoxy, amino, halo, hydroxy and thioalkyl.

71. The compound of claim 1, or a salt or N-oxide thereof, wherein D is unsubstituted thiazolyl or thiazolyl substituted by 1 to 5 substituents independently selected from the group consisting of alkoxy, amino, halo, hydroxy and thioalkyl.

72. The compound of claim 71, or a salt or N-oxide thereof, wherein D is unsubstituted thiazolyl.

73. The compound of claim 71, or a salt or N-oxide thereof, wherein D is substituted thiazolyl substituted by 1 to 3 substituents independently selected from the group consisting of alkoxy, amino, halo, hydroxy and thioalkyl.

74. The compound of claim 73, or a salt or N-oxide thereof, wherein D is 5-chlorothiazol-2-yl.

75. The compound of claim 1, or a salt or N-oxide thereof, wherein D is unsubstituted thiadiazolyl or thiadiazolyl substituted by 1 to 5 substituents independently selected from the group consisting of alkoxy, amino, halo, hydroxy and thioalkyl.

76. The compound of claim 75, or a salt or N-oxide thereof, wherein D is unsubstituted thiadiazolyl.

77. The compound of claim 1, or a salt or N-oxide thereof, wherein D is unsubstituted $C_3$-$C_8$ cycloalkyl.

78. The compound of claim 1, or a salt or N-oxide thereof, wherein D is unsubstituted heterocyclyl or heterocyclyl substituted by 1 to 5 substituents independently selected from unsubstituted acyl, acyl substituted by amino, $C_1$-$C_6$ alkyl and oxo.

79. The compound of claim 78, or a salt or N-oxide thereof, wherein D is unsubstituted pyrrolidin-3-yl or pyrrolidin-3-yl substituted by 1 to 5 substituents independently selected from unsubstituted acyl, acyl substituted by amino, $C_1$-$C_6$ alkyl and oxo.

80. The compound of claim 79, or a salt or N-oxide thereof, wherein D is 1-acetylpyrrolidin-3-yl.

81. The compound of claim 78, or a salt or N-oxide thereof, wherein D is unsubstituted piperidin-3-yl or piperdin-3-yl substituted by 1 to 5 substituents independently selected from unsubstituted acyl, acyl substituted by amino, $C_1$-$C_6$ alkyl and oxo.

82. The compound of claim 81, or a salt or N-oxide thereof, wherein D is 1-(2-amino-2-methylpropanoyl)piperidin-3-yl.

83. The compound of claim 81, or a salt or N-oxide thereof, wherein D is 1-isopropylpiperidin-3-yl.

84. The compound of claim 1, or a salt or N-oxide thereof, wherein E is an unsubstituted 5-membered heteroaryl.

85. The compound of claim 1, or a salt or N-oxide thereof, wherein E is unsubstituted pyrazolyl or pyrazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl.

86. The compound of claim 85, or a salt or N-oxide thereof, wherein E is pyrazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl.

87. The compound of claim 86, or a salt or N-oxide thereof, wherein E is selected from the group consisting of 5-cyclopropylpyrazol-3-yl, 5-cyclopentylpyrazol-3-yl, 5-(isopropyl)pyrazol-3-yl, 3-cyclopropylpyrazol-5-yl, 3-cyclopentylpyrazol-5-yl and 3-(isopropyl)pyrazol-5-yl.

88. The compound of claim 86, or a salt or N-oxide thereof, wherein E is selected from the group consisting of 5-hydroxypyrazol-3-yl, 5-(2-hydroxypropan-2-yl)pyrazol-3-yl, 5-(1-hydroxypropan-2-yl)pyrazol-3-yl, 5-(2-hydroxycyclopropyl)pyrazol-3-yl, and 1-hydroxy-5-isopropylpyrazol 3-yl.

89. The compound of claim 1, or a salt or N-oxide thereof, wherein E is unsubstituted imidazolyl or imidazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl.

90. The compound of claim 1, or a salt or N-oxide thereof, wherein E is unsubstituted-isoxazolyl or isoxazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl.

91. The compound of claim 1, or a salt or N-oxide thereof, wherein E is unsubstituted oxazolyl or oxazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl.

92. The compound of claim 1, or a salt or N-oxide thereof, wherein E is unsubstituted thiazolyl or thiazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl.

93. A compound, or a salt thereof, wherein the compound is selected from the group consisting of:
- 1-(4-(5-cyclopropyl-1H-pyrazol-3-ylamino)-6,7-dihydro-5H-cyclopenta[d]pyrimidin-2-yl)-N-(6-fluoropyridin-3-yl)-2-methylpyrrolidine-2-carboxamide;
- 1-(4-(5-cyclopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
- 1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide;
- 1-(4-(5-cyclopentyl-1H-pyrazol-3-ylamino)-6,7-dihydro-5H-cyclopenta[d]pyrimidin-2-yl)-N-(6-fluoropyridin-3-yl)pyrrolidine-2-carboxamide;
- 1-(4-(5-cyclopropyl-1H-pyrazol-3-ylamino)-6,7-dihydro-5H-cyclopenta[d]pyrimidin-2-yl)-N-(6-fluoropyridin-3-yl)azetidine-2-carboxamide;
- 1-(4-(5-cyclopropyl-1H-pyrazol-3-ylamino)-6,7-dihydro-5H-cyclopenta[d]pyrimidin-2-yl)-N-(pyrazin-2-yl)pyrrolidine-2-carboxamide;
- 1-(4-(5-cyclopropyl-1H-pyrazol-3-ylamino)-6,7-dihydro-5H-cyclopenta[d]pyrimidin-2-yl)-N-(pyrimidin-5-yl)pyrrolidine-2-carboxamide;
- N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
- 1-(4-(5-cyclopropyl-1H-pyrazol-3-ylamino)-6,7-dihydro-5H-cyclopenta[d]pyrimidin-2-yl)-N-(6-fluoropyridin-3-yl)piperidine-2-carboxamide;
- 1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;
- 1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;
- N-(6-fluoropyridin-3-yl)-1-(4-(3-isopropylisoxazol-5-ylamino)-6,7-dihydro-5H-cyclopenta[d]pyrimidin-2-yl)pyrrolidine-2-carboxamide;
- N-(6-fluoropyridin-3-yl)-1-(4-(5-isopropyl-1H-pyrazol-3-ylamino)-5,6,7,8-tetrahydroquinazolin-2-yl)pyrrolidine-2-carboxamide;
- 1-(4-(5-cyclopropyl-1H-pyrazol-3-ylamino)-5,6,7,8-tetrahydroquinazolin-2-yl)-N-(6-fluoropyridin-3-yl)pyrrolidine-2-carboxamide;
- 1-(4-(5-cyclopentyl-1H-pyrazol-3-ylamino)-5,6,7,8-tetrahydroquinazolin-2-yl)-N-(6-fluoropyridin-3-yl)pyrrolidine-2-carboxamide;
- N-(6-fluoropyridin-3-yl)-1-(4-(5-isopropyl-1H-pyrazol-3-ylamino)-6,7-dihydro-5H-cyclopenta[d]pyrimidin-2-yl)piperidine-2-carboxamide;
- 1-(4-(5-cyclopentyl-1H-pyrazol-3-ylamino)-6,7-dihydro-5H-cyclopenta[d]pyrimidin-2-yl)-N-(6-fluoropyridin-3-yl)piperidine-2-carboxamide;
- 1-(4-(5-isopropyl-1H-pyrazol-3-ylamino)-6,7-dihydro-5H-cyclopenta[d]pyrimidin-2-yl)pyrrolidine-2-carboxamide;
- 1-(4-(5-isopropyl-1H-pyrazol-3-ylamino)-6,7-dihydro-5H-cyclopenta[d]pyrimidin-2-yl)-N-methylpyrrolidine-2-carboxamide;
- 1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;
- 1-(4-((5-isopropyl-1H-pyrazol-3-yl)amino)-6,7-dihydro-5H-cyclopenta[d]pyrimidin-2-yl)-N-(pyrrolidin-3-yl)pyrrolidine-2-carboxamide;
- 1-(4-((5-cyclopropyl-1H-pyrazol-3-yl)amino)-6,7-dihydro-5H-cyclopenta[d]pyrimidin-2-yl)-N-(thiazol-2-yl)pyrrolidine-2-carboxamide;
- 1-(4-((5-cyclopropyl-1H-pyrazol-3-yl)amino)-6,7-dihydro-5H-cyclopenta[d]pyrimidin-2-yl)-2-methyl-N-(pyrimidin-4-yl)pyrrolidine-2-carboxamide;
- 1-(4-((5-isopropyl-1H-pyrazol-3-yl)amino)-6,7-dihydro-5H-cyclopenta[d]pyrimidin-2-yl)-N-(piperidin-3-yl)pyrrolidine-2-carboxamide;
- N-(1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
- N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;
- N-(6-aminopyridin-3-yl)-1-(4-((5-cyclopropyl-1H-pyrazol-3-yl)amino)-6,7-dihydro-5H-cyclopenta[d]pyrimidin-2-yl)pyrrolidine-2-carboxamide;
- 1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;
- 1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;
- N-(6-fluoropyridin-3-yl)-1-(4-((5-(1-methylcyclopropyl)-1H-pyrazol-3-yl)amino)-6,7-dihydro-5H-cyclopenta[d]pyrimidin-2-yl)pyrrolidine-2-carboxamide;
- N-(6-fluoropyridin-3-yl)-1-(4-((5-isopropyl-1H-pyrazol-3-yl)amino)-6,7-dihydro-5H-cyclopenta[d]pyrimidin-2-yl)-4,4-dimethylpyrrolidine-2-carboxamide
- 1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;

1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;

4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

4,4-difluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

3-((2-(2-((6-fluoropyridin-3-yl)carbamoyl)pyrrolidin-1-yl)-6,7-dihydro-5H-cyclopenta[d]pyrimidin-4-yl)amino)-1H-pyrazole-5-carboxamide;

N-(6-fluoropyridin-3-yl)-1-(4-((1-isopropyl-1H-imidazol-4-yl)amino)-6,7-dihydro-5H-cyclopenta[d]pyrimidin-2-yl)pyrrolidine-2-carboxamide;

4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;

2-((2-(2-((6-fluoropyridin-3-yl)carbamoyl)pyrrolidin-1-yl)-6,7-dihydro-5H-cyclopenta[d]pyrimidin-4-yl)amino)oxazole-5-carboxamide;

N-(6-fluoropyridin-3-yl)-1-(4-((5-(1-hydroxycyclopropyl)-1H-pyrazol-3-yl)amino)-6,7-dihydro-5H-cyclopenta[d]pyrimidin-2-yl)pyrrolidine-2-carboxamide;

N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;

2-((2-(2-((6-fluoropyridin-3-yl)carbamoyl)pyrrolidin-1-yl)-6,7-dihydro-5H-cyclopenta[d]pyrimidin-4-yl)amino)thiazole-5-carboxamide;

N-(6-fluoropyridin-3-yl)-1-(4-((2-isopropyl-1H-imidazol-5-yl)amino)-6,7-dihydro-5H-cyclopenta[d]pyrimidin-2-yl)pyrrolidine-2-carboxamide;

N-(6-fluoropyridin-3-yl)-1-(4-((5-isopropyl-1H-pyrazol-3-yl)amino)-5,5-dimethyl-6,7-dihydro-5H-cyclopenta[d]pyrimidin-2-yl)pyrrolidine-2-carboxamide;

N-(6-fluoropyridin-3-yl)-1-(4-((5-isopropyl-1H-pyrazol-3-yl)amino)-7,7-dimethyl-6,7-dihydro-5H-cyclopenta[d]pyrimidin-2-yl)pyrrolidine-2-carboxamide;

N-(6-fluoropyridin-3-yl)-1-(4-((5-isopropyl-1H-pyrazol-3-yl)amino)-5,7-dihydrospiro[cyclopenta[d]pyrimidine-6,1'-cyclopropan]-2-yl)pyrrolidine-2-carboxamide;

N-(6-fluoropyridin-3-yl)-1-(4-((5-isopropyl-1H-pyrazol-3-yl)amino)-6-oxo-6,7-dihydro-5H-cyclopenta[d]pyrimidin-2-yl)pyrrolidine-2-carboxamide;

N-(6-fluoropyridin-3-yl)-1-(4-((5-isopropyl-1H-pyrazol-3-yl)amino)-6,6-dimethyl-6,7-dihydro-5H-cyclopenta[d]pyrimidin-2-yl)pyrrolidine-2-carboxamide;

1-(6,6-difluoro-4-((5-isopropyl-1H-pyrazol-3-yl)amino)-6,7-dihydro-5H-cyclopenta[d]pyrimidin-2-yl)-N-(6-fluoropyridin-3-yl)pyrrolidine-2-carboxamide;

N-(6-fluoropyridin-3-yl)-1-(4-((5-isopropyl-1H-pyrazol-3-yl)amino)-5,7-dihydrospiro[cyclopenta[d]pyrimidine-6,2'-oxiran]-2-yl)pyrrolidine-2-carboxamide;

N-(6-fluoropyridin-3-yl)-1-(4-((5-isopropyl-1H-pyrazol-3-yl)amino)-6-thioxo-6,7-dihydro-5H-cyclopenta[d]pyrimidin-2-yl)pyrrolidine-2-carboxamide;

1-(4-(5-cyclopropyl-1H-pyrazol-3-ylamino)-6,7-dihydro-5H-cyclopenta[d]pyrimidin-2-yl)pyrrolidine-2-carboxamide;

1-(4-((5-cyclopropyl-1H-pyrazol-3-yl)amino)-5,6,7,8-tetrahydroquinazolin-2-yl)-N-(thiazol-2-yl)pyrrolidine-2-carboxamide;

1-(4-((5-cyclopropyl-1H-pyrazol-3-yl)amino)-6,7,8,9-tetrahydro-5H-cyclohepta[d]pyrimidin-2-yl)-N-(thiazol-2-yl)pyrrolidine-2-carboxamide;

(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid;

1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;

2-fluoro-5-(1-(4-((5-isopropyl-1H-pyrazol-3-yl)amino)-6,7-dihydro-5H-cyclopenta[d]pyrimidin-2-yl)pyrrolidine-2-carboxamido)pyridine 1-oxide;

2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 1-oxide;

2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 3-oxide;

N-(6-hydroxypyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

1-(4-((5-isopropyl-1H-pyrazol-3-yl)amino)-6,7-dihydro-5H-cyclopenta[d]pyrimidin-2-yl)-N-(6-oxo-1,6-dihydropyridin-3-yl)pyrrolidine-2-carboxamide;

1-(5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

1-(5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

1-(4-((5-hydroxy-1H-pyrazol-3-yl)amino)-6,7-dihydro-5H-cyclopenta[d]pyrimidin-2-yl)-N-(6-hydroxypyridin-3-yl)pyrrolidine-2-carboxamide;

1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

1-(4-(5-isopropyl-1H-pyrazol-3-ylamino)-6,7-dihydro-5H-cyclopenta[d]pyrimidin-2-yl)-N-(pyrimidin-4-yl)pyrrolidine-2-carboxamide;

N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;

4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

N-(6-aminopyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

N-(6-fluoropyridin-3-yl)-1-(4-(5-(2-hydroxypropan-2-yl)-1H-pyrazol-3-ylamino)-6,7-dihydro-5H-cyclopenta[d]pyrimidin-2-yl)pyrrolidine-2-carboxamide;

3-(2-(2-(6-fluoropyridin-3-ylcarbamoyl)pyrrolidin-1-yl)-6,7-dihydro-5H-cyclopenta[d]pyrimidin-4-ylamino)-5-isopropyl-1H-pyrazole 2-oxide;

N-(6-fluoropyridin-3-yl)-1-(4-(1-hydroxy-5-isopropyl-1H-pyrazol-3-ylamino)-6,7-dihydro-5H-cyclopenta[d]pyrimidin-2-yl)pyrrolidine-2-carboxamide;

1-(4-(5-isopropyl-1H-pyrazol-3-ylamino)-6,7-dihydro-5H-cyclopenta[d]pyrimidin-2-yl)-N-(6-(methylthio)pyridin-3-yl)pyrrolidine-2-carboxamide;

N-(6-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

N-(6-fluoropyridin-3-yl)-1-(4-(5-isopropyl-1H-pyrazol-3-ylamino)-6,7-dihydro-5H-cyclopenta[d]pyrimidin-2-yl)-4-oxopyrrolidine-2-carboxamide;

N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;
N-(2-hydroxyethyl)-1-(4-(5-isopropyl-1H-pyrazol-3-ylamino)-6,7-dihydro-5H-cyclopenta[d]pyrimidin-2-yl)pyrrolidine-2-carboxamide;
N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carbothioamide;
N-(2-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
N-(furan-2-ylmethyl)-1-(4-(5-isopropyl-1H-pyrazol-3-ylamino)-6,7-dihydro-5H-cyclopenta[d]pyrimidin-2-yl)pyrrolidine-2-carboxamide;
N-((1H-pyrazol-5-yl)methyl)-1-(4-(5-isopropyl-1H-pyrazol-3-ylamino)-6,7-dihydro-5H-cyclopenta[d]pyrimidin-2-yl)pyrrolidine-2-carboxamide;
1-(4-(5-isopropyl-1H-pyrazol-3-ylamino)-6,7-dihydro-5H-cyclopenta[d]pyrimidin-2-yl)-N-((1-methyl-1H-pyrazol-5-yl)methyl)pyrrolidine-2-carboxamide;
1-(4-(5-isopropyl-1H-pyrazol-3-ylamino)-6,7-dihydro-5H-cyclopenta[d]pyrimidin-2-yl)-N-(oxazol-2-ylmethyl)pyrrolidine-2-carboxamide;
1-(4-(5-isopropyl-1H-pyrazol-3-ylamino)-6,7-dihydro-5H-cyclopenta[d]pyrimidin-2-yl)-N-(thiazol-2-ylmethyl)pyrrolidine-2-carboxamide;
N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;
N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;
1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;
N-(6-fluoropyridin-3-yl)-1-(7-hydroxy-4-(5-isopropyl-1H-pyrazol-3-ylamino)-6,7-dihydro-5H-cyclopenta[d]pyrimidin-2-y771)pyrrolidine-2-carboxamide;
N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide; and
N-(2-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide.

94. A compound, or a salt thereof, wherein the compound is selected from the group consisting of:
(R)-1-(4-(5-cyclopropyl-1H-pyrazol-3-ylamino)-6,7-dihydro-5H-cyclopenta[d]pyrimidin-2-yl)-N-(6-fluoropyridin-3-yl)-2-methylpyrrolidine-2-carboxamide;
(S)-1-(4-(5-cyclopropyl-1H-pyrazol-3-ylamino)-6,7-dihydro-5H-cyclopenta[d]pyrimidin-2-yl)-N-(6-fluoropyridin-3-yl)-2-methylpyrrolidine-2-carboxamide;
(R)-1-(4-(5-cyclopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(S)-1-(4-(5-cyclopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(R)-1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide;
(S)-1-(4-(5-cyclopropyl-1H-pyrazol-3-ylamino)-6,7-dihydro-5H-cyclopenta[d]pyrimidin-2-yl)-N-(pyridin-3-yl)pyrrolidine-2-carboxamide;
(R)-1-(4-(5-cyclopentyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(S)-1-(4-(5-cyclopentyl-1H-pyrazol-3-ylamino)-6,7-dihydro-5H-cyclopenta[d]pyrimidin-2-yl)-N-(6-fluoropyridin-3-yl)pyrrolidine-2-carboxamide;
(R)-1-(4-(5-cyclopropyl-1H-pyrazol-3-ylamino)-6,7-dihydro-5H-cyclopenta[d]pyrimidin-2-yl)-N-(6-fluoropyridin-3-yl)azetidine-2-carboxamide;
(S)-1-(4-(5-cyclopropyl-1H-pyrazol-3-ylamino)-6,7-dihydro-5H-cyclopenta[d]pyrimidin-2-yl)-N-(6-fluoropyridin-3-yl)azetidine-2-carboxamide;
(R)-1-(4-(5-cyclopropyl-1H-pyrazol-3-ylamino)-6,7-dihydro-5H-cyclopenta[d]pyrimidin-2-yl)-N-(pyrazin-2-yl)pyrrolidine-2-carboxamide;
(S)-1-(4-(5-cyclopropyl-1H-pyrazol-3-ylamino)-6,7-dihydro-5H-cyclopenta[d]pyrimidin-2-yl)-N-(pyrazin-2-yl)pyrrolidine-2-carboxamide;
(R)-1-(4-(5-cyclopropyl-1H-pyrazol-3-ylamino)-6,7-dihydro-5H-cyclopenta[d]pyrimidin-2-yl)-N-(pyrimidin-5-yl)pyrrolidine-2-carboxamide;
(S)-1-(4-(5-cyclopropyl-1H-pyrazol-3-ylamino)-6,7-dihydro-5H-cyclopenta[d]pyrimidin-2-yl)-N-(pyrimidin-5-yl)pyrrolidine-2-carboxamide;
(R)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(S)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;
(R)-1-(4-(5-cyclopropyl-1H-pyrazol-3-ylamino)-6,7-dihydro-5H-cyclopenta[d]pyrimidin-2-yl)-N-(6-fluoropyridin-3-yl)piperidine-2-carboxamide;
(S)-1-(4-(5-cyclopropyl-1H-pyrazol-3-ylamino)-6,7-dihydro-5H-cyclopenta[d]pyrimidin-2-yl)-N-(6-fluoropyridin-3-yl)piperidine-2-carboxamide;
(2R,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;
(2S,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;
(2R,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;
(2S,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-hydroxypyrrolidine-2-carboxamide;
(2R,3R)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;
(2S,3S)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;
(2R,3S)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;
(2S,3R)-1-(4-(5-cyclopropyl-1H-pyrazol-3-ylamino)-6,7-dihydro-5H-cyclopenta[d]pyrimidin-2-yl)-N-(6-fluoropyridin-3-yl)-3-hydroxypyrrolidine-2-carboxamide;

(R)—N-(6-fluoropyridin-3-yl)-1-(4-(3-isopropylisox-azol-5-ylamino)-6,7-dihydro-5H-cyclopenta[d]pyrimi-din-2-yl)pyrrolidine-2-carboxamide;
(S)—N-(6-fluoropyridin-3-yl)-1-(4-(3-isopropylisoxazol-5-ylamino)-6,7-dihydro-5H-cyclopenta[d]pyrimidin-2-yl)pyrrolidine-2-carboxamide;
(R)—N-(6-fluoropyridin-3-yl)-1-(4-(5-isopropyl-1H-pyrazol-3-ylamino)-5,6,7,8-tetrahydroquinazolin-2-yl)pyrrolidine-2-carboxamide;
(S)—N-(6-fluoropyridin-3-yl)-1-(4-(5-isopropyl-1H-pyrazol-3-ylamino)-5,6,7,8-tetrahydroquinazolin-2-yl)pyrrolidine-2-carboxamide;
(R)-1-(4-(5-cyclopropyl-1H-pyrazol-3-ylamino)-5,6,7,8-tetrahydroquinazolin-2-yl)-N-(6-fluoropyridin-3-yl)pyrrolidine-2-carboxamide;
(S)-1-(4-(5-cyclopropyl-1H-pyrazol-3-ylamino)-5,6,7,8-tetrahydroquinazolin-2-yl)-N-(6-fluoropyridin-3-yl)pyrrolidine-2-carboxamide;
(R)-1-(4-(5-cyclopentyl-1H-pyrazol-3-ylamino)-5,6,7,8-tetrahydroquinazolin-2-yl)-N-(6-fluoropyridin-3-yl)pyrrolidine-2-carboxamide;
(S)-1-(4-(5-cyclopentyl-1H-pyrazol-3-ylamino)-5,6,7,8-tetrahydroquinazolin-2-yl)-N-(6-fluoropyridin-3-yl)pyrrolidine-2-carboxamide;
(R)—N-(6-fluoropyridin-3-yl)-1-(4-(5-isopropyl-1H-pyrazol-3-ylamino)-6,7-dihydro-5H-cyclopenta[d]pyrimidin-2-yl)piperidine-2-carboxamide;
(S)—N-(6-fluoropyridin-3-yl)-1-(4-(5-isopropyl-1H-pyrazol-3-ylamino)-6,7-dihydro-5H-cyclopenta[d]pyrimidin-2-yl)piperidine-2-carboxamide;
(R)-1-(4-(5-cyclopentyl-1H-pyrazol-3-ylamino)-6,7-dihydro-5H-cyclopenta[d]pyrimidin-2-yl)-N-(6-fluoropyridin-3-yl)piperidine-2-carboxamide;
(S)-1-(4-(5-cyclopentyl-1H-pyrazol-3-ylamino)-6,7-dihydro-5H-cyclopenta[d]pyrimidin-2-yl)-N-(6-fluoropyridin-3-yl)piperidine-2-carboxamide;
(R)-1-(4-(5-isopropyl-1H-pyrazol-3-ylamino)-6,7-dihydro-5H-cyclopenta[d]pyrimidin-2-yl)pyrrolidine-2-carboxamide;
(S)-1-(4-(5-isopropyl-1H-pyrazol-3-ylamino)-6,7-dihydro-5H-cyclopenta[d]pyrimidin-2-yl)pyrrolidine-2-carboxamide;
(R)-1-(4-(5-isopropyl-1H-pyrazol-3-ylamino)-6,7-dihydro-5H-cyclopenta[d]pyrimidin-2-yl)-N-methylpyrrolidine-2-carboxamide;
(S)-1-(4-(5-isopropyl-1H-pyrazol-3-ylamino)-6,7-dihydro-5H-cyclopenta[d]pyrimidin-2-yl)-N-methylpyrrolidine-2-carboxamide;
(2R,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;
(2S,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;
(2R,4S)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;
(2S,4R)-1-(4-(5-cyclopropyl-1H-pyrazol-3-ylamino)-6,7-dihydro-5H-cyclopenta[d]pyrimidin-2-yl)-N-(6-fluoropyridin-3-yl)-4-methoxypyrrolidine-2-carboxamide;
(R)-1-(4-((5-isopropyl-1H-pyrazol-3-yl)amino)-6,7-dihydro-5H-cyclopenta[d]pyrimidin-2-yl)-N—((R)-pyrrolidin-3-yl)pyrrolidine-2-carboxamide;
(S)-1-(4-((5-isopropyl-1H-pyrazol-3-yl)amino)-6,7-dihydro-5H-cyclopenta[d]pyrimidin-2-yl)-N—((S)-pyrrolidin-3-yl)pyrrolidine-2-carboxamide;
(R)-1-(4-((5-isopropyl-1H-pyrazol-3-yl)amino)-6,7-dihydro-5H-cyclopenta[d]pyrimidin-2-yl)-N—((S)-pyrrolidin-3-yl)pyrrolidine-2-carboxamide;
(S)-1-(4-((5-isopropyl-1H-pyrazol-3-yl)amino)-6,7-dihydro-5H-cyclopenta[d]pyrimidin-2-yl)-N—((R)-pyrrolidin-3-yl)pyrrolidine-2-carboxamide;
(R)-1-(4-((5-cyclopropyl-1H-pyrazol-3-yl)amino)-6,7-dihydro-5H-cyclopenta[d]pyrimidin-2-yl)-N-(thiazol-2-yl)pyrrolidine-2-carboxamide;
(S)-1-(4-((5-cyclopropyl-1H-pyrazol-3-yl)amino)-6,7-dihydro-5H-cyclopenta[d]pyrimidin-2-yl)-N-(thiazol-2-yl)pyrrolidine-2-carboxamide;
(R)-1-(4-((5-cyclopropyl-1H-pyrazol-3-yl)amino)-6,7-dihydro-5H-cyclopenta[d]pyrimidin-2-yl)-2-methyl-N-(pyrimidin-4-yl)pyrrolidine-2-carboxamide;
(S)-1-(4-((5-cyclopropyl-1H-pyrazol-3-yl)amino)-6,7-dihydro-5H-cyclopenta[d]pyrimidin-2-yl)-2-methyl-N-(pyrimidin-4-yl)pyrrolidine-2-carboxamide;
(R)-1-(4-((5-isopropyl-1H-pyrazol-3-yl)amino)-6,7-dihydro-5H-cyclopenta[d]pyrimidin-2-yl)-N—((R)-piperidin-3-yl)pyrrolidine-2-carboxamide;
(S)-1-(4-((5-isopropyl-1H-pyrazol-3-yl)amino)-6,7-dihydro-5H-cyclopenta[d]pyrimidin-2-yl)-N—((S)-piperidin-3-yl)pyrrolidine-2-carboxamide;
(R)-1-(4-((5-isopropyl-1H-pyrazol-3-yl)amino)-6,7-dihydro-5H-cyclopenta[d]pyrimidin-2-yl)-N—((S)-piperidin-3-yl)pyrrolidine-2-carboxamide;
(S)-1-(4-((5-isopropyl-1H-pyrazol-3-yl)amino)-6,7-dihydro-5H-cyclopenta[d]pyrimidin-2-yl)-N—((R)-piperidin-3-yl)pyrrolidine-2-carboxamide;
(R)—N—(R)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(S)—N—((S)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(R)—N—((S)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(S)—N—((R)-1-(2-amino-2-methylpropanoyl)piperidin-3-yl)-1-(4-((5-isopropyl-1H-pyrazol-3-yl)amino)-6,7-dihydro-5H-cyclopenta[d]pyrimidin-2-yl)pyrrolidine-2-carboxamide;
(2R,4R)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;
(2S,4S)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;
(2R,4S)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;
(2S,4R)—N-(5-chlorothiazol-2-yl)-1-(4-((5-cyclopropyl-1H-pyrazol-3-yl)amino)-6,7-dihydro-5H-cyclopenta[d]pyrimidin-2-yl)-4-methoxypyrrolidine-2-carboxamide;
(R)—N-(6-aminopyridin-3-yl)-1-(4-((5-cyclopropyl-1H-pyrazol-3-yl)amino)-6,7-dihydro-5H-cyclopenta[d]pyrimidin-2-yl)pyrrolidine-2-carboxamide;

(S)—N-(6-aminopyridin-3-yl)-1-(4-((5-cyclopropyl-1H-pyrazol-3-yl)amino)-6,7-dihydro-5H-cyclopenta[d]pyrimidin-2-yl)pyrrolidine-2-carboxamide;

(2R,4R)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2S,4S)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2R,4S)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2S,4R)-1-(4-((5-cyclopropyl-1H-pyrazol-3-yl)amino)-6,7-dihydro-5H-cyclopenta[d]pyrimidin-2-yl)-4-hydroxy-N-(pyridin-3-yl)pyrrolidine-2-carboxamide;

(2R,4R)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(2S,4S)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(2R,4S)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(2S,4R)-1-(4-((5-cyclopropyl-1H-pyrazol-3-yl)amino)-6,7-dihydro-5H-cyclopenta[d]pyrimidin-2-yl)-4-fluoro-N-(1,2,4-thiadiazol-5-yl)pyrrolidine-2-carboxamide;

(R)—N-(6-fluoropyridin-3-yl)-1-(4-((5-(1-methylcyclopropyl)-1H-pyrazol-3-yl)amino)-6,7-dihydro-5H-cyclopenta[d]pyrimidin-2-yl)pyrrolidine-2-carboxamide;

(S)—N-(6-fluoropyridin-3-yl)-1-(4-((5-(1-methylcyclopropyl)-1H-pyrazol-3-yl)amino)-6,7-dihydro-5H-cyclopenta[d]pyrimidin-2-yl)pyrrolidine-2-carboxamide;

(R)—N-(6-fluoropyridin-3-yl)-1-(4-((5-isopropyl-1H-pyrazol-3-yl)amino)-6,7-dihydro-5H-cyclopenta[d]pyrimidin-2-yl)-4,4-dimethylpyrrolidine-2-carboxamide;

(S)—N-(6-fluoropyridin-3-yl)-1-(4-((5-isopropyl-1H-pyrazol-3-yl)amino)-6,7-dihydro-5H-cyclopenta[d]pyrimidin-2-yl)-4,4-dimethylpyrrolidine-2-carboxamide;

(2R,4R)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;

(2S,4S)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;

(2R,4S)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;

(2S,4R)-1-(4-((5-cyclopropyl-1H-pyrazol-3-yl)amino)-6,7-dihydro-5H-cyclopenta[d]pyrimidin-2-yl)-4-methoxy-N-(1,2,4-thiadiazol-5-yl)pyrrolidine-2-carboxamide;

(2R,4R)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;

(2S,4S)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;

(2R,4S)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;

(2S,4R)-1-(4-((5-cyclopropyl-1H-pyrazol-3-yl)amino)-6,7-dihydro-5H-cyclopenta[d]pyrimidin-2-yl)-N-(6-fluoropyridin-3-yl)-4-(5-methyl-2H-tetrazol-2-yl)pyrrolidine-2-carboxamide;

(2R,4R)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(2S,4S)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(2R,4S)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(2S,4R)-4-fluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(R)-4,4-difluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(S)-4,4-difluoro-N-(6-fluoropyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(R)-3-((2-(2-((6-fluoropyridin-3-yl)carbamoyl)pyrrolidin-1-yl)-6,7-dihydro-5H-cyclopenta[d]pyrimidin-4-yl)amino)-1H-pyrazole-5-carboxamide;

(S)-3-((2-(2-((6-fluoropyridin-3-yl)carbamoyl)pyrrolidin-1-yl)-6,7-dihydro-5H-cyclopenta[d]pyrimidin-4-yl)amino)-1H-pyrazole-5-carboxamide;

(R)—N-(6-fluoropyridin-3-yl)-1-(4-((1-isopropyl-1H-imidazol-4-yl)amino)-6,7-dihydro-5H-cyclopenta[d]pyrimidin-2-yl)pyrrolidine-2-carboxamide;

(S)—N-(6-fluoropyridin-3-yl)-1-(4-((1-isopropyl-1H-imidazol-4-yl)amino)-6,7-dihydro-5H-cyclopenta[d]pyrimidin-2-yl)pyrrolidine-2-carboxamide;

(2R,4R)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;

(2S,4S)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;

(2R,4S)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;

(2S,4R)-4-hydroxy-1-(4-((1-isopropyl-1H-imidazol-4-yl)amino)-6,7-dihydro-5H-cyclopenta[d]pyrimidin-2-yl)-N-(1-isopropylpiperidin-3-yl)pyrrolidine-2-carboxamide;

(R)-2-((2-(2-((6-fluoropyridin-3-yl)carbamoyl)pyrrolidin-1-yl)-6,7-dihydro-5H-cyclopenta[d]pyrimidin-4-yl)amino)oxazole-5-carboxamide;

(S)-2-((2-(2-((6-fluoropyridin-3-yl)carbamoyl)pyrrolidin-1-yl)-6,7-dihydro-5H-cyclopenta[d]pyrimidin-4-yl)amino)oxazole-5-carboxamide;

(R)—N-(6-fluoropyridin-3-yl)-1-(4-((5-(1-hydroxycyclopropyl)-1H-pyrazol-3-yl)amino)-6,7-dihydro-5H-cyclopenta[d]pyrimidin-2-yl)pyrrolidine-2-carboxamide;

(S)—N-(6-fluoropyridin-3-yl)-1-(4-((5-(1-hydroxycyclopropyl)-1H-pyrazol-3-yl)amino)-6,7-dihydro-5H-cyclopenta[d]pyrimidin-2-yl)pyrrolidine-2-carboxamide;

(2R,4R)—N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;

(2S,4S)—N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;

(2R,4S)—N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;

(2S,4R)—N-(6-fluoropyridin-3-yl)-4-hydroxy-1-(4-((1-isopropyl-1H-imidazol-4-yl)amino)-6,7-dihydro-5H-cyclopenta[d]pyrimidin-2-yl)pyrrolidine-2-carboxamide;

(R)-2-((2-(2-((6-fluoropyridin-3-yl)carbamoyl)pyrrolidin-1-yl)-6,7-dihydro-5H-cyclopenta[d]pyrimidin-4-yl)amino)thiazole-5-carboxamide;

(S)-2-((2-(2-((6-fluoropyridin-3-yl)carbamoyl)pyrrolidin-1-yl)-6,7-dihydro-5H-cyclopenta[d]pyrimidin-4-yl)amino)thiazole-5-carboxamide;

(R)—N-(6-fluoropyridin-3-yl)-1-(4-((2-isopropyl-1H-imidazol-5-yl)amino)-6,7-dihydro-5H-cyclopenta[d]pyrimidin-2-yl)pyrrolidine-2-carboxamide;

(S)—N-(6-fluoropyridin-3-yl)-1-(4-((2-isopropyl-1H-imidazol-5-yl)amino)-6,7-dihydro-5H-cyclopenta[d]pyrimidin-2-yl)pyrrolidine-2-carboxamide;

(R)—N-(6-fluoropyridin-3-yl)-1-(4-((5-isopropyl-1H-pyrazol-3-yl)amino)-5,5-dimethyl-6,7-dihydro-5H-cyclopenta[d]pyrimidin-2-yl)pyrrolidine-2-carboxamide;

(S)—N-(6-fluoropyridin-3-yl)-1-(4-((5-isopropyl-1H-pyrazol-3-yl)amino)-5,5-dimethyl-6,7-dihydro-5H-cyclopenta[d]pyrimidin-2-yl)pyrrolidine-2-carboxamide;

(R)—N-(6-fluoropyridin-3-yl)-1-(4-((5-isopropyl-1H-pyrazol-3-yl)amino)-7,7-dimethyl-6,7-dihydro-5H-cyclopenta[d]pyrimidin-2-yl)pyrrolidine-2-carboxamide;

(S)—N-(6-fluoropyridin-3-yl)-1-(4-((5-isopropyl-1H-pyrazol-3-yl)amino)-7,7-dimethyl-6,7-dihydro-5H-cyclopenta[d]pyrimidin-2-yl)pyrrolidine-2-carboxamide;

(R)—N-(6-fluoropyridin-3-yl)-1-(4-((5-isopropyl-1H-pyrazol-3-yl)amino)-6-oxo-6,7-dihydro-5H-cyclopenta[d]pyrimidin-2-yl)pyrrolidine-2-carboxamide;

(S)—N-(6-fluoropyridin-3-yl)-1-(4-((5-isopropyl-1H-pyrazol-3-yl)amino)-6-oxo-6,7-dihydro-5H-cyclopenta[d]pyrimidin-2-yl)pyrrolidine-2-carboxamide;

(R)—N-(6-fluoropyridin-3-yl)-1-(4-((5-isopropyl-1H-pyrazol-3-yl)amino)-6,6-dimethyl-6,7-dihydro-5H-cyclopenta[d]pyrimidin-2-yl)pyrrolidine-2-carboxamide;

(S)—N-(6-fluoropyridin-3-yl)-1-(4-((5-isopropyl-1H-pyrazol-3-yl)amino)-6,6-dimethyl-6,7-dihydro-5H-cyclopenta[d]pyrimidin-2-yl)pyrrolidine-2-carboxamide;

(R)-1-(6,6-difluoro-4-((5-isopropyl-1H-pyrazol-3-yl)amino)-6,7-dihydro-5H-cyclopenta[d]pyrimidin-2-yl)-N-(6-fluoropyridin-3-yl)pyrrolidine-2-carboxamide;

(S)-1-(6,6-difluoro-4-((5-isopropyl-1H-pyrazol-3-yl)amino)-6,7-dihydro-5H-cyclopenta[d]pyrimidin-2-yl)-N-(6-fluoropyridin-3-yl)pyrrolidine-2-carboxamide;

(R)—N-(6-fluoropyridin-3-yl)-1-(4-((5-isopropyl-1H-pyrazol-3-yl)amino)-6-thioxo-6,7-dihydro-5H-cyclopenta[d]pyrimidin-2-yl)pyrrolidine-2-carboxamide;

(S)—N-(6-fluoropyridin-3-yl)-1-(4-((5-isopropyl-1H-pyrazol-3-yl)amino)-6-thioxo-6,7-dihydro-5H-cyclopenta[d]pyrimidin-2-yl)pyrrolidine-2-carboxamide;

(R)-1-(4-(5-cyclopropyl-1H-pyrazol-3-ylamino)-6,7-dihydro-5H-cyclopenta[d]pyrimidin-2-yl)pyrrolidine-2-carboxamide;

(S)-1-(4-(5-cyclopropyl-1H-pyrazol-3-ylamino)-6,7-dihydro-5H-cyclopenta[d]pyrimidin-2-yl)pyrrolidine-2-carboxamide;

(R)-1-(4-((5-cyclopropyl-1H-pyrazol-3-yl)amino)-5,6,7,8-tetrahydroquinazolin-2-yl)-N-(thiazol-2-yl)pyrrolidine-2-carboxamide;

(S)-1-(4-((5-cyclopropyl-1H-pyrazol-3-yl)amino)-5,6,7,8-tetrahydroquinazolin-2-yl)-N-(thiazol-2-yl)pyrrolidine-2-carboxamide;

(R)-1-(4-((5-cyclopropyl-1H-pyrazol-3-yl)amino)-6,7,8,9-tetrahydro-5H-cyclohepta[d]pyrimidin-2-yl)-N-(thiazol-2-yl)pyrrolidine-2-carboxamide;

(S)-1-(4-((5-cyclopropyl-1H-pyrazol-3-yl)amino)-6,7,8,9-tetrahydro-5H-cyclohepta[d]pyrimidin-2-yl)-N-(thiazol-2-yl)pyrrolidine-2-carboxamide;

(2R,4R)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid;

(2S,4S)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid;

(2R,4S)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid;

(2S,4R)-(((1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl)oxy)methyl)phosphonic acid;

(2R,4R)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;

(2S,4S)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;

(2R,4S)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate;

(2S,4R)-1-(4-((5-cyclopropyl-1H-pyrazol-3-yl)amino)-6,7-dihydro-5H-cyclopenta[d]pyrimidin-2-yl)-5-((6-fluoropyridin-3-yl)carbamoyl)pyrrolidin-3-yl isobutyrate (R)-2-fluoro-5-(1-(4-((5-isopropyl-1H-pyrazol-3-yl)amino)-6,7-dihydro-5H-cyclopenta[d]pyrimidin-2-yl)pyrrolidine-2-carboxamido)pyridine 1-oxide;

(S)-2-fluoro-5-(1-(4-((5-isopropyl-1H-pyrazol-3-yl)amino)-6,7-dihydro-5H-cyclopenta[d]pyrimidin-2-yl)pyrrolidine-2-carboxamido)pyridine 1-oxide;

(R)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 1-oxide;

(S)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 1-oxide;

(R)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 3-oxide;

(S)-2-(2-((6-fluoropyridin-3-yl)carbamoyl)pyrrolidin-1-yl)-4-((5-isopropyl-1H-pyrazol-3-yl)amino)-6,7-dihydro-5H-cyclopenta[d]pyrimidine 3-oxide;

(R)—N-(6-hydroxypyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(S)—N-(6-hydroxypyridin-3-yl)-1-(4-((5-isopropyl-1H-pyrazol-3-yl)amino)-6,7-dihydro-5H-cyclopenta[d]pyrimidin-2-yl)pyrrolidine-2-carboxamide;

(R)-1-(4-((5-isopropyl-1H-pyrazol-3-yl)amino)-6,7-dihydro-5H-cyclopenta[d]pyrimidin-2-yl)-N-(6-oxo-1,6-dihydropyridin-3-yl)pyrrolidine-2-carboxamide;

(S)-1-(4-((5-isopropyl-1H-pyrazol-3-yl)amino)-6,7-dihydro-5H-cyclopenta[d]pyrimidin-2-yl)-N-(6-oxo-1,6-dihydropyridin-3-yl)pyrrolidine-2-carboxamide;

(R)-1-((R)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((S)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-((S)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((R)-5-hydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-((5R,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-((5R,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-((5S,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-((5S,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((5R,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((5R,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((5S,7R)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-((5S,7S)-5,7-dihydroxy-4-((5-isopropyl-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-(4-((5-hydroxy-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(S)-1-(4-((5-hydroxy-1H-pyrazol-3-yl)amino)-6,7-dihydro-5H-cyclopenta[d]pyrimidin-2-yl)-N-(6-hydroxypyridin-3-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(pyrimidin-4-yl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(pyrimidin-4-yl)pyrrolidine-2-carboxamide;

(2R,4R)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;

(2R,4S)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;

(2S,4R)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;

(2S,4S)—N-(6-fluoropyridin-3-yl)-4-hydroxy-1-(4-(5-isopropyl-1H-pyrazol-3-ylamino)-6,7-dihydro-5H-cyclopenta[d]pyrimidin-2-yl)pyrrolidine-2-carboxamide;

(2R,4R)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

(2R,4S)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

(2S,4R)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide;

(2S,4S)-4-hydroxy-1-(4-(5-isopropyl-1H-pyrazol-3-ylamino)-6,7-dihydro-5H-cyclopenta[d]pyrimidin-2-yl)-N-(thiazol-2-yl)pyrrolidine-2-carboxamide (R)—N-(6-aminopyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(6-aminopyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-(6-fluoropyridin-3-yl)-1-(4-(5-(2-hydroxypropan-2-yl)-1H-pyrazol-3-ylamino)-6,7-dihydro-5H-cyclopenta[d]pyrimidin-2-yl)pyrrolidine-2-carboxamide;

(S)—N-(6-fluoropyridin-3-yl)-1-(4-(5-(2-hydroxypropan-2-yl)-1H-pyrazol-3-ylamino)-6,7-dihydro-5H-cyclopenta[d]pyrimidin-2-yl)pyrrolidine-2-carboxamide;

(R)-3-(2-(2-(6-fluoropyridin-3-ylcarbamoyl)pyrrolidin-1-yl)-6,7-dihydro-5H-cyclopenta[d]pyrimidin-4-ylamino)-5-isopropyl-1H-pyrazole 2-oxide;

(S)-3-(2-(2-(6-fluoropyridin-3-ylcarbamoyl)pyrrolidin-1-yl)-6,7-dihydro-5H-cyclopenta[d]pyrimidin-4-ylamino)-5-isopropyl-1H-pyrazole 2-oxide;

(R)—N-(6-fluoropyridin-3-yl)-1-(4-(1-hydroxy-5-isopropyl-1H-pyrazol-3-ylamino)-6,7-dihydro-5H-cyclopenta[d]pyrimidin-2-yl)pyrrolidine-2-carboxamide;

(S)—N-(6-fluoropyridin-3-yl)-1-(4-(1-hydroxy-5-isopropyl-1H-pyrazol-3-ylamino)-6,7-dihydro-5H-cyclopenta[d]pyrimidin-2-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(6-(methylthio)pyridin-3-yl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(6-(methylthio)pyridin-3-yl)pyrrolidine-2-carboxamide;

(R)—N-(6-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(6-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-(6-fluoropyridin-3-yl)-1-(4-(5-isopropyl-1H-pyrazol-3-ylamino)-6,7-dihydro-5H-cyclopenta[d]pyrimidin-2-yl)-4-oxopyrrolidine-2-carboxamide;

(S)—N-(6-fluoropyridin-3-yl)-1-(4-(5-isopropyl-1H-pyrazol-3-ylamino)-6,7-dihydro-5H-cyclopenta[d]pyrimidin-2-yl)-4-oxopyrrolidine-2-carboxamide;

(R,R)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R,S)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S,R)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S,S)—N-(1-acetylpyrrolidin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-(2-hydroxyethyl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(2-hydroxyethyl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carbothioamide;

(S)—N-(6-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carbothioamide;

(R)—N-(2-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(2-fluoropyridin-3-yl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-(furan-2-ylmethyl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-(furan-2-ylmethyl)-1-(4-(5-isopropyl-1H-pyrazol-3-ylamino)-6,7-dihydro-5H-cyclopenta[d]pyrimidin-2-yl)pyrrolidine-2-carboxamide;

(R)—N-((1H-pyrazol-5-yl)methyl)-1-(4-(5-isopropyl-1H-pyrazol-3-ylamino)-6,7-dihydro-5H-cyclopenta[d]pyrimidin-2-yl)pyrrolidine-2-carboxamide;

(S)—N-((1H-pyrazol-5-yl)methyl)-1-(4-(5-isopropyl-1H-pyrazol-3-ylamino)-6,7-dihydro-5H-cyclopenta[d]pyrimidin-2-yl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-((1-methyl-1H-pyrazol-5-yl)methyl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-((1-methyl-1H-pyrazol-5-yl)methyl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(oxazol-2-ylmethyl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(oxazol-2-ylmethyl)pyrrolidine-2-carboxamide;

(R)-1-(4-(5-isopropyl-1H-pyrazol-3-ylamino)-6,7-dihydro-5H-cyclopenta[d]pyrimidin-2-yl)-N-(thiazol-2-ylmethyl)pyrrolidine-2-carboxamide;

(S)-1-(4-(5-isopropyl-1H-pyrazol-3-ylamino)-6,7-dihydro-5H-cyclopenta[d]pyrimidin-2-yl)-N-(thiazol-2-ylmethyl)pyrrolidine-2-carboxamide;

(R,R)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;

(R,S)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;

(S,R)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;

(S,S)—N-(6-fluoropyridin-3-yl)-1-(4-(5-(1-hydroxypropan-2-yl)-1H-pyrazol-3-ylamino)-6,7-dihydro-5H-cyclopenta[d]pyrimidin-2-yl)pyrrolidine-2-carboxamide;

(R,R)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;

(R,S)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;

(S,R)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;

(S,S)—N-(6-fluoropyridin-3-yl)-1-(4-(5-(2-hydroxycyclopropyl)-1H-pyrazol-3-ylamino)-6,7-dihydro-5H-cyclopenta[d]pyrimidin-2-yl)pyrrolidine-2-carboxamide;

(R,R)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(R,S)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(S,R)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(S,S)-1-(6-fluoro-4-(5-isopropyl-1H-pyrazol-3-ylamino)-6,7-dihydro-5H-cyclopenta[d]pyrimidin-2-yl)-N-(6-fluoropyridin-3-yl)pyrrolidine-2-carboxamide;

(R,R)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;

(R,S)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;

(S,R)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;

(S,S)—N-(6-fluoropyridin-3-yl)-1-(6-hydroxy-4-(5-isopropyl-1H-pyrazol-3-ylamino)-6,7-dihydro-5H-cyclopenta[d]pyrimidin-2-yl)pyrrolidine-2-carboxamide;

(R,R)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;

(R,S)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;

(S,R)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;

(S,S)—N-(6-fluoropyridin-3-yl)-1-(7-hydroxy-4-(5-isopropyl-1H-pyrazol-3-ylamino)-6,7-dihydro-5H-cyclopenta[d]pyrimidin-2-yl)pyrrolidine-2-carboxamide;

(R)—N-(2-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide; and (S)—N-(2-ethoxypyridin-3-yl)-1-(4-(5-isopropyl-1H-pyrazol-3-ylamino)-6,7-dihydro-5H-cyclopenta[d]pyrimidin-2-yl)pyrrolidine-2-carboxamide.

95. The compound of claim 1, wherein the compound is of the formula (I-A):

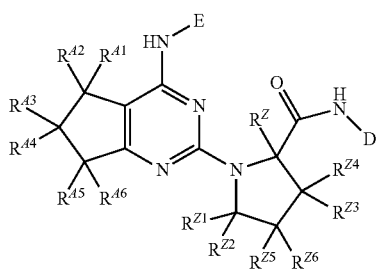

(I-A)

or a salt or N-oxide thereof.

96. The compound of claim 95, or a salt or N-oxide thereof, wherein each of $R^{A1}$, $R^{A2}$, $R^{A3}$, $R^{A4}$, $R^{A5}$ and $R^{A6}$ is independently hydrogen, unsubstituted $C_1$-$C_6$ alkyl, halo, or taken together with a geminal $R^{A(1-6)}$ group and the carbon to which they are attached to form a carbonyl moiety or a thiocarbonyl moiety.

97. The compound of claim 95, or a salt or N-oxide thereof, wherein each of $R^{A1}$, $R^{A2}$, $R^{A3}$, $R^{A4}$, $R^{A5}$ and $R^{A6}$ is independently hydroxy or hydrogen.

98. The compound of claim 95, or a salt or N-oxide thereof, wherein each of $R^{Z1}$, $R^{Z2}$, $R^{Z3}$ and $R^{Z4}$ is hydrogen.

99. The compound of claim 98, or a salt or N-oxide thereof, wherein each of $R^{Z5}$ and $R^{Z6}$ is hydrogen.

100. The compound of claim 98, or a salt or N-oxide thereof, wherein $R^{Z5}$ is hydroxy or —$OR^1$; and $R^{Z6}$ is hydrogen.

101. The compound of claim 95, or a salt or N-oxide thereof, wherein $R^{Z3}$ is hydroxy; and $R^{Z4}$ is hydrogen.

102. The compound of claim 95, or a salt or N-oxide thereof, wherein $R^{Z5}$ is —$OR^1$; and $R^{Z6}$ is hydrogen.

103. The compound of claim 102, or a salt or N-oxide thereof, wherein $R^{Z5}$ is methoxy.

104. The compound of claim 95, or a salt or N-oxide thereof, wherein $R^{Z5}$ is halogen and $R^{Z6}$ is hydrogen.

105. The compound of claim 104, or a salt or N-oxide thereof, wherein $R^{Z5}$ is fluorine.

106. The compound of claim 95, or a salt or N-oxide thereof, wherein each of $R^{Z5}$ and $R^{Z6}$ is independently unsubstituted $C_1$-$C_6$ alkyl.

107. The compound of claim 104, or a salt or N-oxide thereof, wherein each of $R^{Z5}$ and $R^{Z6}$ is methyl.

108. The compound of claim 95, or a salt or N-oxide thereof, wherein $R^{Z5}$ is unsubstituted tetrazolyl or tetrazolyl substituted by $C_1$-$C_6$ alkyl; and $R^{Z6}$ is hydrogen.

109. The compound of claim 108, or a salt or N-oxide thereof, wherein $R^{Z5}$ is tetrazolyl substituted by $C_1$-$C_6$ alkyl.

110. The compound of claim 95, or a salt or N-oxide thereof, wherein each of $R^{Z5}$ and $R^{Z6}$ is independently halogen.

111. The compound of claim 110, or a salt or N-oxide thereof, wherein each of $R^{Z5}$ and $R^{Z6}$ is fluorine.

112. The compound of claim 95, or a salt or N-oxide thereof, wherein $R^{Z5}$ is —O—$C_1$-$C_6$ alkylene-P(O)(OH)$_2$; and $R^{Z6}$ is hydrogen.

113. The compound of claim 95, or a salt or N-oxide thereof, wherein $R^{Z5}$ is —OC(O)$R^8$; and $R^{Z6}$ is hydrogen.

114. The compound of claim 95, or a salt or N-oxide thereof, wherein $R^{Z5}$ and $R^{Z6}$ are taken together with the carbon to which they are attached to form a carbonyl moiety.

115. The compound of claim 95, or a salt or N-oxide thereof, wherein $R^Z$ is hydrogen or methyl.

116. The compound of claim 95, or a salt or N-oxide thereof, wherein D is unsubstituted pyridyl, pyridyl substituted by 1 to 5 substituents independently selected from the group consisting of alkoxy, amino, halo, hydroxy and thioalkyl; unsubstituted pyrimidyl, pyrimidyl substituted by 1 to 5 substituents independently selected from the group consisting of alkoxy, amino, halo, hydroxy and thioalkyl; unsubstituted pyrazinyl, or pyrazinyl substituted by 1 to 5 substituents independently selected from the group consisting of alkoxy, amino, halo, hydroxy and thioalkyl.

117. The compound of claim 116, or a salt or N-oxide thereof, wherein D is selected from the group consisting of 6-fluoro-3-pyridyl, 3-pyridyl, pyrimid-5-yl and pyrazin-2-yl.

118. The compound of claim 95, or a salt or N-oxide thereof, wherein D is unsubstituted $C_1$-$C_6$ alkyl or $C_1$-$C_6$ alkyl substituted by 1 to 5 substituents independently selected from the group consisting of hydroxy, heteroaryl, and heteroaryl substituted by $C_1$-$C_6$ alkyl.

119. The compound of claim 118, or a salt or N-oxide thereof, wherein D is methyl.

120. The compound of claim 118, or a salt or N-oxide thereof, wherein D is methyl substituted with unsubstituted oxazolyl, oxazolyl substituted by $C_1$-$C_6$ alkyl, unsubstituted pyrazolyl, pyrazolyl substituted by $C_1$-$C_6$ alkyl, unsubstituted furanyl, furanyl substituted by $C_1$-$C_6$ alkyl, unsubstituted thiazolyl, or thiazolyl substituted by $C_1$-$C_6$ alkyl.

121. The compound of claim 120, or a salt or N-oxide thereof, wherein D is methyl substituted with oxazol-2-yl, pyrazol-5-yl, 1-methylpyrazol-5-yl, furan-2-yl, or thiazol-2-yl.

122. The compound of claim 95, or a salt or N-oxide thereof, wherein D is unsubstituted piperdin-3-yl or piperdin-3-yl substituted by 1 to 5 substituents independently selected from unsubstituted acyl, acyl substituted by amino.

123. The compound of claim 122, or a salt or N-oxide thereof, wherein D is 1-(2-amino-2-methylpropanoyl)piperidin-3-yl.

124. The compound of claim 122, or a salt or N-oxide thereof, wherein D is 1-isopropylpiperidin-3-yl.

125. The compound of claim 95, or a salt or N-oxide thereof, wherein D is unsubstituted thiazolyl or thiazolyl substituted by 1 to 3 substituents independently selected from the group consisting of alkoxy, amino, halo, hydroxy and thioalkyl.

126. The compound of claim 95, or a salt or N-oxide thereof, wherein D is unsubstituted thiadiazolyl or thiadiazolyl substituted by 1 to 3 substituents independently selected from the group consisting of alkoxy, amino, halo, hydroxy and thioalkyl.

127. The compound of claim 95, or a salt or N-oxide thereof, wherein D is unsubstituted pyrrolidin-3-yl or pyrrolidin-3-yl substituted by 1 to 5 substituents independently selected from unsubstituted acyl, acyl substituted by amino.

128. The compound of claim 95, or a salt or N-oxide thereof, wherein E is unsubstituted pyrazolyl, pyrazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl; unsubstituted isoxazolyl, isoxazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl; unsubstituted imidazolyl, imidazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl; unsubstituted oxazolyl, oxazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl; unsubstituted thiazole thiazolyl, or thiazolyl substituted by 1 to 3 substituents independently selected from the group consisting of unsubstituted acylamino, hydroxy, unsubstituted $C_1$-$C_6$ alkyl, $C_1$-$C_6$ alkyl substituted by hydroxy, unsubstituted $C_3$-$C_8$ cycloalkyl, and $C_3$-$C_8$ cycloalkyl substituted by hydroxy or $C_1$-$C_6$ alkyl.

129. The compound of claim 128, or a salt or N-oxide thereof, wherein E is selected from the group consisting of 5-cyclopropylpyrazol-3-yl, 5-cyclopentylpyrazol-3-yl, 5-(isopropyl)pyrazol-3-yl, 3-cyclopropylpyrazol-5-yl, 3-cyclopentylpyrazol-5-yl, 3-(isopropyl)pyrazol-5-yl, and 3-(isopropyl)isoxazol-5-yl.

130. The compound of claim 128, or a salt or N-oxide thereof, wherein E is selected from the group consisting of 5-hydroxypyrazol-3-yl, 5-(2-hydroxypropan-2-yl)pyrazol-3-yl, 5-(1-hydroxypropan-2-yl)pyrazol-3-yl, 5-(2-hydroxycyclopropyl)pyrazol-3-yl, and 1-hydroxy-5-isopropylpyrazol-3-yl.

131. A pharmaceutical composition comprising a compound of claim 1, or a salt or N-oxide thereof, and a pharmaceutically acceptable carrier.

132. A kit comprising a compound of claim 1, or an N-oxide thereof, or a pharmaceutically acceptable salt thereof.

133. A pharmaceutical composition comprising a compound of claim 93, or a salt thereof, and a pharmaceutically acceptable carrier.

134. A kit comprising a compound of claim 93, or a pharmaceutically acceptable salt thereof.

135. A pharmaceutical composition comprising a compound of claim 94, or a salt thereof, and a pharmaceutically acceptable carrier.

136. A kit comprising a compound of claim 94, or a pharmaceutically acceptable salt thereof.

137. A pharmaceutical composition comprising a compound of claim 95, or a salt or N-oxide thereof, and a pharmaceutically acceptable carrier.

138. A kit comprising a compound of claim 95, or an N-oxide thereof, or a pharmaceutically acceptable salt thereof.

* * * * *